(12) United States Patent
Smider et al.

(10) Patent No.: US 10,562,980 B2
(45) Date of Patent: Feb. 18, 2020

(54) HUMANIZED ANTIBODIES

(71) Applicant: The Scripps Research Institute, La Jolla, CA (US)

(72) Inventors: Vaughn Smider, San Diego, CA (US); Omar A. Bazirgan, San Diego, CA (US); Hongyuan Helen Mao, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 68 days.

(21) Appl. No.: 15/801,251

(22) Filed: Nov. 1, 2017

(65) Prior Publication Data
US 2018/0222999 A1 Aug. 9, 2018

Related U.S. Application Data

(63) Continuation of application No. 14/371,170, filed as application No. PCT/US2013/020910 on Jan. 9, 2013, now abandoned.

(60) Provisional application No. 61/584,680, filed on Jan. 9, 2012.

(51) Int. Cl.
| | |
|---|---|
| *C40B 40/10* | (2006.01) |
| *C07K 16/46* | (2006.01) |
| *C07K 14/54* | (2006.01) |
| *C07K 16/00* | (2006.01) |
| *C07K 16/10* | (2006.01) |

(52) U.S. Cl.
CPC .......... *C07K 16/46* (2013.01); *C07K 14/5421* (2013.01); *C07K 16/00* (2013.01); *C07K 16/005* (2013.01); *C07K 16/1081* (2013.01); *C07K 2317/20* (2013.01); *C07K 2317/24* (2013.01); *C07K 2317/565* (2013.01); *C07K 2318/10* (2013.01); *C07K 2319/00* (2013.01); *C07K 2319/33* (2013.01); *C40B 40/10* (2013.01)

(58) Field of Classification Search
None
See application file for complete search history.

(56) References Cited

U.S. PATENT DOCUMENTS

| | | |
|---|---|---|
| 6,740,747 B2 | 5/2004 | Kaushik et al. |
| 7,196,185 B2 | 3/2007 | Kaushik et al. |
| 7,575,893 B2 | 8/2009 | Simmons |
| 7,592,010 B2 | 9/2009 | Rosen et al. |
| 9,221,902 B2 | 12/2015 | Smider et al. |
| 9,403,904 B2 | 8/2016 | Smider et al. |
| 9,644,021 B2 | 5/2017 | Wang et al. |
| 10,101,333 B2 | 10/2018 | Smider et al. |
| 2003/0088074 A1 | 5/2003 | Hamers et al. |

(Continued)

FOREIGN PATENT DOCUMENTS

| | | |
|---|---|---|
| JP | 2005/522197 | 7/2005 |
| WO | WO 1993/020210 | 10/1993 |

(Continued)

OTHER PUBLICATIONS

Almagro & Fransson, "Humanization of antibodies," Frontiers in Bioscience, 13:1619-33 (2008).

(Continued)

*Primary Examiner* — Christian C Boesen
(74) *Attorney, Agent, or Firm* — Hugh Wang; Thomas Fitting

(57) ABSTRACT

The present disclosure provides humanized antibodies, including antibodies comprising an ultralong CDR3 and uses thereof.

13 Claims, 11 Drawing Sheets

Specification includes a Sequence Listing.

| | | | | | |
|---|---|---|---|---|---|
| BLV1H12 | CTSVHQ | ETKKYQ | SCPDGYRERSDCSNRPACGTSPCCRVSVFGNCLTTLFVSYSYTMYEW | HVDVWGQGLLVTVSS | (SEQ ID NO : 360) |
| BLV5B8 | CTTVHQ | ETRKT | CSDGYIAVDSCGRGQSDGCVNDCNSCYYGWRNCRRQPAIBSYEF | HVDAWGRGLLVTVSS | (SEQ ID NO : 361) |
| BLV5D3 | CSSVTQ | RTHVSR | SCFDGCSDGDCCVDGCCCSAYRCYTFGVRDLSCTSYSITYTYEW | NVDAWGRGLLVTVSS | (SEQ ID NO : 362) |
| BLV8C11 | CTTVHQ | KTTRKT | CCSDAYRYDSGCGSGCDCCGADCYVFGACTFGLDSSYSYIYIYQW | YVDAWGQGLLVTVSS | (SEQ ID NO : 363) |
| BF4E9 | CTTVHQ | IF | CPDGYSYGYGCGYGYGCSGYDCYGYGGYGYGGYSSYSYSYSYEY | YGDAWGQGLLVTVSS | (SEQ ID NO : 364) |
| BF1E1 | CTTVHP | | SPDGYSYGYGCGYGYGCSGYDCYGYGGYGYGGYSSYSYSYS | | (SEQ ID NO : 365) |
| F18 | CTTVHQ | IR | CPDGYGYGCGYGSYGYSGYDCYGYGGYGGYGGYSSYS | | (SEQ ID NO : 366) |

(56) References Cited

U.S. PATENT DOCUMENTS

| | | |
|---|---|---|
| 2003/0170646 A1 | 9/2003 | Kaushik et al. |
| 2003/0215880 A1 | 11/2003 | Burton |
| 2005/0261480 A1 | 11/2005 | Foote |
| 2006/0275254 A1 | 12/2006 | Kim et al. |
| 2007/0071764 A1 | 3/2007 | Sullivan et al. |
| 2009/0148455 A1 | 6/2009 | Fischer et al. |
| 2009/0304580 A1 | 12/2009 | Goldenberg et al. |
| 2010/0311119 A1 | 12/2010 | Hermans et al. |
| 2011/0039761 A1 | 2/2011 | Eckert et al. |
| 2011/0172125 A1 | 7/2011 | Ladner |
| 2011/0293513 A1 | 12/2011 | Govindan et al. |
| 2011/0318339 A1 | 12/2011 | Smider et al. |
| 2012/0058906 A1 | 3/2012 | Smider et al. |
| 2012/0316071 A1 | 12/2012 | Smider et al. |
| 2014/0050720 A1 | 2/2014 | Smider et al. |
| 2014/0086871 A1 | 3/2014 | Smider et al. |
| 2014/0227267 A1 | 8/2014 | Wang et al. |
| 2015/0011431 A1 | 1/2015 | Smider et al. |
| 2015/0376264 A1 | 12/2015 | Wang et al. |
| 2016/0069894 A1 | 3/2016 | Smider et al. |
| 2016/0159928 A1 | 6/2016 | Bazirgan et al. |
| 2016/0168231 A1 | 6/2016 | De Los Rios et al. |
| 2016/0194627 A1 | 7/2016 | Smider et al. |
| 2016/0237156 A1 | 8/2016 | Wang et al. |

FOREIGN PATENT DOCUMENTS

| | | |
|---|---|---|
| WO | WO 1994/018221 A1 | 8/1994 |
| WO | WO 2003/030821 A2 | 4/2003 |
| WO | WO 2003/085086 | 10/2003 |
| WO | WO 2010/028791 A1 | 3/2010 |
| WO | WO 2010/054007 A1 | 5/2010 |
| WO | WO 2010/054010 A1 | 5/2010 |
| WO | WO 2011/044542 A1 | 4/2011 |
| WO | WO 2011/056997 A1 | 5/2011 |
| WO | WO 2002/022809 A2 | 3/2012 |
| WO | WO 2012/170977 A1 | 12/2012 |
| WO | WO 2005/056759 | 6/2013 |
| WO | WO 2013/106485 | 7/2013 |
| WO | WO 2013/106489 | 7/2013 |
| WO | WO 2014/110368 | 7/2014 |
| WO | WO 2015/010100 | 1/2015 |
| WO | WO 2015/017146 | 2/2015 |

OTHER PUBLICATIONS

Choi et al., "Predicting antibody complementarity determining region structures without classification," Molecular BioSystems, 7(12):3327-334 (2011).

Saini et al., "Exceptionally long CDR3H region with multiple cysteine residues in functional bovine IgM antibodies," European Journal of Immunology, 29(8): 2420-2426 (1999).

Smider, "Cow Antibodies: A New Structural Class of Antibody Using Ultralong CDR3s," World ADC, Oct. 16, 2013. Retrieved from http://adc-summit.com/uploads/files/2463_ADC_Nau.

Stanfield et al., "Conservation and diversity in the ultralong third heavy-chain complementarity-determining region of bovine antibodies," Science Immunology (2016) 1 :aaf7962.

Wang et al., "Reshaping Antibody Diversity," Cell,153(6):1379-1393 (2013).

Zhang et al., "An Antibody CDR3-Erythropoietin Fusion Protein," ACS Chem Biol, 8(10):2117-2121 (2013).

Zhang et al., "Functional Antibody CDR3 Fusion Proteins with Enhanced Pharmacological Properties," Angew Chem Int Ed Engl, 52(32):8295-8298 (2013).

Zhang et al., "Rational Design of humanized dual-agonist antibodies," Journal of the American Chemical Society, 137(1):38-41 (2015).

De Genst et al., "Antibody repertoire development in camelids," Developmental and Comparative Immunology, 30(1-2): 187-98 (2006).

Ward et al.,"Binding activities of a repertoire of single immunoglobulin variable domains secreted from *Escherichia coli*," Nature, 341(6242):544-546 (1989).

Griffiths et al., "Human anti-self antibodies with high specificity from phage display libraries," The EMBO Journal, 12(2):725-734 (1993).

Klimka et al., "Human anti-CD30 recombinant antibodies by guided phage antibody selection using cell panning," British Journal of Cancer, 83(2):252-260 (2000).

Ottensmeier et al., "Isotype switch variants reveal clonally related subpopulations in diffuse large B-cell lymphoma," Blood, 96(7):2550-2556 (2000).

Baker, P.J., "The pain of "chronic Lyme disease": moving the discourse in a different direction," The FASEB Journal, 26(1):11-12 (2012).

Brumeanu et al., "Efficient loading of identical viral peptide onto class II molecules by antigenized immunoglobulin and influenza virus," J. Exp. Med 178(5):1795-1799 (1993).

Casset et al., "A peptide mimetic of an anti-CD4 monoclonal antibody by rational design," BBRC 307(1):198-205 (2003).

Haakenson et al., "Diversity in the cow Ultralong CDR H3 Antibody repertoire," Frontiers in Immunology (2018) 9:1262.

Hosseini et al., "Duplicated copies of the bovine JH locus contribute to the Ig repertoire," Int. Immunol. (2004) 16(6):843-852.

Hust et al., "Single chain Fab (scFab) fragment," BMC Biotechnology (2007) 7:14.

Inoue et al., "Affinity transfer to a human protein by CDR3 grafting of camelid VHH," Protein Science. 20(12):1971-1981 (2011).

Lefranc et al., "IMGT, the international ImMunoGeneTics information system." Nucleic Acids Res. Jan. 2009;37(Database issue):D1006-12.

Muyldermans et al., "Distinct Antibody Species: Structural Differences Creating Therapeutic Opportunities," Curr Opin Immunol. Jun. 2016; 40: 7-13.

NCBI, GenBank accession No. DM113215.1 (Jun. 18, 2009).

Paul., "Fv structure and Diversity in Three Dimensions" Fundamental Immunology, 3rd edition Raven Press, NY. 292-295 (1993).

Qin et al., "Fusion protein of CDR mimetic peptide with Fc inhibit TNF-alpha induced cytotoxicity," Molecular Immunology 43(6):660-666.

Qiu et al.,"Small antibody mimetics comprising two complementarity determining regions and a framework region for tumor targeting," Nature Biotechnology 25(8):921-929 (2007).

Rader et al., "The rabbit antibody repertoire as a novel source for the generation of therapeutic human antibodies," Journal of Biological Chemistry. 275:13668-13676 (2000).

Roche et al., "Invited review: Body condition score and its association with dairy cow productivity, health, and welfare," J. Dairy Sci., 92(12):5769-5801 (2009).

Sok et al., "Rapid elicitation of broadly neutralizing antibodies to HIV by immunization in cows," Nature. Aug. 3, 2017; 548(7665): 108-111.

Streltsov et al., "Crystal Structure of the Amyloid-p3 Fragment Provides a Model for Oligomer Formation in Alzheimer's Disease," J. of Neuroscience. 31(4) 1419-1426.

Wells "Additivity of Mutational Effects in Proteins," Biochemistry 29:8509-8517 (1990).

Wold et al., "Antibody Therapeutics in Oncology," Immunotherapy (Los Angel). Mar. 2016; 2(1):pii:108.

Zhao et al., "The bovine antibody repertoire," Developmental and Comparative Immunology. 30:175-186 (2006).

Figure 1

| | | | | |
|---|---|---|---|---|
| BLV1H12 | CTTVHQ | ETKKYQ | SCPMGYRBKSDCSMRPACCTSQCRVSVFGWCITLLNSYSYTNMZW | RVDVWGQGLLV

Figure 2A

Figure 2B (illegible - low resolution sequence listing table)

Figure 2C

Other Representative sequences:

| | | | | | |
|---|---|---|---|---|---|
| UL-58 | CVTVHQ QTHATR | RCPDGYGDSYACKSNYGCSAEGCCRWGPGSGACTGAIYTSPYEW | YVDAW | 57 | (SEQ ID NO : 340) |
| UL-59 | CAAVHQ KTEGQQ | SCPDGYLETRVCFYRMYRCIGWDCCRCSDGSRDNYIMTYSYEF | HVDVW | 56 | (SEQ ID NO : 341) |
| UL-60 | CTTVYQ KTKTKS | GCPDGYSCCYNGRSRSCRFNDCSTYGEVRSLSRSCYTYNYEF | YVDAW | 55 | (SEQ ID NO : 342) |
| UL-61 | CGTVYQ HTKEIK | TCPDGYSDVFTYCPVTCPGWDCCRRNDCGRTRYTVAYSYAL | HVDVW | 54 | (SEQ ID NO : 343) |
| UL-62 | CTTVLQ KTHQQR | GCPAGYQVVDGCFYGDCCRTSYVCGPLTCTSNTATRNYQW | YVDAW | 53 | (SEQ ID NO : 344) |
| UL-63 | CSTVYQ KTEK | KCPDGYTDRRDECPNTCKRFDCENSGGLRCLCSAYISAYEF | HVDAW | 52 | (SEQ ID NO : 345) |
| UL-64 | CTTTHQ RTQK | SCPDYASYDCGSFDDEECSSCRSCTRWCAFTAFYIYTYQF | YIDAW | 51 | (SEQ ID NO : 346) |
| UL-65 | CTTVHQ QTNK | RCPTGYNSGTLCNMIGCSGDECCNYGRVECTSYVWTHNF | YVDAW | 50 | (SEQ ID NO : 347) |
| UL-66 | CTTVHQ KTQRT | SCPSGWTYTCNCRNGCGCYRPSQLCGAYVAVIRTYEF | HVDAW | 49 | (SEQ ID NO : 348) |
| UL-67 | CATVHQ KDK | HCPAGYRSGTLCRMIGCTGDDCCNYDRVECTNYDYTNNF | YVDAW | 49 | (SEQ ID NO : 349) |
| UL-68 | CTAVHQ QTTEKGK | TCPPRSRDNGTRCRDDRYYPWRYSDYTYTYTYEW | HVDAW | 48 | (SEQ ID NO : 350) |
| UL-69 | CTSVHQ KTDV | TCPSGATYRCDCGGRGCGCYDPWCSTTYRGTYTYDF | HVSTW | 47 | (SEQ ID NO : 351) |
| UL-70 | CGTVHQ KTHTQR | TCPDACDVTGDNCKVRRNGDWCGRASKTDTYDF | YVDAW | 46 | (SEQ ID NO : 352) |
| UL-71 | CTTDYQ KTEK | SCPENYYAETGYCMCGSWRCGYGSTTSLIVSYEW | YVDAW | 45 | (SEQ ID NO : 353) |
| UL-72 | CTTVHQ KTNQKW | GCPDGYVRMSGSCCRGSICTNGLFRNTYTYSF | NVSAW | 45 | (SEQ ID NO : 354) |
| UL-73 | CTTVYQ KTKT | NCPDGYNYRSGDCRRWNHWLGEQRVSPTYRYEW | YVDSW | 44 | (SEQ ID NO : 355) |
| UL-74 | CTTVYQ KTTTTK | SCPSGFDNGRRCINGLGDLRDYTYFNKYEW | YVETW | 43 | (SEQ ID NO : 356) |
| UL-75 | CSTVHQ KTEQ | RCLDGYDDRGAYCYTDSVRGLMSWTYKYVYEW | RVQTW | 42 | (SEQ ID NO : 357) |
| UL-76 | CTNVHQ MTIK | TCPDGGSYGWYWPYGYGCNGGVSATYTYEF | YVDAW | 41 | (SEQ ID NO : 358) |
| UL-77 | CTTVYQ KTESVR | SCPDGSMDGWRCRLGTNNWIYSNTYEF | YVDAW | 40 | (SEQ ID NO : 359) |

Figure 3

BLV1H12
SVHQETKKYQSCPDGYRERSDCSNRPACGTSDCCRVSVFGNCLTTLPVSYSYTYNYEWHVD
(SEQ ID NO : 22)

BLV5B8
TVHQETRKTCSDGYIAVDSCGRGQSDGCVNDCNSCYYGWRNCRRQPAIHSYEFHVD
(SEQ ID NO : 23)

BLV5D3
SVTQRTHVSRSCPDGCSDGDGCVDGCCCSAYRCYTPGVRDLSCTSYSITYTYEWNVD
(SEQ ID NO : 24)

BLV8C11
TVHQKTTRKTCCSDAYRYDSGCGSGCDCCGADCYVFGACTFGLDSSYSYIYIYQWYVD
(SEQ ID NO : 25)

BF4E9
TVHQIFCPDGYSYGYGCGYGYGCSGYDCYGYGGYGYGGYGGYSSYSYSYSYEYYGD
(SEQ ID NO : 26)

BF1H1
TVHPSPDGYSYGYGCGYGYGCSGYDCYGYGGYGYGGYGGYSSYSYSYS
(SEQ ID NO : 27)

F18
TVHQIRCPDGYGYGYGCGYGSYGYSGYDCYGYGGYGGYGGYGGYSSYS
(SEQ ID NO : 28)

Figure 4

Bovine VH-UL:

```
caggtgcagctgcgggagtcgggcccagcctggtgaagccctcacagaccctctcgtc
 Q  V  Q  L  R  E  S  G  P  S  L  V  K  P  S  Q  T  L  S  L
acctgcacggcctctggattctcattgagcgacaaggctgtaggctgggtccgccagct
 T  C  T  A  S  G  F  S  L  S  D  K  A  V  G  W  V  R  Q  A
ccaggaaggcgctggagtggtcggtggtatagacactggtggaagcacaggctataac
 P  G  K  A  L  E  W  L  G  G  I  D  T  G  G  S  T  G  Y  N
ccaggcctgaaatcccggctcagcatcaccaaggacaactccaagagccaagtctctctg
 P  G  L  K  S  R  L  S  I  T  K  D  N  S  K  S  Q  V  S  L
tcagtgagcagcgtgacaactgaggactcggccacatactactgtactactgtgcaccag  (SEQ ID NO: 367)
 S  V  S  S  V  T  T  E  D  S  A  T  Y  Y  C  T  T  V  R  Q  (SEQ ID NO: 29)

QVQLRESGPSLVKPSQTLSLTCTASGFSLSDKAVGWVRQAPGKALEWLGGIDTGGSTGYN
PGLKSRLSITKDNSKSQVSLSVSSVTTEDSATYYCTTVRQ   (SEQ ID NO: 29)
```

Figure 5A 4-39:
Cagctgcagctgcaggagtcggggccaggactggtgaagccttcggagaccctgtccctcacctgcactgtctctgg
tggctccatcagcagtagtagttactactggggctggatccgccagcccccagggaaggggctggagtggattggga
gtatctattatagtgggagcacctactacaacccgtccctcaagagtcgagtcaccatatccgtagacacgtccaag
aaccagttctccctgaagctgagctctgtgaccgccgcagacacggctgtgtattactgtgcgagacacacagtgag
ggg
(SEQ ID NO: 368)

QLQLQESGPGLVKPSETLSLTCTVSGGSISSSYYWGWIRQPPGKGLEWIGSIYYSGSTYYNPSLKSRVTISVDTSK
NQFSLKLSSVTAADTAVYYCAR
(SEQ ID NO: 31)

4-59*03:
Caggtgcagctgcaggagtcgggcccaggactggtgaagccttcggagaccctgtccctcacctgcactgtctctgg
tggctccatcagtagttactactggagctggatccggcagcccccagggaagggactggagtggattgggtatatct
attacagtgggagcaccaactacaaccctccctcaagagtcgagtcaccatatcagtagacacgtccaagaaccaa
ttctccctgaagctgagctctgtgaccgctgcggacacggccgtgtattactgtgcg
(SEQ ID NO: 369)

QVQLQESGPGLVKPSETLSLTCTVSGGSISSYYWSWIRQPPGKGLEWIGYIYYSGSTNYNPSLKSRVTISVDTSKNQ
FSLKLSSVTAADTAVYYCA
(SEQ ID NO: 32)

4-34*09:
Cagytgcagctgcaggagtcgggcccaggactggtgaagccttcacagaccctgtccctcacctgcgctgtctatgg
tgggtccttcagtggttactactggagctggatccgccagcccccagggaaggggctggagtggattgggaaatca
atcatagtggaagcaccaactacaacccgtccctcaagagtcgagttaccatatcagtagacacgtctaagaaccag
ttctccctgaagctgagctctgtgactgccgcgggacacggccgtgtattactgtgcgaga
(SEQ ID NO: 370)

QVQLQESGPGLVKPSQTLSLTCAVYGGSFSGYYWSWIRQPPGKGLEWIGEINHSGSTNYNPSLKSRVTISVDTSKNQ
FSLKLSSVTAADTAVYYCAR
(SEQ ID NO: 33)

4-34*02:
Caggtgcagctacaacagtggggcgcaggactgttgaagcttggagaccctgtccctcacctgcgctgtctatgg
tgggtccttcagtggttactactggagctggatccgccagcccccagggaagggctggagtggattgggaaatca
atcatagtggaagcaccaactacaacccgtccctcaagagtcgagtcaccatatcagtagacacgtccaagaaccag
ttctccctgaagctgagctctgtgaccgccgcggacacggctgtgtattactgtgcgagagg
(SEQ ID NO: 371)

QVQLQQWGAGLLKPSETLSLTCAVYGGSFSGYYWSWIRQPPGKGLEWIGEINHSGSTNYNPSLKSPVTISVDTSKNQ
FSLKLSSVTAADTAVYYCAR
(SEQ ID NO: 34)

Figure 5B

```
4-39     QLQLQESGPGLVKPSETLSLTCTVSGGSISSSSYYWGWIRQPPGKGLEWIGSIYYSGST  60
4-59*03  QVQLQESGPGLVKPSETLSLTCTVSGGSISS--YYWSWIRQPPGKGLEWIGYIYYSGSTN 58
4-34*02  QVQLQQWGAGLLKPSETLSLTCAVYGGSPSG--YYWSWIRQPPGKGLEWIGRINHSGSTN 58
4-34*09  QVQLQESGPGLVKPSQTLSLTCAVYGGSPSG--YYWSWIRQPPGKGLEWIGRINHSGSTN 58
VH-UL    QVQLRESGPSLVKPSQTLSLTCTASGFSLSD--FAVGWVRQAPGKALEWLGGIDTGGSTG 58
         *:**::  *.,*;***;****:***;  *  *;*;    ,*;**,***,**:;* *  :***

4-39     YNPSLKSRVTISVDTSKNQFSLKLSSVTAADTAVYYCAR------ 99 (SEQ ID NO: 31)
4-59*03  YNPSLKSRVTISVDTSKNQFSLKLSSVTAADTAVYYCA------- 96 (SEQ ID NO: 32)
4-34*02  YNPSLKSRVTISVDTSKNQFSLKLSSVTAADTAVYYCAR------ 97 (SEQ ID NO: 33)
4-34*09  YNPSLKSRVTISVDTSKNQFSLKLSSVTAADTAVYYCAR------ 97 (SEQ ID NO: 34)
VH-UL    YNPGLKSRLSITKDNSKSQVSLSVSSVTTEDSATYYCTTVHQTQ 102 (SEQ ID NO: 29)
         ***.******;:**; *;**.*,**,;,*****;
```

Figure 6

BLV1H12 VL:

Caggctgtgctgaatcagccatcatccgtgtccgggtccctgggccagagggtctccatcacctgctctggaagcag
cagcaatgttggaaatggatatgtgagctggtaccaactgatcccaggatcggccccagaacccctcatctatggtg
acaccagtcgagcctcggggtccccgaccgattctccggctccaggtctgggaacacagccaccctgaccatcagc
tcgctccaggctgaggacgaggcagattatttctgtgcatctgctgaggatagtagcagtaatgctgttttcggcag
cgggaccaaactgaccgtcctg
(SEQ ID NO: 372)

QAVLNQPSSVSGSLGQRVSITCSGSSSNVGNGYVSWYQLIPGSAPRPLIYGDTSRASGVPDRFSGSRSGNTATLTIS
SLQAEDEADYFCASAEDSSSNAVFGSGTTLTVL
(SEQ ID NO: 35)

Figure 7A

VL1-47:
Cagtctgtgctgactcagccaccctcagcgtctgggaccccgggcagagggtcaccatctcttgttctggaagcag
ctccaacatcggaagtaattatgtatactggtaccagcagctcccaggaacggcccccaaactcctcatctatagga
ataatcagcggccctcaggggtccctgaccgattctctggctccaagtctggcacctcagcctccctggccatcagt
gggctccggtccgaggatgaggctgattattactgtgcagcatgggatgacagcctgagtggtcc
(SEQ ID NO: 373)

QSVLTQPPSASGTPGQRVTISCSGSSSNIGSNYVYWYQQLPGTAPKLLIYRNNQRPSGVPDRFSGSKSGTSASLAIS
GLRSEDEADYYCAAWDDSLSG
(SEQ ID NO: 36)

VL1-40*1:
Cagtctgtgctgacgcagccgccctcagtgtctggggcccagggcagagggtcaccatctcctgcactgggagcag
ctccaacatcggggcaggttatgatgtacactggtaccagcagcttccaggaacagcccccaaactcctcatctatg
gtaacagcaatcggccctcaggggtccctgaccgattctctggctccaagtctggcacctcagcctccctggccatc
actggactccaggctgaggatgaggctgattattactgcagtccatatgacagcagcctgagtggttc
(SEQ ID NO: 374)

QSVLTQPPSVSGAPGQRVTISCTGSSSNIGAGYDVHWYQQLPGTAPKLLIYGNSNRPSGVPDRFSGSKSGTSASLAI
TGLQAEDEADYYCQSYDSSLSG
(SEQ ID NO: 37)

VL1-51 *01:
Cagtctgtgttgacgcagccgccctcagtgtctgggccccaggacagaaggtcaccatctcctgctctggaagcag
ctccaacattgggaataattatgtatcctggtaccagcagctcccaggaacagcccccaaactcctcatttatgaca
ataataagcgaccctcagggattcctgaccgattctctggctccaagtctggcacgtcagccaccctgggcatcacc
ggactccagactggggacgaggccgattattactgcggaacatgggatagcagcctgagtgctgg
(SEQ ID NO: 375)

QSVLTQPPSVSAAPGQKVTISCSGSSSNIGNNYVSWYQQLPGTAPKLLIYDNNKRPSGIPDRFSGSKSGTSATLGIT
GLQTGDEADYYCGTWDSSLSA
(SEQ ID NO: 38)

VL2-18*02:
Cagtctgccctgactcagcctccctccgtgtccgggtctcctggacagtcagtcaccatctcctgcactggaaccagcagtgacgt
tggtagttataaccgtgtctcctggtaccagcagcccccaggcacagcccccaaactcatgatttatgaggtcagtaatcggcct
cagggtccctgatcgcttctctggctccaagtctggcaacacggcctcctgaccatctctgggctccaggctgaggacgaggct
gattattactgcagctcatatacaagcagcagcacttc
(SEQ ID NO: 376)

QSALTQPPSVSGSPGQSVTISCTGTSSDVGSYNRVSWYQQPPGTAPKLMIYEVSNRPSGVPDRFSGSKSGNTASLTI
SGLQAEDEADYYCSSYTSSSTF
(SEQ ID NO: 39)

Figure 7B

```
V11-47      QSVLTQPPSASGTPGQRVTISCSGSSSNIGSNY-VYWYQQLPGTAPKLLIYRNNQRPSGV 59
V11-51      QSVLTQPPSVSAPGQKVTISCSGSSSNIGNNY-VSWYQQLPGTAPKLLIYDNNKRPSGI 59
V11-40*1    QSVLTQPPSVSGAPGQRVTISCTGSSSNIGAGYDVHWYQQLPGTAPKLLIYGNSNRPSGV 60
V12-19*02   QSALTQPPSVSGSPGQSVTISCTGTSSDVGGYNPVSWYQQPPGTAPKLMIYEVSNRPSGV 60
V11x (cow)  QAVLTQPSSVSGSLGQRVSITCSGSSSNVGNGY-VSWYQLIPGSAPRTLIYGUTSKASGV 59
            *::****:*:,*.:. ** *:*:*:*:**:*      * **:  **:***:;**  ,,*,**;

V11-47      PDRFSGSKSGTSASLAISGLRSEDEADYYCAAWDDSLSG 98  (SEQ ID NO: 36)
V11-51      PDRFSGSKSGTSATLGITGLQTSDEADYYCGTWDSSLSA 98  (SEQ ID NO: 37)
V11-40*1    PDRFSGSKSGTSASLAITGLQAEDEADYYCQSYDSSLSG 99  (SEQ ID NO: 38)
V12-19*02   PDRFSGSKSGNTASLTISGLQAEDEADYYCSSYTSSSTF 99  (SEQ ID NO: 39)
V11x        PDRFSGSKSGNTATLTISGLQAEDEADYFCASAEDSSSN 98  (SEQ ID NO: 35)
            ********:**:*:*:* *;,*;; *****:*  ;   ,*  ;
```

HUMANIZED ANTIBODIES

CROSS-REFERENCE TO RELATED APPLICATIONS

This application is a continuation of application Ser. No. 14/371,170, which is a U.S. National Stage Application under 35 U.S.C. § 371 of International Patent Application No. PCT/US2013/020910, filed Jan. 9, 2013, which claims the benefit of U.S. Provisional Application No. 61/584,680, filed Jan. 9, 2012, the entire contents of which are each incorporated by reference.

Incorporated herein by reference is the Sequence Listing being concurrently submitted via EFS-Web as an ASCII text file named 17886-026-999_SEQ_LISTING.txt, of file size 354,780 bytes, created on Nov. 1, 2017.

FIELD

The present disclosure relates to humanized antibodies, including antibodies comprising an ultralong CDR3.

BACKGROUND

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some bovine antibodies have unusually long VH CDR3 sequences compared to other vertebrates. For example, about 10% of IgM contains "ultralong" CDR3 sequences, which can be up to 61 amino acids long. These unusual CDR3s often have multiple cysteines. Functional VH genes form through a process called V(D)J recombination, wherein the D-region encodes a significant proportion of CDR3. A unique D-region encoding an ultralong sequence has been identified in cattle. Ultralong CDR3s are partially encoded in the cattle genome, and provide a unique characteristic of their antibody repertoire in comparison to humans. Kaushik et al. (U.S. Pat. Nos. 6,740,747 and 7,196,185) disclose several bovine germline D-gene sequences unique to cattle stated to be useful as probes and a bovine VDJ cassette stated to be useful as a vaccine vector.

SUMMARY

The present disclosure provides humanized antibodies, including antibodies comprising an ultralong CDR3, methods of making same, and uses thereof.

The present disclosure provides a humanized antibody or binding fragment thereof comprising an ultralong CDR3.

In some embodiments, the humanized antibody or binding fragment thereof comprises one or more human variable region framework sequences.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

In some embodiments of each or any of the above or below mentioned embodiments, the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4X_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

In some embodiments of each or any of the above or below mentioned embodiments, the ultralong CDR3 comprises 2 to 6 disulfide bonds.

In some embodiments of each or any of the above or below mentioned embodiments, the ultralong CDR3 comprises SEQ ID NO: 40 or a derivative thereof.

In some embodiments of each or any of the above or below mentioned embodiments, the ultralong CDR3 comprises amino acid residues 3-6 of any of one SEQ ID NO: 1-4.

In some embodiments of each or any of the above or below mentioned embodiments, the ultralong CDR3 comprises a non-human DH or a derivative thereof.

In some embodiments of each or any of the above or below mentioned embodiments, the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiments of each or any of the above or below mentioned embodiments, the ultralong CDR3 comprises a JH sequence or a derivative thereof.

In some embodiments of each or any of the above or below mentioned embodiments, the JH sequence is SEQ ID NO: 13, SEQ ID NO: 14, SEQ ID NO: 15, SEQ ID NO: 16, or SEQ ID NO: 17.

In some embodiments of each or any of the above or below mentioned embodiments, the ultralong CDR3 comprises: a non-human or human VH sequence (e.g., a germline VH) or a derivative thereof; a non-human DH sequence or a derivative thereof; and/or JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the additional amino acid sequence is selected from the group consisting of: IR, IF, SEQ ID NO: 18, SEQ ID NO: 19, SEQ ID NO: 20 or SEQ ID NO: 21.

In some embodiments of each or any of the above or below mentioned embodiments, the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments of each or any of the above or below mentioned embodiments, the ultralong CDR3 comprises a bovine sequence, a non-bovine sequence, an antibody sequence, or a non-antibody sequence.

In some embodiments of each or any of the above or below mentioned embodiments, the non-antibody sequence is a synthetic sequence.

In some embodiments of each or any of the above or below mentioned embodiments, the non-antibody sequence is a cytokine sequence, a lymphokine sequence, a chemokine sequence, a growth factor sequence, a hormone sequence, or a toxin sequence.

In some embodiments of each or any of the above or below mentioned embodiments, the non-antibody sequence is an IL-8 sequence, an IL-21 sequence, an SDF-1 (alpha) sequence, a somatostatin sequence, a chlorotoxin sequence, a Pro-TxII sequence, or a ziconotide sequence.

In some embodiments of each or any of the above or below mentioned embodiments, the non-antibody sequence is any one of SEQ ID NOS: 475-481.

In some embodiments of each or any of the above or below mentioned embodiments, the non-antibody sequence replaces at least a portion of the ultralong CDR3.

In some embodiments of each or any of the above or below mentioned embodiments, the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

In some embodiments of each or any of the above or below mentioned embodiments, the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the ultralong CDR3 comprises a $CX^1X^2X^3X^4X^5$ motif.

In some embodiments of each or any of the above or below mentioned embodiments, the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the $(X^aX^b)_z$ motif is YXYXYX.

In some embodiments of each or any of the above or below mentioned embodiments, the ultralong CDR3 comprises a $X^1X^2X^3X^4X^5X_n$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), and wherein n is 27-54.

In some embodiments of each or any of the above or below mentioned embodiments, the ultralong CDR3 comprises $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the $X^1X^2X^3X^4X^5$ motif is TTVHQ (SEQ ID NO: 153) or TSVHQ (SEQ ID NO: 154), and wherein the $(X^aX^b)_z$ motif is YXYXYX.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CXCX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95), and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4C$ $CXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_5CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{12}C$ (SEQ ID NO: 104), $CXCX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_5CX_3CXCX_4CCX_5CCCX_6C$ (SEQ ID NO: 111), $CX_5CX_3CXCX_2CXCCX_6CX_5CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_5CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_2CX_2CX_3C$ (SEQ ID NO: 142), $CX_5CX_4CX_4CX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the ultralong CDR3 is a ruminant CDR3.

In some embodiments of each or any of the above or below mentioned embodiments, the ruminant is a cow.

In some embodiments of each or any of the above or below mentioned embodiments, the humanized antibody or binding fragment thereof comprises a human heavy chain variable region framework sequence.

In some embodiments of each or any of the above or below mentioned embodiments, the humanized antibody or binding fragment thereof comprises a human heavy chain germline sequence or is a derived from a human heavy chain germline sequence.

In some embodiments of each or any of the above or below mentioned embodiments, the humanized antibody or binding fragment thereof comprises a human heavy chain germline sequence that is a VH4 family member germline sequence.

In some embodiments of each or any of the above or below mentioned embodiments, the humanized antibody or binding fragment thereof comprises a VH4-34 germline sequence.

In some embodiments of each or any of the above or below mentioned embodiments, the humanized antibody or binding fragment thereof comprises a human heavy chain germline sequence that is derived from the VH4-34 germline sequence.

In some embodiments of each or any of the above or below mentioned embodiments, the VH4-34 germline sequence comprises a CDR1 comprising a Gly31Asp and Tyr32Lys substitution based on Kabat numbering.

In some embodiments of each or any of the above or below mentioned embodiments, the VH4-34 germline sequence comprises a CDR2 comprising a Glu50Ser substitution based on Kabat numbering.

In some embodiments of each or any of the above or below mentioned embodiments, the VH4-34 germline sequence comprises a CDR1 comprising Ala23Thr, Val24Ala, Tyr25Ser, Gly27Phe, Phe29Leu, Gly31Asp, Tyr32Lys, Tyr33Ala, Trp34Val, and Ser35Gly substitutions, and a CDR2 comprising Ile48Leu, Glu50Ser, Asn52Asp, His53Thr, Ser54Gly, Ser56Asn, and Asn58Gly substitutions, based on Kabat numbering.

In some embodiments of each or any of the above or below mentioned embodiments, the humanized antibody or binding fragment thereof comprises the amino acid sequence set forth in SEQ ID NO: 461, 462, 463, 464, 465, 466, 467, 468, or 469.

In some embodiments of each or any of the above or below mentioned embodiments, the humanized antibody or binding fragment thereof comprises the amino acid sequence set forth in SEQ ID NO: 470.

In some embodiments of each or any of the above or below mentioned embodiments, the humanized antibody or binding fragment thereof comprises the amino acid sequence set forth in SEQ ID NO: 461, 462, 463, 464, 465, 466, 467, 468, or 469; and the amino acid sequence set forth in SEQ ID NO: 470.

In some embodiments of each or any of the above or below mentioned embodiments, the humanized antibody or binding fragment thereof comprises the amino acid sequence set forth in SEQ ID NO: 461, 462, 463, 464, 465, 466, 467, 468, or 469; the amino acid sequence set forth in SEQ ID NO: 470; and a peptide sequence, wherein the peptide sequence is positioned between SEQ ID NO: 461, 462, 463, 464, 465, 466, 467, 468, or 469, and SEQ ID NO: 470.

In some embodiments of each or any of the above or below mentioned embodiments, the peptide sequence is a bovine sequence, a non-bovine sequence, an antibody sequence, or a non-antibody sequence.

In some embodiments of each or any of the above or below mentioned embodiments, the humanized antibody or binding fragment thereof comprises a human light chain variable region framework sequence.

In some embodiments of each or any of the above or below mentioned embodiments, the humanized antibody or binding fragment thereof comprises a light chain variable region sequence that is a lambda light chain variable region sequence.

In some embodiments of each or any of the above or below mentioned embodiments, the lambda light chain variable region sequence is a bovine lambda light chain variable region sequence or derived from a bovine lambda light chain variable region sequence.

In some embodiments of each or any of the above or below mentioned embodiments, the lambda light chain variable region sequence is a human lambda light chain variable region sequence or derived from a human lambda light chain variable region sequence.

In some embodiments of each or any of the above or below mentioned embodiments, the human lambda light chain variable region sequence is a VL1-51 germline sequence.

In some embodiments of each or any of the above or below mentioned embodiments, the human lambda light chain variable region sequence is derived from a VL1-51 germline sequence.

In some embodiments of each or any of the above or below mentioned embodiments, the VL1-51 germline sequence comprises a CDR1 comprising Ile29Val and Asn32Gly substitution based on Kabat numbering.

In some embodiments of each or any of the above or below mentioned embodiments, the VL1-51 germline sequence comprises a CDR2 comprising a substitution of DNN to GDT.

In some embodiments of each or any of the above or below mentioned embodiments, the VL1-51 germline sequence comprises a CDR2 comprising a substitution of DNNKRP (SEQ ID NO: 471) to GDTSRA (SEQ ID NO: 472).

In some embodiments of each or any of the above or below mentioned embodiments, the VL1-51 germline sequence comprises a S2A, T5N, P8S, A12G, A13S, and P14L substitution based on Kabat numbering.

In some embodiments of each or any of the above or below mentioned embodiments, the VL1-51 germline sequence comprises a S2A, T5N, P8S, A12G, A13S, and P14L substitution based on Kabat numbering, and a CDR2 comprising a substitution of DNN to GDT.

In some embodiments of each or any of the above or below mentioned embodiments, the humanized antibody or binding fragment thereof comprising the amino acid sequence set forth in SEQ ID NO: 440, 441, 442, 443, or 444.

The present disclosure also provides polynucleotides encoding the humanized antibody or binding fragment thereof disclosed herein.

The present disclosure also provides polynucleotides encoding a humanized antibody or binding fragment thereof that comprises an ultralong CDR3.

The present disclosure also provides polynucleotides encoding a humanized variable region that comprises an ultralong CDR3.

The present disclosure also provides vectors that comprise the polynucleotides disclosed herein.

The present disclosure also provides host cells comprising the vectors disclosed herein.

The present disclosure also provides a nucleic acid library comprising a plurality of polynucleotides comprising sequences coding for humanized antibodies or binding fragments thereof, wherein the antibodies or binding fragments thereof comprise an ultralong CDR3.

The present disclosure also provides a library of humanized antibodies or binding fragments thereof, wherein the antibodies or binding fragments thereof comprise an ultralong CDR3.

In some embodiments of each or any of the above or below mentioned embodiments, the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the ultralong CDR3 is 35 amino acids in length or longer.

In some embodiments of each or any of the above or below mentioned embodiments, the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the ultralong CDR3 comprises 3 or more cysteine residues.

In some embodiments of each or any of the above or below mentioned embodiments, the antibodies or binding fragments thereof comprise a cysteine motif.

In some embodiments of each or any of the above or below mentioned embodiments, the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

In some embodiments of each or any of the above or below mentioned embodiments, the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCCX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), CX₇CX₇CX₂CX₂CX₃C (SEQ ID NO: 142), CX₉CX₄CX₄CCX₆C (SEQ ID NO: 143), CX₇CXCX₃CXCX₆C (SEQ ID NO: 144), CX₇CXCX₄CXCX₄C (SEQ ID NO: 145), CX₉CX₅CX₄C (SEQ ID NO: 146), CX₃CX₆CX₈C (SEQ ID NO: 147), CX₁₀CXCX₄C (SEQ ID NO: 148), CX₁₀CCX₄C (SEQ ID NO: 149), CX₁₅C (SEQ ID NO: 150), CX₁₀C (SEQ ID NO: 151), and CX₉C (SEQ ID NO: 152).

In some embodiments of each or any of the above or below mentioned embodiments, the ultralong CDR3 comprises 2 to 6 disulfide bonds.

In some embodiments of each or any of the above or below mentioned embodiments, the ultralong CDR3 comprises SEQ ID NO: 40 or a derivative thereof.

In some embodiments of each or any of the above or below mentioned embodiments, the ultralong CDR3 comprises amino acid residues 3-6 of any of one SEQ ID NO: 1-4.

In some embodiments of each or any of the above or below mentioned embodiments, the ultralong CDR3 comprises a non-human DH or a derivative thereof.

In some embodiments of each or any of the above or below mentioned embodiments, the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiments of each or any of the above or below mentioned embodiments, the ultralong CDR3 comprises a JH sequence or a derivative thereof.

In some embodiments of each or any of the above or below mentioned embodiments, the JH sequence is SEQ ID NO: 13, SEQ ID NO: 14, SEQ ID NO: 15, SEQ ID NO: 16, or SEQ ID NO: 17.

In some embodiments of each or any of the above or below mentioned embodiments, the ultralong CDR3 comprises: a non-human VH sequence or a derivative thereof; a non-human DH sequence or a derivative thereof; and/or a JH sequence or derivative thereof.

In some embodiments of each or any of the above or below mentioned embodiments, the ultralong CDR3 comprises an additional amino acid sequence comprising two to six amino acid residues or more positioned between the VH sequence and the DH sequence.

In some embodiments of each or any of the above or below mentioned embodiments, the additional amino acid sequence is selected from the group consisting of: IR, IF, SEQ ID NO: 18, SEQ ID NO: 19, SEQ ID NO: 20 or SEQ ID NO: 21.

In some embodiments of each or any of the above or below mentioned embodiments, the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments of each or any of the above or below mentioned embodiments, the ultralong CDR3 comprises a non-bovine sequence or a non-antibody sequence.

In some embodiments of each or any of the above or below mentioned embodiments, the non-antibody sequence is a synthetic sequence.

In some embodiments of each or any of the above or below mentioned embodiments, the non-antibody sequence is a cytokine sequence, a lymphokine sequence, a chemokine sequence, a growth factor sequence, a hormone sequence, or a toxin sequence.

In some embodiments of each or any of the above or below mentioned embodiments, the non-antibody sequence is an IL-8 sequence, an IL-21 sequence, an SDF-1 (alpha) sequence, a somatostatin sequence, a chlorotoxin sequence, a Pro-TxII sequence, or a ziconotide sequence.

In some embodiments of each or any of the above or below mentioned embodiments, the non-antibody sequence is any one of SEQ ID NOS: 475-481.

In some embodiments of each or any of the above or below mentioned embodiments, the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

In some embodiments of each or any of the above or below mentioned embodiments, the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the ultralong CDR3 comprises a $CX^1X^2X^3X^4X^5$ motif.

In some embodiments of each or any of the above or below mentioned embodiments, the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO:

223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the $(X^aX^b)_z$ motif is YXYXYX.

In some embodiments of each or any of the above or below mentioned embodiments, the ultralong CDR3 comprises a $X^1X^2X^3X^4X^5X_n$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), and wherein n is 27-54.

In some embodiments of each or any of the above or below mentioned embodiments, the ultralong CDR3 comprises $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the ultralong CDR3 comprises a $X^1X^2X^3X^4X^5X_n(X^aX^b)_z$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the $X^1X^2X^3X^4X^5$ motif is TTVHQ (SEQ ID NO: 153) or TSVHQ (SEQ ID NO: 154), and wherein the $(X^aX^b)_z$ motif is YXYXYX.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CXCX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_5CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and a $(X^aX^b)_z$ motif, $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4C$ $CXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{1}20$ (SEQ ID NO: 104), $CXCX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CXCCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and ba $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the ultralong CDR3 comprises an additional sequence that is a linker.

In some embodiments of each or any of the above or below mentioned embodiments, the linker is linked to a C-terminus, a N-terminus, or both C-terminus and N-terminus of the non-antibody sequence.

In some embodiments of each or any of the above or below mentioned embodiments, the ultralong CDR3 is a ruminant CDR3.

In some embodiments of each or any of the above or below mentioned embodiments, the ruminant is a cow.

In some embodiments of each or any of the above or below mentioned embodiments, the humanized antibody or binding fragment thereof comprises a human heavy chain variable region framework sequence.

In some embodiments of each or any of the above or below mentioned embodiments, the humanized antibody or binding fragment thereof comprises a human heavy chain germline sequence or is a derived from a human heavy chain germline sequence.

In some embodiments of each or any of the above or below mentioned embodiments, the humanized antibody or binding fragment thereof comprises a human heavy chain germline sequence that is a VH4 family member germline sequence.

In some embodiments of each or any of the above or below mentioned embodiments, the humanized antibody or binding fragment thereof comprises a VH4-34 germline sequence.

In some embodiments of each or any of the above or below mentioned embodiments, the humanized antibody or binding fragment thereof comprises a human heavy chain germline sequence that is derived from VH4-34.

In some embodiments of each or any of the above or below mentioned embodiments, the VH4-34 germline sequence comprises a CDR1 comprising a Gly31Asp and Tyr32Lys substitution based on Kabat numbering.

In some embodiments of each or any of the above or below mentioned embodiments, the VH4-34 germline sequence comprises a CDR2 comprising a Glu50Ser substitution based on Kabat numbering.

In some embodiments of each or any of the above or below mentioned embodiments, the VH4-34 germline sequence comprises a CDR1 comprising Ala23Thr, Val24Ala, Tyr25Ser, Gly27Phe, Phe29Leu, Gly31Asp, Tyr32Lys, Tyr33Ala, Trp34Val, and Ser35Gly substitutions, and a CDR2 comprising Ile48Leu, Glu50Ser, Asn52Asp, His53Thr, Ser54Gly, Ser56Asn, and Asn58Gly substitutions, based on Kabat numbering.

In some embodiments of each or any of the above or below mentioned embodiments, the humanized antibody or binding fragment thereof comprises the amino acid sequence set forth in SEQ ID NO: 470.

In some embodiments of each or any of the above or below mentioned embodiments, the humanized antibody or binding fragment thereof comprises the amino acid sequence set forth in SEQ ID NO: 461, 462, 463, 464, 465, 466, 467, 468, or 469; and the amino acid sequence set forth in SEQ ID NO: 470.

In some embodiments of each or any of the above or below mentioned embodiments, the humanized antibody or binding fragment thereof comprises the amino acid sequence set forth in SEQ ID NO: 461, 462, 463, 464, 465, 466, 467, 468, or 469; the amino acid sequence set forth in SEQ ID NO: 470; and a peptide sequence, wherein the peptide sequence is positioned between SEQ ID NO: 461, 462, 463, 464, 465, 466, 467, 468, or 469, and SEQ ID NO: 470.

In some embodiments of each or any of the above or below mentioned embodiments, the peptide sequence is a bovine sequence, a non-bovine sequence, an antibody sequence, or a non-antibody sequence.

In some embodiments of each or any of the above or below mentioned embodiments, the humanized antibody or binding fragment thereof comprises a lambda light chain variable region sequence.

In some embodiments of each or any of the above or below mentioned embodiments, the humanized antibody or binding fragment thereof comprises a light chain variable region sequence that is a lambda light chain variable region sequence.

In some embodiments of each or any of the above or below mentioned embodiments, the lambda light chain variable region sequence is a bovine lambda light chain variable region sequence.

In some embodiments of each or any of the above or below mentioned embodiments, the lambda light chain variable region sequence is a human lambda light chain variable region sequence.

In some embodiments of each or any of the above or below mentioned embodiments, the human lambda light chain variable region sequence is VL1-51.

In some embodiments of each or any of the above or below mentioned embodiments, the human lambda light chain variable region sequence is derived from VL1-51.

In some embodiments of each or any of the above or below mentioned embodiments, the VL1-51 germline sequence comprises a CDR1 comprising Ile29Val and Asn32Gly substitution based on Kabat numbering.

In some embodiments of each or any of the above or below mentioned embodiments, the VL1-51 germline sequence comprises a CDR2 comprising a substitution of DNN to GDT.

In some embodiments of each or any of the above or below mentioned embodiments, the VL1-51 germline sequence comprises a CDR2 comprising a substitution of DNNKRP (SEQ ID NO: 471) to GDTSRA (SEQ ID NO: 472).

In some embodiments of each or any of the above or below mentioned embodiments, the VL1-51 germline sequence comprises a S2A, T5N, P8S, A12G, A13S, and P14L substitution based on Kabat numbering.

In some embodiments of each or any of the above or below mentioned embodiments, the VL1-51 germline sequence comprises a S2A, T5N, P8S, A12G, A13S, and P14L substitution based on Kabat numbering, and a CDR2 comprising a substitution of DNN to GDT.

In some embodiments of each or any of the above or below mentioned embodiments, the humanized antibody or binding fragment thereof comprising the amino acid sequence set forth in SEQ ID NO: 440, 441, 442, 443, or 444.

In some embodiments of each or any of the above or below mentioned embodiments, the humanized antibodies or binding fragments thereof are present in a spatially addressed format.

The present disclosure also provides a method of humanizing an antibody variable region comprising the step of genetically combining a nucleic acid sequence encoding a non-human ultralong CDR3 with a nucleic acid sequence encoding a human variable region framework (FR) sequence.

The present disclosure also provides a method of generating a library of humanized antibodies that comprises an ultralong CDR3, the method comprising: combining a nucleic acid sequence encoding an ultralong CDR3 with a nucleic acid sequence encoding a human variable region framework (FR) sequence to produce nucleic acids encoding for humanized antibodies that comprises an ultralong CDR3; and expressing the nucleic acids encoding for humanized antibodies that comprises an ultralong CDR3 to generate a library of humanized antibodies that comprises an ultralong CDR3.

The present disclosure also provides a method of generating a library of humanized antibodies or binding fragments thereof comprising an ultralong CDR3 and which comprises a non-antibody sequence, the method comprising: combining a nucleic acid sequence encoding an ultralong CDR3, a nucleic acid sequence encoding a human variable region framework (FR) sequence, and a nucleic acid sequence encoding a non-antibody sequence to produce nucleic acids encoding humanized antibodies or binding fragments thereof comprising an ultralong CDR3 and a non-antibody sequence, and expressing the nucleic acids encoding humanized antibodies or binding fragments thereof comprising an ultralong CDR3 and a non-antibody sequence to generate a library of humanized antibodies or binding fragments thereof comprising an ultralong CDR3 and a non-antibody sequence. In some embodiments, the ultralong CDR3 comprises a bovine, a non-bovine, an antibody, or a non-antibody sequence.

The present disclosure also provides a library of humanized antibodies or binding fragments thereof comprising an ultralong CDR3 which comprises a non-bovine or a non-antibody sequence.

The present disclosure also provides a method of generating a library of humanized antibodies or binding fragments thereof comprising an ultralong CDR3 which comprises a cysteine motif, the method comprising: combining a human variable region framework (FR) sequence, and a nucleic acid sequence encoding an ultralong CDR3 and a cysteine motif; introducing one or more nucleotide changes to the nucleic acid sequence encoding one or more amino acid residues that are positioned between one or more cysteine residues in the cysteine motif for nucleotides encoding different amino acid residues to produce nucleic acids encoding humanized antibodies or binding fragments thereof comprising an ultralong CDR3 and a cysteine motif with one or more nucleotide changes introduced between one or more cysteine residues in the cysteine domain; and expressing the nucleic acids encoding humanized antibodies or binding fragments thereof comprising an ultralong CDR3 and a cysteine motif with one or more nucleotide changes introduced between one or more cysteine residues in the cysteine domain to generate a library of humanized antibodies or binding fragments thereof comprising an ultralong CDR3 and a cysteine motif with one or more amino acid changes introduced between one or more cysteine residues in the cysteine domain.

The present disclosure also provides a library of humanized antibodies or binding fragments thereof comprising an ultralong CDR3 which comprises a cysteine motif, wherein the antibodies or binding fragments comprise one or more substitutions of amino acid residues that are positioned between cysteine residues in the cysteine motif.

The present disclosure also provides a method of generating a library of humanized antibodies or binding fragments thereof comprising a bovine ultralong CDR3, the method comprising: combining a nucleic acid sequence encoding a human variable region framework (FR) sequence and a nucleic acid encoding a bovine ultralong CDR3, and expressing the nucleic acids encoding a human variable region framework (FR) sequence and a nucleic acid encoding a bovine ultralong CDR3 to generate a library of humanized antibodies or binding fragments thereof comprising a bovine ultralong CDR3.

The present disclosure provides humanized antibodies, including antibodies comprising a CDR3 scaffold, methods of making same, and uses thereof.

The present disclosure provides a humanized antibody or binding fragment thereof comprising a CDR3 scaffold.

In some embodiments, the CDR3 scaffold comprises one or more human variable region framework sequences.

The present disclosure also provides a library of humanized antibodies or binding fragments thereof comprising a bovine ultralong CDR3.

In some embodiments of each or any of the above or below mentioned embodiments, the CDR3 scaffold comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

In some embodiments of each or any of the above or below mentioned embodiments, the CDR3 scaffold is 35 amino acids in length or longer, 40 amino acids in length or longer, 45 amino acids in length or longer, 50 amino acids in length or longer, 55 amino acids in length or longer, or 60 amino acids in length or longer.

In some embodiments of each or any of the above or below mentioned embodiments, the CDR3 scaffold is 35 amino acids in length or longer.

In some embodiments of each or any of the above or below mentioned embodiments, the CDR3 scaffold comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

In some embodiments of each or any of the above or below mentioned embodiments, the CDR3 scaffold comprises 3 or more cysteine residues.

In some embodiments of each or any of the above or below mentioned embodiments, the CDR3 scaffold comprises a cysteine motif.

In some embodiments of each or any of the above or below mentioned embodiments, the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

In some embodiments of each or any of the above or below mentioned embodiments, the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCCX_4CX_2CXCCXCX_4CX_3C$ (SEQ ID NO: 114), $CX_{10}CXCX_3CX_2CXCCX_4CX_5CXC$ (SEQ ID NO: 115), $CX_5CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCCX_5C$ (SEQ ID NO: 123), $CX_9CX_7CX_4CCXCX_7CX_3C$ (SEQ ID NO: 124), $CX_5CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), CX$_8$CX$_2$CX$_4$CCX$_4$CX$_3$CX$_3$C (SEQ ID NO: 129), CX$_7$CX$_5$CXCX$_4$CCX$_7$CX$_4$C (SEQ ID NO: 130), CX$_{11}$CX$_3$CX$_4$CCCX$_8$CX$_2$C (SEQ ID NO: 131), CX$_2$CX$_3$CX$_4$CCX$_4$CX$_5$CX$_{15}$C (SEQ ID NO: 132), CX$_9$CX$_5$CX$_4$CCX$_7$C (SEQ ID NO: 133), CX$_9$CX$_7$CX$_3$CX$_2$CX$_6$C (SEQ ID NO: 134), CX$_9$CX$_5$CX$_4$CCX$_{14}$C (SEQ ID NO: 135), CX$_9$CX$_5$CX$_4$CCX$_8$C (SEQ ID NO: 136), CX$_9$CX$_6$CX$_4$CCXC (SEQ ID NO: 137), CX$_5$CCX$_7$CX$_4$CX$_{12}$ (SEQ ID NO: 138), CX$_{10}$CX$_3$CX$_4$CCX$_4$C (SEQ ID NO: 139), CX$_9$CX$_4$CCX$_5$CX$_4$C (SEQ ID NO: 140), CX$_{10}$CX$_3$CX$_4$CX$_7$CXC (SEQ ID NO: 141), CX$_7$CX$_7$CX$_2$CX$_2$CX$_3$C (SEQ ID NO: 142), CX$_9$CX$_4$CX$_4$CCX$_6$C (SEQ ID NO: 143), CX$_7$CXCX$_3$CXCX$_6$C (SEQ ID NO: 144), CX$_7$CXCX$_4$CXCX$_4$C (SEQ ID NO: 145), CX$_9$CX$_5$CX$_4$C (SEQ ID NO: 146), CX$_3$CX$_6$CX$_8$C (SEQ ID NO: 147), CX$_{10}$CXCX$_4$C (SEQ ID NO: 148), CX$_{10}$CCX$_4$C (SEQ ID NO: 149), CX$_{15}$C (SEQ ID NO: 150), CX$_{10}$C (SEQ ID NO: 151), and CX$_9$C (SEQ ID NO: 152).

In some embodiments of each or any of the above or below mentioned embodiments, the CDR3 scaffold comprises 2 to 6 disulfide bonds.

In some embodiments of each or any of the above or below mentioned embodiments, the X$^1$X$^2$X$^3$X$^4$X$^5$ motif in the CDR3 scaffold is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

In some embodiments of each or any of the above or below mentioned embodiments, the CDR3 scaffold comprises a CX$^1$X$^2$X$^3$X$^4$X$^5$ motif.

In some embodiments of each or any of the above or below mentioned embodiments, the CX$^1$X$^2$X$^3$X$^4$X$^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

In some embodiments of each or any of the above or below mentioned embodiments, the CDR3 scaffold comprises a (X$^a$X$^b$)$_z$ motif, wherein X$^a$ is any amino acid residue, X$^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the (X$^a$X$^b$)$_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

In some embodiments of each or any of the above or below mentioned embodiments, the (X$^a$X$^b$)$_z$ motif is YXYXYX.

In some embodiments of each or any of the above or below mentioned embodiments, the CDR3 scaffold comprises a X$^1$X$^2$X$^3$X$^4$X$^5$X$_n$ motif, wherein X$^1$ is threonine (T), glycine (G), alanine (A), serine (S), or valine (V), wherein X$^2$ is serine (S), threonine (T), proline (P), isoleucine (I), alanine (A), valine (V), or asparagine (N), wherein X$^3$ is valine (V), alanine (A), threonine (T), or aspartic acid (D), wherein X$^4$ is histidine (H), threonine (T), arginine (R), tyrosine (Y), phenylalanine (F), or leucine (L), and wherein X$^5$ is glutamine (Q), and wherein n is 27-54.

In some embodiments of each or any of the above or below mentioned embodiments, the CDR3 scaffold comprises X$_n$(X$^a$X$^b$)$_z$ motif, wherein X$^a$ is any amino acid residue, X$^b$ is an aromatic amino acid selected from the group consisting of: tyrosine (Y), phenylalanine (F), tryptophan (W), and histidine (H), wherein n is 27-54, and wherein z is 1-4.

In some embodiments of each or any of the above or below mentioned embodiments, the CDR3 scaffold comprises a X$^1$X$^2$X$^3$X$^4$X$^5$X$_n$(X$^a$X$^b$)$_z$ motif, herein X$_1$ is threonine (T), glycine (G), alanine (A), serine (S), or valine (V), wherein X$_2$ is serine (S), threonine (T), proline (P), isoleucine (I), alanine (A), valine (V), or asparagine (N), wherein X$_3$ is valine (V), alanine (A), threonine (T), or aspartic acid (D), wherein X$_4$ is histidine (H), threonine (T), arginine (R), tyrosine (Y), phenylalanine (F), or leucine (L), wherein X$_5$ is glutamine (Q), X$^a$ is any amino acid residue, X$^b$ is an aromatic amino acid selected from the group consisting of:

tyrosine (Y), phenylalanine (F), tryptophan (W), and histidine (H), wherein n is 27-54, and wherein z is 1-4.

In some embodiments of each or any of the above or below mentioned embodiments, the $X^1X^2X^3X^4X^5$ motif in the CDR3 scaffold is TTVHQ (SEQ ID NO: 153) or TSVHQ (SEQ ID NO: 154), and wherein the $(X^aX^b)_z$ motif is YXYXYX.

In some embodiments of each or any of the above or below mentioned embodiments, the CDR3 scaffold comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the CDR3 scaffold comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX\ C$ (SEQ ID NO: 96), $CX_6CX_2CX_5CX_4C\ CXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{1}20$ (SEQ ID NO: 104), $CXCX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_5CCCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CXCCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCX_4CX_{54}CXC$ (SEQ ID NO: 123), $CX_5CX_7CX_4CCXCX_7CX_3C$ (SEQ ID NO: 124), $CX_5CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_5CX_5CX_4CCX_7C$ (SEQ ID NO: 133), $CX_5CX_7CX_3CX_2CX_6C$ (SEQ ID NO: 134), $CX_5CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

In some embodiments of each or any of the above or below mentioned embodiments, the CDR3 scaffold comprises SEQ ID NO: 40 or a derivative thereof.

In some embodiments of each or any of the above or below mentioned embodiments, the CDR3 scaffold comprises amino acid residues 3-6 of any of one SEQ ID NO: 1-4.

In some embodiments of each or any of the above or below mentioned embodiments, the CDR3 scaffold comprises a non-human DH or a derivative thereof.

In some embodiments of each or any of the above or below mentioned embodiments, the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12

In some embodiments of each or any of the above or below mentioned embodiments, the CDR3 scaffold comprises a JH sequence or a derivative thereof.

In some embodiments of each or any of the above or below mentioned embodiments, the JH sequence is SEQ ID NO: 13, SEQ ID NO: 14, SEQ ID NO: 15, SEQ ID NO: 16, or SEQ ID NO: 17.

In some embodiments of each or any of the above or below mentioned embodiments, the CDR3 scaffold comprises: a non-human VH sequence or a derivative thereof; a non-human DH sequence or a derivative thereof; and/or a JH sequence or derivative thereof.

In some embodiments of each or any of the above or below mentioned embodiments, the CDR3 scaffold comprises an additional amino acid sequence comprising two to six amino acid residues or more positioned between the VH sequence and the DH sequence.

In some embodiments of each or any of the above or below mentioned embodiments, the additional amino acid sequence is selected from the group consisting of: IR, IF, SEQ ID NO: 18, SEQ ID NO: 19, SEQ ID NO: 20 or SEQ ID NO: 21.

In some embodiments of each or any of the above or below mentioned embodiments, the CDR3 scaffold comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

In some embodiments of each or any of the above or below mentioned embodiments, the CDR3 scaffold is a ruminant CDR3 scaffold.

In some embodiments of each or any of the above or below mentioned embodiments, the ruminant is a cow.

The present disclosure also provides a library comprising the CDR3 scaffold disclosed herein.

The present disclosure also provides a polynucleotide encoding the CDR3 scaffold disclosed herein.

The present disclosure also provides a vector comprising any of the polynucleotides disclosed herein.

The present disclosure also provides a host cell comprising any of the vectors disclosed herein.

The present disclosure also provides

In some embodiments of each or any of the above or below mentioned embodiments, the cell is a bacteria, virus, or bacteriophage.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1 shows a sequence alignment of exemplary bovine-derived antibody variable region sequences designated BLV1H12, BLV5B8, BLV5D3, BLV8C11, BF4E9, BF1H1, or F18 that comprise an ultralong CDR3 sequence.

FIG. 2A-C depicts ultralong CDR3 sequences. (Top) Translation from the germline $V_H$BUL, $D_H2$, and $J_H$. The 5 full length ultralong CDR H3s reported in the literature contain between four and eight cysteines and are not highly homologous to one another; however, some conservation of cysteine residues with $D_H2$ could be found when the first cysteine of these CDR H3s was "fixed" prior to alignment. Four of the seven sequences (BLV1H12, BLV5D3, BLV8C11, and BF4E9) contain four cysteines in the same positions as $D_H2$, but also have additional cysteines. BLV5B8 has two cysteines in common with the germline $D_H2$. This limited homology with some cysteine conservation suggests that mutation of $D_H2$ could generate these sequences. B-L1 and B-L2 are from initial sequences from bovine spleen, and the remaining are selected ultralong CDR H3 sequences from deep sequencing data. The first group contains the longest CDR H3s identified, and appear clonally related. The * indicates a sequence represented 167 times, suggesting it was strongly selected for function. Several of the eight-cysteine sequences appear selected for function as they were represented multiple times, indicated in parentheses. Other representative sequences of various lengths are indicated in the last group. The framework cysteine and tryptophan residues that define the CDR H3 boundaries are double-underlined. The sequences BLV1H12 through UL-77 (left-most column) presented in Tables 2A-C are depicted broken apart into four segments to identify the segments of amino acid residues that are derived from certain germline sequences and V/D/J joining sequences. Moving from left to right, the first segment is derived from the $V_H$ germline and is represented in the disclosure as a $X^1X^2X^3X^4X^5$ motif. The second segment represents sequences from V-D joining and is represented in the disclosure as $X_n$. The third segment is a string of amino acid residues derived from $D_H2$ germline, and the fourth segment is a string of amino acid residues derived from $J_H1$ germline region.

FIG. 3 depicts a sequence alignment of exemplary bovine-derived ultralong CDR3 sequences designated BLV1H12, BLV5B8, BLV5D3, BLV8C11, BF4E9, BF1H1, or F18.

FIG. 4 shows an exemplary bovine germline heavy chain variable region ($V_H$) sequence designated VH-UL suitable for modification or use with an ultralong CDR3 sequence.

FIG. 5A-B shows exemplary human germline heavy chain variable region sequences designated 4-39, 4-59*03, 4-34*09, and 4-34*02 that are suitable for modification or use with an ultralong CDR3 sequence (A) and an alignment of these sequences (B).

FIG. 6 shows an exemplary bovine light chain variable region sequence designated BLV1H12 suitable for modification or use with an ultralong CDR 3 sequence (e.g., a heavy chain variable region sequence comprising an ultralong CDR3 sequence).

FIG. 7A-B shows exemplary light chain variable region sequences designated VI1-47, VI1-40*1, VI1-51*01, and VI2-18*02 that are suitable for modification or use with an ultralong CDR 3 sequence (A) and an alignment of these sequences (B).

DETAILED DESCRIPTION

The present disclosure provides humanized antibodies comprising ultralong CDR3 sequences, along with materials for (e.g., protein sequences, genetic sequences, cells, libraries) and methods of making the antibodies (e.g., humanizing methods, library methods). Such humanized antibodies may be useful for the treatment or prevention of a variety of disease states or disorders.

The present disclosure also provides humanized antibodies comprising ultralong CDR3 sequences, wherein the CDR3 sequences are 35 amino acids in length or longer (e.g., 40 or longer, 45 or longer, 50 or longer, 55 or longer, 60 or longer) and/or wherein the CDR3 sequences have at least 3 cysteine residues or more (e.g., 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues). Such antibodies, as described herein, bind (e.g., specifically or selectively bind) a variety of targets, including, for example protein targets such as transmembrane proteins (e.g., GPCRs, ion channels, transporter, cell surface receptors).

The present disclosure also provides methods and materials for the preparation or making of humanized antibodies comprising ultralong CDR3 sequences. Such materials include proteins, genetic sequences, cells and libraries. Such methods include methods of humanization and method of making and screening libraries.

The present disclosure provides a humanized antibody or binding fragment thereof comprising an ultralong CDR3. In some embodiments, the ultralong CDR3 may be 35 amino acids in length or longer, 40 amino acids in length or longer, 45 amino acids in length or longer, 50 amino acids in length or longer, 55 amino acids in length or longer, or 60 amino acids in length or longer. In some embodiments, the ultralong CDR3 may comprise 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues. The ultralong CDR3 may comprise a cysteine motif including, for example, where the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95). Alternatively, the ultralong CDR3 may comprise a cysteine motif including, for example, where the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_5CCX_4CX_2CXCCXCX_4CX_3C$ (SEQ ID NO: 114), $CX_{10}CXCX_2CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCCX_5C$ (SEQ ID NO: 123), $CX_5CX_7CX_4CCXCX_7CX_3C$ (SEQ ID NO: 124), $CX_9CX_5CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4X_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

The present disclosure provides a humanized antibody or binding fragment thereof comprising an ultralong CDR3, wherein the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q). In some embodiments, the $X^1X^2X^3X^4X^5$ motif may be TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

The present disclosure provides a humanized antibody or binding fragment thereof comprising an ultralong CDR3, wherein the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4. In some embodiments, the $(X^aX^b)_z$ motif may be CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

The present disclosure provides a humanized antibody or binding fragment thereof comprising an ultralong CDR3, wherein the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

The present disclosure provides a humanized antibody or binding fragment thereof comprising an ultralong CDR3, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}X_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_7CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95), and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

The present disclosure provides a humanized antibody or binding fragment thereof comprising an ultralong CDR3, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_5CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_5CX_5CX_4CCX_7C$ (SEQ ID NO: 133), $CX_5CX_7CX_2CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4X_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

The present disclosure also provides methods of generating a library of humanized antibodies that comprises an ultralong CDR3, comprising: combining a nucleic acid sequence encoding an ultralong CDR3 with a nucleic acid sequence encoding a human variable region framework (FR) sequence to produce nucleic acids encoding for humanized antibodies that comprises an ultralong CDR3; and expressing the nucleic acids encoding for humanized antibodies that comprises an ultralong CDR3 to generate a library of humanized antibodies that comprises an ultralong CDR3.

The present disclosure also provides methods of generating a library of humanized antibodies or binding fragments thereof comprising an ultralong CDR3 that comprises a non-antibody sequence, comprising: combining a nucleic acid sequence encoding an ultralong CDR3, a nucleic acid sequence encoding a human variable region framework (FR) sequence, and a nucleic acid sequence encoding a non-antibody sequence to produce nucleic acids encoding humanized antibodies or binding fragments thereof comprising an ultralong CDR3 and a non-antibody sequence, and expressing the nucleic acids encoding humanized antibodies or binding fragments thereof comprising an ultralong CDR3 and a non-antibody sequence to generate a library of humanized antibodies or binding fragments thereof comprising an ultralong CDR3 and a non-antibody sequence.

The present disclosure also provides libraries of humanized antibodies or binding fragments thereof comprising an ultralong CDR3 that comprises a non-antibody sequence.

The present disclosure also provides methods of generating a library of humanized antibodies or binding fragments thereof comprising an ultralong CDR3 that comprises a cysteine motif, comprising: combining a human variable region framework (FR) sequence, and a nucleic acid sequence encoding an ultralong CDR3 and a cysteine motif; introducing one or more nucleotide changes to the nucleic acid sequence encoding one or more amino acid residues that are positioned between one or more cysteine residues in the cysteine motif for nucleotides encoding different amino acid residues to produce nucleic acids encoding humanized antibodies or binding fragments thereof comprising an ultralong CDR3 and a cysteine motif with one or more nucleotide changes introduced between one or more cysteine residues in the cysteine domain; and expressing the nucleic acids encoding humanized antibodies or binding fragments thereof comprising an ultralong CDR3 and a cysteine motif with one or more nucleotide changes introduced between one or more cysteine residues in the cysteine domain to generate a library of humanized antibodies or binding fragments thereof comprising an ultralong CDR3 and a cysteine motif with one or more amino acid changes introduced between one or more cysteine residues in the cysteine domain.

The present disclosure also provides libraries of humanized antibodies or binding fragments thereof comprising an ultralong CDR3 that comprises a cysteine motif, wherein the antibodies or binding fragments comprise one or more substitutions of amino acid residues that are positioned between cysteine residues in the cysteine motif.

The present disclosure also provides methods of generating a library of humanized antibodies or binding fragments thereof comprising a bovine ultralong CDR3, comprising: combining a nucleic acid sequence encoding a human variable region framework (FR) sequence and a nucleic acid encoding a bovine ultralong CDR3, and expressing the nucleic acids encoding a human variable region framework (FR) sequence and a nucleic acid encoding a bovine ultralong CDR3 to generate a library of humanized antibodies or binding fragments thereof comprising a bovine ultralong CDR3.

The present disclosure also provides a CDR3 scaffold comprising a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

Proteins

The present disclosure provides humanized antibodies comprising ultralong CDR3 sequences.

In an embodiment, the present disclosure provides a humanized antibody comprising an ultralong CDR3, wherein the CDR3 is 35 amino acids in length or more (e.g., 40 or more, 45 or more, 50 or more, 55 or more, 60 or more). Such a humanized antibody may comprise at least 3 cysteine residues or more (e.g., 4 or more, 6 or more, 8 or more) within the ultralong CDR3.

In another embodiment, the present disclosure provides a humanized antibody comprising an ultralong CDR3, wherein the CDR3 is 35 amino acids in length or more and is derived from or based on a non-human sequence. The ultralong CDR3 sequence may be derived from any species that naturally produces ultralong CDR3 antibodies, including ruminants such as cattle (Bos taurus).

In another embodiment, the present disclosure provides a humanized antibody comprising an ultralong CDR3, wherein the CDR3 is 35 amino acids in length or more and is derived from a non-antibody sequence. The non-antibody sequence may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be of human or non-human origin and may comprise a portion of a non-antibody protein such as a peptide or domain. The non-antibody sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the humanized antibody.

In another embodiment, the present disclosure provides a humanized antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides for a humanized antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides a humanized antibody comprising an ultralong CDR3, wherein the CDR3 is 35 amino acids in length or more and comprises at least 3 cysteine residues or more, wherein the partially human ultralong CDR3 is a component of an immunoconjugate.

In another embodiment, the present disclosure provides a humanized antibody comprising an ultralong CDR3, wherein the CDR3 is 35 amino acids in length or more and comprises at least 3 cysteine residues or more, wherein the humanized antibody comprising an ultralong CDR3 binds to a transmembrane protein target. Such transmembrane targets may include, but are not limited to, GPCRs, ion channels, transporters, and cell surface receptors.

Genetic Sequences

The present disclosure provides genetic sequences (e.g., genes, nucleic acids, polynucleotides) encoding humanized antibodies comprising ultralong CDR sequences.

The present disclosure also provides genetic sequences (e.g., genes, nucleic acids, polynucleotides) encoding an ultralong CDR3.

In an embodiment, the present disclosure provides genetic sequences encoding a humanized antibody comprising an ultralong CDR3, wherein the CDR3 is 35 amino acids in length or more (e.g., 40 or more, 45 or more, 50 or more, 55 or more, 60 or more). Such a humanized antibody may comprise at least 3 cysteine residues or more (e.g., 4 or more, 6 or more, 8 or more) within the ultralong CDR3.

In another embodiment, the present disclosure provides genetic sequences encoding a humanized antibody comprising an ultralong CDR3, wherein the CDR3 is 35 amino acids in length or more and is derived from or based on a non-human sequence. The genetic sequences encoding the ultralong CDR3 may be derived from any species that naturally produces ultralong CDR3 antibodies, including ruminants such as cattle (Bos taurus).

In another embodiment, the present disclosure provides genetic sequences encoding a humanized antibody comprising an ultralong CDR3, wherein the CDR3 is 35 amino acids in length or more and is derived from a non-antibody protein sequence. The genetic sequences encoding the non-antibody protein sequences may be derived from any protein family including, but not limited to, chemokines, growth factors, peptides, cytokines, cell surface proteins, serum proteins, toxins, extracellular matrix proteins, clotting factors, secreted proteins, etc. The non-antibody protein sequence may be of human or non-human origin and may comprise a portion of a non-antibody protein such as a peptide or domain. The non-antibody protein sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the humanized antibody.

In another embodiment, the present disclosure provides genetic sequences encoding a humanized antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides genetic sequences encoding a humanized antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides genetic sequences encoding a humanized antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides genetic sequences encoding a humanized antibody comprising an ultralong CDR3 wherein the CDR3 is 35 amino acids in length or more and comprises at least 3 cysteine residues or more and wherein the humanized antibody comprising an ultralong CDR3 binds to a transmembrane protein target. Such transmembrane targets may include, but are not limited to, GPCRs, ion channels, transporters, and cell surface receptors.

Libraries and Arrays

The present disclosure provides collections, libraries, and arrays of humanized antibodies comprising ultralong CDR3 sequences.

In an embodiment, the present disclosure provides a library or an array of humanized antibodies comprising ultralong CDR3 sequences wherein at least two members of the library or array differ in the positions of at least one of the cysteines in the ultralong CDR3 sequence. Structural diversity may be enhanced through different numbers of cysteines in the ultralong CDR3 sequence (e.g., at least 3 or more cysteine residues such as 4 or more, 6 or more and 8 or more) and/or through different disulfide bond formation, and hence different loop structures.

In another embodiment, the present disclosure provides for a library or an array of humanized antibodies comprising ultralong CDR3 sequences wherein at least two members of the library or the array differ in at least one amino acid located between cysteines in the ultralong CDR3. In this regard, members of the library or the array can contain cysteines in the same positions of CDR3, resulting in similar overall structural folds, but with fine differences brought about through different amino acid side chains. Such libraries or arrays may be useful for affinity maturation.

In another embodiment, the present disclosure provides libraries or arrays of humanized antibodies comprising ultralong CDR3 sequences wherein at least two of the ultralong CDR3 sequences differ in length (e.g., 35 amino acids in length or more such as 40 or more, 45 or more, 50 or more, 55 or more and 60 or more). The amino acid and cysteine content may or may not be altered between the members of the library or the array. Different lengths of ultralong CDR3 sequences may provide for unique binding sites, including, for example, due to steric differences, as a result of altered length.

In another embodiment, the present disclosure provides libraries or arrays of humanized antibodies comprising ultralong CDR3 sequences wherein at least two members of the library differ in the human framework used to construct the humanized antibody comprising an ultralong CDR3.

In another embodiment, the present disclosure provides libraries or arrays of humanized antibodies comprising ultralong CDR3 sequences wherein at least two members of the library or the array differ in having a non-antibody protein sequence that comprises a portion of the ultralong CDR3. Such libraries or arrays may contain multiple non-antibody protein sequences, including for chemokines, growth factors, peptides, cytokines, cell surface proteins, serum proteins, toxins, extracellular matrix proteins, clotting factors, secreted proteins, viral or bacterial proteins, etc. The non-antibody protein sequence may be of human or non-human origin and may be comprised of a portion of a non-antibody protein such as a peptide or domain. The non-antibody protein sequence of the ultralong CDR3 may contain mutations from its natural sequence, including amino acid changes (e.g., substitutions), or insertions or deletions. Engineering additional amino acids at the junction between the non-antibody sequence within the ultralong CDR3 may be done to facilitate or enhance proper folding of the non-antibody sequence within the humanized antibody.

The libraries or the arrays of the present disclosure may be in several formats well known in the art. The library or the array may be an addressable library or an addressable array. The library or array may be in display format, for example, the antibody sequences may be expressed on phage, ribosomes, mRNA, yeast, or mammalian cells.

Cells

The present disclosure provides cells comprising genetic sequences encoding humanized antibodies comprising ultralong CDR3 sequences.

In an embodiment, the present disclosure provides cells expressing a humanized antibody comprising an ultralong CDR3. The cells may be prokaryotic or eukaryotic, and a humanized antibody comprising an ultralong CDR3 may be expressed on the cell surface or secreted into the media. When displayed on the cell surface a humanized antibody preferentially contains a motif for insertion into the plasmid membrane such as a membrane spanning domain at the C-terminus or a lipid attachment site. For bacterial cells, a humanized antibody comprising an ultralong CDR3 may be secreted into the periplasm. When the cells are eukaryotic, they may be transiently transfected with genetic sequences encoding a humanized antibody comprising an ultralong CDR3. Alternatively, a stable cell line or stable pools may be created by transfecting or transducing genetic sequences encoding a humanized antibody comprising an ultralong CDR3 by methods well known to those of skill in the art. Cells can be selected by fluorescence activated cell sorting (FACS) or through selection for a gene encoding drug resistance. Cells useful for producing humanized antibodies comprising ultralong CDR3 sequences include prokaryotic cells like *E. coli*, eukaryotic cells like the yeasts *Saccharo-*

*myces cerevisiae* and *Pichia pastoris*, chinese hamster ovary (CHO) cells, monkey cells like COS-1, or human cells like HEK-293, HeLa, SP-1.

Humanization Methods

The present disclosure provides methods for making humanized antibodies comprising ultralong CDR3 sequences, comprising the steps of engineering an ultralong CDR3 sequence derived from a non-human CDR3 into a human framework. The human framework may be of germline origin, or may be derived from non-germline (e.g. mutated or affinity matured) sequences. Genetic engineering techniques well known to those in the art, including as disclosed herein, may be used to generate a hybrid DNA sequence containing a human framework and a non-human ultralong CDR3. Unlike human antibodies which may be encoded by V region genes derived from one of seven families, bovine antibodies which produce ultralong CDR3 sequences appear to utilize a single V region family which may be considered to be most homologous to the human VH4 family. In a preferred embodiment where ultralong CDR3 sequences derived from cattle are to be humanized to produce an antibody comprising an ultralong CDR3, human V region sequences derived from the VH4 family may be genetically fused to a bovine-derived ultralong CDR3 sequence. Exemplary VH4 germline gene sequences in the human antibody locus are shown in FIG. 5A (e.g., SEQ ID NOS: 31-34; and 368-371).

The present disclosure also provides methods of humanizing an antibody variable region comprising the step of genetically combining a nucleic acid sequence encoding a non-human ultralong CDR3 (ULCDR3) with a nucleic acid sequence encoding a human variable region framework (FR) sequence. Also provided are methods of making a humanized antibody variable region comprising selecting a human framework sequence comprising FR1, FR2, and FR3; selecting a CDR1 sequence; selecting a CDR2 sequence; selecting an ultralong CDR3 sequence; and combining the sequences as FR1-CDR1-FR2-CDR2-FR3-ULCDR3. Also provided are methods of making a humanized antibody variable region sequence comprising selecting a human antibody variable region sequence comprising a sequence encoding FR1-CDR1-FR2-CDR2-FR3; selecting a sequence encoding a non-human ultralong CDR3 (ULCDR3); and genetically fusing the human sequence of step (a) in frame with the non-human sequence of step (b) to generate a sequence encoding FR1-CDR1-FR2-CDR2-FR3-ULCDR3.

In an embodiment, the present disclosure provides a fusion of a human VH4 framework sequence to a bovine-derived ultralong CDR3, for example, as may be accomplished through the following steps. First, the second cysteine of a V region genetic sequence is identified along with the nucleotide sequence encoding the second cysteine. Generally, the second cysteine marks the boundary of the framework and CDR3 two residues upstream (N-terminal) of the CDR3. Second, the second cysteine in a bovine-derived V region sequence is identified which similarly marks 2 residues upstream (N-terminal) of the CDR3. Third, the genetic material encoding the human V region is combined with the genetic sequence encoding the ultralong CDR3. Thus, a genetic fusion may be made, wherein the ultralong CDR3 sequence is placed in frame of the human V region sequence. Preferably a humanized antibody comprising an ultralong CDR3 is as near to human in amino acid composition as possible. Optionally, a J region sequence may be mutated from bovine-derived sequence to a human sequence. Also optionally, a humanized heavy chain may be paired with a human light chain.

In another embodiment, the present disclosure provides pairing of a human ultralong CDR3 heavy chain with a non-human light chain.

In another embodiment, the present disclosure provides pairing of a humanized heavy chain comprising an ultralong CDR3 with a human light chain. Preferably the light chain is homologous to a bovine light chain known to pair with a bovine ultralong CDR3 heavy chain. An exemplary bovine light chain is shown in FIG. 7A (e.g., SEQ ID NO: 36-39; and 373-376).

Library Methods

The present disclosure provides methods for making libraries comprising humanized antibodies comprising ultralong CDR3 sequences. Methods for making libraries of spatially addressed libraries are described in WO 2010/054007. Methods of making libraries in yeast, phage, *E. coli*, or mammalian cells are well known in the art.

The present disclosure also provides methods of screening libraries of humanized antibodies comprising ultralong CDR3 sequences.

Definitions

Figure 2A:
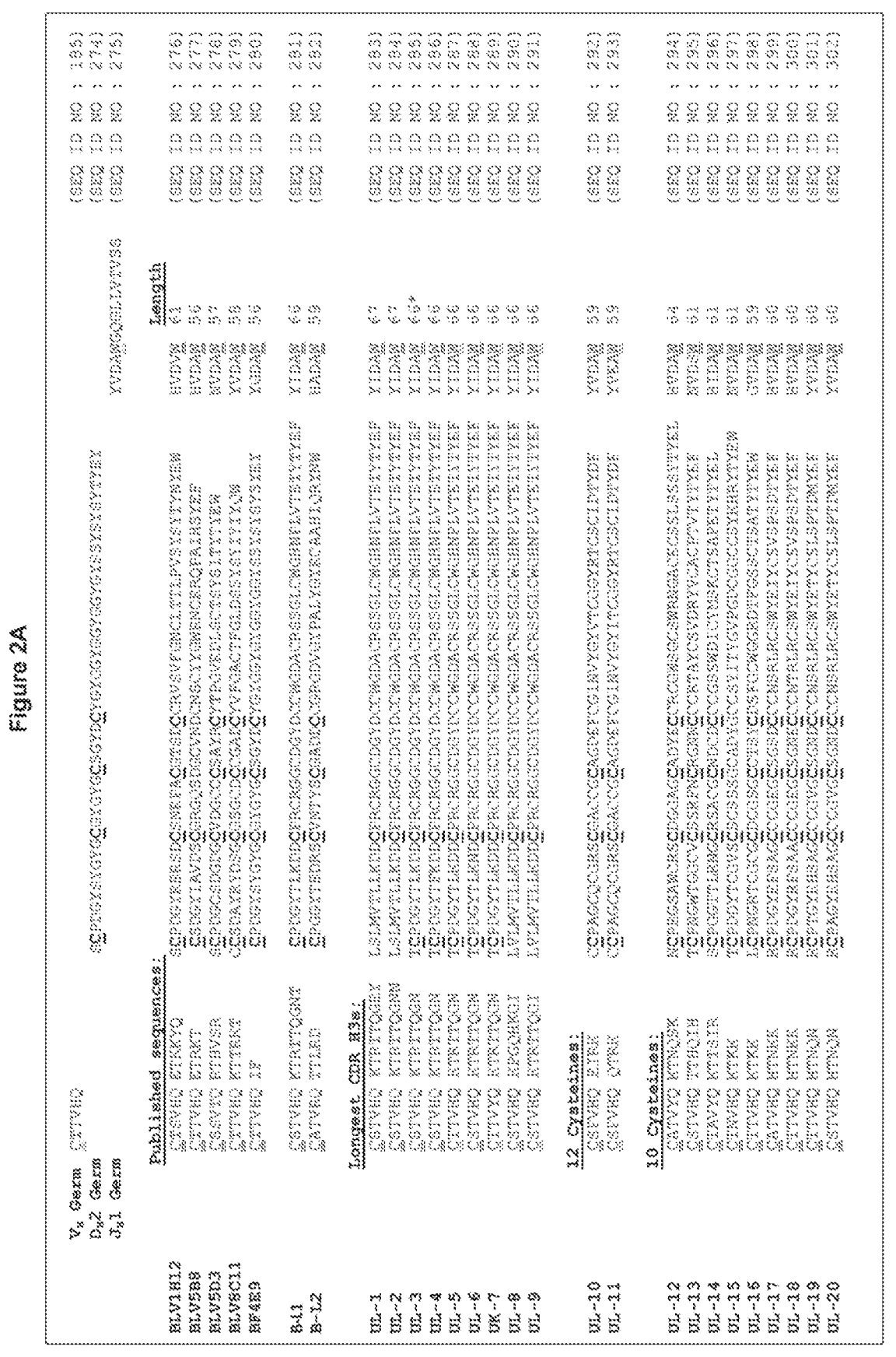

An "ultralong CDR3" or an "ultralong CDR3 sequence", used interchangeably herein, comprises a CDR3 or CDR3 sequence that is not derived from a human antibody sequence. An ultralong CDR3 may be 35 amino acids in length or longer, for example, 40 amino acids in length or longer, 45 amino acids in length or longer, 50 amino acids in length or longer, 55 amino acids in length or longer, or 60 amino acids in length or longer. The length of the ultralong CDR3 may include a non-antibody sequence. An ultralong CDR3 may comprise a non-antibody sequence, including, for example, an interleukin sequence, a hormone sequence, a cytokine sequence, a toxin sequence, a lymphokine sequence, a growth factor sequence, a chemokine sequence, a toxin sequence, or combinations thereof. Preferably, the ultralong CDR3 is a heavy chain CDR3 (CDR-H3 or CDRH3). Preferably, the ultralong CDR3 is a sequence derived from or based on a ruminant (e.g., bovine) sequence. An ultralong CDR3 may comprise at least 3 or more cysteine residues, for example, 4 or more cysteine residues, 6 or more cysteine residues, 8 or more cysteine residues, 10 or more cysteine residues, or 12 or more cysteine residues (e.g., 3, 4, 5, 6, 7, 8, 9, 10, 11, 12 or more). An ultralong CDR3 may comprise one or more of the following motifs: a cysteine motif, a $X^1X^2X^3X^4X^5$ motif, a $CX^1X^2X^3X^4X^5$ motif, or a $(X^aX^b)_z$ motif. A "cysteine motif" is a segment of amino acid residues in an ultralong CDR3 that comprises 3 or more cysteine residues including, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues. A cysteine motif may comprise an amino acid sequence selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CXCX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95). Alternatively, a cysteine motif may comprise an amino acid sequence selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{12}C$ (SEQ ID NO: 104), $CX_6CX_2CXCCX_4CX_5CX_5CX_3CXC$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX_9C$ (SEQ ID NO: 121), $CCX_9CX_3CXCCX_3CX_5C$ (SEQ ID NO: 122), $CX_9CX_2CX_3CX_4CCX_4CX_{54}CXC$ (SEQ ID NO: 123), $CX_9CX_7CX_4CCXCX_7CX_3C$ (SEQ ID NO: 124), $CX_5CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_5CX_5CX_4CCX_{14}C$ (SEQ ID NO: 135), $CX_5CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152). A cysteine motif is preferably positioned within an ultralong CDR3 between a $X^1X^2X^3X^4X^5$ motif and a $(X^aX^b)_z$ motif. A "$X^1X^2X^3X^4X^5$ motif" is a series of five consecutive amino acid residues in an ultralong CDR3, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q). In some embodiments, the $X^1X^2X^3X^4X^5$ motif may be TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184). A "$CX^1X^2X^3X^4X^5$ motif" is a series of six consecutive amino acid residues in an ultralong CDR3, wherein the first amino acid residue is cysteine, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q). In some embodiments, the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216). A "$(X^a X^b)_z$" motif is a repeating series of two amino acid residues in an ultralong CDR3, wherein $X^a$ is any amino acid residue, $X^b$ is an aromatic amino acid selected from the group consisting of: tyrosine (Y), phenylalanine (F), tryptophan (W), and histidine (H), and wherein z is 1-4. In some embodiments, the $(X^a X^b)_z$ motif may comprise CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKVVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273). In some embodiments, the $(X^a X^b)_z$ motif is YXYXYX. An ultralong CDR3 may comprise an amino acid sequence that is derived from or based on SEQ ID NO: 40 (see, e.g., amino acid residues 3-6 of SEQ ID NO: 1-4; see also, e.g., VH germline sequences in FIGS. 2A-C). A variable region that comprises an ultralong CDR3 may include an amino acid sequence that is SEQ ID NO: 1 (CTTVHQ), SEQ ID NO:2 (CTSVHQ), SEQ ID NO:3 (CSSVTQ) or SEQ ID NO: 4 (CTTVHP). Such a sequence may be derived from or based on a bovine germline VH gene sequence (e.g., SEQ ID NO: 1). An ultralong CDR3 may comprise a sequence derived from or based on a non-human DH gene sequence, for example, SEQ ID NO: 5 (see also, e.g., Koti, et al. (2010) Mol. Immunol. 47: 2119-2128), or alternative sequences such as SEQ ID NO: 6, 7, 8, 9, 10, 11 or 12 (see also, e.g., DH2 germline sequences in FIGS. 2A-C). An ultralong CDR3 may comprise a sequence derived from or based on a JH sequence, for example, SEQ ID NO: 13 (see also, e.g., Hosseini, et al. (2004) Int. Immunol. 16: 843-852), or alternative sequences such as SEQ ID NO: 14, 15, 16 or 17 (see also, e.g., JH1 germline sequences in FIGS. 2A-C). In an embodiment, an ultralong CDR3 may comprise a sequence derived from or based on a non-human VH sequence (e.g., SEQ ID NO: 1, 2, 3 or 4; alternatively VH sequences in FIGS. 2A-C) and/or a sequence derived from or based on a non-human DH sequence (e.g., SEQ ID NO: 5, 6, 7, 8, 9, 10, 11 or 12; alternatively DH sequences in FIGS. 2A-C) and/or a sequence derived from or based on a JH sequence (e.g., SEQ ID NO: 13, 14, 15, 16, or 17; alternatively JH sequences in FIGS. 2A-C), and optionally an additional sequence comprising two to six amino acids or more (e.g., IR, IF, SEQ ID NO: 18, 19, 20 or 21) such as, for example, between the VH derived sequence and the DH derived sequence. In another embodiment, an ultralong CDR3 may comprise a sequence derived from or based on SEQ ID NO: 22, 23, 24, 25, 26, 27, or 28 (see also, e.g., SEQ ID NOs: 276-359 in FIGS. 2A-C).

An "isolated" biological molecule, such as the various polypeptides, polynucleotides, and antibodies disclosed herein, refers to a biological molecule that has been identified and separated and/or recovered from at least one component of its natural environment.

"Antagonist" refers to any molecule that partially or fully blocks, inhibits, or neutralizes an activity (e.g., biological activity) of a polypeptide. Also encompassed by "antagonist" are molecules that fully or partially inhibit the transcription or translation of mRNA encoding the polypeptide. Suitable antagonist molecules include, e.g., antagonist antibodies or antibody fragments; fragments or amino acid sequence variants of a native polypeptide; peptides; antisense oligonucleotides; small organic molecules; and nucleic acids that encode polypeptide antagonists or antagonist antibodies. Reference to "an" antagonist encompasses a single antagonist or a combination of two or more different antagonists.

"Agonist" refers to any molecule that partially or fully mimics a biological activity of a polypeptide. Also encompassed by "agonist" are molecules that stimulate the transcription or translation of mRNA encoding the polypeptide. Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

An "isolated" antibody refers to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody (e.g., as determined by the Lowry method), and preferably to more than 99% by weight, (2) to a degree sufficient to obtain at least 15 residues of N-terminal or internal amino acid sequence (e.g., by use of a spinning cup sequenator), or (3) to homogeneity by SDS-PAGE under reducing or nonreducing conditions (e.g., using Coomassie™ blue or, preferably, silver stain). Isolated antibody includes the antibody in situ within recombinant cells since at least one component of the antibody's natural environment will not be present. Similarly, isolated antibody includes the antibody in medium around recombinant cells. An isolated antibody may be prepared by at least one purification step.

An "isolated" nucleic acid molecule refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that express an antibody where, for example, the nucleic acid molecule is in a chromosomal location different from that of natural cells.

Variable domain residue numbering as in Kabat or amino acid position numbering as in Kabat, and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (e.g., residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Substantially similar," or "substantially the same", refers to a sufficiently high degree of similarity between two numeric values (generally one associated with an antibody disclosed herein and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

An "on-rate" or "rate of association" or "association rate" or "$k_{on}$" can be determined with a surface plasmon resonance technique such as Biacore (e.g., Biacore A100, Biacore™-2000, Biacore™-3000, Biacore, Inc., Piscataway, N.J.) carboxymethylated dextran biosensor chips (CM5, Biacore Inc.) and according to the supplier's instructions.

"Vector" refers to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. Accordingly, "plasmid" and "vector" may, at times, be used interchangeably as the plasmid is a commonly used form of vector.

"Gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post transcriptional cleavage and polyadenylation.

"Polynucleotide," or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), 37 (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide" refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Stringent hybridization conditions" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. For example, recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this disclosure. It is understood that once a recombinant nucleic acid is made and introduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, e.g., through the expression of a recombinant nucleic acid as depicted above.

"Percent (%) amino acid sequence identity" with respect to a peptide or polypeptide sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MegAlign (DNASTAR) software. Those skilled in the art can determine appropriate parameters for measuring alignment, including any algorithms needed to achieve maximal alignment over the full length of the sequences being compared.

"Polypeptide," "peptide," "protein," and "protein fragment" may be used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles disclosed herein. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Antibodies" (Abs) and "immunoglobulins" (Igs) are glycoproteins having similar structural characteristics. While antibodies may exhibit binding specificity to a specific antigen, immunoglobulins may include both antibodies and other antibody-like molecules which generally lack antigen specificity. Polypeptides of the latter kind are, for example, produced at low levels by the lymph system and at increased levels by myelomas.

"Antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured. An antibody may refer to immunoglobulins and immunoglobulin portions, whether natural or partially or wholly synthetic, such as recombinantly produced, including any portion thereof containing at least a portion of the variable region of the immunoglobulin molecule that is sufficient to form an antigen binding site. Hence, an antibody or portion thereof includes any protein having a binding domain that is homologous or substantially homologous to an immunoglobulin antigen binding site. For example, an antibody may refer to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, VH, chains VH-CH1 chains and VH-CH1-CH2-CH3 chains), and each light chain can be a full-length light chain or a thereof sufficient to form an antigen binding site (e.g. light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region. For example, a full-length antibody is an antibody having two full-length heavy chains (e.g. VH-CH1-CH2-CH3 or VH-CH1-CH2-CH3-CH4) and two full-length light chains (VL-CL) and hinge regions, such as antibodies produced by antibody secreting B cells and antibodies with the same domains that are produced synthetically. Additionally, an "antibody" refers to a protein of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively.

"Variable" refers to the fact that certain portions of the variable domains (also referred to as variable regions) differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. CDRs include those specified as Kabat, Chothia, and IMGT as shown herein within the variable region sequences. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" refers to an antibody fragment which contains an antigen-recognition and antigen-binding site. In a two-chain Fv species, this region consists of a dimer of one heavy and one light chain variable domain in non-covalent association. In a single chain Fv (scFv) species, one heavy chain and one light chain variable domain can be covalently linked by a flexible peptide linker such that the light and heavy chains can associate in a "dimeric" structure analogous to that in a two-chain Fv (scFv) species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', $F(ab')2$, single-chain Fvs (scFv), Fv, dsFv, diabody, Fd and Fd' fragments Fab fragments, Fd fragments, scFv fragments, linear antibodies, single-chain antibody molecules, and multispecific antibodies formed from antibody fragments (see, for example, Methods in Molecular Biology, Vol 207: Recombinant Antibodies for Cancer Therapy Methods and Protocols (2003); Chapter 1; p 3-25, Kipriyanov). Other known fragments include, but are not limited to, scFab fragments (Hust et al., BMC Biotechnology (2007), 7:14). In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. For another example, an antibody fragment or antibody portion refers to any portion of a full-length antibody that is less than full length but contains at least a portion of the variable region of the antibody sufficient to form an antigen binding site (e.g. one or more CDRs) and thus retains the binding specificity and/or an activity of the full-length antibody; antibody fragments include antibody derivatives produced by enzymatic treatment of full-length antibodies, as well as synthetically, e.g. recombinantly produced derivatives.

A "dsFv" refers to an Fv with an engineered intermolecular disulfide bond, which stabilizes the VH-VL pair.

A "Fd fragment" refers to a fragment of an antibody containing a variable domain (VH) and one constant region domain (CH1) of an antibody heavy chain.

A "Fab fragment" refers to an antibody fragment that contains the portion of the full-length antibody that would results from digestion of a full-length immunoglobulin with papain, or a fragment having the same structure that is produced synthetically, e.g. recombinantly. A Fab fragment contains a light chain (containing a VL and CL portion) and another chain containing a variable domain of a heavy chain (VH) and one constant region domain portion of the heavy chain (CH1); it can be recombinantly produced.

A "$F(ab')2$ fragment" refers to an antibody fragment that results from digestion of an immunoglobulin with pepsin at pH 4.0-4.5, or a synthetically, e.g. recombinantly, produced antibody having the same structure. The $F(ab')2$ fragment contains two Fab fragments but where each heavy chain portion contains an additional few amino acids, including cysteine residues that form disulfide linkages joining the two fragments; it can be recombinantly produced.

A "Fab' fragment" refers to a fragment containing one half (one heavy chain and one light chain) of the F(ab')2 fragment.

A "Fd' fragment refers to a fragment of an antibody containing one heavy chain portion of a F(ab')2 fragment.

A "Fv' fragment" refers to a fragment containing only the VH and VL domains of an antibody molecule.

A "scFv fragment" refers to an antibody fragment that contains a variable light chain (VL) and variable heavy chain (VH), covalently connected by a polypeptide linker in any order. The linker is of a length such that the two variable domains are bridged without substantial interference. Exemplary linkers are (Gly-Ser)n residues with some Glu or Lys residues dispersed throughout to increase solubility.

Diabodies are dimeric scFv; diabodies typically have shorter peptide linkers than scFvs, and they preferentially dimerize.

"HsFv" refers to antibody fragments in which the constant domains normally present in a Fab fragment have been substituted with a heterodimeric coiled-coil domain (see, e.g., Arndt et al. (2001) J Mol Biol. 7:312:221-228).

"Hypervariable region", "HVR", or "HV", as well as "complementary determining region" or "CDR", may refer to the regions of an antibody variable domain which are hypervariable in sequence and/or form structurally defined loops. Generally, antibodies comprise six hypervariable or CDR regions; three in the VH (H1, H2, H3), and three in the VL (L1, L2, L3). A number of hypervariable region or CDR delineations are in use and are encompassed herein. The Kabat Complementarity Determining Regions (Kabat CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, (Chothia "CDRs") and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

IMGT refers to the international ImMunoGeneTics Information System, as described by Lefrace et al., Nucl. Acids, Res. 37; D1006-D1012 (2009), including for example, IMGT designated CDRs for antibodies.

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., Supra for each of these definitions.

"Framework" or "FR" residues are those variable domain residues other than the hypervariable region residues as herein defined. "Framework regions" (FRs) are the domains within the antibody variable region domains comprising framework residues that are located within the beta sheets; the FR regions are comparatively more conserved, in terms of their amino acid sequences, than the hypervariable regions.

"Monoclonal antibody" refers to an antibody from a population of substantially homogeneous antibodies, that is, for example, the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations which typically include different antibodies directed against different determinants (e.g., epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806;

5,569,825; 5,591,669; 5,545,807; WO 1997/17852; U.S. Pat. Nos. 5,545,807; 5,545,806; 5,569,825; 5,625,126; 5,633,425; and 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995)).

"Humanized" or "Human engineered" forms of non-human (e.g., murine) antibodies are chimeric antibodies that contain amino acids represented in human immunoglobulin sequences, including, for example, wherein minimal sequence is derived from non-human immunoglobulin. For example, humanized antibodies may be human antibodies in which some hypervariable region residues and possibly some FR residues are substituted by residues from analogous sites in non-human (e.g., rodent) antibodies. Alternatively, humanized or human engineered antibodies may be non-human (e.g., rodent) antibodies in which some residues are substituted by residues from analogous sites in human antibodies (see, e.g., U.S. Pat. No. 5,766,886). Humanized antibodies include human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody, including, for example non-antibody sequences such as a chemokine, growth factor, peptide, cytokine, cell surface protein, serum protein, toxin, extracellular matrix protein, clotting factor, or secreted protein sequence. These modifications may be made to further refine antibody performance. Humanized antibodies include human engineered antibodies, for example, as described by U.S. Pat. No. 5,766,886, including methods for preparing modified antibody variable domains. A humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. A humanized antibody optionally may also comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

"Hybrid antibodies" refer to immunoglobulin molecules in which pairs of heavy and light chains from antibodies with different antigenic determinant regions are assembled together so that two different epitopes or two different antigens can be recognized and bound by the resulting tetramer.

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). Humanized antibody refers to a subset of chimeric antibodies.

"Single-chain Fv" or "scFv" antibody fragments may comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see e.g., Pluckthun, in The Pharmacology of Monoclonal Antibodies, vol. 113, Rosenburg and Moore eds., Springer-Verlag, New York, pp. 269-315 (1994).

An "antigen" refers to a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

"Epitope" or "antigenic determinant", used interchangeably herein, refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. Antibodies may bind to the same or a different epitope on an antigen. Antibodies may be characterized in different epitope bins. Whether an antibody binds to the same or different epitope as another antibody (e.g., a reference antibody or benchmark antibody) may be determined by competition between antibodies in assays (e.g., competitive binding assays).

Competition between antibodies may be determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay or enzyme-linked immunosorbent assay (EIA or ELISA), sandwich competition assay including an ELISA assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using 1-125 label (see Morel et al., Molec. Immunol. 25(1): 7-15 (1988)); solid phase direct biotin-avidin EIA (Cheung et al., Virology 176:546-552 (1990)); and direct labeled RIA (Moldenhauer et al., Scand. J. Immunol., 32:77-82 (1990)). Competition binding assays may be performed using Surface Plasmon Resonance (SPR), for example, with a Biacore® instrument for kinetic analysis of binding interactions. In such an assay, a humanized antibody comprising an ultralong CDR3 of unknown epitope specificity may be evaluated for its ability to compete for binding against a comparator antibody (e.g., a BA1 or BA2 antibody as described herein). An assay may involve the use of purified antigen bound to a solid surface or cells bearing either of these, an unlabeled test immunoglobulin and a labeled reference immunoglobulin. Competitive inhibition may be measured by determining the amount of label bound to the solid surface or cells in the presence of the test immunoglobulin. Usually the test immunoglobulin is present in excess. An assay (competing antibodies) may include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50%, or at least about 70%, or at least about 80%, or at least about 90%, or at least about 95%, or at least about 99% or about 100% for a competitor antibody.

That an antibody "selectively binds" or "specifically binds" means that the antibody reacts or associates more frequently, more rapidly, with greater duration, with greater affinity, or with some combination of the above to an antigen or an epitope than with alternative substances, including unrelated proteins. "Selectively binds" or "specifically binds" may mean, for example, that an antibody binds to a protein with a $K_D$ of at least about 0.1 mM, or at least about 1 μM or at least about 0.1 μM or better, or at least about 0.01 μM or better. Because of the sequence identity between homologous proteins in different species, specific binding can include an antibody that recognizes a given antigen in more than one species.

"Non-specific binding" and "background binding" when used in reference to the interaction of an antibody and a protein or peptide refer to an interaction that is not dependent on the presence of a particular structure (e.g., the antibody is binding to proteins in general rather that a particular structure such as an epitope).

"Diabodies" refer to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et. al., Proc. Natl. Acad. Sci. USA, 90:6444-6448 (1993).

A "human antibody" refers to one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody refers to one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Natl. Acad. Sci. USA 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulates homeostasis of immunoglobulins. For example, antibody variants with improved or diminished binding to FcRs have been described (see, e.g., Shields et al. J. Biol. Chem. 9(2): 6591-6604 (2001)).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, for example, as described in Gazzano-Santoro et al., J. Immunol. Methods 202:163 (1996), may be performed.

Polypeptide variants with altered Fc region amino acid sequences and increased or decreased Clq binding capability have been described (e.g., see, also, Idusogie et al. J. Immunol. 164: 4178-4184 (2000)).

"Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide.

"Blocking" antibody or an "antagonist" antibody refers to one which inhibits or reduces biological activity of the antigen it binds. Preferred blocking antibodies or antagonist antibodies substantially or completely inhibit the biological activity of the antigen.

"Agonist" antibody refers to an antibody which mimics (e.g., partially or fully) at least one of the functional activities of a polypeptide of interest.

"Acceptor human framework" refers to a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Disorder" or "disease" refers to any condition that would benefit from treatment with a substance/molecule (e.g., a humanized antibody comprising an ultralong CDR3 as disclosed herein) or method disclosed herein. This includes chronic and acute disorders or diseases including those pathological conditions which predispose the mammal to the disorder in question.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or disorder.

"Individual" (e.g., a "subject") refers to a vertebrate, preferably a mammal, more preferably a human. Mammals include, but are not limited to, farm animals (such as cows), sport animals, pets (such as cats, dogs and horses), primates, mice and rats.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

"Providing a prognosis", "prognostic information", or "predictive information" refer to providing information, including for example the presence of cancer cells in a subject's tumor, regarding the impact of the presence of cancer (e.g., as determined by the diagnostic methods of the present disclosure) on a subject's future health (e.g., expected morbidity or mortality, the likelihood of getting cancer, and the risk of metastasis).

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented.

"Providing a diagnosis" or "diagnostic information" refers to any information, including for example the presence of cancer cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

A "human consensus framework" refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein refers to a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Antigen-binding site" refers to the interface formed by one or more complementary determining regions. An antibody molecule has two antigen combining sites, each containing portions of a heavy chain variable region and portions of a light chain variable region. The antigen combining sites can contain other portions of the variable region domains in addition to the CDRs.

An "antibody light chain" or an "antibody heavy chain" refers to a polypeptide comprising the VL or VH, respectively. The VL is encoded by the minigenes V (variable) and J (junctional), and the VH by minigenes V, D (diversity), and J. Each of VL or VH includes the CDRs as well as the framework regions. In this application, antibody light chains and/or antibody heavy chains may, from time to time, be collectively referred to as "antibody chains." These terms encompass antibody chains containing mutations that do not disrupt the basic structure of VL or VH, as one skilled in the art will readily recognize.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide bonded. From N- to C-terminus, each heavy chain has a variable region (V H), also called a variable heavy domain or a heavy chain variable domain, followed by three constant domains (CH1, CH2, and CH3). Similarly, from N- to C-terminus, each light chain has a variable region (V L), also called a variable light domain or a light chain variable domain, followed by a constant light (CL) domain. The light chain of an antibody may be assigned to one of two types, called kappa (κ) and lambda (K), based on the amino acid sequence of its constant domain.

"Combinatorial library" refers to collections of compounds formed by reacting different combinations of interchangeable chemical "building blocks" to produce a collection of compounds based on permutations of the building blocks. For an antibody combinatorial library, the building blocks are the component V, D and J regions (or modified forms thereof) from which antibodies are formed. For purposes herein, the terms "library" or "collection" are used interchangeably.

A "combinatorial antibody library" refers to a collection of antibodies (or portions thereof, such as Fabs), where the antibodies are encoded by nucleic acid molecules produced by the combination of V, D and J gene segments, particularly human V, D and J germline segments. The combinatorial libraries herein typically contain at least 50 different antibody (or antibody portions or fragment) members, typically at or about 50, 100, 500, 103, 1×103, 2×103, 3×103, 4×103, 5×103, 6×103, 7×103, 8×103, 9×103, 1×104, 2×104, 3×104, 4×104, 5×104, 6×104, 7×104, 8×104, 9×104, 1×105, 2×105, 3×105, 4×105, 5×105, 6×105, 7×105, 8×105, 9×105, 106, 107, 108, 109, 1010, or more different members. The resulting libraries or collections of antibodies or portions thereof, can be screened for binding to a target protein or modulation of a functional activity.

A "human combinatorial antibody library" refers to a collection of antibodies or portions thereof, whereby each member contains a VL and VH chains or a sufficient portion thereof to form an antigen binding site encoded by nucleic acid containing human germline segments produced as described herein.

A "variable germline segment" refers to V, D and J groups, subgroups, genes or alleles thereof. Gene segment sequences are accessible from known database (e.g., National Center for Biotechnology Information (NCBI), the international ImMunoGeneTics information System® (IMGT), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). Tables 3-5 list exemplary human variable germline segments. Sequences of exemplary VH, DH, JH, Vκ, Jκ, Vλ and or Jλ, germline segments are set forth in SEQ ID NOS: 10-451 and 868. For purposes herein, a germline segment includes modified sequences thereof, that are modified in accord with the rules of sequence compilation provided herein to permit practice of the method. For example, germline gene segments include those that contain one amino acid deletion or insertion at the 5' or 3' end compared to any of the sequences of nucleotides set forth in SEQ ID NOS:10-451, 868.

"Compilation," "compile," "combine," "combination," "rearrange," "rearrangement," or other similar terms or grammatical variations thereof refers to the process by which germline segments are ordered or assembled into nucleic acid sequences representing genes. For example, variable heavy chain germline segments are assembled such that the VH segment is 5' to the DH segment which is 5' to the JH segment, thereby resulting in a nucleic acid sequence encoding a VH chain. Variable light chain germline segments are assembled such that the VL segment is 5' to the JL segment, thereby resulting in a nucleic acid sequence encoding a VL chain. A constant gene segment or segments also can be assembled onto the 3' end of a nucleic acid encoding a VH or VL chain.

"Linked," or "linkage" or other grammatical variations thereof with reference to germline segments refers to the joining of germline segments. Linkage can be direct or indirect. Germline segments can be linked directly without additional nucleotides between segments, or additional nucleotides can be added to render the entire segment in-frame, or nucleotides can be deleted to render the resulting segment in-frame. It is understood that the choice of linker nucleotides is made such that the resulting nucleic acid molecule is in-frame and encodes a functional and productive antibody.

"In-frame" or "linked in-frame" with reference to linkage of human germline segments means that there are insertions and/or deletions in the nucleotide germline segments at the joined junctions to render the resulting nucleic acid molecule in-frame with the 5' start codon (ATG), thereby producing a "productive" or functional full-length polypeptide. The choice of nucleotides inserted or deleted from germline segments, particularly at joints joining various VD, DJ and VJ segments, is in accord with the rules provided in the method herein for V(D)J joint generation. For example, germline segments are assembled such that the VH segment is 5' to the DH segment which is 5' to the JH segment. At the junction joining the VH and the DH and at the junction joining the DH and JH segments, nucleotides can be inserted or deleted from the individual VH, DH or JH segments, such that the resulting nucleic acid molecule containing the joined VDJ segments are in-frame with the 5' start codon (ATG).

A portion of an antibody includes sufficient amino acids to form an antigen binding site.

A "reading frame" refers to a contiguous and non-overlapping set of three-nucleotide codons in DNA or RNA. Because three codons encode one amino acid, there exist three possible reading frames for given nucleotide sequence, reading frames 1, 2 or 3. For example, the sequence ACTGGTCA will be ACT GGT CA for reading frame 1, A CTG GTC A for reading frame 2 and AC TGG TCA for reading frame 3. Generally for practice of the method described herein, nucleic acid sequences are combined so that the V sequence has reading frame 1.

A "stop codon" refers to a three-nucleotide sequence that signals a halt in protein synthesis during translation, or any sequence encoding that sequence (e.g. a DNA sequence encoding an RNA stop codon sequence), including the amber stop codon (UAG or TAG)), the ochre stop codon (UAA or TAA)) and the opal stop codon (UGA or TGA)). It is not necessary that the stop codon signal termination of translation in every cell or in every organism. For example, in suppressor strain host cells, such as amber suppressor strains and partial amber suppressor strains, translation proceeds through one or more stop codon (e.g. the amber stop codon for an amber suppressor strain), at least some of the time.

A "variable heavy" (VH) chain or a "variable light" (VL) chain (also termed VH domain or VL domain) refers to the polypeptide chains that make up the variable domain of an antibody. For purposes herein, heavy chain germline segments are designated as VH, DH and JH, and compilation thereof results in a nucleic acid encoding a VH chain. Light chain germline segments are designated as VL or JL, and include kappa and lambda light chains (Vκ and Jκ; Vλ and Jλ.) and compilation thereof results in a nucleic acid encoding a VL chain. It is understood that a light chain is either a kappa or lambda light chain, but does not include a kappa/lambda combination by virtue of compilation of a Vκ and Jλ.

A "degenerate codon" refers to three-nucleotide codon that specifies the same amino acid as a codon in a parent nucleotide sequence. One of skill in the art is familiar with degeneracy of the genetic code and can identify degenerate codons.

"Diversity" with respect to members in a collection refers to the number of unique members in a collection. Hence, diversity refers to the number of different amino acid sequences or nucleic acid sequences, respectively, among the analogous polypeptide members of that collection. For example, a collection of polynucleotides having a diversity of 104 contains 104 different nucleic acid sequences among the analogous polynucleotide members. In one example, the provided collections of polynucleotides and/or polypeptides have diversities of at least at or about 102, 103, 104, 105, 106, 107, 108, 109, 1010 or more.

"Sequence diversity" refers to a representation of nucleic acid sequence similarity and is determined using sequence alignments, diversity scores, and/or sequence clustering. Any two sequences can be aligned by laying the sequences side-by-side and analyzing differences within nucleotides at every position along the length of the sequences. Sequence alignment can be assessed in silico using Basic Local Alignment Search Tool (BLAST), an NCBI tool for comparing nucleic acid and/or protein sequences. The use of BLAST for sequence alignment is well known to one of skill in the art. The Blast search algorithm compares two sequences and calculates the statistical significance of each match (a Blast score). Sequences that are most similar to each other will have a high Blast score, whereas sequences that are most varied will have a low Blast score.

A "polypeptide domain" refers to a part of a polypeptide (a sequence of three or more, generally 5 or 7 or more amino acids) that is a structurally and/or functionally distinguishable or definable. Exemplary of a polypeptide domain is a part of the polypeptide that can form an independently folded structure within a polypeptide made up of one or more structural motifs (e.g. combinations of alpha helices and/or beta strands connected by loop regions) and/or that is recognized by a particular functional activity, such as enzymatic activity or antigen binding. A polypeptide can have one, typically more than one, distinct domains. For example, the polypeptide can have one or more structural domains and one or more functional domains. A single polypeptide domain can be distinguished based on structure and function. A domain can encompass a contiguous linear sequence of amino acids. Alternatively, a domain can encompass a plurality of non-contiguous amino acid portions, which are non-contiguous along the linear sequence of amino acids of the polypeptide. Typically, a polypeptide contains a plurality of domains. For example, each heavy chain and each light chain of an antibody molecule contains a plurality of immunoglobulin (Ig) domains, each about 110 amino acids in length.

An "Ig domain" refers to a domain, recognized as such by those in the art, that is distinguished by a structure, called the Immunoglobulin (Ig) fold, which contains two beta-pleated sheets, each containing anti-parallel beta strands of amino acids connected by loops. The two beta sheets in the Ig fold are sandwiched together by hydrophobic interactions and a conserved intra-chain disulfide bond. Individual immunoglobulin domains within an antibody chain further can be distinguished based on function. For example, a light chain contains one variable region domain (VL) and one constant region domain (CL), while a heavy chain contains one variable region domain (VH) and three or four constant region domains (CH). Each VL, CL, VH, and CH domain is an example of an immunoglobulin domain.

A "variable domain" with reference to an antibody refers to a specific Ig domain of an antibody heavy or light chain that contains a sequence of amino acids that varies among different antibodies. Each light chain and each heavy chain has one variable region domain (VL, and, VH). The variable domains provide antigen specificity, and thus are responsible for antigen recognition. Each variable region contains CDRs that are part of the antigen binding site domain and framework regions (FRs).

A "constant region domain" refers to a domain in an antibody heavy or light chain that contains a sequence of amino acids that is comparatively more conserved among antibodies than the variable region domain. Each light chain has a single light chain constant region (CL) domain and each heavy chain contains one or more heavy chain constant region (CH) domains, which include, CH1, CH2, CH3 and CH4. Full-length IgA, IgD and IgG isotypes contain CH1, CH2 CH3 and a hinge region, while IgE and IgM contain CH1, CH2 CH3 and CH4. CH1 and CL domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g. through interactions with various cells, biomolecules and tissues.

An "antibody or portion thereof that is sufficient to form an antigen binding site" means that the antibody or portion thereof contains at least 1 or 2, typically 3, 4, 5 or all 6 CDRs of the VH and VL sufficient to retain at least a portion of the binding specificity of the corresponding full-length antibody containing all 6 CDRs. Generally, a sufficient antigen binding site at least requires CDR3 of the heavy chain (CDRH3). It typically further requires the CDR3 of the light chain (CDRL3). As described herein, one of skill in the art knows and can identify the CDRs based on Kabat or Chothia numbering (see, e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). For example, based on Kabat numbering, CDR-L1 corresponds to residues L24-L34; CDR-L2 corresponds to residues L50-L56; CDR-L3 corresponds to residues L89-L97; CDR-H1 corresponds to residues H31-H35, 35a or 35b depending on the length; CDR-H2 corresponds to residues H50-H65; and CDR-H3 corresponds to residues H95-H102.

A "peptide mimetic" refers to a peptide that mimics the activity of a polypeptide. For example, an erythropoietin (EPO) peptide mimetic is a peptide that mimics the activity of Epo, such as for binding and activation of the EPO receptor.

An "address" refers to a unique identifier for each locus in a collection whereby an addressed member (e.g. an antibody) can be identified. An addressed moiety is one that can be identified by virtue of its locus or location. Addressing can be effected by position on a surface, such as a well of a microplate. For example, an address for a protein in a microwell plate that is F9 means that the protein is located in row F, column 9 of the microwell plate. Addressing also can be effected by other identifiers, such as a tag encoded with a bar code or other symbology, a chemical tag, an electronic, such RF tag, a color-coded tag or other such identifier.

An "array" refers to a collection of elements, such as antibodies, containing three or more members.

A "spatial array" refers to an array where members are separated or occupy a distinct space in an array. Hence, spatial arrays are a type of addressable array. Examples of spatial arrays include microtiter plates where each well of a plate is an address in the array. Spacial arrays include any arrangement wherein a plurality of different molecules, e.g., polypeptides, are held, presented, positioned, situated, or supported. Arrays can include microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. Furthermore, arrays can also include a plurality of sub-arrays. A plurality of sub-arrays encompasses an array where more than one arrangement is used to position the polypeptides. For example, multiple 96-well plates could constitute a plurality of sub-arrays and a single array.

An "addressable library" or "spatially addressed library" refers to a collection of molecules such as nucleic acid molecules or protein agents, such as antibodies, in which each member of the collection is identifiable by virtue of its address.

An "addressable array" refers to one in which the members of the array are identifiable by their address, the position in a spatial array, such as a well of a microtiter plate, or on a solid phase support, or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are located at identifiable loci on the surface of a solid phase or directly or indirectly linked to or otherwise associated with the identifiable label, such as affixed to a microsphere or other particulate support (herein referred to as beads) and suspended in solution or spread out on a surface.

"An addressable combinatorial antibody library" refers to a collection of antibodies in which member antibodies are identifiable and all antibodies with the same identifier, such as position in a spatial array or on a solid support, or a chemical or RF tag, bind to the same antigen, and generally are substantially the same in amino acid sequence. For purposes herein, reference to an "addressable arrayed combinatorial antibody library" means that the antibody members are addressed in an array.

"In silico" refers to research and experiments performed using a computer. In silico methods include, but are not limited to, molecular modeling studies, biomolecular docking experiments, and virtual representations of molecular structures and/or processes, such as molecular interactions. For purposes herein, the antibody members of a library can be designed using a computer program that selects component V, D and J germline segments from among those input into the computer and joins them in-frame to output a list of nucleic acid molecules for synthesis. Thus, the recombination of the components of the antibodies in the collections or libraries provided herein, can be performed in silico by combining the nucleotide sequences of each building block in accord with software that contains rules for doing so. The process could be performed manually without a computer, but the computer provides the convenience of speed.

A "database" refers to a collection of data items. For purposes herein, reference to a database is typically with reference to antibody databases, which provide a collection of sequence and structure information for antibody genes and sequences. Exemplary antibody databases include, but are not limited to, IMGT®, the international ImMunoGeneTics information system (imgt.cines.fr; see e.g., Lefranc et al. (2008) Briefings in Bioinformatics, 9:263-275), National Center for Biotechnology Information (NCBI), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). A database also can be created by a user to include any desired sequences. The database can be created such that the sequences are inputted in a desired format (e.g., in a particular reading frame; lacking stop codons; lacking signal sequences). The database also can be created to include sequences in addition to antibody sequences.

"Screening" refers to identification or selection of an antibody or portion thereof from a collection or library of antibodies and/or portions thereof, based on determination of the activity or property of an antibody or portion thereof. Screening can be performed in any of a variety of ways, including, for example, by assays assessing direct binding (e.g. binding affinity) of the antibody to a target protein or by functional assays assessing modulation of an activity of a target protein.

"Activity towards a target protein" refers to binding specificity and/or modulation of a functional activity of a target protein, or other measurements that reflects the activity of an antibody or portion thereof towards a target protein.

A "target protein" refers to candidate proteins or peptides that are specifically recognized by an antibody or portion thereof and/or whose activity is modulated by an antibody or portion thereof. A target protein includes any peptide or protein that contains an epitope for antibody recognition. Target proteins include proteins involved in the etiology of a disease or disorder by virtue of expression or activity. Exemplary target proteins are described herein.

"Hit" refers to an antibody or portion thereof identified, recognized or selected as having an activity in a screening assay.

"Iterative" with respect to screening means that the screening is repeated a plurality of times, such as 2, 3, 4, 5 or more times, until a "Hit" is identified whose activity is optimized or improved compared to prior iterations.

"High-throughput" refers to a large-scale method or process that permits manipulation of large numbers of molecules or compounds, generally tens to hundred to thousands of compounds. For example, methods of purification and screening can be rendered high-throughput. High-throughput methods can be performed manually. Generally, however, high-throughput methods involve automation, robotics or software.

Basic Local Alignment Search Tool (BLAST) is a search algorithm developed by Altschul et al. (1990) to separately search protein or DNA databases, for example, based on sequence identity. For example, blastn is a program that compares a nucleotide query sequence against a nucleotide sequence database (e.g. GenBank). BlastP is a program that compares an amino acid query sequence against a protein sequence database.

A BLAST bit score is a value calculated from the number of gaps and substitutions associated with each aligned sequence. The higher the score, the more significant the alignment.

A "human protein" refers to a protein encoded by a nucleic acid molecule, such as DNA, present in the genome of a human, including all allelic variants and conservative variations thereof. A variant or modification of a protein is a human protein if the modification is based on the wildtype or prominent sequence of a human protein.

"Naturally occurring amino acids" refer to the 20 L-amino acids that occur in polypeptides. The residues are those 20 α-amino acids found in nature which are incorporated into protein by the specific recognition of the charged tRNA molecule with its cognate mRNA codon in humans.

"Non-naturally occurring amino acids" refer to amino acids that are not genetically encoded. For example, a non-natural amino acid is an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

"Nucleic acids" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

A "peptide" refers to a polypeptide that is from 2 to 40 amino acids in length.

The amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

An "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

"Amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3552-3559 (1969), and adopted 37 C.F.R. §§ 1.821-1.822, abbreviations for amino acid residues are shown below:

| SYMBOL | | |
|---|---|---|
| 1-Letter | 3-Letter | AMINO ACID |
| Y | Tyr | Tyrosine |
| G | Gly | Glycine |
| F | Phe | Phenylalanine |

-continued

| SYMBOL | | AMINO ACID |
|---|---|---|
| 1-Letter | 3-Letter | |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH2 or to a carboxyl-terminal group such as COOH. The abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:1726). Each naturally occurring L-amino acid is identified by the standard three letter code (or single letter code) or the standard three letter code (or single letter code) with the prefix "L-"; the prefix "D-" indicates that the stereoisomeric form of the amino acid is D.

An "immunoconjugate" refers to an antibody conjugated to one or more heterologous molecule(s), including but not limited to a cytotoxic agent. An immunoconjugate may include non-antibody sequences.

General Techniques

The present disclosure relies on routine techniques in the field of recombinant genetics. Basic texts disclosing the general methods of use in this present disclosure include Sambrook and Russell, Molecular Cloning: A Laboratory Manual 3d ed. (2001); Kriegler, Gene Transfer and Expression: A Laboratory Manual (1990); and Ausubel et al., Current Protocols in Molecular Biology (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, Tetrahedron Letters, 22:1859-1862 (1981), using an automated synthesizer, as described in Van Devanter et al., Nucleic Acids Res., 12:6159-6168 (1984). Purification of oligonucleotides is by either native polyacrylamide gel electrophoresis or by anion-exchange chromatography as described in Pearson & Reanier, J. Chrom., 255:137-149 (1983). The sequence of the cloned genes and synthetic oligonucleotides can be verified after cloning using, e.g., the chain termination method for sequencing double-stranded templates of Wallace et al., Gene, 16:21-26 (1981).

The nucleic acids encoding recombinant polypeptides of the present disclosure may be cloned into an intermediate vector before transformation into prokaryotic or eukaryotic cells for replication and/or expression. The intermediate vector may be a prokaryote vector such as a plasmid or shuttle vector.

Humanized Antibodies with Ultralong CDR3 Sequences

To date, cattle are the only species where ultralong CDR3 sequences have been identified. However, other species, for example other ruminants, may also possess antibodies with ultralong CDR3 sequences.

Exemplary antibody variable region sequences comprising an ultralong CDR3 sequence identified in cattle include those designated as: BLV1H12 (see, SEQ ID NO: 22), BLV5B8 (see, SEQ ID NO: 23), BLV5D3 (see, SEQ ID NO: 24) and BLV8C11 (see, SEQ ID NO: 25) (see, e.g., Saini, et al. (1999) Eur. J. Immunol. 29: 2420-2426; and Saini and Kaushik (2002) Scand. J. Immunol. 55: 140-148); BF4E9 (see, SEQ ID NO: 26) and BF1H1 (see, SEQ ID NO: 27) (see, e.g., Saini and Kaushik (2002) Scand. J. Immunol. 55: 140-148); and F18 (see, SEQ ID NO: 28) (see, e.g., Berens, et al. (1997) Int. Immunol. 9: 189-199).

In an embodiment, bovine antibodies are identified and humanized. Multiple techniques exist to identify antibodies.

Antibodies of the present disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Phage display libraries of bovine antibodies may be a source of bovine antibody gene sequences, including ultralong CDR3 sequences.

Typically, a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Human variable region framework sequences that may be used for humanization include but are not limited to: framework sequences selected using the "best-fit" method (see, e.g., Sims et al. J. Immunol. 151:2296 (1993)); framework sequences derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151: 2623 (1993)); human mature (somatically mutated) framework sequences or human germline framework sequences (see, e.g., Almagro and Fransson, Front. Biosci. 13:1619-1633 (2008)); and framework sequences derived from screening FR libraries (see, e.g., Baca et al., Biol. Chem. 272:10678-10684 (1997) and Rosok et al., J. Biol. Chem. 271:22611-22618 (1996)).

Humanized antibodies with ultralong CDR3 sequences may also include engineered non-antibody sequences, such as cytokines or growth factors, into the CDR3 region, such that the resultant humanized antibody is effective, for example, in inhibiting tumor metastasis. Non-antibody sequences may include an interleukin sequence, a hormone sequence, a cytokine sequence, a toxin sequence, a lymphokine sequence, a growth factor sequence, a chemokine sequence, a toxin sequence, or combinations thereof. Non-antibody sequences may be human, non-human, or synthetic. In some embodiments, the cytokine or growth factor may be shown to have an antiproliferative effect on at least one cell population. Such cytokines, lymphokines, growth factors, or other hematopoietic factors include M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFo1, TNF1, TNF2, G-CSF, Meg-CSF, GM-CSF, thrombopoietin, stem cell factor, and erythropoietin. Additional growth factors for use in humanized antibodies and/or pharmaceutical compositions of the present disclosure include: angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-S, latent transforming growth factor-1, transforming growth factor-1 binding protein I, transforming growth factor-1 binding protein II, transforming growth factor-1 binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Exemplary non-antibody sequences include interleukin 8 (IL-8, SEQ ID NO: 475), interleukin 21 (IL-21, SEQ ID NO: 480), CXCL12/SDF-1alpha (SEQ ID NO: 479), somatostain (SEQ ID NO: 477), ProTx-II (SEQ ID NO: 481), chlorotoxin (SEQ ID NO: 478), and ziconotide (SEQ ID NO: 476).

A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

The humanized antibodies comprising an ultralong CDR3 as disclosed herein are preferably monoclonal. Also encompassed within the scope of the disclosure are Fab, Fab', Fab'-SH and F(ab')$_2$ fragments of the humanized antibodies comprising an ultralong CDR3 as provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies.

The humanized antibodies comprising an ultralong CDR3 as disclosed herein can be made using a hybridoma cell-based method first described by Kohler et al., Nature, 256:495 (1975), or may be made by recombinant DNA methods.

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed.

The hybridoma cells may be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, myeloma cell lines may be murine myeloma lines, such as those derived from MOPC-21 and MPC-11 mouse tumors available from the Salk Institute Cell Distribution Center, San Diego, Calif. USA, and SP-2 or $X_{63}$-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of humanized antibodies comprising an ultralong CDR3. For example, the binding specificity of monoclonal antibodies produced by hybridoma cells may be determined by immunoprecipitation or by an in vitro binding assay, such as an enzyme-linked immunoadsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The humanized antibodies comprising an ultralong CDR3 as disclosed herein may be made by using combinatorial libraries to screen for synthetic antibody clones with the desired activity or activities. For example, synthetic antibody clones are selected by screening phage libraries containing phage that display various fragments of antibody variable regions (e.g., scFv or Fab) fused to phage coat protein. Such phage libraries may be panned, for example, by affinity chromatography against the desired antigen. Clones expressing antibody fragments capable of binding to the desired antigen may be adsorbed to the antigen and thus separated from the non-binding clones in the library. The binding clones may then be eluted from the antigen, and can be further enriched by additional cycles of antigen adsorption/elution. Any of the humanized antibodies comprising an ultralong CDR3 as disclosed herein may be obtained by designing a suitable antigen screening procedure to select for the phage clone of interest followed by construction of a full length antibody comprising an ultralong CDR3 clone using the VH and VL (e.g., from scFv or Fab) sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions, one each from the light (VL) and heavy (VH) chains, that both present three hypervariable loops or complementarity-determining regions (CDRs). Variable domains may be displayed functionally on phage, either as single-chain Fv (scFv, also referred to as single-chain antibody (SCA)) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). scFv or SCA encoding phage clones and Fab encoding phage clones may be separately or collectively referred to as "Fv phage clones" or "Fv clones".

Repertoires of VH and VL genes may be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire may be cloned to provide a single source of human antibodies to a wide range of non-self and also self antigens without any immunization as described by Griffiths et al., EMBO J. 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. Protein pIII may include truncated forms of pIII. The antibody fragments can be displayed as single chain Fv fragments, in which VH and VL domains are connected on the same polypeptide chain by a flexible polypeptide spacer, (e.g., as described by Marks et al., J. Mol. Biol., 222: 581-597 (1991)), or as Fab fragments, in which one chain is fused to pIII (e.g., a truncated pIII) and the other is secreted into the bacterial host cell periplasm where assembly of a Fab-coat protein structure which becomes displayed on the phage surface by displacing some of the wild type coat proteins, (e.g., as described in Hoogenboom et al., Nucl. Acids Res., 19: 4133-4137 (1991)).

Nucleic acid encoding antibody variable gene segments (including VH and VL segments) are recovered from the cells of interest and and may be amplified or copies made by recombinant DNA techniques (e.g., Kunkel mutagenesis). For example, in the case of rearranged VH and VL gene libraries, the desired DNA may be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes may be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). For amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To enhance or maximize complementarity, degeneracy may be incorporated in the primers as described in Orlandi et al. (1989) or Sastry et al. (1989). Library diversity may be enhanced or maximized by using PCR primers targeted to each V-gene family in order to amplify available VH and VL arrangements present in the immune cell nucleic acid sample, for example, as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction may can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes may be derived in vitro from V gene segments. Most of the human VH-gene segments have been cloned and sequenced (e.g., reported in Tomlinson et al., J. Mol. Biol., 227: 776-798 (1992)), and mapped (e.g., reported in Matsuda et al., Nature Genet., 3: 88-94 (1993); these cloned segments (including all the major conformations of the H1 and H2 loop) may be used to generate diverse VH gene repertoires with PCR primers encoding H3 loops of diverse sequence and length as described in Hoogenboom and Winter, J. Mol. Biol., 227: 381-388 (1992). VH repertoires may also be made with all the sequence diversity focused in a long H3 loop of a single length as described in Barbas et al., Proc. Natl. Acad. Sci. USA, 89: 4457-4461 (1992). Human Vκ and Vλ. segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments may be constructed by combining VH and VL gene repertoires together in several ways. Each repertoire may be created in different vectors, and the vectors recombined in vitro, for example, as described in Hogrefe et al., Gene, 128: 119-126 (1993), or in vivo by combinatorial infection, for example, the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These large libraries may provide large numbers of diverse antibodies of good affinity ($K_d^{-1}$ of about 10-8 M).

Alternatively, the repertoires may be cloned sequentially into the same vector, for example, as described in Barbas et al., Proc. Natl. Acad. Sci. USA, 88: 7978-7982 (1991), or assembled together by PCR and then cloned, for example, as described in Clackson et al., Nature, 352: 624-628 (1991). PCR assembly may also be used to join VH and VL DNAs with DNA encoding a flexible peptide spacer to form single chain Fv (scFv) repertoires. In yet another technique, "in cell PCR assembly" may be used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7 M^{-1}$), but affinity maturation may also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation may be performed by randomly mutating one or more CDRs, for example, using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the 10-9 M range.

The phage library samples are contacted with an immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g., as described in Barbas et al., Proc. Natl. Acad. Sci. USA, 88: 7978-7982 (1991), or by alkali, (e.g., as described in Marks et al., J. Mol. Biol., 222: 581-597 (1991)), or by antigen competition, (e.g., in a procedure similar to the antigen competition method of Clackson et al., Nature, 352: 624-628 (1991)). Phages may be enriched 20-1,000-fold in a single round of selection. Moreover, the enriched phages may be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) may be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) may be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

DNA encoding the hybridoma-derived monoclonal antibodies or phage display Fv clones disclosed herein is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Recombinant expression in bacteria of antibody-encoding DNA has been described by Better et al., U.S. Pat. No. 6,204,023 (see also, e.g., Skerra et al., Curr. Opinion in Immunol., 5: 256 (1993) and Pluckthun, Immunol. Revs, 130: 151 (1992)).

DNA encoding Fv clones as disclosed herein may be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions may be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred Fv clone embodiment, aFv clone derived from human variable DNA is fused to human constant region DNA to form coding sequence(s) for all human, full or partial length heavy and/or light chains.

DNA encoding a humanized antibody comprising an ultralong CDR3 derived from a hybridoma disclosed herein may also be modified, for example, by substituting the coding sequence for human heavy- and light-chain constant domains in place of homologous murine sequences derived from the hybridoma clone (e.g., as in the method of Morrison et al., Proc. Natl. Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies disclosed herein.

Antibody Genes and Proteins

The present disclosure provides antibody genes and proteins including, for example, humanized antibody genes or proteins that comprise an ultralong CDR3 sequence and/or a CDR3 scaffold. The present disclosure additionally provides VH, DH, and JH sequences useful in the preparation of ultralong CDR3 sequences. Such sequences may comprise motifs (e.g., cysteine motifs) as described herein including those as described in the many embodiments disclosed herein. In some embodiments, the antibodies disclosed herein may selectively or specifically bind to an epitope of a target protein. In some embodiments, the antibody may be an antagonist (e.g., blocking) antibody or an agonist antibody.

The variable region of the heavy and light chains are encoded by multiple germline gene segments separated by non-coding regions, or introns, and often are present on different chromosomes. For example, the genes for the human immunoglobulin heavy chain region contains approximately 65 variable (VH) genes, 27 Diversity (DH) genes, and 6 Joining (JH) genes. The human kappa (κ) and lambda (λ) light chains are also each encoded by a similar number of VL and JL gene segments, but do not include any D gene segments. Exemplary VH, DH, JH and VL (Vκ or Vλ) and JL (Jκ or Jλ) germline gene segments are set forth in WO 2010/054007.

During B cell differentiation germline DNA is rearranged whereby one DH and one JH gene segment of the heavy chain locus are recombined, which is followed by the joining of one VH gene segment forming a rearranged VDJ gene that encodes a VH chain. The rearrangement occurs only on a single heavy chain allele by the process of allelic exclusion. Allelic exclusion is regulated by in-frame or "productive" recombination of the VDJ segments, which occurs in only about one-third of VDJ recombinations of the variable heavy chain. When such productive recombination events first occur in a cell, this result in production of a p heavy chain that gets expressed on the surface of a pre-B cell and transmits a signal to shut off further heavy chain recombination, thereby preventing expression of the allelic heavy chain locus. The surface-expressed p heavy chain also acts to activate the kappa (κ) locus for rearrangement. The lambda (λ) locus is only activated for rearrangement if the κ recombination is unproductive on both loci. The light chain rearrangement events are similar to the heavy chain, except that only the VL and JL segments are recombined. Before primary transcription of each, the corresponding constant chain gene is added. Subsequent transcription and RNA splicing leads to mRNA that is translated into an intact light chain or heavy chain.

The variable regions of antibodies confer antigen binding and specificity due to recombination events of individual germline V, D and J segments, whereby the resulting recombined nucleic acid sequences encoding the variable region domains differ among antibodies and confer antigen-specificity to a particular antibody. The variation, however, is limited to three complementarity determining regions (CDR1, CDR2, and CDR3) found within the N-terminal domain of the heavy (H) and (L) chain variable regions. The CDRs are interspersed with regions that are more conserved, termed "framework regions" (FR). The extent of the framework region and CDRs has been precisely defined (see e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Each VH and VL is typically composed of three CDRs and four FRs arranged from the amino terminus to carboxy terminus in the following order: FR1, CDR1, FR2, CDR2, FR3, CDR3 and FR4. Sequence variability among VL and VH domains is generally limited to the CDRs, which are the regions that form the antigen binding site. For example, for the heavy chain, generally, VH genes encode the N-terminal three framework regions, the first two complete CDRs and the first part of the third CDR), the DH gene encodes the central portion of the third CDR, and the JH gene encodes the last part of the third CDR and the fourth framework region. For the light chain, the VL genes encode the first CDR and second CDR. The third CDR (CDRL3) is formed by the joining of the VL and JL gene segments. Hence, CDRs 1 and 2 are exclusively encoded by germline V gene segment sequences. The VH and VL chain CDR3s form the center of the Ag-binding site, with CDRs 1 and 2 form the outside boundaries; the FRs support the scaffold by orienting the H and L CDRs. On average, an antigen binding site typically requires at least four of the CDRs make contact with the antigen's epitope, with CDR3 of both the heavy and light chain being the most variable and contributing the most specificity to antigen binding (see, e.g., Janis Kuby, Immunology, Third Edition, New York, W.H. Freeman and Company, 1998, pp. 115-118). CDRH3, which includes all of the D gene segment, is the most diverse component of the Ab-binding site, and typically plays a critical role in defining the specificity of the Ab. In addition to sequence variation, there is variation in the length of the CDRs between the heavy and light chains.

The constant regions, on the other hand, are encoded by sequences that are more conserved among antibodies. These domains confer functional properties to antibodies, for example, the ability to interact with cells of the immune system and serum proteins in order to cause clearance of infectious agents. Different classes of antibodies, for example IgM, IgD, IgG, IgE and IgA, have different constant regions, allowing them to serve distinct effector functions.

These natural recombination events of V, D, and J, can provide nearly $2 \times 10^7$ different antibodies with both high affinity and specificity. Additional diversity is introduced by nucleotide insertions and deletions in the joining segments and also by somatic hypermutation of V regions. The result is that there are approximately $10^{10}$ antibodies present in an individual with differing antigen specificities.

Antibodies include bovine antibody BLVH12 (e.g., heavy chain variable region set forth in SEQ ID NO: 482, and light chain variable region set forth in SEQ ID NO: 483); and bovine antibody BLV5B8 (e.g., heavy chain variable region set forth in SEQ ID NO: 484, and light chain variable region set forth in SEQ ID NO: 485)

Antibody Fragments

The present disclosure encompasses antibody fragments. In certain circumstances there are advantages of using antibody fragments, rather than whole antibodies. The smaller size of the fragments allows for rapid clearance, and may lead to improved access to solid tumors. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). Antibody fragments can be made by various techniques, including but not limited to proteolytic digestion of an intact antibody as well as production by recombinant host cells (e.g. *E. coli* or phage), as described herein.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments (see, e.g., U.S. Pat. No. 6,204,023). Antibody fragments can be isolated from antibody phage libraries as discussed above. Alternatively, Fab'-SH fragments can be directly recovered from *E. coli* and chemically coupled to form $F(ab')_2$ fragments (see, e.g., Carter et al., Bio/Technology 10: 163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues (see, e.g., in U.S. Pat. No. 5,869,046). Other techniques for the production of antibody fragments will be apparent to the skilled practitioner. In other embodiments, the antibody of choice is a single chain Fv fragment (scFv or single chain antibody (SCA)). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, Supra. The antibody fragment may also be a "linear antibody", for example, as described in U.S. Pat. No. 5,641,870. Such linear antibody fragments may be monospecific or bispecific.

Humanized Antibodies

The present disclosure provides humanized antibodies comprising an ultralong CDR3. Humanized antibodies may include human engineered antibodies (see, e.g., Studnicka et al. (1994) Protein Eng. 7(6) 805-814; and U.S. Pat. No. 5,766,886). Various methods for humanizing non-human antibodies are known in the art. For example, a humanized antibody can have one or more amino acid residues introduced into it from a source which is human or non-human. Humanization may be performed following the method of Studnicka (see, e.g., Studnicka et al. (1994) Protein Eng. 7(6) 805-814; and U.S. Pat. No. 5,766,886), including the preparation of modified antibody variable domains. Humanization may alternatively be performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" or "human engineered" antibodies are chimeric antibodies, including wherein substantially less than an intact human variable domain has been substituted by or incorporated into the corresponding sequence from a non-human species. For example, humanized antibodies may be human antibodies in which some hypervariable region residues and possibly some FR residues are substituted by residues from analogous sites in rodent antibodies. Alternatively, humanized or human engineered antibodies may be non-human (e.g, rodent) antibodies in which some residues are substituted by residues from analogious sites in human antibodies (see, e.g., Studnicka et al. (1994) Protein Eng. 7(6) 805-814; and U.S. Pat. No. 5,766,886).

The choice of human variable domains, both light and heavy, to be used in making the humanized antibodies is important to reduce antigenicity. For example, to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the humanized antibodies comprising an ultralong CDR3 may be deimmunized. Methods of deimmunizing an antibody or protein are well known in the art. The immunogenicity of therapeutic proteins such as antibodies is thought to result from the presence of T-cell epitopes which can bind MHC class II molecules and generate a proliferative and cytokine response in CD4+ helper T-cells. These CD4+ helper cells then collaborate with B-cells to generate an antibody response against the therapeutic protein. Removal of the T-cell epitopes are thought to be key steps in deimmunizing a recombinant protein. T-cell epitopes can be predicted by in silico algorithms that identify residues required for binding MHC. Alternatively, epitopes can be identified directly by utilizing peripheral blood mononuclear cells from panels of human donors and measuring their response against the therapeutic protein when incubated with antigen presenting cells. Such in silico and in vitro systems are well known in the art [Jones T D, Crompton L J, Carr F J, Baker M P. Methods Mol Biol. 2009; 525:405-23, Deimmunization of monoclonal antibodies; and Baker M, and Jones T D. The identification and removal of immunogenicity in therapeutic proteins. Curr. Opin. Drug Discovery Dev. 2007; (2007); 10(2): 219-227]. When peptides are identified that bind MHC II or otherwise stimulate CD4+ cell activation, the residues of the peptide can be mutated one by one and tested for T-cell activation until a mutation is found which disrupts MHC II binding and T-cell activation. Such mutations, when found in an individual peptide, can be encoded directly in the recombinant therapeutic protein. Incubation of the whole protein with antigen presenting cells will not induce a significant CD4+ response, indicating successful deimmunization.

Bispecific Antibodies

Bispecific antibodies are monoclonal, preferably human or humanized, antibodies that have binding specificities for at least two different antigens. For example, one of the binding specificities may be for a first antigen and the other may be for any other antigen. Exemplary bispecific antibodies may bind to two different epitopes of the same protein. Bispecific antibodies may also be used to localize cytotoxic agents to cells which express a particular protein. These antibodies possess a binding arm specific for the particular protein and an arm which binds the cytotoxic agent (e.g., saporin, anti-interferon-α, vinca alkaloid, ricin A chain, methotrexate or radioactive isotope hapten). Bispecific antibodies may be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al., EMBO J., 10: 3655 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are not of particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure may facilitate the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules may can be engineered to maximize the percentage of heterodimers which are recovered from recombinant cell culture. The preferred interface comprises at least a part of the $C_{H3}$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate may be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies may be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced may be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. See, e.g., Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol., 152:5368 (1994).

Antibodies with more than two valencies are contemplated. For example, trispecific antibodies can be prepared. See, e.g., Tutt et al. J. Immunol. 147: 60 (1991). Multivalent Antibodies A multivalent antibody may be internalized (and/or catabolized) faster than a bivalent antibody by a cell expressing an antigen to which the antibodies bind. The antibodies of the present disclosure may be multivalent antibodies (which are other than of the IgM class) with three or more antigen binding sites (e.g., tetravalent antibodies), which may be produced by recombinant expression of nucleic acid encoding the polypeptide chains of the antibody. The multivalent antibody may comprise a dimerization domain and three or more antigen binding sites. A preferred dimerization domain may comprise (or consist of) an Fc region or a hinge region. In this scenario, the antibody will comprise an Fc region and three or more antigen binding sites amino-terminal to the Fc region. A preferred multivalent antibody may comprise (or consist of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-($X_1$)n-VD2-($X_2$)n-Fc, wherein VD1 is a first variable domain, VD2 is a second variable domain, Fc is one polypeptide chain of an Fc region, $X_1$ and $X_2$ represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. A multivalent antibody may preferably further comprises at least two (and preferably four) light chain variable domain polypeptides. A multivalent antibody may, for instance, comprise from about two to about eight light chain variable domain polypeptides. The light chain variable domain polypeptides may comprise a light chain variable domain and, optionally, further comprise a CL domain.

Antibody Variants

In some embodiments, amino acid sequence modification(s) of the humanized antibodies comprising an ultralong CDR3 as described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody have been described (see, e.g., US 2003/0157108, US 2004/0093621. Antibodies with a bisecting N-acetylglucosamine (GlcNAc) in the carbohydrate attached to an Fc region of the antibody have been described (see, e.g., WO 2003/011878, and U.S. Pat. No. 6,602,684). Antibodies with at least one galactose residue in the oligosaccharide attached to an Fc region of the antibody WO 1997/30087; see, also, WO 1998/58964 and WO 1999/22764 concerning antibodies with altered carbohydrate attached to the Fc region thereof). Antigen-binding molecules with modified glycosylation have been described (see, e.g., WO 99/54342, U.S. Pat. Nos. 6,602,684 and 7,517,670, and US 2004/0072290; see also, e.g., U.S. Pat. Nos. 7,214,775 and 7,682,610).

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614 (now U.S. Pat. No. 6,946,292) US 2002/0164328 (now U.S. Pat. No. 7,064,191); US 2004/0093621; US 2004/0132140; US 2004/0110704; US 2004/0110282 (now U.S. Pat. No. 7,749, 753); US 2004/0109865; WO 2003/085119; WO 2003/ 084570; WO 2005/035586; WO 2005/035778; WO2005/ 053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: Cys, Ser, Thr, Asn, Gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides disclosed herein, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods disclosed herein may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (e.g., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624,821; and WO94/29351 concerning other examples of Fc region variants. WO00/42072 and WO 2004/056312 describe antibody variants with improved or diminished binding to FcRs. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). These antibodies comprise an Fc reg on with one or more substitutions therein which improve binding of the Fc region to FcRn. Polypeptide variants with altered Fc region amino acid sequences and increased or decreased C1q binding capability are described in U.S. Pat. No. 6,194,551, WO99/51642. See, also, Idusogie et al. J. Immunol. 164:4178-4184 (2000).

In certain embodiments, the present disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRII only, whereas monocytes express FcγRI, FcγRII and FcγRII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see, Bruggemann, M. et al., Exp. Med. 166:1351-1361 (1987)). Alternatively, non-radioactive assays methods may be employed (see, for example, ACTI™ non-radioactive cytotoxicity assay for flow cytometry (CellTecl1r1ology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1qbinding assays may also be carried out to confirm that the antibody is unable to bind Clq and hence lacks CDC activity. See, e.g., Clq and C3c binding ELISA in WO 2006/029879 and WO 2005/100402. To assess complement activation, a CDC assay may be performed (see, for example, Gazzano-Santoro et al., Immunol. Methods 202:163 (1996); Cragg, M. S. et al., Blood 101: 1045-1052 (2003); and Cragg, M. S, and M. J. Glennie, Blood 103:27382743 (2004)). FcRn binding and in vivo clearance/half life determinations can also be performed using methods known in the art (see, e.g., Petkova, S. B. et al., Int'l Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) Clq binding and/or Complement Dependent Cytotoxicity (CDC), e.g., as described in U.S. Pat. No. 6,194,551, WO 99/51642, and Idusogie et al. Immunol. 164: 41784184 (2000).

Antibodies with increased half lives and improved binding to the neonatal Fc receptor (FcRn), which is responsible for the transfer of maternal IgGs to the fetus (Guyer et al., Immunol. 117:587 (1976) and Kim et al., Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

Antibody Derivatives

The humanized antibodies comprising an ultralong CDR3 as disclosed herein may be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells and Recombinant Methods

For recombinant production of an antibody or fragment thereof as disclosed herein, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). In an exemplary embodiment, nucleic acid encoding a humanized antibody comprising an ultralong CDR3, a variable region comprising an ultralong CDR3, or an ultralong CDR3, is isolated and inserted into a replicable vector for further cloning (amplification of the DNA) or for expression. Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a partially human ultralong CDR3 antibody chain under the direction of the polyhedrin promoter or other strong baculovirus promoters.

a. Generating Antibodies Using Prokaryotic or Eukaryotic Host Cells:

i. Vector Construction

Polynucleotide sequences encoding polypeptide components of the antibodies disclosed herein can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence. Additionally, V regions comprising an ultralong CDR3 may optionally be fused to a C-region to produce an antibody comprising constant regions.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies have been described (see, e.g., U.S. Pat. No. 5,648,237).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vectors disclosed herein may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector disclosed herein. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include: an ara B promoter, a PhoA promoter, β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (e.g., Siebenlist et al. (1980) Cell 20: 269) using linkers or adaptors to supply any required restriction sites.

Suitable bacterial promoters are well known in the art and fully described in scientific literature such as Sambrook and Russell, supra, and Ausubel et al, supra. Bacterial expression systems for expressing antibody chains of the recombinant catalytic polypeptide are available in, e.g., E. coli, Bacillus sp., and Salmonella (Palva et al., Gene, 22:229-235 (1983); Mosbach et al., Nature, 302:543-545 (1983)).

In one aspect disclosed herein, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence should be one that is recognized and processed (e.g., cleaved by a signal peptidase) by the host cell. For prokaryotic host cells that do not recognize and process the signal sequences native to the heterologous polypeptides, the signal sequence is substituted by a prokaryotic signal sequence selected, for example PelB, OmpA, alkaline phosphatase, penicillinase, lpp, or heat-stable enterotoxin II (STII) leaders, LamB, PhoE, and MBP. In one embodiment disclosed herein, the signal sequences used in both cistrons of the expression system are STII signal sequences or variants thereof.

In another aspect, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits (see e.g., Proba and Pluckthun Gene, 159:203 (1995)).

Suitable host cells for cloning or expression of antibody-encoding vectors include prokaryotic or eukaryotic cells described herein. In one embodiment, the host cell is eukaryotic, e.g. a Chinese Hamster Ovary (CHO) cell, Human Embryonic Kidney (HEK) cell or lymphoid cell (e.g., YO, NSO, Sp20 cell). For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22: 1409-1414 (2004), and Li et al., Nat. Biotech. 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Plant cell cultures can also be utilized as hosts. See, e.g. U.S. Pat. Nos. 5,959,177, 6,040,498, 6,420,548, 7,125, 978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., Gen VII'0I. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (V ERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., Annals NI'. Acad. Sci. 383:44-68 (1982); MRC 5 cells; and FS4 cells. Other useful mammalian host cell lines include Chinese hamster ovary (CHO) cells, including DHFR' CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

ii. Antibody Production

For recombinant production of a partially human ultralong CDR3 antibody, nucleic acid encoding a humanized antibody comprising an ultralong CDR3 is inserted into one or more expression vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Host cells are transformed with such expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides disclosed herein are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli,* the pH is preferably from about 6.8 to about 7.4, and more preferably about 7.0.

If an inducible promoter is used in the expression vector disclosed herein, protein expression is induced under conditions suitable for the activation of the promoter. For example, an ara B or phoA promoter may be used for controlling transcription of the polypeptides. A variety of inducers may be used, according to the vector construct employed, as is known in the art.

The expressed polypeptides of the present disclosure are secreted into and recovered from the periplasm of the host cells or transported into the culture media. Protein recovery from the periplasm typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins that are transported into the culture media may be isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Antibody production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides disclosed herein, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells. (see e.g., Chen et al. (1999) J Bio Chem 274:19601-19605; U.S. Pat. Nos. 6,083,715; 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210).

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available (see, e.g., Joly et al. (1998), supra; U.S. Pat. Nos. 5,264,365; 5,508,192; Hara et al., Microbial Drug Resistance, 2:63-72 (1996)).

E. coli strains deficient for proteolytic enzymes and transformed with plasmids overexpressing one or more chaperone proteins may be used as host cells in the expression systems disclosed herein.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products disclosed herein. Protein A is a 41 kD cell wall protein from Staphylococcus aureas which binds with a high affinity to the Fc region of antibodies (see, e.g., Lindmark et al (1983) J. Immunol. Meth. 62:1-13). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (e.g., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this disclosure by higher eukaryotes is often increased by inserting an enhancer sequence into the vector. Many enhancer sequences are now known from mammalian genes (globin, elastase, albumin, α-fetoprotein, and insulin). An enhancer from a eukaryotic cell virus may also be used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least both genes into the host cell capable of expressing germline antibody polypeptide.

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Reissue 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Soluble forms of antibody or fragment present either in the cytoplasm or released from the periplasmic space may be further purified using methods known in the art, for example Fab fragments are released from the bacterial periplasmic space by osmotic shock techniques.

If inclusion bodies comprising an antibody or fragment have formed, they can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The soluble antibody or fragment can then be analyzed using gel electrophoresis, immunoprecipitation or the like. If it is desired to isolate a solubilized antibody or antigen binding fragment isolation may be accomplished using standard methods such as those set forth below and in Marston et al. (Meth. Enz., 182:264-275 (1990)).

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

In some cases, an antibody or fragment may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/ dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Immunoconjugates

The disclosure also provides immunoconjugates (interchangeably termed "antibody-drug conjugates" or "ADC"), comprising any of the humanized antibodies comprising an ultralong CDR3 as described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate).

The use of antibody-drug conjugates for the local delivery of cytotoxic or cytostatic agents. For example, drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) Supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10: 1025-1028; Mandler et al (2002) Bioconjugate Chem. 13:786-791), maytansinoids (EP 1391213; Liu et al., (1996) Proc. Natl.

Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin may be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

a. Maytansine and Maytansinoids

In some embodiments, the immunoconjugate comprises a humanized antibody (full length or fragments) comprising an ultralong CDR3 as disclosed herein conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and EP 0 425 235. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. Nos. 5,208,020, 6,441, 163, or EP Patent 0 425 235, Chari et al., Cancer Research 52:127-131 (1992). Antibody-maytansinoid conjugates comprising the linker component SMCC may be prepared. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

b. Auristatins and Dolastatins

In some embodiments, the immunoconjugate comprises an antibody disclosed herein conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, (see, e.g., U.S. Pat. No. 7,498,298).

Typically, peptide-based drug moieties can be prepared by forming a peptide bond between two or more amino acids and/or peptide fragments. Such peptide bonds can be prepared, for example, according to the liquid phase synthesis method (see, e.g., E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al. (1998) Anti-Cancer Drug Design 13:243-277; Pettit, G. R., et al. Synthesis, 1996, 719-725; and Pettit et al. (1996) J. Chem. Soc. Perkin Trans. 1 5:859-863. See also Doronina (2003) Nat Biotechnol 21(7):778-784; U.S. Pat. No. 7,498,289, (disclosing, linkers and methods of preparing monomethylvaline compounds such as MMAE and MMAF conjugated to linkers).

c. Calicheamicin

In other embodiments, the immunoconjugate comprises an antibody disclosed herein conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Structural analogues of calicheamicin which may be used include, but are not limited to, $\gamma_1'$, $\alpha_2'$, $\alpha_3'$, N-acetyl-$\gamma_1'$, PSAG and $\theta_1'$ (see, e.g., Hinman et al., Cancer Research 53:3336-3342 (1993), Lode et al., Cancer Research 58:2925-2928 (1998) and the aforementioned U.S. patents). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

d. Other Cytotoxic Agents

Other antitumor agents that can be conjugated to the antibodies disclosed herein include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present disclosure further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{25}$, $Y^{90}$, $Re^{186}$, $Re^{88}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radiolabels or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds disclosed herein expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

e. Preparation of Antibody Drug Conjugates

In the antibody drug conjugates (ADC) disclosed herein, an antibody (Ab) is conjugated to one or more drug moieties (D), e.g., about 1 to about 20 drug moieties per antibody, through a linker (L). An ADC of Formula I [Ab-(L-D)$_p$] may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are disclosed herein (see, e.g., U.S. Pat. No. 7,498,298).

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, e.g., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates disclosed herein may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Engineered Hybridomas

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed. Hybridomas. Including bovine hybridomas, may be a source of bovine antibody gene sequences, including ultralong CDR3 sequences.

Transgenic Mammals

A nucleic acid sequence encoding a germline antibody polypeptide of the present disclosure can be introduced into a non-human mammal to generate a transgenic animal that expresses the germline antibody polypeptide. Unlike the transgenic animal models more commonly seen, the transgene expressed by the transgenic mammals of the present disclosure need not replace at least one allele of the endogenous coding sequence responsible for the variable regions of antibody chains following somatic recombination. Due to allelic exclusion, the presence of an exogenous, post-somatic rearrangement version of the germline V region DNA will inhibit the endogenous alleles of pre-somatic rearrangement V minigenes from undergoing somatic rearrangement and contributing to the makeup of antibody chains this mammal may produce. Thus, when exposed to a particular antigen, the mammal will generate heterologous antibodies comprising one endogenously rearranged antibody chain, and one transgenic gene which was rearranged a priori. Such heterologous antibodies are invaluable in research and in treating certain conditions in live subjects. On the other hand, a method that directs the integration of the transgene to the locus of an endogenous allele will fully serve the purpose of practicing the present disclosure as well.

The general methods of generating transgenic animals have been well established and frequently practiced. For reviews and protocols for generating transgenic animals and related methods for genetic manipulations, see, e.g., Mansour et al., Nature 336:348-352 (1988); Capecchi et al., Trends Genet. 5:70-76 (1989); Capecchi, Science 244:1288-1292 (1989); Capecchi et al., Current Communications in Molecular Biology, pp 45-52, Capecchi, M. R. (ed.), Cold Spring Harbor Press, Cold Spring Harbor, N.Y. (1989); Frohman et al., Cell 56: 145-147 (1989); Brinster et al., Proc. Natl. Acad. Sci. USA 82:4438-4442 (1985); Evans et. al., Nature 292:154-156 (1981); Bradley et al., Nature 309:255-258 (1984); Gossler et al., Proc. Natl. Acad. Sci. USA 83:9065-9069 (1986); Robertson et al., Nature 322: 445-448 (1986); Jaenisch Science 240:1468-1474 (1988); and Siedel, G. E., Jr., "Critical review of embryo transfer procedures with cattle" in Fertilization and Embryonic Development in Vitro, page 323, L. Mastroianni, Jr. and J. D. Biggers, ed., Plenum Press, New York, N.Y. (1981).

An exemplary transgenic animal of the present disclosure is mouse, whereas a number of other transgenic animals can also be produced using the same general method. These animals include, but are not limited to: rabbits, sheep, cattle, and pigs (Jaenisch Science 240:1468-1474 (1988); Hammer et al., J. Animal. Sci. 63:269 (1986); Hammer et al. Nature 315:680 (1985); Wagner et al., Theriogenology 21:29 (1984)).

Pharmaceutical Compositions

Humanized antibodies comprising an ultralong CDR3, antibody fragments, nucleic acids, or vectors disclosed herein can be formulated in compositions, especially pharmaceutical compositions. Such compositions with humanized antibodies comprising an ultralong CDR3 comprise a therapeutically or prophylactically effective amount of a humanized antibodies comprising an ultralong CDR3, antibody fragment, nucleic acid, or vector disclosed herein in admixture with a suitable carrier, e.g., a pharmaceutically acceptable agent. Typically, humanized antibodies comprising an ultralong CDR3, antibody fragments, nucleic acids, or vectors disclosed herein are sufficiently purified for administration before formulation in a pharmaceutical composition.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of humanized antibodies comprising an ultralong CDR3, antibody fragments, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., humanized antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(−)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of a humanized antibody comprising an ultralong CDR3 to hyaluronic acid polymer.

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which a humanized antibody comprising an ultralong CDR3, antibody fragment, nucleic acid, or vector disclosed herein has been absorbed or encapsulated. Where an implantation device is used, the device may be implanted into any suitable tissue or organ, and delivery of a humanized antibody comprising an ultralong CDR3 antibody fragment, nucleic acid, or vector disclosed herein can be directly through the device via bolus, or via continuous administration, or via catheter using continuous infusion.

A pharmaceutical composition comprising a humanized antibody comprising an ultralong CDR3, antibody fragment, nucleic acid, or vector disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations containing humanized antibodies comprising an ultralong CDR3, antibody fragments, nucleic acids, or vectors disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of a humanized antibody comprising an ultralong CDR3, antibody fragment, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

In some embodiments, humanized antibodies comprising an ultralong CDR3 or fragments thereof are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG1, IgG2, IgG3, or IgG4) that is responsible for increasing the in vivo serum half-life of the IgG molecule.

A salvage receptor binding epitope may include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also WO 97/34631 and WO 96/32478 which describe Fc variants and their interaction with the salvage receptor.

Mutation of residues within Fc receptor binding sites may result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g., replacing an IgG1 residue with a corresponding IgG2 residue at that position). For example, it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g., a composition comprising a humanized antibody comprising an ultralong CDR3 alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises a humanized antibody comprising an ultralong CDR3 as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the humanized antibody comprising an ultralong CDR3 composition.

The following are examples of the methods and compositions of the disclosure. It is understood that various other embodiments may be practiced, given the general description provided above.

EXAMPLES

Example 1. Generation of a Humanized Antibody with an Ultralong CDR3 Sequence At least 7 antibody heavy chain variable region sequences are publicly available that comprise an ultralong CDR3 of bovine origin. These sequences are shown in the alignment in FIG. 1. As shown in FIG. 1, the ultralong CDR3s present within these variable region sequences range in length from 56 to 61 amino acids. Strikingly, the sequence alignment indicates that the amino acid residues positioned in the N-terminal ends of the CDR3s are particularly conserved. Following the first cysteine residue in each of these variable region sequences, an amino acid sequence pattern of "TTVHQ" (SEQ ID NO: 153) and variants thereof are found. This is unusual in that most heavy chain variable regions of most species end with the amino acid sequence "CAK" or "CAR". This unusual sequence motif (e.g., "TTVHQ" (SEQ ID NO: 153)) may be characteristic of the structure of an ultralong CDR3.

Additionally, the *Bos taurus* genome was searched and an undescribed heavy chain variable region DNA sequence in the antibody locus was found that encodes a "CTTVHQ" motif (e.g., SEQ ID NO: 1). This variable region sequence is designated herein as VH-UL (SEQ ID NO: 29). This sequence motif, discovered for the first time in searching the cow genome, is important in antibodies that comprise an ultralong CDR3.

To produce a humanized antibody comprising an ultralong CDR3, human variable regions for acceptor human frameworks were identified that are homologous to the bovine-derived VH-UL sequence (SEQ ID NO: 29). Several members of the human VH4 family were identified as being homologous to the VH-UL sequence, however none of VH4 family members contained a "CTTVHQ" motif (SEQ ID NO: 185). The sequences VH4-34*02 (SEQ ID NO: 33), VH4-39 (SEQ ID NO: 31), and VH4-59*03 (SEQ ID NO: 32) are the most homologous to the VH-UL sequence (see, e.g., FIG. 4B).

In a first exemplary method to produce a humanized antibody comprising an ultralong CDR3, a VH4-39 human acceptor framework (SEQ ID NO: 31) is used. The nucleotides encoding the last two amino acid residues of VH4-39 (e.g., "AR") are removed from the VH4-39 human acceptor framework, and nucleotides encoding a "TTVHQ" motif (SEQ ID NO: 153) are added to the 3' end of the DNA sequence encoding the VH4-39 human acceptor framework after the nucleotides that encode the second cysteine residue of the VH4-39 human acceptor framework (e.g., after the nucleotides that code for amino acid position 97 of SEQ ID NO: 31). Next, the DNA encoding a portion of the ultralong CDR3 from BLV1H12 (e.g., the portion of the ultralong CDR3 beginning at the first glutamic acid residue (E) in BLV1H12; ETKKYQSCPDGYRERSDCSNRPACGTSDC-CRVSVFGNCLTTLPVSYSYTYNYEWHVD) is fused to the 3' end of the polynucleotide encoding the "TTVHQ" motif (SEQ ID NO: 153). Finally, DNA encoding a partial human JH4 region, beginning with the conserved tryptophan residue common to J region sequences, is added to the 3' end of the portion of the ultralong CDR3 sequence derived from BLV1H12. The following antibody gene encoding a partially human antibody comprising an ultralong CDR3 is derived:

```
                                        (SEQ ID NO: 377)
cagctgcagctgcaggagtcgggcccaggactggtgaagccttcggaga ccctgtccctcacctgcactgtctctggtggctccatcagcagtagtag ttactactggggctggatccgccagcccccagggaaggggctggagtgg attgggagtatctattatagtgggagcacctactacaacccgtccctca agagtcgagtcaccatatccgtagacacgtccaagaaccagttctccct gaagctgagctctgtgaccgccgcagacacggctgtgtattactgtact actgtgcaccagGAAACAAAAAAATACCAAAGTTGTCCTGATGGGTATA

GAGAACGTTCGGATTGTAGTAACAGACCTGCTTGTGGTACTAGTGATTG

TTGTCGTGTTAGTGTTTTTGGTAATTGTCTTACTACTCTTCCTGTGAGT

TATAGTTATACTTACAATTACGAATGGCACGTCGATGTCTGGGGCCAGG

GAACCCTGGTCACCGTCTCCTCAG
```

Regular Font—derived from human VH4-39
Underlined—derived from VH-UL
BOLD BLACK—ultralong CDR3, derived from cow BLVH12
ITALICS—derived from human JH4

The amino acid sequence as translated from this partially human variable region gene is:

```
cagctgcagctgcaggagtcgggcccaggactggtgaagccttcggagaccctgtccctc
 Q   L   Q   L   Q   E   S   G   P   G   L   V   K   P   S   E   T   L   S   L acctgcactgtctctggtggctccatcagcagtagtagttactactggggctggatccgc
 T   C   T   V   S   G   G   S   I   S   S   S   S   Y   Y   W   G   W   I   R
```

```
                        -continued
cagccccagggaaggggctggagtggattgggagtatctattatagtgggagcacctac
 Q  P  P  G  K  G  L  E  W  I  G  S  I  Y  Y  S  G  S  T  Y tacaacccgtccctcaagagtcgagtcaccatatccgtagacacgtccaagaaccagttc
 Y  N  P  S  L  K  S  R  V  T  I  S  V  D  T  S  K  N  Q  F tccctgaagctgagctctgtgaccgccgcagacacggctgtgtattactgtactactgtg
 S  L  K  L  S  S  V  T  A  A  D  T  A  V  Y  Y  C  T  T  V caccaggaaacaaaaaaataccaaagttgtcctgatgggtatagagaacgttcggattgt
 H  Q  E  T  K  K  Y  Q  S  C  P  D  G  Y  R  E  R  S  D  C agtaacagacctgcttgtggtactagtgattgttgtcgtgttagtgttttggtaattgt
 S  N  R  P  A  C  G  T  S  D  C  C  R  V  S  V  F  G  N  C cttactactcttcctgtgagttatagttatacttacaattacgaatggcacgtcgatgtc
 L  T  T  L  P  V  S  Y  S  Y  T  Y  N  Y  E  W  H  V  D  V tggggccagggaaccctggtcaccgtctcctcag  (SEQ ID NO: 377)
 W  G  Q  G  T  L  V  T  V  S  S    (SEQ ID NO: 378)
```

In an embodiment, this humanized VH sequence is recombinantly fused in-frame with a human heavy chain constant region and paired with a light chain for recombinant antibody production.

In another exemplary method to produce a humanized antibody comprising an ultralong CDR3, an ultralong CDR3 derived from BLV5B8 (SEQ ID NO: 7) is incorporated into the VH4-34 human acceptor framework (e.g., 4-34*02 (SEQ ID NO: 33); or 4-34*09 (SEQ ID NO: 34), along with a portion of the human JH2 region to produce a humanized antibody comprising an ultralong CDR3. Next, the nucleotides encoding the last two amino acid residues of the VH4-34 human acceptor framework (e.g., "AR") are removed from the VH4-34 human acceptor framework, and nucleotides encoding a "TTVHQ" motif are added to the 3' end of the VH4-34 human acceptor framework after the nucleotides that code for the second conserved cysteine residue in the VH4-34 human acceptor framework (e.g., after the nucleotides that code for amino acid position 95 of SEQ ID NOS: 33 or 34). Finally, DNA encoding a partial human JH2 region, beginning with the conserved tryptophan residue common to J region sequences, is added to the 3' end of the portion of the ultralong CDR3 sequence derived from BLV5B8. Thus, the following sequence encoding a humanized antibody variable region comprising an ultralong CDR3 is produced:

```
                                                (SEQ ID NO: 379)
caggtgcagctacaacagtggggcgcaggactgttgaagccttcggagac cctgtccctcacctgcgctgtctatggtgggtccttcagtggttactact ggagctggatccgccagccccagggaaggggctggagtggattggggaa atcaatcatagtggaagcaccaactacaacccgtccctcaagagtcgagt caccatatcagtagacacgtccaagaaccagttctccctgaagctgagct ctgtgaccgccgcggacacggctgtgtattactgtActactgtgcaccag

GAAACCAGAAAAACCTGTTCTGATGGTTATATGGCTGTAGATAGTTGTGG

TCGTGGTCAGAGTGATGGTTGTGTCAATGATTGCAATTGTTGTTATTATG

GTTGGCGGAACTGTCGCAGGCAGCCTGCAATTCAAAGTTACGAATTTCAC

GTCGATGCCTGGGGCCGTGGCACCCTGGTCACTGTCTCCTCAG
```

Regular Font—derived from human VH4-39
Underlined—derived from VH-UL
BOLD BLACK—ultralong CDR3, derived from cow BLVH12
ITALICS—derived from human JH2

The amino acid sequence as translated from this partially human variable region gene is:

```
caggtgcagctacaacagtggggcgcaggactgttgaagccttcggagaccctgtccctc
 Q  V  Q  L  Q  Q  W  G  A  G  L  L  K  P  S  E  T  L  S  L acctgcgctgtctatggtgggtccttcagtggttactactggagctggatccgccagccc
 T  C  A  V  Y  G  G  S  F  S  G  Y  Y  W  S  W  I  R  Q  P ccagggaaggggctggagtggattggggaaatcaatcatagtggaagcaccaactacaac
 P  G  K  G  L  E  W  I  G  E  I  N  H  S  G  S  T  N  Y  N ccgtccctcaagagtcgagtcaccatatcagtagacacgtccaagaaccagttctccctg
 P  S  L  K  S  R  V  T  I  S  V  D  T  S  K  N  Q  F  S  L aagctgagctctgtgaccgccgcggacacggctgtgtattactgtactactgtgcaccag
 K  L  S  S  V  T  A  A  D  T  A  V  Y  Y  C  T  T  V  H  Q gaaaccagaaaaacctgttctgatggttatatggctgtagatagttgtggtcgtggtcag
 E  T  R  K  T  C  S  D  G  Y  M  A  V  D  S  C  G  R  G  Q agtgatggttgtgtcaatgattgcaattgttgttattatggttggcggaactgtcgcagg
 S  D  G  C  V  N  D  C  N  C  C  Y  Y  G  W  R  N  C  R  R cagcctgcaattcaaagttacgaatttcacgtcgatgcctggggccgtggcaccctggtc
 Q  P  A  I  Q  S  Y  E  F  H  V  D  A  W  G  R  G  T  L  V Actgtctcctcag (SEQ ID NO: 379)
 T  V  S  S    (SEQ ID NO: 380)
```

In an embodiment, this humanized VH sequence is then recombinantly fused in-frame with a human heavy chain constant region and paired with a light chain for recombinant antibody production.

The library of amplified antibody variable regions were then subjected to deep sequencing. Briefly, bar-coded primers (Table 1) for each of the three cows (MID1, MID10, and MID11) were used to amplify $V_H$ from bovine spleen cDNA.

TABLE 1

Bar-coded primers for deep sequencing

| Primer # | Isotype | Primers |
|---|---|---|
| MID1 FW | IgG | CCTATCCCCTGTGTGCCTTGGCAGTCTCAGACGAGTGCGTTTGAGCGACA AGGCTGTAGGCTG (SEQ ID NO: 381) |
| MID1 RV | IgG | CCATCTCATCCCTGCGTGTCTCCGACTCAGACGAGTGCGTCTTTCGGGGC TGTGGTGGAGGC (SEQ ID NO: 382) |
| MID10 FW | IgM | CCTATCCCCTGTGTGCCTTGGCAGTCTCAGTCTCTATGCGTTGAGCGACA AGGCTGTAGGCTG (SEQ ID NO: 383) |
| MID10 RV | IgM | CCATCTCATCCCTGCGTGTCTCCGACTCAGTCTCTATGCGAGTGAAGACT CTCGGGTGTGATTCAC (SEQ ID NO: 384) |
| MID11 FW | IgM | CCTATCCCCTGTGTGCCTTGGCAGTCTCAGTGATACGTCTTTGAGCGACA AGGCTGTAGGCTG (SEQ ID NO: 385) |
| MID11 RV | IgM | CCATCTCATCCCTGCGTGTCTCCGACTCAGTGATACGTCTAGTGAAGACTC TCGGGTGTGATTCAC (SEQ ID NO: 386) |

Thus, any heavy chain variable region can be paired with a light chain variable region to produce a recombinant antibody. Bovine antibodies containing ultralong VH CDR3s typically pair with a restricted set of lambda light chains. Several human VL sequences can be used to pair with the sequences above, including VL1-47, VL1-40, VL1-51, VL2-18, which are homologous to the lambda region derived from Bos taurus.

Example 2: Generation of Libraries of Polynucleotides Encoding Antibodies Comprising an Ultralong CDR3

Libraries of polynucleotides encoding antibodies that comprise an ultralong CDR3 may be constructed by any method known in the art. Such polynucleotide libraries may be present within a plurality of vectors (e.g., a library of vectors) including, for example, vectors present within a plurality of host cells (e.g., a library of host cells). The libraries may present in any known format including, in a spatially addressed format (see, e.g., WO 11/056997; and Mao et al. (2010) Nat Biotech 28:1195-1202).

In an exemplary method, bovine spleen and lymph nodes were obtained from Animal Technologies (Tyler, Tex.), or from Texas A&M University. Total RNA was isolated from bovine tissues from three different cows (MID1, MID10, and MID 11) using TRIzol reagent (Invitrogen, Carlsbad, Calif., USA) followed by on column digestion of DNA using the RNeasy Mini Kit (Qiagen, Valencia, Calif., USA). Alternatively, cDNA may be obtained from the lymph nodes of a bovine immunized with an antigen (e.g., BVDV). Next, RNA quantity and quality were assessed with Nanodrop (Thermal Scientific), Qubit RNA and Agilent 2100 Bioanalyzer (Agilent, Santa Clara, Calif., USA), following the manufacturer's protocols. Total RNA was used as a template for cDNA synthesis catalyzed by Superscript II (Invitrogen).

Next, the amplicons of $V_H$ were purified from 2% agarose gels and deep sequenced according to Roche 454 GS FLX instructions. Multiple alignments were performed with the MUSCLE algorithm (Edgar (2004) Nucleic Acids Research 32:1792-1797). MUSCLE was executed to generate multiple long CDR H3 nucleotide alignments with relatively high gap open (−20.0) and gap extend (−10.0) penalties due to the large amount of heterogeneity observed in the sequences. Local alignment was executed using the Smith-Waterman algorithm with the following settings, match score=2.0, mismatch penalty=−1.0, gap opening penalty=−2.0, and gap extension penalty=−0.5. CDR H3s were defined by the third residue following the conserved cysteine in framework 3 to the residue immediately preceding the conserved tryptophan in framework 4. $V_H$BUL was identified by BLAST searching the bovine genome (assembly Btau_4.6.1) with multiple ultralong $V_H$ sequences identified by deep sequencing. The deep sequencing identified a total of 11,728 ultralong CDR3 sequences with having a length between 44 and 69 amino acid residues. The results of the deep sequencing are summarized in Table 2 below.

TABLE 2

Summary of deep sequencing results from bovine spleen

| Source (Bar code) | Cow#1 (MID1) | Cow#1 (MID10) | Cow#2 (MID11) |
|---|---|---|---|
| Ig Class | IgG | IgM | IgM |
| CDR H3 length range | 44-66 | 44-68 | 44-69 |
| Number of unique cysteine patterns | 655 | 449 | 847 |
| Total number of unique long CDR H3 sequences | 5633 | 1639 | 4456 |

The results of the deep sequencing also revealed that ultralong CDR3 comprise a cysteine motif (e.g., a pattern of cysteine residues) that comprises between 3 and 12 cysteine residues. Representative examples of cysteine patterns are shown for the deep sequencing run for three different cows (MID1, MID10, and MID11) as well as their abundance in the run (Tables 3-5). The cysteines in the ultralong CDR3 regions are symbolized as "C". The amino acids between two cysteines are symbolized as "$X_n$". Exemplary sequences comprising cysteine motifs identified from the deep sequencing are presented in FIGS. 2A-C.

TABLE 3

Cysteine patterns identified in ultralong CDR3s from MID1

| Cysteine pattern (MID1) | SEQ ID NO | Abundance (%) |
|---|---|---|
| $CX_{10}CX_5CX_5CXCX_7C$ | 41 | 10.44% |
| $CX_{10}CX_6CX_5CXCX_{15}C$ | 42 | 8.11% |
| $CX_{11}CXCX_5C$ | 43 | 5.22% |
| $CX_{11}CX_5CX_5CXCX_7C$ | 44 | 2.56% |
| $CX_{10}CX_6CX_5CXCX_{13}C$ | 45 | 1.47% |
| $CX_{10}CX_5CXCX_4CX_8C$ | 46 | 1.19% |
| $CX_{10}CX_6CX_6CXCX_7C$ | 47 | 1.08% |
| $CX_{10}CX_4CX_7CXCX_8C$ | 48 | 1.05% |
| $CX_{10}CX_4CX_7CXCX_7C$ | 49 | 0.91% |
| $CX_{13}CX_8CX_8C$ | 50 | 0.91% |
| $CX_{10}CX_6CX_5CXCX_7C$ | 51 | 0.59% |
| $CX_{10}CX_5CX_5C$ | 52 | 0.57% |
| $CX_{10}CX_5CX_6CXCX_7C$ | 53 | 0.50% |
| $CX_{10}CX_6CX_5CX_7CX_9C$ | 54 | 0.43% |
| $CX_9CX_7CX_5CXCX_7C$ | 55 | 0.41% |
| $CX_{10}CX_6CX_5CXCX_9C$ | 56 | 0.36% |
| $CX_{10}CXCX_4CX_5CX_{11}C$ | 57 | 0.32% |
| $CX_7CX_3CX_6CX_5CXCX_5CX_{10}C$ | 58 | 0.32% |
| $CX_{10}CXCX_4CX_5CXCX_2CX_3C$ | 59 | 0.30% |
| $CX_{16}CX_5CXC$ | 60 | 0.23% |

TABLE 4

Cysteine patterns identified in ultralong CDR3s from MID10

| Cysteine pattern (MID10) | SEQ ID NO | Abundance (%) |
|---|---|---|
| $CX_{10}CXCX_4CX_5CXCX_2CX_3C$ | 59 | 2.87% |
| $CX_{10}CX_5CX_5C$ | 52 | 0.73% |
| $CX_{10}CXCX_4CX_5CX_{11}C$ | 57 | 0.67% |
| $CX_6CX_4CXCX_4CX_5C$ | 61 | 0.61% |
| $CX_{11}CX_4CX_5CX_6CX_3C$ | 62 | 0.55% |
| $CX_8CX_2CX_6CX_5C$ | 63 | 0.43% |
| $CX_{10}CX_5CX_5CXCX_{10}C$ | 64 | 0.37% |
| $CX_{10}CXCX_6CX_4CXC$ | 65 | 0.31% |

TABLE 4-continued

Cysteine patterns identified in ultralong CDR3s from MID10

| Cysteine pattern (MID10) | SEQ ID NO | Abundance (%) |
|---|---|---|
| $CX_{10}CX_5CX_5CXCX_2C$ | 66 | 0.31% |
| $CX_{14}CX_2CX_3CXCXC$ | 67 | 0.31% |
| $CX_{15}CX_5CXC$ | 68 | 0.31% |
| $CX_4CX_6CX_9CX_2CX_{11}C$ | 69 | 0.31% |
| $CX_6CX_4CX_5CX_5CX_{12}C$ | 70 | 0.31% |
| $CX_7CX_3CXCXCX_4CX_5CX_9C$ | 71 | 0.31% |
| $CX_{10}CX_6CX_5C$ | 72 | 0.24% |
| $CX_7CX_3CX_5CX_5CX_9C$ | 73 | 0.24% |
| $CX_7CX_5CXCX_2C$ | 74 | 0.24% |
| $CX_{10}CXCX_6C$ | 75 | 0.18% |
| $CX_{10}CX_3CX_3CX_5CX_7CXCX_6C$ | 76 | 0.18% |
| $CX_{10}CX_4CX_5CX_{12}CX_2C$ | 77 | 0.18% |

TABLE 5

Cysteine patterns identified in ultralong CDR3s from MID11

| Cysteine pattern (MID11) | SEQ ID NO | Abundance (%) |
|---|---|---|
| $CX_{12}CX_4CX_5CXCXCX_9CX_3C$ | 78 | 1.19% |
| $CX_{12}CX_4CX_5CX_{12}CX_2C$ | 79 | 0.96% |
| $CX_{10}CX_6CX_5CXCX_{11}C$ | 80 | 0.92% |
| $CX_{16}CX_5CXCXCX_{14}C$ | 81 | 0.70% |
| $CX_{10}CX_5CXCX_8CX_6C$ | 82 | 0.52% |
| $CX_{12}CX_4CX_5CX_8CX_2C$ | 83 | 0.49% |
| $CX_{12}CX_5CX_5CXCX_8C$ | 84 | 0.47% |
| $CX_{10}CX_6CX_5CXCX_4CXCX_9C$ | 85 | 0.45% |
| $CX_{11}CX_4CX_5CX_8CX_2C$ | 86 | 0.45% |
| $CX_{10}CX_6CX_5CX_8CX_2C$ | 87 | 0.43% |
| $CX_{10}CX_6CX_5CXCX_8C$ | 88 | 0.36% |
| $CX_{10}CX_6CX_5C$ | 72 | 0.31% |
| $CX_{10}CX_6CX_5CXCX_3CX_8CX_2C$ | 89 | 0.29% |
| $CX_{10}CX_6CX_5CX_3CX_8C$ | 90 | 0.29% |
| $CX_{10}CX_6CX_5CXCX_2CX_6CX_5C$ | 91 | 0.25% |
| $CX_7CX_6CX_3CX_3CX_9C$ | 92 | 0.25% |
| $CX_9CX_8CX_5CX_6CX_5C$ | 93 | 0.22% |
| $CX_{10}CX_2CX_2CX_7CXCX_{11}CX_5C$ | 94 | 0.20% |
| $CX_{10}CX_6CX_5CXCX_{13}C$ | 45 | 0.20% |
| $CX_{10}CX_6CX_5CXCX_2CX_8CX_4C$ | 95 | 0.20% |

Bovine V_H regions were amplified from cDNA prepared in example 9 using primers 5'-TTGAGCGACAAGGCTG-TAGGCTG-3' (SEQ ID NO: 387) and 5'-CTTTCGGGGCT-GTGGTGG-AGGC-3' (SEQ ID NO: 388) producing a library of antibody variable region cDNA biased for ultralong CDRs. Next, the mixture of $V_H$ regions was assembled by overlap PCR with bovine CH1 and human IgG Fc. Briefly, EcoRI and NheI sites were incorporated for ligation into pFUSE expression vector, to afford a full-length heavy chain library ready for expression in mammalian cells. The ligation product was transformed into E. coli and 500 single E. coli transformants were picked. Each transformant was then grown overnight in a separate vessel and DNA from each colony was extracted using Qiagen minprep kits (Qiagen, Inc.) and sequenced by BATJ, Inc. (San Diego, Calif.) using the oligo 5'-AGATCCAAGCTGTGACCGGC-3' (SEQ ID NO: 389). Sequences were analyzed using VectorNTI (Invitrogen, Inc. Carlsbad, Calif.). Duplicative sequences, sequences with no insert, and sequences encoding a CDR shorter than 35 residues were excluded. 132 clones containing unique long CDR heavy chain sequences were selected. Each heavy chain in the 132 member library was then co-transfected in parallel with pFUSE expression vector encoding the invariant bovine light chain BLV1H12 (SEQ ID NO: 412) into 293T cells, to generate a small spatially addressed library (Mao et al. (2010) Nat Biotech 28:1195-1202). 130,000 293T cells per well were plated in 24 well plates and grown overnight in 500 ul DMEM media (Invitrogen) with 10% FBS (Invitrogen), and Penicillin/streptomycin/glutamine (Invitrogen) at 37° C. and 5% $CO_2$. 0.5 μg of Hc-encoding pFuse vector and 0.5 μg of Lc-encoding pFuse vector were added to 25 μl of optimem (Invitrogen). 1 μl of Lipofectamine 2000 or 293Fectin transfection reagent (Invitrogen) was added to 25 μl of optimem, and incubated 5 minutes. Next, the DNA-optimem mix and transfection reagent-optimem mix were combined and incubated 15 minutes, added to 293T cells, and allowed to incubate on cells 4-6 hours. Then media was aspirated from wells and replaced with fresh media, and cells were allowed to grow and secrete IgG into the media for 4 days. Cell-culture supernatants containing IgG were harvested in 96 well format for further testing. The chimeric antibodies were quantified by sandwich ELISA detecting human F and screened for binding to BVDV by ELISA.

Antibodies were then secreted into culture media and harvested in a 96 well format to generate a small spatially addressed library for further testing including, screening for binding to BVDV by ELISA. For example, an ELISA was conducted to screen the antibody library for binding to BVDV. Briefly, killed BVDV (0.2 μg) in 100 μL DPBS was coated on 96-well MaxiSorp ELISA plates (Nunc) for 1 hour at 37° C. Next, the plates were blocked with 200 μL 3% BSA solution in DPBST, Dulbecco's phosphate buffered saline, 0.25% Tween 20) for 1 hour at 37° C. Samples were then incubated with 3% BSA in DPBST for 1 hour at 37° C. Subsequently, wells were washed 5 times with 200 μL DPBST. Next, Goat Anti-Human IgG (Fc)—HRP conjugated antibody (KPL Inc.) was added at a 1:1,000 dilution in blocking solution and incubated for 1 hour at 37° C. Wells were then washed 10 times with 200 μL DPBST. A 100 μL working solution of QuantaBlu (Pierce) was added to each well and incubated for 5 minutes at room temperature before plates were read in a SpectraMax M5 plate reader at ex325/em420 nm. Several candidate binders were identified. Clone H12 has a 63-residue CDR3 with 6 cysteine residues and was able to strongly bind BVDV in a dose dependent fashion.

Additionally, binding of the chimeric recombinant antibodies to BVDV antigens was evaluated by immunocytometric analysis of transfected human embryonic kidney (HEK) 293A cells (Invitrogen), as previously described (see, e.g., Njongmeta et al. (2012) Vaccine 30:1624-1635). Briefly, HEK 293A monolayers grown in 6-well tissue culture plates were transfected with 2 μg/well of plasmid (pCDNA3.3, Invitrogen) encoding BVDV antigens (NPro, E2, or non-structural proteins NS2-3) using Lipofectamine 2000 reagent (Invitrogen), and incubated for 48 hr at 37° C. with 5% $CO_2$. The monolayers were fixed with ice-cold 100% methanol for 10 minutes, rinsed with PBS, and after blocking for 1 hour with PBS containing 5% fetal bovine serum (blocking buffer), the monolayers were incubated at room temperature for 1 hr with 10 μg/ml of a mouse anti-FLAG M2-alkaline phosphatase (AP)-conjugate (Sigma) in blocking buffer or 10 μg/ml of the chimeric recombinant antibodies (H12 or B8). Monolayers transfected with empty vector were similarly reacted to serve as negative controls and, following washes in blocking buffer, the monolayers probed with the chimeric recombinant antibodies were incubated with a ½₀₀ dilution of AP-conjugated goat anti-Human IgG (Fc specific) mAb (Sigma) in blocking buffer for 1 hr. Following washes in blocking buffer, the AP activity in all the wells was detected using Fast Red AS-MX substrate (Sigma). Stained cells were visualized and photographed using an IS70 inverted optical microscope (Olympus, Japan) equipped with a camera. H12 strongly binds HEK293A cells transfected with the NS2-3 non-structural proteins of BVDV but weakly bound to untransfected cells while B8 had weak binding to both HEK293A cells transfected with the NS2-3 non-structural proteins of BVDV and untransfected cells.

Example 3: Construction of Vector Comprising an Antibody with an Ultralong CDR3

Any vector known in the art may be used, or may be modified to be used, for cloning and/or expression of a nucleotide sequence encoding a heavy chain variable region that comprises an ultralong CDR3. Such vectors may optionally comprise, or be modified to comprise, a nucleotide sequence encoding the Fc portion of a human immunoglobulin (e.g., IgG) linked to the nucleotide sequence encoding the heavy chain variable region comprising an ultralong CDR3. Additionally, the nucleotide sequence encoding the heavy chain variable region comprising the ultralong CDR3 may be modified according to known methods such that the ultralong CDR3 can accept a nucleotide sequence encoding a non-bovine (e.g., non-antibody or human) sequence including, for example, by unidirectional cloning with restriction enzymes. Any vector known in the art may also be used, or may be modified to be used, for cloning and/or expression of a nucleotide sequence encoding a light chain variable region.

In an exemplary method, a vector may be modified by recombinant techniques to comprise a nucleotide sequence encoding a heavy chain variable region having an ultralong CDR3 linked to a nucleotide sequence encoding an IgG Fc. Briefly, a nucleotide sequence encoding CH1-CH2-CH3 of human IgG1 (SEQ ID NO: 390) was amplified by PCR and assembled via strand overlap elongation. Next, a compatible cohesive-end strategy was employed to replace the human Fc sequence encoded in vector pFUSE-hIgG2-Fc2 (SEQ ID NO: 457, InVivogen, San Diego Calif.) with CH1-CH2-CH3 of human IgG1, which destroyed the existing 3' NheI site in the pFUSE-hIgG2-Fc2 vector and generated an NheI site at the 5' end of SEQ ID NO: 390. The modified pFUSE-hIgG2-Fc2 vector ("HC pFuse", SEQ ID NO: 458) allows insertion of VH fragments between the signal sequence and the nucleotide sequence encoding CH1-CH2-CH3 of human IgG1 using the existing EcoRI site and the newly introduced NheI site. For example, the VH region from bovine antibody BLV1H12 (SEQ ID NO: 392) was amplified by PCR and subcloned in-frame between the signal sequence and nucleotide sequence encoding CH1-CH2-CH3 of human IgG1 in the HC pFuse vector using EcoRI and NheI restriction enzymes generating SEQ ID NO: 393.

Alternatively, nucleotide sequences encoding non-bovine sequences were inserted into the nucleotide sequence encoding the CDR3 of BLV1H12 heavy chain. Briefly, a pair of BsaI sites were introduced by PCR strand overlap extension into the nucleotide sequence encoding the CDR3 of BLV1H12 (SEQ ID NO: 395). The modified nucleotide sequence incorporating the BsaI sites within the CDR3 encoding sequence of BLV1H12 was then subcloned in-frame between the signal sequence and the nucleotide sequence encoding CH1-CH2-CH3 of human IgG1 in the HC pFuse vector described above using EcoRI and NheI restriction enzymes. Next, non-antibody sequences including cDNA encoding for interleukin 8 (IL-8, SEQ ID NO: 475), interleukin 21 (IL-21, SEQ ID NO: 480) and CXCL12/SDF-1alpha (SEQ ID NO: 479) (Origene) and oligoprimers encoding the peptide hormone somatostatin (SEQ ID NO: 477), the venom peptides ProTx-II (SEQ ID NO: 481) and chlorotoxin (SEQ ID NO: 478), and the synthetic conotoxin peptide ziconotide (SEQ ID NO: 476) (IDTDNA) were modified by PCR amplification using oligoprimers with BsaI flanks to comprise BsaI flanks to produce non-bovine sequences with BsaI flanks for insertion into the CDR3 of BLV1H12. Next, the BsaI flanks in the modified non-antibody sequences were cut with BsaI and ligated, in frame, with the BLV1H12 BsaI digested vector, thereby inserting the nucleotide sequence encoding the non-antibody sequence into the BLV1H12 heavy chain variable region and replacing a portion (e.g., cysteine-rich portion) of the ultralong CDR3, and in-frame with the sequence encoding BVL1H12 variable region and CH1-CH2-CH3.

Similarly, a vector was modified by recombinant techniques to comprise a nucleotide sequence encoding a light chain. Briefly, the BLV1H12 light chain sequence (SEQ ID NO: 412) was amplified by PCR to introduce EcoRI and NheI ends. The BLV1H12 light chain variable region sequence was then digested with EcoRI and NheI and subcloned into pFUSE-hIgG2-Fc2, deleting the portion of pFUSE-hIgG2-Fc2 encoding Fc, and replacing it with only light chain sequence (SEQ ID NO: 459).

In addition, overlap PCR was used to amplify and join sequence from BLV1H12 light chain variable region and human lambda light chain constant region (SEQ ID NO: 474). This was amplified by PCR to introduce EcoRI and NheI ends. The hybrid BLV1H12 with human lambda sequence was then digested with EcoRI and NheI and subcloned into pFUSE-hIgG2-Fc2, deleting the portion of pFUSE-hIgG2-Fc2 encoding Fc, and replacing it with only light chain sequence.

Example 4: Expression of Polynucleotides Coding for Antibodies that Comprise an Ultralong CDR3

Polynucleotides coding for antibodies comprising an ultralong CDR3 may be expressed including, transiently expressed, in a host cell by any method known in the art.

In an exemplary method, the vectors comprising the heavy and light chains generated in Example 2 may be transfected into either 293T cells or Freestyle™ 293-F cells.

For example, 130,000 293T cells per well were plated in 24 well plates and grown overnight in 500 μl DMEM media (Invitrogen) with 10% FBS (Invitrogen), and penicillin/streptomycin/glutamine (Invitrogen) at 37° C. and 5% $CO_2$. Next, 0.5 μg of Heavy chain-encoding pFuse vector (e.g., generated in Example 2) and 0.5 μg of Light chain-encoding pFuse vector (e.g., generated in Example 2) were added to 25 μl of Opti-MEM (Invitrogen). Subsequently, 1 μl of Lipofectamine 2000 or 293Fectin transfection reagent (Invitrogen) was added to 25 μl of Opti-MEM, and incubated 5 minutes. Then the dna-Opti-MEM solution and transfection reagent-Opti-MEM solution were combined and incubated for 15 minutes, added to 293T cells, and allowed to incubate on cells for 4-6 hours. Then media was aspirated from wells and replaced with fresh media, and the cells were allowed to grow and secrete IgG into the media for 2-6 days.

Additionally, for example, $1\times10^6$ 293Freestyle suspension cells/ml were grown overnight in Freestyle™293 Expression Medium (Invitrogen), and penicillin/streptomycin/glutamine (Invitrogen) at 37° C. and 5% $CO_2$. Next, for each milliliter of cells, a 30 μl solution was made in buffer PBS comprising 0.5 μg Heavy chain-encoding pFuse DNA and 0.5 μg of Lc-encoding pFuse. Additionally, for each milliliter of cells, a solution comprising 1 μl of 293Fectin transfection reagent was added to 30 μl PBS and incubated 5 minutes. Subsequently, the DNA and lipofectamine solutions were combined and incubated 15 minutes before adding the mixture to the cells. The cells were then allowed to grow and secrete IgG into media for 2-6 days.

After the growth period for the 293T cells or Freestyle™ 293-F suspension cells, media was harvested, and IgG secreted into the supernatant was evaluated by sandwich ELISA. Briefly, Fc-specific anti Human IgG (Cat 12136, Sigma-Aldrich) was diluted 1:1000 in PBS and coated onto maxisorp plates (Nunc). Next, plates were blocked with 2% BSA in TBST, washed, and IgG secreted supernatants were incubated for 1 hour. After washing with TBST, the appropriate HRP conjugated anti-Light chain antibody is diluted 1:1000 in TBST and incubated 1 hour (anti kappa-HRP, Cat#A-7164, Sigma-Aldrich; anti-lambda-HRP, Cat#2070-05, Southern Biotech). After washing with TBST, HRP was detected with TMB (Cat#TMBS-1000-01, BioFX), and neutralized with 0.6M $H_2SO_4$. Subsequently, absorbance (A450) was measured, and compared to a standard curve of known IgG concentration to determine the concentration of human antibody in cell culture supernatant.

The yield of antibody from supernatants from cells transfected with heavy chain constructs encoding BLV1H12 with human CH1-CH2-CH3 and a replacement of at least a portion of CDR3 (generated in Example 3) and a light chain construct encoding BLV1H12 LV-human lambda LC was determined by ELISA, and normalized to the yield of BLV1H12-IL8 (Table 6). The ELISA indicated that some sequences (e.g., zinconotide) that were used to replace a portion of CDR3 have a minor impact on expression of the antibody, while some sequences (e.g., somatostatin, chlorotoxin, SDF1(alpha), IL21) that were used to replace a portion of CDR3 had a modest impact on expression of the antibody, and other sequences (ProTxII) had an even greater impact on expression of the antibody, as compared to BLV1H12-1L8 (the highest expressor) (Table 6).

TABLE 6

Expression yield of BLV1H12 with replacements to Long CDR3

| Heavy Chain V region | Light Chain | Normalized Yield (% of highest expressor) |
|---|---|---|
| BLV1H12-IL8 | BLV1H12-HuLambdaC | 100 |
| BLV1H12-Ziconotide | BLV1H12-HuLambdaC | 94.7 |
| BLV1H12-Somatostatin | BLV1H12-HuLambdaC | 46.5 |
| BLV1H12-Chlorotoxin | BLV1H12-HuLambdaC | 39.7 |
| BLV1H12-SDF1(alpha) | BLV1H12-HuLambdaC | 38.9 |
| BLV1H12-IL21 | BLV1H12-HuLambdaC | 32.3 |
| BLV1H12-ProTxII | BLV1H12-HuLambdaC | 2.1 |

Example 5: Evaluation of Human Germline Sequences Comprising an Ultralong CDR3 with a Non-Bovine Sequence Human germline sequences that comprise an ultralong CDR3 may be evaluated by any method known in the art to identify those human germline sequences that permit expression of an ultralong CDR3 that comprises a non-bovine sequence.

In an exemplary method, overlap PCR was used to insert BsaI sites into human germline variable regions VH1-24, VH1-46, VH1-69, VH3-23, VH4-4, and VH4-34. Next, PCR was used to introduce EcoRI and NheI sites for sub-cloning in between the signal sequence and CH1-CH2-CH3 region of the HC pFuse vector comprising BLV1H12 generated in Example 2. Subsequently, the IL-8-GSG cassette (SEQ ID NO: 399) was introduced into the BsaI sites of each human germline construct, giving VH1-24+CDR3-1L8 (SEQ ID NO: 425), VH1-46+CDR3-1L8 (SEQ ID NO: 426), VH1-69+CDR3-1L8 (SEQ ID NO: 427), VH3-23+CDR3-1L8 (SEQ ID NO: 428), VH4-4+CDR3-1L8 (SEQ ID NO: 429), and VH4-34+CDR3-1L8 (SEQ ID NO: 430). Next, each pFuse vector encoding a human germline heavy chain and CDR3-1L8 construct was co-transfected with pFuse vector encoding BLV1H12 LV (SEQ ID NO: 474), and allowed to express and secrete these IgGs into the media as described in Example 4. ELISA was then used to determine IgG yield as described in Example 4. Yields of the constructs were determined, and normalized to the highest expressing construct. Surprisingly, the CDR3 from cow is not readily transposable to any human heavy chain variable region. VH4-4 had the highest yield, despite VH4-34 having the closest sequence homology to the BLV1H12 sequence (Table 7).

TABLE 7

Expression Yield of Humanized Heavy Chains with Ultralong CDR3s (removed last column of values, with IgG nM, only showing normalized values.

| Heavy Chain Variable Region: | Normalized Yield (% of highest expressor) |
|---|---|
| BLV1H12 + CDR3IL8 | 100 |
| BLV1H12 | 58.4 |
| VH1-24 BLVCDR3IL8 | 4.4 |
| VH1-46 BLVCDR3IL8 | 2.4 |
| VH1-69 BLVCDR3IL8 | 1.4 |
| VH3-23 BLVCDR3IL8 | 14.7 |
| VH4-4 BLVCDR3IL8 | 22.5 |
| VH4-34 BLVCDR3IL8 | 5.4 |

Example 6: Evaluation of Antibodies that Comprise an Ultralong CDR3 with a Non-Bovine Sequence Antibodies comprising an ultralong CDR3 with a non-bovine sequence (e.g., a replacement of at least a portion of the CDR3 with a non-bovine sequence) including, humanized antibodies, may be evaluated by any method known in the art for binding of the non-bovine sequence to its binding partner including, for example, flow cytometry.

In an exemplary method, BLV1H12 IgG comprising a CDR3 with an IL-8 insert (e.g., the IL-8 sequence replaced a portion of the CDR3) was evaluated for binding to CXCR1 expressing cells by flow cytometry. Briefly, a cell line expressing functionally validated CXCR1 derived from U2OS cells was obtained from DiscoveRx and cultured per manufacturer's instructions (Cat#93-0226C3, DiscoveRx Corporation, Freemont, Calif.). The parental cell line U2OS was obtained from ATCC and cultured under the same conditions as the CXCR1 cells. Cell culture supernatants were then tested for binding to cells by flow cytometry. The adherent U2OS or CXCR1-U2OS cells were dissociated with Accutase (Innovative Cell Technologies, Inc., San Diego, Calif.), neutralized with an equal volume of media containing 10% serum, centrifuged at 1000 g, and resuspended in PBS with 2% BSA. Next, cells were dispensed into microtiter plates to achieve between 30,000 to 300,000 cells per well, centrifuged again, and resuspended in cell culture supernatant containing expressed IgG, or a dilution of IgG-containing cell culture supernatant. A fluorescent-conjugated anti-Human Fc antibody was used to detect binding of the expressed antibody to cells. Subsequently, cell fluorescence was measured by flow cytometry (e.g., FACS), and median Arbitrary Fluorescence Units (AFU) were calculated for each combination of antibody and cell type tested, revealing the extent of IgG binding to those cells. The ratio of median fluorescence (IgG binding) of CXCR1-U2OS cells versus U2OS parental cells shows that the BLV1H12 IgG comprising a CDR3 with an IL-8 insert has specificity for CXCR1 (Table 8).

TABLE 8

Binding of BLV1H12 frameworks to CXCR1 U2OS cells

| | ULcowV (Median Arbitrary Fluorescence Units (AFU)) | ULcowV + IL8 (Median Arbitrary Fluorescence Units (AFU)) |
|---|---|---|
| Parental U2OS | 4 | 76 |
| CXCR1-U2OS | 4 | 707 |

Additionally, the human germline CDR3-1L8 IgGs described in Example 5 were evaluated for binding to CXCR1 expressing cells by flow cytometry as described above. IgG binding to CXCR1-U2OS cells is indicated by higher fluorescence values, but non-specific binding to U2OS parental cells is also detectable. For a given IgG with CDR3-IL-8, specific binding to CXCR1 is revealed by the ratio of fluorescence on CXCR1-U2OS cells to the fluorescence on parental U2OS cells (Table 9). While the BLV1H12 supported strong and specific binding to CXCR1 (Table 8), the IL-8 in human germline IgGs showed either weaker binding to CXCR1, or non-specific interaction as seen in strong binding to both CXCR1-U2OS cells as well as the parental control cells. The most specific interaction to CXCR1 of IL-8 within a human germline IgG was seen with VH4-34.

TABLE 9

Binding of IgGs with CDR3-IL8 to CXCR1 U2OS cells

| IgG with HC V region: | Parental U2OS | CXCR1-U2OS | Ratio of CXCR1/Parental |
|---|---|---|---|
| BLV1H12 | 5 | 9 | 1.9 |
| VH1-24 + CDR3-IL8 | 5 | 23 | 4.3 |
| VH1-46 + CDR3-IL8 | 5 | 6 | 1.1 |
| VH1-69 + CDR3-IL8 | 20 | 78 | 4.0 |
| VH3-23 + CDR3-IL8 | 534 | 1443 | 2.7 |
| VH4-4 + CDR3-IL8 | 1007 | 3079 | 3.1 |
| VH4-34 + CDR3-IL8 | 70 | 648 | 9.3 |

In another exemplary method, IL-8 activation of the CXCR1 receptor was tested using the CXCR1-U2OS DiscoveRx cells described above (Cat#93-0226C3, DiscoveRx). The DiscoveRx cells are engineered such that upon activation by ligand, the resultant beta-arrestin recruitment to the GPCR also causes activation of a luminescent reporter enzyme present cell line. Lysis reagents and luminescence substrate are included in the PathHunter Detection Kit (Cat#93-001, DiscoveRx) which was used following manufacturer's instructions. U2OS-CXCR1 cells were plated at 15,000 cells per well and serum starved overnight in EMEM media without serum. Next, media was removed and cells were incubated 1 hour at 37° C. with 80 µl of 1:1 EMEM and PBS, containing dilutions of either IL-8 or IgG with IL-8 insertion in CDR3, or control antibody. After 1 hour, 40 µl of PathHunter Detection reagent mix was added. Subsequently, after an hour at room temperature the luminescence in each well was measured using a luminescence plate reader. Higher luminescence signal reveals more activation of the CXCR1 receptor at the tested concentrations of IL-8 or IgG. IgGs were purified by scaling up the transfection method of Example 4, and purification of the IgG from media using protein A sepharose following manufacturer's instructions (Cat#17-1279-03 GE Healthcare) and dialysis post-elution into PBS. Protein yield was determined by A280 and calculated molar extinction coefficient. Increasing concentrations of BLV1H12-1L8 IgG activated CXCR1 somewhat similarly to the activation observed with IL-8, whereas increasing concentration of BLV1H12 IgG had no effect on CXCR1 activation (Table 10).

TABLE 10

Activation of CXCR1 by IL-8 as soluble cytokine or as CDR3 replacement

| nM | IL-8 (average RLU) | BLV1H12-IL8 IgG (average RLU) | IgG_BVL1H12 IgG (average RLU) |
|---|---|---|---|
| 500.00 | 5720 | 6641 | 484 |
| 166.67 | 6770 | 6207 | 525 |
| 55.56 | 7365 | 5509 | 511 |
| 18.52 | 7295 | 5071 | 529 |
| 6.17 | 5869 | 4428 | 517 |
| 2.06 | 4110 | 3645 | 495 |
| 0.69 | 1939 | 2651 | 516 |
| 0.23 | 940 | 1515 | 455 |
| 0.08 | 504 | 822 | 461 |
| 0.01 | 440 | 435 | 460 |

Additionally, antibodies in which IL-8 was grafted into the VH4-4 human germline variable region were tested for activation of CXCR1. IgG with VH4-4+CDR3-1L8 (SEQ ID NO: 429) was compared to BLV1H12+CDR3-IL8, and IgGVH4-4 CDR3 BsaI (lacking the IL-8 insert) (SEQ ID NO: 431). A single concentration of soluble IL-8 was tested as a positive control for assay function at 31.5 nM and gave activation of 55525 average RLU. (Table 11). Although the IgG with insertion of IL-8 into the human VH4-4 variable region did activate CXCR1, it was not as potent in equal dose to the IgG with BLV1H12 sequence.

TABLE 11

Activation of CXCR1 by IgGs with CDR3 IL-8

| IgG (nM) | BLV1H12 + CDR3-IL8 (average RLU) | VH4-4 + CDR3-IL8 (average RLU) | VH4-4 + CDR3-BsaI (average RLU) |
|---|---|---|---|
| 261.500 | 56349 | 36481 | 7545 |
| 87.167 | 52128 | 29623 | 7139 |
| 29.056 | 47621 | 24889 | 7104 |
| 9.685 | 39280 | 15545 | 7174 |
| 3.228 | 34544 | 10233 | 7034 |
| 1.076 | 23700 | 8012 | 7184 |
| 0.359 | 13278 | 7338 | 6687 |
| 0.120 | 8867 | 7513 | 7331 |
| 0.040 | 7736 | 7323 | 6973 |
| 0.013 | 7329 | 6956 | 7048 |
| 0.004 | 7240 | 7067 | 7387 |
| 0.001 | 7437 | 7142 | 7500 |

Example 7: Modification of Humanized Antibodies Comprising an Ultralong CDR3

Humanized antibodies generated in Example 5 may be modified to comprise one or more amino acid substitutions in heavy chain CDR1 and/or CDR2. Such amino acid substitutions may be introduced into a human germline CDR1 and CDR2 at positions that are hypothesized to interact with CDR3.

In an exemplary method, certain residues in VH4-34 CDR1 and/or CDR2 were substituted with corresponding CDR1 and/or CDR2 residues from BLV1H12. Briefly, the pFuse vector encoding heavy chain VH4-34 CDR3-1L8 was modified by overlap PCR to replace all of CDR1 with sequence from BLV1H12 (VH4-34+CDR3-IL8_CDR1 Cow, SEQ ID NO: 432) or all of CDR2 with sequence from BLV1H12 (VH4-34+CDR3-IL8_CDR2 Cow, SEQ ID NO: 433). Additionally, overlap PCR was used to introduce point mutants G31D and Y32K into CDR1 (VH4-34+CDR3-IL8_CDR1 G31D, Y32K, SEQ ID NO: 434) or point mutant E50S into CDR2 (VH4-34+CDR3-IL8_CDR2 E50S, SEQ ID NO: 435). These heavy chain constructs were paired with BLV1H12 light chain and were expressed as described in Example 4. Yield and CXCR1 binding were determined as described in Example 6 (Table 12).

TABLE 12

CDR1 and 2 modification of VH4-34 CDR3-IL8 IgG

| Heavy chain | IgG Yield normalized | FACS CXCR1/Parental Ratio |
|---|---|---|
| BLV1H12 | 100 | 1.9 |
| VH4-34 + CDR3-IL8 | 20 | 9.3 |
| VH4-34 + CDR3-IL8 + Cow CDR1 | 29 | 2.1 |
| VH4-34 + CDR3-IL8 + Cow CDR2 | 9 | 8.0 |
| VH4-34 + CDR3-IL8 + E31D, Y32K | 19 | 8.1 |
| VH4-34 + CDR3-IL8 + E50S | 27 | 4.0 |

Example 8: Pairing of Heavy Chain Comprising an Ultralong CDR3 with a Human Light Chain Antibodies that comprise an ultralong CDR3 including, antibodies that comprise an ultralong CDR3 where at least a portion of the CDR3 has been replaced by a non-bovine sequence, may be paired with a human light chain.

In an exemplary method, BLV1H12+CDR3-1L8 flexibility to pair productively with human germline light chains was explored by co-transfecting pFuse vector encoding heavy chain BLV1H12+CDR3-1L8 with pFuse vectors encoding each of several human germline light chains (e.g., SEQ ID NOs: 445-456), or BLV1H12 light chain (SEQ ID NO: 412). These human germline light chain sequences were synthesized (Genscript, Inc) and amplified by PCR as in Example 3 for subcloning via EcoRI and NheI into the pFUSE LC vector. BLV1H12+CDR3-1L8 encoding pFUSE vector was cotransfected with pFUSE vectors encoding light chains as in Example 3. Secreted IgGs were then tested by FACS as in Example 5 for specific binding to CXCR1 cells (Table 13). Human germ line light chains did not readily support the function of IL-8 when expressed as BLV1H12+CDR3.

TABLE 13

Evaluation of BLV1H12 + CDR3-IL8 when paired with germline human light chains

| Light chain | FACS CXCR1/ Parental Ratio |
| --- | --- |
| A20J1 | 0.8 |
| A27J3 | 0.9 |
| L6J1 | 0.8 |
| L25J1 | 1.3 |
| V1-2J7 | 0.8 |
| V1-7J1 | 0.6 |
| V1-11J2 | 0.8 |
| V1-13J5 | 2.9 |
| V1-16J6 | 0.6 |
| V2-13J2 | 0.9 |
| V2-14J4 | 1.0 |
| V2-15J7 | 1.1 |
| V2-17J2 | 2.0 |
| V3-4J1 | 1.2 |
| V5-4J2 | 0.8 |
| BLV1H12 | 5.0 |

Alternatively, using the BLV1H12 light chain variable region as a guide, the human germline sequences identified with closest homology were V1-47 and V1-51. These light chain sequences were synthesized (SEQ ID NO: 455, 456) (IDTDNA, Inc.) with the desired EcoRI and NheI restriction sites for subcloning into the pFuse vector. Subsequently, pFuse vector encoding V1-47 or V1-51 were paired with pFuse vectors encoding VH4-34+CDR3-IL8, the VH4-34+CDR3-1L8 with the CDR1 or CDR2 modifications described in Example 6 (SEQ ID NOs: 432-435), as well as vectors encoding the combinations of both CDR1 and CDR2 modifications (e.g., VH4-34+CDR3-IL8_CDR1 Cow_CDR2 Cow, SEQ ID NO: 436; VH4-34+CDR3-IL8_CDR1 Cow_CDR2 E50S, SEQ ID NO: 437; VH4-34+CDR3-IL8_CDR1 G31D,Y32K_CDR2 Cow, SEQ ID NO: 438; VH4-34+CDR3-IL8_CDR1 G31D,Y32K_CDR2 E50S, SEQ ID NO: 439). These IgGs were expressed, yield was determined by ELISA, and CXCR1 binding specificity was measured by flow cytometry as described above (Table 14).

TABLE 14

Expression yield and CXCR1 specificity for VH4-34 CDR3-IL8 IgGs having CDR1 and CDR2 modifications and paired with Lc V1-47 or V1-51

| HC VH4-34 CDR3-IL8+ | | nM IgG | | CXCR1/Parental Ratio | |
| --- | --- | --- | --- | --- | --- |
| Hc-CDR1 | HC-CDR2 | V1-47 | V1-51 | V1-47 | V1-51 |
| G31D Y32K | VH4-34 | 1 | 2.5 | 3.6 | 3 |
| Cow | VH4-34 | 3 | 8.5 | 5.1 | 2.4 |
| VH4-34 | VH4-34 | 1.5 | −0.4 | 2.6 | 2.9 |
| G31D Y32K | E50S | 2 | 4.6 | 1.4 | 3 |
| Cow | E50S | — | 22.8 | 2.6 | 3.1 |
| VH4-34 | E50S | 3.3 | 3.3 | 3.3 | 1.8 |
| G31D Y32K | Cow | −0.1 | 2.3 | 2 | 2.6 |
| Cow | Cow | 0.7 | 4.9 | 4.6 | 3.1 |
| VH4-34 | Cow | 0.6 | 0.6 | 2.5 | 3.9 |

Example 9: Modification of Human Light Chain and Pairing with Heavy Chain Comprising an Ultralong CDR3

Human germline light chains including, light chains that may be paired with a heavy chain comprising an ultralong CDR3, may be modified by any method known in the art. Such modifications may include the substitution of certain amino acid residues in the human light chain to those residues at corresponding positions in a bovine light chain sequence. The modified light chains may improve the yield of the antibody comprising the ultralong CDR3 and/or increase its binding specificity.

In an exemplary method, variants of V1-51 were made by overlap PCR and subcloned into pFuse vector for expression as described in Example 4. The engineered variants of V1-51 had: i) substitutions I29V and N32G introduced in CDR1 (SEQ ID NO: 440), ii) residues DNN (amino acids 51-53) in CDR2 changed to GDT (SEQ ID NO: 441), iii) residues DNNKRP (SEQ ID NO: 471) in and near CDR2 changed to GDTSRA (SEQ ID NO: 472), or iv) the 14 residues at the N-terminus were made identical to the first 14 resides of BLV1H12 light chain with point mutations S2A, T5N, P8S, A12G, A13S, and P14L (SEQ ID NO: 443) or v) combining the changes set forth in ii) and iv) (SEQ ID NO: 444). These V1-51 variants were paired with heavy chains encoding VH4-34+CDR3-1L8 (SEQ ID NO: 430), VH4-34+CDR3-IL8_CDR1 Cow (SEQ ID NO: 432), VH4-34+CDR3-IL8_CDR2 Cow (SEQ ID NO: 433), or VH4-34+CDR3-IL8_CDR1 Cow_CDR2 Cow, (SEQ ID NO: 436). Transfections and ELISA were carried out as described above, and flow cytometry was used to evaluate CXCR1 binding specificity as previously described, with the modification that cells were resuspended in 2% BSA in PBS plus 2 ug/ml Heparin sulfate, and IgGs were normalized to 10 nM during incubation on cells. Only certain combinations of heavy and light chains supported detectable expression (Table 15). Those combinations that expressed heavy and light chains were tested for CXCR1 binding specificity (Table 16).

TABLE 15

Expression yield (nM IgG) for VH4-34 + CDR3-IL8 variants and V1-51 variants

|  | | VH4-34 CDR3-IL8 | VH4-34 CDR3-IL8 CDR1-Cow | VH4-34 CDR3-IL8 CDR2-Cow | VH4-34 CDR3-IL8 CDR1-Cow &CDR2-Cow |
|---|---|---|---|---|---|
| | Hc CDR1:<br>CDR2: | Human<br>Human | Cow<br>Human | Human<br>Cow | Cow<br>Cow |
| V1-51 | | 1 | 5 | 0 | 13 |
| V1-51 CDR1 I29V, N32G | | -1 | 5 | 0 | 3 |
| V1-51 CDR2 DNN to GDT | | -1 | 23 | -1 | 5 |
| V1-51 CDR2 DNNKRP (SEQ ID NO: 471) to GDTSRA (SEQ ID NO: 472) | | -1 | 4 | 1 | 23 |
| V1-51 S2A, T5N, P8S, A12G, A13S, P14L | | 0 | 38 | -1 | 22 |
| V1-51 S2A, T5N, P8S, A12G, A13S, P14L & DNN to GDT | | 0 | 37 | 0 | 1 |

TABLE 16

CXCR1 specificity for VH4-34 + CDR3-IL8 variants and V1-51 variants

|  | | VH4-34 CDR3-IL8 | VH4-34 CDR3-IL8 CDR1-Cow | VH4-34 CDR3-IL8 CDR2-Cow | VH4-34 CDR3-IL8 CDR1-Cow &CDR2-Cow |
|---|---|---|---|---|---|
| | Hc CDR1:<br>CDR2: | Human<br>Human | Cow<br>Human | Human<br>Cow | Cow<br>Cow |
| V1-51 | | nt | 7.2 | nt | 11.1 |
| V1-51 CDR1 I29V, N32G | | nt | 8.9 | nt | 11.8 |
| V1-51 CDR2 DNN to GDT | | nt | 5.6 | nt | 16.7 |
| V1-51 CDR2 DNNKRP (SEQ ID NO: 471) to GDTSRA (SEQ ID NO: 472) | | nt | 8.0 | nt | 6.9 |
| V1-51 S2A, T5N, P8S, A12G, A13S, P14L | | nt | 4.7 | nt | 12.2 |
| V1-51 S2A, T5N, P8S, A12G, A13S, P14L & DNN to GDT | | nt | 6.8 | nt | |

Example 10: Preparation of Antibody Libraries with Ultralong CDR3 Sequences

Libraries may be generated that comprise an ultralong CDR3 including, for example libraries that comprise at least a portion of an ultralong CDR3, within an antibody framework (e.g., a heavy chain framework). Such libraries may comprise a diversity of ultralong CDR3 sequences, a diversity of one or more residues that are positioned between one or more cysteine residues in the cysteine domain of the ultralong CDR3, or a diversity of non-bovine peptides that may be inserted (e.g., replace a portion of) in the ultralong CDR3. The antibody framework may be derived from a bovine sequence such as VH-UL, a human germline sequence, or a modified human germline sequence such as described in Example 7. Heavy chains with diverse ultralong CDR3 may be paired with light chains of bovine, human, or modified composition (see, e.g., Example 9) for expression of a library of antibody or antibody fragments comprising a diverse ultralong CDR3.

In an exemplary method, a library is generated in which the library comprises a diversity of ultralong CDR3 sequences (e.g., the diversity in the library resides in that the library contains a plurality of diverse ultralong CDR3 sequences). For example, a plurality of diverse ultralong CDR3 sequences is obtained from cDNA extracted from the spleen and/or lymph nodes from either immunized or non-immunized cows. Alternatively, a plurality of diverse ultralong CDR3 sequences is captured as information from cDNA by sequencing technology, such as described in Example 2. cDNA-derived cow sequences are then amplified from the isolated cDNA or synthesized from sequencing of cDNA, and diverse CDR3 sequences are inserted into an antibody framework for expression of IgGs with ultralong CDR3 sequences, producing a library of IgGs with CDR3s derived from cows. The IgG library can exist in any format, including as a spatially addressed array see, e.g., WO 11/056997; and Mao et al. (2010) Nat Biotech 28:1195-1202).

In another exemplary method, a library is generated in which members of the library comprise an ultralong CDR3 with a certain cysteine domain, or multiple cysteine domains, wherein the members are diverse in one or more residues that are positioned between one or more cysteine residues in the cysteine domain. For example, in the sequence $CX_{10}CX_5CX_5CXCX_7C$ (SEQ ID NO: 41), a library is generated whereby any X residue is changed, or combination of X residues are changed, to produce diversity within CDR3. Such diversity is introduced by degenerate nucleotide synthesis, error prone PCR, gene synthesis, or any other method known in the art to make changes in nucleotide sequences. These ultralong CDR3 loops are then integrated with sequence encoding the antibody framework. Heavy chain sequences are then paired with human or modified human light chain sequences for co-transfection and expression to comprise an antibody library engineered from bovine CDR3s.

In another exemplary method, a library is generated in which members of the library comprise an ultralong CDR3 with diversity in a non-bovine sequence inserted into (e.g., replace a portion of) the ultralong CDR3. Ultralong CDR3s tolerate large non-bovine sequence insertions (e.g., cytokines, peptide hormones, signaling domains, and constituent proteins of arthropod toxins or reptile venoms) including, for example, cysteine rich insertions, within an antibody framework, and support the independent function of the peptide encoded by the non-bovine sequence, as demonstrated in Example 4 and Example 6. Sequences encoding non-bovine sequences are amplified by PCR from cDNA or synthesized, and incorporated with or without linker sequences, into an antibody sequence such that they are expressed within, in place of, or replace at least a portion of, an ultralong CDR3. Exemplary methods to insert a non-bovine sequence into a vector for expression are set forth in Example 3 above. Heavy chain sequences are then paired with human or modified human light chain for co-transfection and expression. For example, a non-bovine sequence is inserted into HC pFUSE, encoding VH4-34*02 with CDR1 and CDR3 modifications from BLV1H12. Briefly, the portion of the HC pFuse vector comprising a BsaI cassette (see, Example 3; bolded in the sequence below) which is flanked on both sides by a portion of an ultralong CDR3 (underlined sequence below) is replaced by a non-bovine sequence.

(SEQ ID NO: 472)
caggtgcagctacagcagtggggcgcaggactgttgaagccttcggagac gctgtccctcacctgcacagcaagcgggttttcactgagcgacaaggcag tgggatggattcgccagccccagggaaggggctggagtggattggggaa atcaatcatagtggaagcaccaactacaacccgtccctcaagagtcgagt caccatatcagtagacacgtccaagaaccagttctccctgaagctgagct ctgtgaccgccgcggacacggctgtgtattactgt<u>acctctgtgcaccag</u> gaaactaagaaataccagagcgagacctactatggttcgggtctctctta tacctacaattatgaatgg<u>catgtggatgtctggggacagggcctgctgg</u> tgacagtctctagtgctagc

After replacement of the BsaI cassette with the non-bovine sequence the non-bovine sequence (referred to as insert in bold text in the sequence below) is positioned such that it is flanked on both sides by a portion of the ultralong CDR3.

(SEQ ID NO: 473)
qvqlqqwgagllkpsetlsltctasgfslsdkavgwirqppgkgle wigeinhsgstnynpslksrvtisvdtsknqfslklssvtaadtavyy ct<u>svhqet</u>kkyqs-insert-<u>sytynyew</u>hydvwgqgllvtvssas Heavy chain sequences are then paired with human or modified human light chain for co-transfection and expression.

Embodiments of the present subject matter described above, some of which are set forth below, may be beneficial alone or in combination, with one or more other embodiments. Such embodiments include:

Embodiment 1

A humanized antibody or binding fragment thereof comprising an ultralong CDR3. In some embodiments, the humanized antibody or binding fragment thereof comprises one or more human variable region framework sequences.

Embodiment 2

The humanized antibody or binding fragment thereof of Embodiment 1, wherein the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

Embodiment 3

The humanized antibody or binding fragment thereof of Embodiment 2, wherein the ultralong CDR3 is 35 amino acids in length or longer.

Embodiment 4

The humanized antibody or binding fragment thereof of Embodiment 1, wherein the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

Embodiment 5

The humanized antibody or binding fragment thereof of Embodiment 4, wherein the ultralong CDR3 comprises 3 or more cysteine residues.

Embodiment 6

The humanized antibody or binding fragment thereof of Embodiment 1, wherein the antibodies or binding fragments thereof comprise a cysteine motif.

Embodiment 7

The humanized antibody or binding fragment thereof of Embodiment 6, wherein the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_6CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

Embodiment 8

The humanized antibody or binding fragment thereof of Embodiment 6, wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCCX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CCX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

Embodiment 9

The humanized antibody or binding fragment thereof of Embodiment 1, wherein the ultralong CDR3 comprises 2 to 6 disulfide bonds.

Embodiment 10

The humanized antibody or binding fragment thereof of Embodiment 1, wherein the ultralong CDR3 comprises SEQ ID NO: 40 or a derivative thereof.

Embodiment 11

The humanized antibody or binding fragment thereof of Embodiment 1, wherein the ultralong CDR3 comprises amino acid residues 3-6 of any of one SEQ ID NO: 1-4.

Embodiment 12

The humanized antibody or binding fragment thereof of Embodiment 1, wherein the ultralong CDR3 comprises a non-human DH or a derivative thereof.

Embodiment 13

The humanized antibody or binding fragment thereof of Embodiment 12, wherein the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

Embodiment 14

The humanized antibody or binding fragment thereof of Embodiment 1, wherein the ultralong CDR3 comprises a JH sequence or a derivative thereof.

Embodiment 15

The humanized antibody or binding fragment thereof of Embodiment 14, wherein the JH sequence is SEQ ID NO: 13, SEQ ID NO: 14, SEQ ID NO: 15, SEQ ID NO: 16, or SEQ ID NO: 17.

Embodiment 16

The humanized antibody or binding fragment thereof of Embodiment 1, wherein the ultralong CDR3 comprises: a non-human VH sequence or a derivative thereof; a non-human DH sequence or a derivative thereof; and/or a JH sequence or derivative thereof.

Embodiment 17

The humanized antibody or binding fragment thereof of Embodiment 16, wherein the ultralong CDR3 comprises an additional amino acid sequence comprising two to six amino acid residues or more positioned between the VH sequence and the DH sequence.

Embodiment 18

The humanized antibody or binding fragment thereof of Embodiment 17, wherein the additional amino acid sequence is selected from the group consisting of: IR, IF, SEQ ID NO: 18, SEQ ID NO: 19, SEQ ID NO: 20 or SEQ ID NO: 21.

Embodiment 19

The humanized antibody or binding fragment thereof of Embodiment 1, wherein the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

Embodiment 20

The humanized antibody or binding fragment thereof of Embodiment 1, wherein the ultralong CDR3 comprises a non-bovine sequence or a non-antibody sequence.

Embodiment 21

The humanized antibody or binding fragment thereof of Embodiment 20, wherein the non-antibody sequence is a synthetic sequence.

Embodiment 22

The humanized antibody or binding fragment thereof of Embodiment 20, wherein the non-antibody sequence is a cytokine sequence, a lymphokine sequence, a chemokine sequence, a growth factor sequence, a hormone sequence, or a toxin sequence.

Embodiment 23

The humanized antibody or binding fragment thereof of Embodiment 20, wherein the non-antibody sequence is an IL-8 sequence, an IL-21 sequence, an SDF-1 (alpha) sequence, a somatostatin sequence, a chlorotoxin sequence, a Pro-TxII sequence, or a ziconotide sequence.

Embodiment 24

The humanized antibody or binding fragment thereof of Embodiment 20, wherein the non-antibody sequence is any one of SEQ ID NOS: 475-481.

Embodiment 25

The humanized antibody or binding fragment thereof of Embodiment 20, wherein the non-antibody sequence replaces at least a portion of the ultralong CDR3.

Embodiment 26

The humanized antibody or binding fragment thereof of Embodiment 1, wherein the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

Embodiment 27

The humanized antibody or binding fragment thereof of Embodiment 26, wherein the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

Embodiment 28

The humanized antibody or binding fragment thereof of Embodiment 1, wherein the ultralong CDR3 comprises a $CX^1X^2X^3X^4X^5$ motif.

Embodiment 29

The humanized antibody or binding fragment thereof of Embodiment 28, wherein the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

Embodiment 30

The humanized antibody or binding fragment thereof of Embodiment 1, wherein the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 31

The humanized antibody or binding fragment thereof of Embodiment 30, wherein the $(X^aX^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

Embodiment 32

The humanized antibody or binding fragment thereof of Embodiment 30, wherein the $(X^aX^b)_z$ motif is YXYXYX.

Embodiment 33

The humanized antibody or binding fragment thereof of Embodiment 1, wherein the ultralong CDR3 comprises a $X^1X^2X^3X^4X^5X_n$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), and wherein n is 27-54.

Embodiment 34

The humanized antibody or binding fragment thereof of Embodiment 1, wherein the ultralong CDR3 comprises $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 35

The humanized antibody or binding fragment thereof of Embodiment 1, wherein the ultralong CDR3 comprises a $X^1X^2X^3X^4X^5X_n(X^aX^b)_z$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 36

The humanized antibody or binding fragment thereof of Embodiment 35, wherein the $X^1X^2X^3X^4X^5$ motif is TTVHQ (SEQ ID NO: 153) or TSVHQ (SEQ ID NO: 154), and wherein the $(X^aX^b)_z$ motif is YXYXYX.

Embodiment 37

The humanized antibody or binding fragment thereof of Embodiment 1, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CXCX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 38

The humanized antibody or binding fragment thereof of Embodiment 1, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4C$ $CXCX_4CX_6CXC$ (SEQ ID NO: 97), $CX_7CXCX_5CX_4CCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_120$ (SEQ ID NO: 104), $CXCX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_5CX_7CX_4CXCX_2CX_5CX_2C$ (SEQ ID NO: 110), $CX_5CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX_5C$ (SEQ ID NO: 121), $CCX_9CX_3CXCCX_3CX_5C$ (SEQ ID NO: 122), $CX_9CX_2CX_3CX_4CCX_4CX_{54}CXC$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_5CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 39

The humanized antibody or binding fragment thereof of Embodiment 20, wherein the ultralong CDR3 comprises an additional sequence that is a linker.

Embodiment 40

The humanized antibody or binding fragment thereof of Embodiment 39, wherein the linker is linked to a C-terminus, a N-terminus, or both C-terminus and N-terminus of the non-antibody sequence.

Embodiment 41

The humanized antibody or binding fragment thereof of Embodiment 1, wherein the ultralong CDR3 is a ruminant CDR3.

Embodiment 42

The humanized antibody or binding fragment thereof of Embodiment 41, wherein the ruminant is a cow.

Embodiment 43

The humanized antibody or binding fragment thereof of Embodiment 1, wherein the humanized antibody or binding fragment thereof comprises a human heavy chain germline sequence that is a VH4 family member germline sequence.

Embodiment 44

The humanized antibody or binding fragment thereof of Embodiment 1, wherein the humanized antibody or binding fragment thereof comprises a VH4-34 germline sequence.

Embodiment 45

The humanized antibody or binding fragment thereof of Embodiment 44, wherein the humanized antibody or binding fragment thereof comprises a human heavy chain germline sequence that is derived from the VH4-34 germline sequence.

Embodiment 46

The humanized antibody or binding fragment thereof of Embodiment 45, wherein the VH4-34 germline sequence comprises a CDR1 comprising a Gly31Asp and Tyr32Lys substitution based on Kabat numbering.

Embodiment 47

The humanized antibody or binding fragment thereof of Embodiment 45, wherein the VH4-34 germline sequence comprises a CDR2 comprising a Glu50Ser substitution based on Kabat numbering.

Embodiment 48

The humanized antibody or binding fragment thereof of Embodiment 45, wherein the VH4-34 germline sequence comprises a CDR1 comprising Ala23Thr, Val24Ala, Tyr25Ser, Gly27Phe, Phe29Leu, Gly31Asp, Tyr32Lys, Tyr33Ala, Trp34Val, and Ser35Gly substitutions, and a CDR2 comprising Ile48Leu, Glu50Ser, Asn52Asp, His53Thr, Ser54Gly, Ser56Asn, and Asn58Gly substitutions, based on Kabat numbering.

Embodiment 49

The humanized antibody or binding fragment thereof of Embodiment 1, wherein the humanized antibody or binding fragment thereof comprises the amino acid sequence set forth in SEQ ID NO: 461, 462, 463, 464, 465, 466, 467, 468, or 469.

Embodiment 50

The humanized antibody or binding fragment thereof of Embodiment 1, wherein the humanized antibody or binding fragment thereof comprises the amino acid sequence set forth in SEQ ID NO: 470.

Embodiment 51

The humanized antibody or binding fragment thereof of Embodiment 1, wherein the humanized antibody or binding fragment thereof comprises the amino acid sequence set forth in SEQ ID NO: 461, 462, 463, 464, 465, 466, 467, 468, or 469; and the amino acid sequence set forth in SEQ ID NO: 470.

Embodiment 52

The humanized antibody or binding fragment thereof of Embodiment 1, wherein the humanized antibody or binding fragment thereof comprises the amino acid sequence set forth in SEQ ID NO: 461, 462, 463, 464, 465, 466, 467, 468, or 469; the amino acid sequence set forth in SEQ ID NO: 470; and a peptide sequence, wherein the peptide sequence is positioned between SEQ ID NO: 461, 462, 463, 464, 465, 466, 467, 468, or 469, and SEQ ID NO: 470.

Embodiment 53

The humanized antibody or binding fragment thereof of Embodiment 52, wherein the peptide sequence is a bovine sequence, a non-bovine sequence, an antibody sequence, or a non-antibody sequence.

Embodiment 54

The humanized antibody or binding fragment thereof of Embodiment 1, wherein the humanized antibody or binding fragment thereof comprises a light chain variable region sequence that is a lambda light chain variable region sequence.

Embodiment 55

The humanized antibody or binding fragment thereof of Embodiment 54, wherein the lambda light chain variable region sequence is a bovine lambda light chain variable region sequence.

Embodiment 56

The humanized antibody or binding fragment thereof of Embodiment 54, wherein the lambda light chain variable region sequence is a human lambda light chain variable region sequence.

Embodiment 57

The humanized antibody or binding fragment thereof of Embodiment 56, wherein the human lambda light chain variable region sequence is a VL1-51 germline sequence.

Embodiment 58

The humanized antibody or binding fragment thereof of Embodiment 56, wherein the human lambda light chain variable region sequence is derived from a VL1-51 germline sequence.

Embodiment 59

The humanized antibody or binding fragment thereof of Embodiment 58, wherein the VL1-51 germline sequence comprises a CDR1 comprising Ile29Val and Asn32Gly substitution based on Kabat numbering.

Embodiment 60

The humanized antibody or binding fragment thereof of Embodiment 58, wherein the VL1-51 germline sequence comprises a CDR2 comprising a substitution of DNN to GDT.

Embodiment 61

The humanized antibody or binding fragment thereof of Embodiment 58, wherein the VL1-51 germline sequence comprises a CDR2 comprising a substitution of DNNKRP (SEQ ID NO: 471) to GDTSRA (SEQ ID NO: 472).

Embodiment 62

The humanized antibody or binding fragment thereof of Embodiment 58, wherein the VL1-51 germline sequence comprises a S2A, T5N, P8S, A12G, A13S, and P14L substitution based on Kabat numbering.

Embodiment 63

The humanized antibody or binding fragment thereof of Embodiment 58, wherein the VL1-51 germline sequence comprises a S2A, T5N, P8S, A12G, A13S, and P14L substitution based on Kabat numbering, and a CDR2 comprising a substitution of DNN to GDT.

Embodiment 64

The humanized antibody or binding fragment thereof of Embodiment 1, wherein the humanized antibody or binding fragment thereof comprising the amino acid sequence set forth in SEQ ID NO: 440, 441, 442, 443, or 444.

Embodiment 65

A polynucleotide encoding the humanized antibody or binding fragment thereof of any one of Embodiments 1-64.

Embodiment 66

A polynucleotide encoding a humanized antibody or binding fragment thereof that comprises an ultralong CDR3.

Embodiment 67

A polynucleotide encoding a humanized variable region that comprises an ultralong CDR3.

Embodiment 68

A vector comprising the polynucleotide of any one of Embodiments 65-67.

Embodiment 69

A host cell comprising the vector of Embodiment 68.

Embodiment 70

A nucleic acid library comprising a plurality of polynucleotides comprising sequences coding for humanized antibodies or binding fragments thereof, wherein the antibodies or binding fragments thereof comprise an ultralong CDR3.

Embodiment 71

A library of humanized antibodies or binding fragments thereof, wherein the antibodies or binding fragments thereof comprise an ultralong CDR3. In some embodiments, the humanized antibodies or binding fragments thereof in the library comprise one or more human variable region framework sequences.

Embodiment 72

The library of Embodiment 71, wherein the ultralong CDR3 is 35 amino acids in length or longer, 40 amino acids in length or longer, 45 amino acids in length or longer, 50 amino acids in length or longer, 55 amino acids in length or longer, or 60 amino acids in length or longer.

Embodiment 73

The library of Embodiment 72, wherein the ultralong CDR3 is 35 amino acids in length or longer.

Embodiment 74

The library of Embodiment 71, wherein the ultralong CDR3 comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

Embodiment 75

The library of Embodiment 74, wherein the ultralong CDR3 comprises 3 or more cysteine residues.

Embodiment 76

The library of Embodiment 71, wherein the antibodies or binding fragments thereof comprise a cysteine motif.

Embodiment 77

The library of Embodiment 76, wherein the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

Embodiment 78

The library of Embodiment 76, wherein the cysteine motif is selected from the group consisting of: $CCX_3CXCX_3CX_2CCXCX_5CXCX_5CXC$ (SEQ ID NO: 96), $CX_6CX_2CX_5CX_4C\ CXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{12}C$ (SEQ ID NO: 104), $CXCX_2CX_3CCCX_4CX_5CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_5CX_3CX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX_5C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

Embodiment 79

The library of Embodiment 71, wherein the ultralong CDR3 comprises 2 to 6 disulfide bonds.

Embodiment 80

The library of Embodiment 71, wherein the ultralong CDR3 comprises SEQ ID NO: 40 or a derivative thereof.

Embodiment 81

The library of Embodiment 71, wherein the ultralong CDR3 comprises amino acid residues 3-6 of any of one SEQ ID NO: 1-4.

Embodiment 82

The library of Embodiment 71, wherein the ultralong CDR3 comprises a non-human DH or a derivative thereof.

Embodiment 83

The library of Embodiment 82, wherein the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12

Embodiment 84

The library of Embodiment 71, wherein the ultralong CDR3 comprises a JH sequence or a derivative thereof.

Embodiment 85

The library of Embodiment 84, wherein the JH sequence is SEQ ID NO: 13, SEQ ID NO: 14, SEQ ID NO: 15, SEQ ID NO: 16, or SEQ ID NO: 17.

Embodiment 86

The library of Embodiment 71, wherein the ultralong CDR3 comprises: a non-human VH sequence or a derivative thereof; a non-human DH sequence or a derivative thereof; and/or a JH sequence or derivative thereof.

Embodiment 87

The library of Embodiment 86, wherein the ultralong CDR3 comprises an additional amino acid sequence comprising two to six amino acid residues or more positioned between the VH sequence and the DH sequence.

Embodiment 88

The library of Embodiment 87, wherein the additional amino acid sequence is selected from the group consisting of: IR, IF, SEQ ID NO: 18, SEQ ID NO: 19, SEQ ID NO: 20 or SEQ ID NO: 21.

Embodiment 89

The library of Embodiment 88, wherein the ultralong CDR3 comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

Embodiment 90

The library of Embodiment 71, wherein the ultralong CDR3 comprises a non-bovine sequence or a non-antibody sequence.

Embodiment 91

The library of Embodiment 90, wherein the non-antibody sequence is a synthetic sequence.

Embodiment 92

The library of Embodiment 90, wherein the non-antibody sequence is a cytokine sequence, a lymphokine sequence, a chemokine sequence, a growth factor sequence, a hormone sequence, or a toxin sequence.

Embodiment 93

The library of Embodiment 90, wherein the non-antibody sequence is an IL-8 sequence, an IL-21 sequence, an SDF-1 (alpha) sequence, a somatostatin sequence, a chlorotoxin sequence, a Pro-TxII sequence, or a ziconotide sequence.

Embodiment 94

The library of Embodiment 90, wherein the non-antibody sequence is any one of SEQ ID NOS: 475-481.

Embodiment 95

The library of Embodiment 71, wherein the ultralong CDR3 comprises a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

Embodiment 96

The library of Embodiment 95, wherein the $X^1X^2X^3X^4X^5$ motif is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

Embodiment 97

The library of Embodiment 95, wherein the ultralong CDR3 comprises a $CX^1X^2X^3X^4X^5$ motif.

Embodiment 98

The library of Embodiment 97, wherein the $CX^1X^2X^3X^4X^5$ motif is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

Embodiment 99

The humanized antibody or binding fragment thereof of Embodiment 71, wherein the ultralong CDR3 comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 100

The humanized antibody or binding fragment thereof of Embodiment 99, wherein the $(X^a X^b)_z$ motif is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

Embodiment 101

The humanized antibody or binding fragment thereof of Embodiment 99, wherein the $(X^a X^b)_z$ motif is YXYXYX.

Embodiment 102

The library of Embodiment 71, wherein the ultralong CDR3 comprises a $X^1 X^2 X^3 X^4 X^5 X_n$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), and wherein n is 27-54.

Embodiment 103

The library of Embodiment 71, wherein the ultralong CDR3 comprises $X_n(X^a X^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 104

The library of Embodiment 71, wherein the ultralong CDR3 comprises a $X_1 X^2 X_3 X^4 X_5 X_n(X^a X^b)_z$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 105

The library of Embodiment 104, wherein the $X^1 X^2 X^3 X^4 X^5$ motif is TTVHQ (SEQ ID NO: 153) or TSVHQ (SEQ ID NO: 154), and wherein the $(X^a X^b)Z$ motif is YXYXYX.

Embodiment 106

The library of Embodiment 71, wherein the ultralong CDR3 comprises: a $CX^1 X^2 X^3 X^4 X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CXCXCXC$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and a $(X^aX^b)_z$ motif, $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 107

The library of Embodiment 71, wherein the ultralong CDR3 comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{12}C$ (SEQ ID NO: 104), $CX_6CX_2CXCCX_4CX_5CX_5CX_3CXC$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_5CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX$ (SEQ ID NO: 121), $CCX_9CX_3CXCCX_3CX_5C$ (SEQ ID NO: 122), $CX_9CX_2CX_3CX_4CCX_4CX_{54}CXC$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_5CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 108

The library of Embodiment 90, wherein the ultralong CDR3 comprises an additional sequence that is a linker.

Embodiment 109

The library of Embodiment 108, wherein the linker is linked to a C-terminus, a N-terminus, or both C-terminus and N-terminus of the non-antibody sequence.

Embodiment 110

The library of Embodiment 71, wherein the ultralong CDR3 is a ruminant CDR3.

Embodiment 111

The library of Embodiment 110, wherein the ruminant is a cow.

Embodiment 112

The library of Embodiment 71, wherein the humanized antibody or binding fragment thereof comprises a human heavy chain germline sequence that is a VH4 family member germline sequence.

Embodiment 113

The library of Embodiment 71, wherein the humanized antibody or binding fragment thereof comprises a VH4-34 germline sequence.

Embodiment 114

The library of Embodiment 71, wherein the humanized antibody or binding fragment thereof comprises a human heavy chain germline sequence that is derived from VH4-34.

Embodiment 115

The library of Embodiment 114, wherein the VH4-34 germline sequence comprises a CDR1 comprising a Gly31Asp and Tyr32Lys substitution based on Kabat numbering.

Embodiment 116

The library of Embodiment 114, wherein the VH4-34 germline sequence comprises a CDR2 comprising a Glu50Ser substitution based on Kabat numbering.

Embodiment 117

The library of Embodiment 114, wherein the VH4-34 germline sequence comprises a CDR1 comprising Ala23Thr, Val24Ala, Tyr25Ser, Gly27Phe, Phe29Leu, Gly31Asp, Tyr32Lys, Tyr33Ala, Trp34Val, and Ser35Gly substitutions, and a CDR2 comprising Ile48Leu, Glu50Ser, Asn52Asp, His53Thr, Ser54Gly, Ser56Asn, and Asn58Gly substitutions, based on Kabat numbering.

Embodiment 118

The library of Embodiment 71, wherein the humanized antibody or binding fragment thereof comprises the amino acid sequence set forth in SEQ ID NO: 470.

Embodiment 119

The library of Embodiment 71, wherein the humanized antibody or binding fragment thereof comprises the amino acid sequence set forth in SEQ ID NO: 461, 462, 463, 464, 465, 466, 467, 468, or 469; and the amino acid sequence set forth in SEQ ID NO: 470.

Embodiment 120

The library of Embodiment 71, wherein the humanized antibody or binding fragment thereof comprises the amino acid sequence set forth in SEQ ID NO: 461, 462, 463, 464, 465, 466, 467, 468, or 469; the amino acid sequence set forth in SEQ ID NO: 470; and a peptide sequence, wherein the peptide sequence is positioned between SEQ ID NO: 461, 462, 463, 464, 465, 466, 467, 468, or 469, and SEQ ID NO: 470.

Embodiment 121

The library of Embodiment 120, wherein the peptide sequence is a bovine sequence, a non-bovine sequence, an antibody sequence, or a non-antibody sequence.

Embodiment 122

The library of Embodiment 71, wherein the humanized antibody or binding fragment thereof comprises a light chain variable region sequence that is a lambda light chain variable region sequence.

Embodiment 123

The library of Embodiment 122, wherein the lambda light chain variable region sequence is a bovine lambda light chain variable region sequence.

Embodiment 124

The library of Embodiment 122, wherein the lambda light chain variable region sequence is a human lambda light chain variable region sequence.

Embodiment 125

The library of Embodiment 124, wherein the human lambda light chain variable region sequence is VL1-51.

Embodiment 126

The library of Embodiment 124, wherein the human lambda light chain variable region sequence is derived from VL1-51.

Embodiment 127

The library of Embodiment 126, wherein the VL1-51 germline sequence comprises a CDR1 comprising Ile29Val and Asn32Gly substitution based on Kabat numbering.

Embodiment 128

The library of Embodiment 126, wherein the VL1-51 germline sequence comprises a CDR2 comprising a substitution of DNN to GDT.

Embodiment 129

The library of Embodiment 126, wherein the VL1-51 germline sequence comprises a CDR2 comprising a substitution of DNNKRP (SEQ ID NO: 471) to GDTSRA (SEQ ID NO: 472).

Embodiment 130

The library of Embodiment 126, wherein the VL1-51 germline sequence comprises a S2A, T5N, P8S, A12G, A13S, and P14L substitution based on Kabat numbering.

Embodiment 131

The library of Embodiment 126, wherein the VL1-51 germline sequence comprises a S2A, T5N, P8S, A12G, A13S, and P14L substitution based on Kabat numbering, and a CDR2 comprising a substitution of DNN to GDT.

Embodiment 132

The library of Embodiment 71, wherein the humanized antibody or binding fragment thereof comprising the amino acid sequence set forth in SEQ ID NO: 440, 441, 442, 443, or 444.

Embodiment 133

The library of any one of Embodiments 71-132, wherein the humanized antibodies or binding fragments thereof are present in a spatially addressed format.

Embodiment 134

A method of humanizing an antibody variable region comprising the step of genetically combining a nucleic acid sequence encoding a non-human ultralong CDR3 with a nucleic acid sequence encoding a human variable region framework (FR) sequence.

Embodiment 135

A method of generating a library of humanized antibodies that comprises an ultralong CDR3, the method comprising: combining a nucleic acid sequence encoding an ultralong CDR3 with a nucleic acid sequence encoding a human variable region framework (FR) sequence to produce nucleic acids encoding for humanized antibodies that comprises an ultralong CDR3; and expressing the nucleic acids encoding for humanized antibodies that comprises an ultralong CDR3 to generate a library of humanized antibodies that comprises an ultralong CDR3.

Embodiment 136

A method of generating a library of humanized antibodies or binding fragments thereof comprising an ultralong CDR3 that comprises a non-antibody sequence, the method comprising: combining a nucleic acid sequence encoding an ultralong CDR3, a nucleic acid sequence encoding a human variable region framework (FR) sequence, and a nucleic acid sequence encoding a non-antibody sequence to produce nucleic acids encoding humanized antibodies or binding fragments thereof comprising an ultralong CDR3 and a non-antibody sequence, and expressing the nucleic acids encoding humanized antibodies or binding fragments thereof comprising an ultralong CDR3 and a non-antibody sequence to generate a library of humanized antibodies or binding fragments thereof comprising an ultralong CDR3 and a non-antibody sequence.

Embodiment 137

A library of humanized antibodies or binding fragments thereof comprising an ultralong CDR3 that comprises a non-antibody sequence.

Embodiment 138

A method of generating a library of humanized antibodies or binding fragments thereof comprising an ultralong CDR3 that comprises a cysteine motif, the method comprising: combining a human variable region framework (FR) sequence, and a nucleic acid sequence encoding an ultralong CDR3 and a cysteine motif; introducing one or more nucleotide changes to the nucleic acid sequence encoding one or more amino acid residues that are positioned between one or more cysteine residues in the cysteine motif for nucleotides encoding different amino acid residues to produce nucleic acids encoding humanized antibodies or binding fragments thereof comprising an ultralong CDR3 and a cysteine motif with one or more nucleotide changes introduced between one or more cysteine residues in the cysteine domain; and expressing the nucleic acids encoding humanized antibodies or binding fragments thereof comprising an ultralong CDR3 and a cysteine motif with one or more nucleotide changes introduced between one or more cysteine residues in the cysteine domain to generate a library of humanized antibodies or binding fragments thereof comprising an ultralong CDR3 and a cysteine motif with one or more amino acid changes introduced between one or more cysteine residues in the cysteine domain.

Embodiment 139

A library of humanized antibodies or binding fragments thereof comprising an ultralong CDR3 that comprises a cysteine motif, wherein the antibodies or binding fragments comprise one or more substitutions of amino acid residues that are positioned between cysteine residues in the cysteine motif.

Embodiment 140

A method of generating a library of humanized antibodies or binding fragments thereof comprising a bovine ultralong CDR3, the method comprising: combining a nucleic acid sequence encoding a human variable region framework (FR) sequence and a nucleic acid encoding a bovine ultralong CDR3, and expressing the nucleic acids encoding a human variable region framework (FR) sequence and a nucleic acid encoding a bovine ultralong CDR3 to generate a library of humanized antibodies or binding fragments thereof comprising a bovine ultralong CDR3.

Embodiment 141

A library of humanized antibodies or binding fragments thereof comprising a bovine ultralong CDR3.

Embodiment 142

A CDR3 scaffold comprising a $X^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q).

Embodiment 143

The CDR3 scaffold of Embodiment 142, wherein the CDR3 scaffold is 35 amino acids in length or longer, 40 amino acids in length or longer, 45 amino acids in length or longer, 50 amino acids in length or longer, 55 amino acids in length or longer, or 60 amino acids in length or longer.

Embodiment 144

The CDR3 scaffold of Embodiment 143, wherein the CDR3 scaffold is 35 amino acids in length or longer.

Embodiment 145

The CDR3 scaffold of Embodiment 143, wherein the CDR3 scaffold comprises 3 or more cysteine residues, 4 or more cysteine residues, 5 or more cysteine residues, 6 or more cysteine residues, 7 or more cysteine residues, 8 or more cysteine residues, 9 or more cysteine residues, 10 or more cysteine residues, 11 or more cysteine residues, or 12 or more cysteine residues.

Embodiment 146

The CDR3 scaffold of Embodiment 145, wherein the CDR3 scaffold comprises 3 or more cysteine residues.

Embodiment 147

The CDR3 scaffold of Embodiment 142, wherein the CDR3 scaffold comprises a cysteine motif.

Embodiment 148

The CDR3 scaffold of Embodiment 147, wherein the cysteine motif is selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CXCXCXC$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CX_8CX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CXCX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95).

Embodiment 149

The CDR3 scaffold of Embodiment 147, wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CXCXCXC$ (SEQ ID NO: 103), $CCX_6CCX_5CCCX_4CX_4CX_{12}C$ (SEQ ID NO: 104), $CX_6CX_2CX_3CCCX_4CX_3CX_3C$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_5CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCCX_4CX_9C$ (SEQ ID NO: 121), $CCX_9CX_3CXCCX_3CX_5C$ (SEQ ID NO: 122), $CX_9CX_2CX_3CX_4CCX_4CX_5C$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_5CX_5CX_4CCX_{14}C$ (SEQ ID NO: 135), $CX_5CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4X_4C$ (SEQ ID NO: 139), $CX_9CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152).

Embodiment 150

The CDR3 scaffold of Embodiment 142, wherein the CDR3 scaffold comprises 2 to 6 disulfide bonds.

Embodiment 151

The CDR3 scaffold of Embodiment 142, wherein the $X^1X^2X^3X^4X^5$ motif in the CDR3 scaffold is TTVHQ (SEQ ID NO: 153), TSVHQ (SEQ ID NO: 154), SSVTQ (SEQ ID NO: 155), STVHQ (SEQ ID NO: 156), ATVRQ (SEQ ID NO: 157), TTVYQ (SEQ ID NO: 158), SPVHQ (SEQ ID NO: 159), ATVYQ (SEQ ID NO: 160), TAVYQ (SEQ ID NO: 161), TNVHQ (SEQ ID NO: 162), ATVHQ (SEQ ID NO: 163), STVYQ (SEQ ID NO: 164), TIVHQ (SEQ ID NO: 165), AIVYQ (SEQ ID NO: 166), TTVFQ (SEQ ID NO: 167), AAVFQ (SEQ ID NO: 168), GTVHQ (SEQ ID NO: 169), ASVHQ (SEQ ID NO: 170), TAVFQ (SEQ ID NO: 171), ATVFQ (SEQ ID NO: 172), AAAHQ (SEQ ID NO: 173), VVVYQ (SEQ ID NO: 174), GTVFQ (SEQ ID NO: 175), TAVHQ (SEQ ID NO: 176), ITVHQ (SEQ ID NO: 177), ITAHQ (SEQ ID NO: 178), VTVHQ (SEQ ID NO: 179); AAVHQ (SEQ ID NO: 180), GTVYQ (SEQ ID NO: 181), TTVLQ (SEQ ID NO: 182), TTTHQ (SEQ ID NO: 183), or TTDYQ (SEQ ID NO: 184).

Embodiment 152

The CDR3 scaffold of Embodiment 142, wherein the CDR3 scaffold comprises a $CX^1X^2X^3X^4X^5$ motif.

Embodiment 153

The CDR3 scaffold of Embodiment 152, wherein the $CX^1X^2X^3X^4X^5$ motif in the CDR3 scaffold is CTTVHQ (SEQ ID NO: 185), CTSVHQ (SEQ ID NO: 186), CSSVTQ (SEQ ID NO: 187), CSTVHQ (SEQ ID NO: 188), CATVRQ (SEQ ID NO: 189), CTTVYQ (SEQ ID NO: 190), CSPVHQ (SEQ ID NO: 191), CATVYQ (SEQ ID NO: 192), CTAVYQ (SEQ ID NO: 193), CTNVHQ (SEQ ID NO: 194), CATVHQ (SEQ ID NO: 195), CSTVYQ (SEQ ID NO: 196), CTIVHQ (SEQ ID NO: 197), CAIVYQ (SEQ ID NO: 198), CTTVFQ (SEQ ID NO: 199), CAAVFQ (SEQ ID NO: 200), CGTVHQ (SEQ ID NO: 201), CASVHQ (SEQ ID NO: 202), CTAVFQ (SEQ ID NO: 203), CATVFQ (SEQ ID NO: 204), CAAAHQ (SEQ ID NO: 205), CVVVYQ (SEQ ID NO: 206), CGTVFQ (SEQ ID NO: 207), CTAVHQ (SEQ ID NO: 208), CITVHQ (SEQ ID NO: 209), CITAHQ (SEQ ID NO: 210), CVTVHQ (SEQ ID NO: 211); CAAVHQ (SEQ ID NO: 212), CGTVYQ (SEQ ID NO: 213), CTTVLQ (SEQ ID NO: 214), CTTTHQ (SEQ ID NO: 215), or CTTDYQ (SEQ ID NO: 216).

Embodiment 154

The CDR3 scaffold of Embodiment 142, wherein the CDR3 scaffold comprises a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 155

The CDR3 scaffold of Embodiment 154, wherein the $(X^aX^b)_z$ motif in the CDR3 scaffold is CYTYNYEF (SEQ ID NO: 217), HYTYTYDF (SEQ ID NO: 218), HYTYTYEW (SEQ ID NO: 219), KHRYTYEW (SEQ ID NO: 220), NYIYKYSF (SEQ ID NO: 221), PYIYTYQF (SEQ ID NO: 222), SFTYTYEW (SEQ ID NO: 223), SYIYIYQW (SEQ ID NO: 224), SYNYTYSW (SEQ ID NO: 225), SYSYSYEY (SEQ ID NO: 226), SYTYNYDF (SEQ ID NO: 227), SYTYNYEW (SEQ ID NO: 228), SYTYNYQF (SEQ ID NO: 229), SYVWTHNF (SEQ ID NO: 230), TYKYVYEW (SEQ ID NO: 231), TYTYTYEF (SEQ ID NO: 232), TYTYTYEW (SEQ ID NO: 233), VFTYTYEF (SEQ ID NO: 234), AYTYEW (SEQ ID NO: 235), DYIYTY (SEQ ID NO: 236), IHSYEF (SEQ ID NO: 237), SFTYEF (SEQ ID NO: 238), SHSYEF (SEQ ID NO: 239), THTYEF (SEQ ID NO: 240), TWTYEF (SEQ ID NO: 241), TYNYEW (SEQ ID NO: 242), TYSYEF (SEQ ID NO: 243), TYSYEH (SEQ ID NO: 244), TYTYDF (SEQ ID NO: 245), TYTYEF (SEQ ID NO: 246), TYTYEW (SEQ ID NO: 247), AYEF (SEQ ID NO: 248), AYSF (SEQ ID NO: 249), AYSY (SEQ ID NO: 250), CYSF (SEQ ID NO: 251), DYTY (SEQ ID NO: 252), KYEH (SEQ ID NO: 253), KYEW (SEQ ID NO: 254), MYEF (SEQ ID NO: 255), NWIY (SEQ ID NO: 256), NYDY (SEQ ID NO: 257), NYQW (SEQ ID NO: 258), NYSF (SEQ ID NO: 259), PYEW (SEQ ID NO: 260), RYNW (SEQ ID NO: 261), RYTY (SEQ ID NO: 262), SYEF (SEQ ID NO: 263), SYEH (SEQ ID NO: 264), SYEW (SEQ ID NO: 265), SYKW (SEQ ID NO: 266), SYTY (SEQ ID NO: 267), TYDF (SEQ ID NO: 268), TYEF (SEQ ID NO: 269), TYEW (SEQ ID NO: 270), TYQW (SEQ ID NO: 271), TYTY (SEQ ID NO: 272), or VYEW (SEQ ID NO: 273).

Embodiment 156

The CDR3 scaffold of Embodiment 154, wherein the $(X^aX^b)_z$ motif in the CDR3 scaffold is YXYXYX.

Embodiment 157

The CDR3 scaffold of Embodiment 142, wherein the CDR3 scaffold comprises a $X^1X^2X^3X^4X^5X_n$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q), and wherein n is 27-54.

Embodiment 158

The CDR3 scaffold of Embodiment 142, wherein the CDR3 scaffold comprises a $X_n(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 159

The CDR3 scaffold of Embodiment 142, wherein the CDR3 scaffold comprises a $X_1X^2X_3X^4X_5X_n(X^aX^b)_z$ motif, wherein $X_1$ is threonine (T), glycine (G), alanine (A), serine (S), or valine (V), wherein $X_2$ is serine (S), threonine (T), proline (P), isoleucine (I), alanine (A), valine (V), or asparagine (N), wherein $X_3$ is valine (V), alanine (A), threonine (T), or aspartic acid (D), wherein $X_4$ is histidine (H), threonine (T), arginine (R), tyrosine (Y), phenylalanine (F), or leucine (L), wherein $X_5$ is glutamine (Q), $X^a$ is any amino acid residue, $X^b$ is an aromatic amino acid selected from the group consisting of: tyrosine (Y), phenylalanine (F), tryptophan (W), and histidine (H), wherein n is 27-54, and wherein z is 1-4.

Embodiment 160

The CDR3 scaffold of Embodiment 159, wherein the $X^1X^2X^3X^4X^5$ motif in the CDR3 scaffold is TTVHQ (SEQ ID NO: 153) or TSVHQ (SEQ ID NO: 154), and wherein the $(X^aX^b)_z$ motif is YXYXYX.

Embodiment 161

The CDR3 scaffold of Embodiment 142, wherein the CDR3 scaffold comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: $CX_{10}CX_5CX_5CXCX_7C$ (SEQ ID NO: 41), $CX_{10}CX_6CX_5CXCX_{15}C$ (SEQ ID NO: 42), $CX_{11}CXCX_5C$ (SEQ ID NO: 43), $CX_{11}CX_5CX_5CXCX_7C$ (SEQ ID NO: 44), $CX_{10}CX_6CX_5CXCX_{13}C$ (SEQ ID NO: 45), $CX_{10}CX_5CXCX_4CX_8C$ (SEQ ID NO: 46), $CX_{10}CX_6CX_6CXCX_7C$ (SEQ ID NO: 47), $CX_{10}CX_4CX_7CXCX_8C$ (SEQ ID NO: 48), $CX_{10}CX_4CX_7CXCX_7C$ (SEQ ID NO: 49), $CX_{13}CX_8CX_8C$ (SEQ ID NO: 50), $CX_{10}CX_6CX_5CXCX_7C$ (SEQ ID NO: 51), $CX_{10}CX_5CX_5C$ (SEQ ID NO: 52), $CX_{10}CX_5CX_6CXCX_7C$ (SEQ ID NO: 53), $CX_{10}CX_6CX_5CX_7CX_9C$ (SEQ ID NO: 54), $CX_9CX_7CX_5CXCX_7C$ (SEQ ID NO: 55), $CX_{10}CX_6CX_5CXCX_9C$ (SEQ ID NO: 56), $CX_{10}CXCX_4CX_5CX_{11}C$ (SEQ ID NO: 57), $CX_7CX_3CX_6CX_5CXCX_5CX_{10}C$ (SEQ ID NO: 58), $CX_{10}CXCX_4CX_5CXCX_2CX_3C$ (SEQ ID NO: 59), $CX_{16}CX_5CXC$ (SEQ ID NO: 60), $CX_6CX_4CXCX_4CX_5C$ (SEQ ID NO: 61), $CX_{11}CX_4CX_5CX_6CX_3C$ (SEQ ID NO: 62), $CX_8CX_2CX_6CX_5C$ (SEQ ID NO: 63), $CX_{10}CX_5CX_5CXCX_{10}C$ (SEQ ID NO: 64), $CX_{10}CXCX_6CX_4CXC$ (SEQ ID NO: 65), $CX_{10}CX_5CX_5CXCX_2C$ (SEQ ID NO: 66), $CX_{14}CX_2CX_3CXCXC$ (SEQ ID NO: 67), $CX_{15}CX_5CXC$ (SEQ ID NO: 68), $CX_4CX_6CX_9CX_2CX_{11}C$ (SEQ ID NO: 69), $CX_6CX_4CX_5CX_5CX_{12}C$ (SEQ ID NO: 70), $CX_7CX_3CXCXCX_4CX_5CX_9C$ (SEQ ID NO: 71), $CX_{10}CX_6CX_5C$ (SEQ ID NO: 72), $CX_7CX_3CX_5CX_5CX_9C$ (SEQ ID NO: 73), $CX_7CX_5CXCX_2C$ (SEQ ID NO: 74), $CX_{10}CXCX_6C$ (SEQ ID NO: 75), $CX_{10}CX_3CX_3CX_5CX_7CXCX_6C$ (SEQ ID NO: 76), $CX_{10}CX_4CX_5CX_{12}CX_2C$ (SEQ ID NO: 77), $CX_{12}CX_4CX_5CXCXCX_9CX_3C$ (SEQ ID NO: 78), $CX_{12}CX_4CX_5CX_{12}CX_2C$ (SEQ ID NO: 79), $CX_{10}CX_6CX_5CXCX_{11}C$ (SEQ ID NO: 80), $CX_{16}CX_5CXCXCX_{14}C$ (SEQ ID NO: 81), $CX_{10}CX_5CXCX_8CX_6C$ (SEQ ID NO: 82), $CX_{12}CX_4CX_5CX_8CX_2C$ (SEQ ID NO: 83), $CX_{12}CX_5CX_5CXCX_8C$ (SEQ ID NO: 84), $CX_{10}CX_6CX_5CX_5CXCX_4CXCX_9C$ (SEQ ID NO: 85), $CX_{11}CX_4CX_5CX_8CX_2C$ (SEQ ID NO: 86), $CX_{10}CX_6CX_5CX_8CX_2C$ (SEQ ID NO: 87), $CX_{10}CX_6CX_5CXCX_8C$ (SEQ ID NO: 88), $CX_{10}CX_6CX_5CXCX_3CXCX_2C$ (SEQ ID NO: 89), $CX_{10}CX_6CX_5CX_3CX_8C$ (SEQ ID NO: 90), $CX_{10}CX_6CX_5CXCX_2CX_6CX_5C$ (SEQ ID NO: 91), $CX_7CX_6CX_3CX_3CX_9C$ (SEQ ID NO: 92), $CX_9CX_8CX_5CX_6CX_5C$ (SEQ ID NO: 93), $CX_{10}CX_2CX_2CX_7CXCX_{11}CX_5C$ (SEQ ID NO: 94), and $CX_{10}CX_6CX_5CXCX_2CX_8CX_4C$ (SEQ ID NO: 95); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 162

The CDR3 scaffold of Embodiment 142, wherein the CDR3 scaffold comprises: a $CX^1X^2X^3X^4X^5$ motif, wherein $X^1$ is threonine (T), glycine (G), alanine (A), serine (S), or valine (V), wherein $X^2$ is serine (S), threonine (T), proline (P), isoleucine (I), alanine (A), valine (V), or asparagine (N), wherein $X^3$ is valine (V), alanine (A), threonine (T), or aspartic acid (D), wherein $X^4$ is histidine (H), threonine (T), arginine (R), tyrosine (Y), phenylalanine (F), or leucine (L), and wherein $X^5$ is glutamine (Q); a cysteine motif selected from the group consisting of: wherein the cysteine motif is selected from the group consisting of: $CCX_3CXCX_3CX_2CCXCX_5CX_9CX_5CXC$ (SEQ ID NO: 96), $CX_6CX_2CX_5CX_4CCXCX_4CX_6CXC$ (SEQ ID NO: 97), $CX_7CXCX_5CX_4CCCX_4CX_6CXC$ (SEQ ID NO: 98), $CX_9CX_3CXCX_2CXCCCX_6CX_4C$ (SEQ ID NO: 99), $CX_5CX_3CXCX_4CX_4CCX_{10}CX_2CC$ (SEQ ID NO: 100), $CX_5CXCX_1CXCX_3CCX_3CX_4CX_{10}C$ (SEQ ID NO: 101), $CX_9CCCX_3CX_4CCCX_5CX_6C$ (SEQ ID NO: 102), $CCX_8CX_5CX_4CX_3CX_4CCXCX_1C$ (SEQ ID NO: 103), $CCX_6CCX_5CCCX_4CX_4CX_{12}C$ (SEQ ID NO: 104), $CX_6CX_2CX_3CCXCX_5CX_3CXC$ (SEQ ID NO: 105), $CX_3CX_5CX_6CX_4CCXCX_5CX_4CXC$ (SEQ ID NO: 106), $CX_4CX_4CCX_4CX_4CXCX_{11}CX_2CXC$ (SEQ ID NO: 107), $CX_5CX_2CCX_5CX_4CCX_3CCX_7C$ (SEQ ID NO: 108), $CX_5CX_5CX_3CX_2CXCCX_4CX_7CXC$ (SEQ ID NO: 109), $CX_3CX_7CX_3CX_4CCXCX_2CX_5CX_2C$ (SEQ ID NO: 110), $CX_9CX_3CXCX_4CCX_5CCCX_6C$ (SEQ ID NO: 111), $CX_9CX_3CXCX_2CXCCX_6CX_3CX_3C$ (SEQ ID NO: 112), $CX_8CCXCX_3CCX_3CXCX_3CX_4C$ (SEQ ID NO: 113), $CX_9CCX_4CX_2CXCCXCX_4CX_3C$ (SEQ ID NO: 114), $CX_{10}CXCX_3CX_2CXCCX_4CX_5CXC$ (SEQ ID NO: 115), $CX_9CXCX_3CX_2CXCCX_4CX_5CXC$ (SEQ ID NO: 116), $CX_6CCXCX_5CX_4CCXCX_5CX_2C$ (SEQ ID NO: 117), $CX_6CCXCX_3CXCCX_3CX_4CC$ (SEQ ID NO: 118), $CX_6CCXCX_3CXCX_2CXCX_4CX_8C$ (SEQ ID NO: 119), $CX_4CX_2CCX_3CXCX_4CCX_2CX_3C$ (SEQ ID NO: 120), $CX_3CX_5CX_3CCX_4CX_4CX_9C$ (SEQ ID NO: 121), $CCX_9CX_3CXCCX_3CX_5C$ (SEQ ID NO: 122), $CX_9CX_2CX_3CX_4CCX_4CX_{54}CXC$ (SEQ ID NO: 123), $CX_9CX_7CX_4CCXCX_7CX_3C$ (SEQ ID NO: 124), $CX_9CX_3CCCX_{10}CX_2CX_3C$ (SEQ ID NO: 125), $CX_3CX_5CX_5CX_4CCX_{10}CX_6C$ (SEQ ID NO: 126), $CX_9CX_5CX_4CCXCX_5CX_4C$ (SEQ ID NO: 127), $CX_7CXCX_6CX_4CCCX_{10}C$ (SEQ ID NO: 128), $CX_8CX_2CX_4CCX_4CX_3CX_3C$ (SEQ ID NO: 129), $CX_7CX_5CXCX_4CCX_7CX_4C$ (SEQ ID NO: 130), $CX_{11}CX_3CX_4CCCX_8CX_2C$ (SEQ ID NO: 131), $CX_2CX_3CX_4CCX_4CX_5CX_{15}C$ (SEQ ID NO: 132), $CX_9CX_5CX_4CCX_7C$ (SEQ ID NO: 133), $CX_9CX_7CX_3CX_2CX_6C$ (SEQ ID NO: 134), $CX_9CX_5CX_4CCX_{14}C$ (SEQ ID NO: 135), $CX_9CX_5CX_4CCX_8C$ (SEQ ID NO: 136), $CX_9CX_6CX_4CCXC$ (SEQ ID NO: 137), $CX_5CCX_7CX_4CX_{12}$ (SEQ ID NO: 138), $CX_{10}CX_3CX_4CX_4C$ (SEQ ID NO: 139), $CX_5CX_4CCX_5CX_4C$ (SEQ ID NO: 140), $CX_{10}CX_3CX_4CX_7CXC$ (SEQ ID NO: 141), $CX_7CX_7CX_2CX_2CX_3C$ (SEQ ID NO: 142), $CX_9CX_4CX_4CCX_6C$ (SEQ ID NO: 143), $CX_7CXCX_3CXCX_6C$ (SEQ ID NO: 144), $CX_7CXCX_4CXCX_4C$ (SEQ ID NO: 145), $CX_9CX_5CX_4C$ (SEQ ID NO: 146), $CX_3CX_6CX_8C$ (SEQ ID NO: 147), $CX_{10}CXCX_4C$ (SEQ ID NO: 148), $CX_{10}CCX_4C$ (SEQ ID NO: 149), $CX_{15}C$ (SEQ ID NO: 150), $CX_{10}C$ (SEQ ID NO: 151), and $CX_9C$ (SEQ ID NO: 152); and a $(X^aX^b)_z$ motif, wherein $X^a$ is any amino acid residue, $X^b$ is an aromatic amino acid selected from the group consisting of: tyrosine (Y), phenylalanine (F), tryptophan (W), and histidine (H), and wherein z is 1-4.

Embodiment 163

The CDR3 scaffold of Embodiment 142, wherein the CDR3 scaffold comprises SEQ ID NO: 40 or a derivative thereof.

Embodiment 164

The CDR3 scaffold of Embodiment 142, wherein the CDR3 scaffold comprises amino acid residues 3-6 of any of one SEQ ID NO: 1-4.

Embodiment 165

The CDR3 scaffold of Embodiment 142, wherein the CDR3 scaffold comprises a non-human DH or a derivative thereof.

Embodiment 166

The CDR3 scaffold of Embodiment 165, wherein the non-human DH is SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12

Embodiment 167

The CDR3 scaffold of Embodiment 142, wherein the CDR3 scaffold comprises a JH sequence or a derivative thereof.

Embodiment 168

The CDR3 scaffold of Embodiment 167, wherein the JH sequence is SEQ ID NO: 13, SEQ ID NO: 14, SEQ ID NO: 15, SEQ ID NO: 16, or SEQ ID NO: 17.

Embodiment 169

The CDR3 scaffold of Embodiment 142, wherein the CDR3 scaffold comprises: a non-human VH sequence or a derivative thereof; a non-human DH sequence or a derivative thereof; and/or a JH sequence or derivative thereof.

Embodiment 170

The CDR3 scaffold of Embodiment 169, wherein the CDR3 scaffold comprises an additional amino acid sequence comprising two to six amino acid residues or more positioned between the VH sequence and the DH sequence.

Embodiment 171

The CDR3 scaffold of Embodiment 170, wherein the additional amino acid sequence is selected from the group consisting of: IR, IF, SEQ ID NO: 18, SEQ ID NO: 19, SEQ ID NO: 20 or SEQ ID NO: 21.

Embodiment 172

The CDR3 scaffold of Embodiment 142, wherein the CDR3 scaffold comprises a sequence derived from or based on SEQ ID NO: 22, SEQ ID NO: 23, SEQ ID NO: 24, SEQ ID NO: 25, SEQ ID NO: 26, SEQ ID NO: 27, or SEQ ID NO: 28.

Embodiment 173

The CDR3 scaffold of Embodiment 142, wherein the CDR3 scaffold is a ruminant CDR3 scaffold.

Embodiment 174

The CDR3 scaffold of Embodiment 173, wherein the ruminant is a cow.

Embodiment 175

A library comprising the CDR3 scaffold of any one of Embodiments 142-174.

Embodiment 176

A polynucleotide encoding the CDR3 scaffold of any one of Embodiments 142-174.

Embodiment 177

A vector comprising the polynucleotide of Embodiment 176.

Embodiment 178

A host cell comprising the vector of Embodiment 177.

Embodiment 179

The host cell of Embodiment 178, wherein the cell is a bacteria, virus, or bacteriophage.

For the disclosure herein, the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the exemplary embodiments (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the exemplary embodiments and does not pose a limitation on the scope of the exemplary embodiments otherwise claimed. No language in the specification should be construed as indicating any non-claimed element essential to the practice of the exemplary embodiments.

Groupings of alternative elements or embodiments disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the exemplary embodiments. Of course, variations on these described embodiments will become apparent to those of ordinary skill in the art upon reading the foregoing description. The inventor expects skilled artisans to employ such variations as appropriate, and the inventors intend for the embodiments to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications. Each of the above-cited references is individually incorporated herein by reference in their entirety.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Exemplary embodiments so claimed are inherently or expressly described and enabled herein.

In closing, it is to be understood that the exemplary embodiments disclosed herein are illustrative of the principles of the present disclosure. Other modifications that can be employed are within the scope of the disclosure. Thus, by way of example, but not of limitation, alternative configurations of the present exemplary embodiments can be utilized in accordance with the teachings herein. Accordingly, the present exemplary embodiments are not limited to that precisely as shown and described.

The invention claimed is:

1. A humanized antibody or binding fragment thereof comprising a variable heavy chain comprising an ultralong CDR3 in which the CDR3 is replaced by a CDR3 scaffold which is 45 amino acids in length or longer and comprises a $X^1X^2X^3X^4X^5Xn(X^aX^b)z$ motif,
wherein the $X^1X^2X^3X^4X^5$ motif is TTVHQ (SEQ ID NO:153) or TSVHQ (SEQ ID NO:154),
wherein, for $X_n$, X is any amino acid and n is 27-54, and
wherein the $(X^aX^b)^z$ motif is YXYXYX with X being any amino acid.

2. The humanized antibody or binding fragment thereof of claim 1, wherein the ultralong CDR3 is 50 amino acids in length or longer.

3. The humanized antibody or binding fragment thereof of claim 1, wherein the ultralong CDR3 comprises 3 or more cysteine residues.

4. The humanized antibody or binding fragment thereof of claim 1, wherein the ultralong CDR3 comprises:
a non-human VH sequence or a derivative thereof;
a non-human DH sequence or a derivative thereof; and/or
a JH sequence or derivative thereof.

5. The humanized antibody or binding fragment thereof of claim 1, wherein the ultralong CDR3 comprises a non-bovine sequence or a non-antibody sequence.

6. The humanized antibody or binding fragment thereof of claim 1, wherein the humanized antibody or binding fragment thereof comprises the amino acid sequence set forth in SEQ ID NO: 461, 462, 463, 464, 465, 466, 467, 468, or 469 and the amino acid sequence set forth in SEQ ID NO: 470.

7. A library of humanized antibodies or binding fragments thereof, wherein the library comprises antibodies or binding fragments thereof of claim 1.

8. The humanized antibody or binding fragment thereof of claim 5, wherein the non-antibody sequence is a cytokine sequence, a lymphokine sequence, a chemokine sequence, a growth factor sequence, a hormone sequence, or a toxin sequence.

9. The humanized antibody or binding fragment thereof of claim 5, wherein the non-antibody sequence is an IL-8 sequence, an IL-21 sequence, an SDF-1 (alpha) sequence, a somatostatin sequence, a chlorotoxin sequence, a Pro-TxII sequence, or a ziconotide sequence.

10. The humanized antibody or binding fragment thereof of claim 5, wherein the ultralong CDR3 comprises an additional linker sequence, wherein the linker is linked to a C-terminus, a N-terminus, or both C-terminus and N-terminus of the non-antibody sequence.

11. The humanized antibody or binding fragment thereof of claim 1, wherein the humanized antibody or binding fragment thereof comprises the amino acid sequence set forth in SEQ ID NO: 461, 462, 463, 464, 465, 466, 467, 468, or 469; the amino acid sequence set forth in SEQ ID NO:470; and a peptide sequence, wherein the peptide sequence is positioned between SEQ ID NO: 461, 462, 463, 464, 465, 466, 467, 468, or 469, and SEQ ID NO: 470.

12. The humanized antibody or binding fragment thereof of claim 1, wherein the humanized antibody or binding fragment comprises a light chain variable region sequence that is a lambda light chain variable region sequence.

13. The humanized antibody or binding fragment thereof of claim 11, wherein the humanized antibody or binding fragment comprises a light chain variable region sequence that is a lambda light chain variable region sequence.

* * * * *

SEQUENCE LISTING

```
<160> NUMBER OF SEQ ID NOS: 485

<210> SEQ ID NO 1
<211> LENGTH: 6
<212> TYPE: PRT
<213> ORGANISM: Artificial sequence
<220> FEATURE:
<223> OTHER INFORMATION: Synthesized: VH sequence (germline, BLV5B8,
      BLV8C11, BF4E9, and F18)

<400> SEQUENCE: 1

Cys Thr Thr Val His Gln
1               5

<210> SEQ ID NO 2
<211> LENGTH: 6
<212> TYPE: PRT
<213> ORGANISM: Artificial sequence
<220> FEATURE:
<223> OTHER INFORMATION: Synthesized: VH sequence (BLV1H12)

<400> SEQUENCE: 2

Cys Thr Ser Val His Gln
1               5

<210> SEQ ID NO 3
<211> LENGTH: 6
<212> TYPE: PRT
<213> ORGANISM: Artificial sequence
<220> FEATURE:
<223> OTHER INFORMATION: Synthesized: VH sequence (BLV5D3)

<400> SEQUENCE: 3

Cys Ser Ser Val Thr Gln
1               5

<210> SEQ ID NO 4
<211> LENGTH: 6
<212> TYPE: PRT
```

```
<213> ORGANISM: Artificial sequence
<220> FEATURE:
<223> OTHER INFORMATION: Synthesized: VH sequence (BF1H1)

<400> SEQUENCE: 4

Cys Thr Thr Val His Pro
1               5

<210> SEQ ID NO 5
<211> LENGTH: 48
<212> TYPE: PRT
<213> ORGANISM: Artificial sequence
<220> FEATURE:
<223> OTHER INFORMATION: Synthesized: Germline sequence derived from DH2
      gene

<400> SEQUENCE: 5

Ser Cys Pro Asp Gly Tyr Ser Tyr Gly Tyr Cys Gly Tyr Gly Tyr
1               5                   10                  15

Gly Cys Ser Gly Tyr Asp Cys Tyr Gly Tyr Gly Gly Tyr Gly Gly Tyr
            20                  25                  30

Gly Gly Tyr Gly Tyr Ser Ser Tyr Ser Tyr Ser Tyr Thr Tyr Glu Tyr
        35                  40                  45

<210> SEQ ID NO 6
<211> LENGTH: 48
<212> TYPE: PRT
<213> ORGANISM: Artificial sequence
<220> FEATURE:
<223> OTHER INFORMATION: Synthesized: Sequence derived from DH gene
      (BLV1H12)

<400> SEQUENCE: 6

Ser Cys Pro Asp Gly Tyr Arg Glu Arg Ser Asp Cys Ser Asn Arg Pro
1               5                   10                  15

Ala Cys Gly Thr Ser Asp Cys Cys Arg Val Ser Val Phe Gly Asn Cys
            20                  25                  30

Leu Thr Thr Leu Pro Val Ser Tyr Ser Tyr Thr Tyr Asn Tyr Glu Trp
        35                  40                  45

<210> SEQ ID NO 7
<211> LENGTH: 44
<212> TYPE: PRT
<213> ORGANISM: Artificial sequence
<220> FEATURE:
<223> OTHER INFORMATION: Synthesized: Sequence derived from DH gene
      (BLV5B8)

<400> SEQUENCE: 7

Cys Ser Asp Gly Tyr Ile Ala Val Asp Ser Cys Gly Arg Gly Gln Ser
1               5                   10                  15

Asp Gly Cys Val Asn Asp Cys Asn Ser Cys Tyr Tyr Gly Trp Arg Asn
            20                  25                  30

Cys Arg Arg Gln Pro Ala Ile His Ser Tyr Glu Phe
        35                  40

<210> SEQ ID NO 8
<211> LENGTH: 44
<212> TYPE: PRT
<213> ORGANISM: Artificial sequence
<220> FEATURE:
<223> OTHER INFORMATION: Synthesized: Sequence derived from DH gene
      (BLV5D3)

<400> SEQUENCE: 8
```

Ser Cys Pro Asp Gly Cys Ser Asp Gly Asp Gly Cys Val Asp Gly Cys
1               5                   10                  15

Cys Cys Ser Ala Tyr Arg Cys Tyr Thr Pro Gly Val Arg Asp Leu Ser
            20                  25                  30

Cys Thr Ser Tyr Ser Ile Thr Tyr Thr Tyr Glu Trp
            35                  40

<210> SEQ ID NO 9
<211> LENGTH: 45
<212> TYPE: PRT
<213> ORGANISM: Artificial sequence
<220> FEATURE:
<223> OTHER INFORMATION: Synthesized: Sequence derived from DH gene
      (BLV8C11)

<400> SEQUENCE: 9

Cys Cys Ser Asp Ala Tyr Arg Tyr Asp Ser Gly Cys Gly Ser Gly Cys
1               5                   10                  15

Asp Cys Cys Gly Ala Asp Cys Tyr Val Phe Gly Ala Cys Thr Phe Gly
            20                  25                  30

Leu Asp Ser Ser Tyr Ser Tyr Ile Tyr Ile Tyr Gln Trp
            35                  40                  45

<210> SEQ ID NO 10
<211> LENGTH: 47
<212> TYPE: PRT
<213> ORGANISM: Artificial sequence
<220> FEATURE:
<223> OTHER INFORMATION: Synthesized: Sequence derived from DH gene
      (BF4E9)

<400> SEQUENCE: 10

Cys Pro Asp Gly Tyr Ser Tyr Gly Tyr Gly Cys Gly Tyr Gly Tyr Gly
1               5                   10                  15

Cys Ser Gly Tyr Asp Cys Tyr Gly Tyr Gly Tyr Gly Tyr Gly Gly
            20                  25                  30

Tyr Gly Gly Tyr Ser Ser Tyr Ser Tyr Ser Tyr Ser Tyr Glu Tyr
            35                  40                  45

<210> SEQ ID NO 11
<211> LENGTH: 44
<212> TYPE: PRT
<213> ORGANISM: Artificial sequence
<220> FEATURE:
<223> OTHER INFORMATION: Synthesized: Sequence derived from DH gene
      (BF1H1)

<400> SEQUENCE: 11

Ser Pro Asp Gly Tyr Ser Tyr Gly Tyr Gly Cys Gly Tyr Gly Tyr Gly
1               5                   10                  15

Cys Ser Gly Tyr Asp Cys Tyr Gly Tyr Gly Tyr Gly Tyr Gly Gly
            20                  25                  30

Tyr Gly Gly Tyr Ser Ser Tyr Ser Tyr Ser Tyr Ser
            35                  40

<210> SEQ ID NO 12
<211> LENGTH: 42
<212> TYPE: PRT
<213> ORGANISM: Artificial sequence
<220> FEATURE:
<223> OTHER INFORMATION: Synthesized: Sequence derived from DH gene
      (F18)

-continued

```
<400> SEQUENCE: 12

Cys Pro Asp Gly Tyr Gly Tyr Gly Tyr Gly Cys Gly Tyr Gly Ser Tyr
1               5                   10                  15

Gly Tyr Ser Gly Tyr Asp Cys Tyr Gly Tyr Gly Tyr Gly Tyr
            20                  25                  30

Gly Gly Tyr Gly Gly Tyr Ser Ser Tyr Ser
        35                  40

<210> SEQ ID NO 13
<211> LENGTH: 15
<212> TYPE: PRT
<213> ORGANISM: Artificial sequence
<220> FEATURE:
<223> OTHER INFORMATION: Synthesized: Germline sequence derived from JH1
      gene

<400> SEQUENCE: 13

Tyr Val Asp Ala Trp Gly Gln Gly Leu Leu Val Thr Val Ser Ser
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: Synthesized: Sequence derived from JH gene
      (BLV1H12)

<400> SEQUENCE: 14

His Val Asp Val Trp Gly Gln Gly Leu Leu Val Thr Val Ser Ser
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: Synthesized: Sequence derived from JH gene
      (BLV5B8)

<400> SEQUENCE: 15

His Val Asp Ala Trp Gly Arg Gly Leu Leu Val Thr Val Ser Ser
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Synthesized: Sequence derived from JH gene
      (BLV5D3)

<400> SEQUENCE: 16

Asn Val Asp Ala Trp Gly Arg Gly Leu Leu Val Thr Val Ser Ser
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Synthesized: Sequence derived from JH gene
      (BLV8C11 or BF4E9)

<400> SEQUENCE: 17

Tyr Gly Asp Ala Trp Gly Gln Gly Leu Leu Val Thr Val Ser Ser
```

<210> SEQ ID NO 18
<211> LENGTH: 6
<212> TYPE: PRT
<213> ORGANISM: Artificial sequence
<220> FEATURE:
<223> OTHER INFORMATION: Synthesized: Sequence derived from CDR3
      (BLV1H12)

<400> SEQUENCE: 18

Glu Thr Lys Lys Tyr Gln
1               5

<210> SEQ ID NO 19
<211> LENGTH: 5
<212> TYPE: PRT
<213> ORGANISM: Artificial sequence
<220> FEATURE:
<223> OTHER INFORMATION: Synthesized: Sequence derived from CDR3
      (BLV5B8)

<400> SEQUENCE: 19

Glu Thr Arg Lys Thr
1               5

<210> SEQ ID NO 20
<211> LENGTH: 6
<212> TYPE: PRT
<213> ORGANISM: Artificial sequence
<220> FEATURE:
<223> OTHER INFORMATION: Synthesized: Sequence derived from CDR3
      (BLV5D3)

<400> SEQUENCE: 20

Arg Thr His Val Ser Arg
1               5

<210> SEQ ID NO 21
<211> LENGTH: 6
<212> TYPE: PRT
<213> ORGANISM: Artificial sequence
<220> FEATURE:
<223> OTHER INFORMATION: Synthesized: Sequence derived from CDR3
      (BLV8C11)

<400> SEQUENCE: 21

Lys Thr Thr Arg Lys Thr
1               5

<210> SEQ ID NO 22
<211> LENGTH: 61
<212> TYPE: PRT
<213> ORGANISM: Artificial sequence
<220> FEATURE:
<223> OTHER INFORMATION: Synthesized: ultralong CDR3 sequence (BLV1H12)

<400> SEQUENCE: 22

Ser Val His Gln Glu Thr Lys Lys Tyr Gln Ser Cys Pro Asp Gly Tyr
1               5                   10                  15

Arg Glu Arg Ser Asp Cys Ser Asn Arg Pro Ala Cys Gly Thr Ser Asp
            20                  25                  30

Cys Cys Arg Val Ser Val Phe Gly Asn Cys Leu Thr Thr Leu Pro Val
        35                  40                  45

Ser Tyr Ser Tyr Thr Tyr Asn Tyr Glu Trp His Val Asp
    50                  55                  60

<210> SEQ ID NO 23
<211> LENGTH: 56
<212> TYPE: PRT
<213> ORGANISM: Artificial sequence
<220> FEATURE:
<223> OTHER INFORMATION: Synthesized: ultralong CDR3 sequence (BLV5B8)

<400> SEQUENCE: 23

```
Thr Val His Gln Glu Thr Arg Lys Thr Cys Ser Asp Gly Tyr Ile Ala
1               5                   10                  15

Val Asp Ser Cys Gly Arg Gly Gln Ser Asp Gly Cys Val Asn Asp Cys
            20                  25                  30

Asn Ser Cys Tyr Tyr Gly Trp Arg Asn Cys Arg Arg Gln Pro Ala Ile
        35                  40                  45

His Ser Tyr Glu Phe His Val Asp
    50                  55
```

<210> SEQ ID NO 24
<211> LENGTH: 57
<212> TYPE: PRT
<213> ORGANISM: Artificial sequence
<220> FEATURE:
<223> OTHER INFORMATION: Synthesized: ultralong CDR3 sequence (BLV5D3)

<400> SEQUENCE: 24

```
Ser Val Thr Gln Arg Thr His Val Ser Arg Ser Cys Pro Asp Gly Cys
1               5                   10                  15

Ser Asp Gly Asp Gly Cys Val Asp Gly Cys Cys Cys Ser Ala Tyr Arg
            20                  25                  30

Cys Tyr Thr Pro Gly Val Arg Asp Leu Ser Cys Thr Ser Tyr Ser Ile
        35                  40                  45

Thr Tyr Thr Tyr Glu Trp Asn Val Asp
    50                  55
```

<210> SEQ ID NO 25
<211> LENGTH: 58
<212> TYPE: PRT
<213> ORGANISM: Artificial sequence
<220> FEATURE:
<223> OTHER INFORMATION: Synthesized: ultralong CDR3 sequence (BLV8C11)

<400> SEQUENCE: 25

```
Thr Val His Gln Lys Thr Thr Arg Lys Thr Cys Cys Ser Asp Ala Tyr
1               5                   10                  15

Arg Tyr Asp Ser Gly Cys Gly Ser Gly Cys Asp Cys Cys Gly Ala Asp
            20                  25                  30

Cys Tyr Val Phe Gly Ala Cys Thr Phe Gly Leu Asp Ser Ser Tyr Ser
        35                  40                  45

Tyr Ile Tyr Ile Tyr Gln Trp Tyr Val Asp
    50                  55
```

<210> SEQ ID NO 26
<211> LENGTH: 56
<212> TYPE: PRT
<213> ORGANISM: Artificial sequence
<220> FEATURE:
<223> OTHER INFORMATION: Synthesized: ultralong CDR3 sequence (BF4E9)

<400> SEQUENCE: 26

```
Thr Val His Gln Ile Phe Cys Pro Asp Gly Tyr Ser Tyr Gly Tyr Gly
1               5                   10                  15
```

Cys Gly Tyr Gly Tyr Gly Cys Ser Gly Tyr Asp Cys Tyr Gly Tyr Gly
                20                  25                  30

Gly Tyr Gly Tyr Gly Gly Tyr Gly Tyr Ser Ser Tyr Ser Tyr Ser
            35                  40                  45

Tyr Ser Tyr Glu Tyr Tyr Gly Asp
        50                  55

<210> SEQ ID NO 27
<211> LENGTH: 48
<212> TYPE: PRT
<213> ORGANISM: Artificial sequence
<220> FEATURE:
<223> OTHER INFORMATION: Synthesized: ultralong CDR3 sequence (BF1H1)

<400> SEQUENCE: 27

Thr Val His Pro Ser Pro Asp Gly Tyr Ser Tyr Gly Tyr Gly Cys Gly
1               5                   10                  15

Tyr Gly Tyr Gly Cys Ser Gly Tyr Asp Cys Tyr Gly Tyr Gly Gly Tyr
                20                  25                  30

Gly Tyr Gly Gly Tyr Gly Gly Tyr Ser Ser Tyr Ser Tyr Ser Tyr Ser
            35                  40                  45

<210> SEQ ID NO 28
<211> LENGTH: 48
<212> TYPE: PRT
<213> ORGANISM: Artificial sequence
<220> FEATURE:
<223> OTHER INFORMATION: Synthesized: ultralong CDR3 sequence (F18)

<400> SEQUENCE: 28

Thr Val His Gln Ile Arg Cys Pro Asp Gly Tyr Gly Tyr Gly Tyr Gly
1               5                   10                  15

Cys Gly Tyr Gly Ser Tyr Gly Tyr Ser Gly Tyr Asp Cys Tyr Gly Tyr
                20                  25                  30

Gly Gly Tyr Gly Gly Tyr Gly Gly Tyr Gly Gly Tyr Ser Ser Tyr Ser
            35                  40                  45

<210> SEQ ID NO 29
<211> LENGTH: 100
<212> TYPE: PRT
<213> ORGANISM: Artificial sequence
<220> FEATURE:
<223> OTHER INFORMATION: Synthesized: exemplary heavy chain variable
      region sequence suitable for modification or use with an ultralong
      CDR3 sequence (VH-UL)

<400> SEQUENCE: 29

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
                20                  25                  30

Ala Val Gly Trp Val Arg Gln Ala Pro Gly Lys Ala Leu Glu Trp Leu
            35                  40                  45

Gly Gly Ile Asp Thr Gly Gly Ser Thr Gly Tyr Asn Pro Gly Leu Lys
        50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Thr Val His Gln

<210> SEQ ID NO 30
<211> LENGTH: 97
<212> TYPE: PRT
<213> ORGANISM: Artificial sequence
<220> FEATURE:
<223> OTHER INFORMATION: Synthesized: exemplary light chain variable
region sequence suitable for modification or use with an ultralong
CDR3 sequence (VL1X)

<400> SEQUENCE: 30

```
Gln Ala Val Leu Thr Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
    50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser
```

<210> SEQ ID NO 31
<211> LENGTH: 99
<212> TYPE: PRT
<213> ORGANISM: Artificial sequence
<220> FEATURE:
<223> OTHER INFORMATION: Synthesized: exemplary heavy chain variable
region sequence suitable for modification or use with an ultralong
CDR 3 sequence (VH4-39)

<400> SEQUENCE: 31

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg
```

<210> SEQ ID NO 32
<211> LENGTH: 96
<212> TYPE: PRT
<213> ORGANISM: Artificial sequence
<220> FEATURE:
<223> OTHER INFORMATION: Synthesized: Human germline heavy chain
variable region sequence 4-59*03

<400> SEQUENCE: 32

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

<210> SEQ ID NO 33
<211> LENGTH: 97
<212> TYPE: PRT
<213> ORGANISM: Artificial sequence
<220> FEATURE:
<223> OTHER INFORMATION: Synthesized: Human germline heavy chain
      variable region sequence 4-34*02

<400> SEQUENCE: 33

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 34
<211> LENGTH: 97
<212> TYPE: PRT
<213> ORGANISM: Artificial sequence
<220> FEATURE:
<223> OTHER INFORMATION: Synthesized: Human germline heavy chain
      variable region sequence 4-34*09

<400> SEQUENCE: 34

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

```
<210> SEQ ID NO 35
<211> LENGTH: 110
<212> TYPE: PRT
<213> ORGANISM: Artificial sequence
<220> FEATURE:
<223> OTHER INFORMATION: Synthsized: Bovine light chain variable region
      sequence BLV1H12

<400> SEQUENCE: 35

Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu
            100                 105                 110

<210> SEQ ID NO 36
<211> LENGTH: 98
<212> TYPE: PRT
<213> ORGANISM: Artificial sequence
<220> FEATURE:
<223> OTHER INFORMATION: Synthesized: Human germline light chain
      variable region sequence VL1-47

<400> SEQUENCE: 36

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly

<210> SEQ ID NO 37
<211> LENGTH: 99
<212> TYPE: PRT
<213> ORGANISM: Artificial sequence
<220> FEATURE:
<223> OTHER INFORMATION: Synthesized: Human germline light chain
      variable region sequence VL1-40*1

<400> SEQUENCE: 37

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

```
Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly
```

<210> SEQ ID NO 38
<211> LENGTH: 98
<212> TYPE: PRT
<213> ORGANISM: Artificial sequence
<220> FEATURE:
<223> OTHER INFORMATION: Synthesized: Human germline light chain
      variable region sequence VL1-51*01

<400> SEQUENCE: 38

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala
```

<210> SEQ ID NO 39
<211> LENGTH: 99
<212> TYPE: PRT
<213> ORGANISM: Artificial sequence
<220> FEATURE:
<223> OTHER INFORMATION: Synthesized: Human germline light chain
      variable region sequence VL2-18*02

<400> SEQUENCE: 39

```
Gln Ser Ala Leu Thr Gln Pro Pro Ser Val Ser Gly Ser Pro Gly Gln
 1               5                  10                  15

Ser Val Thr Ile Ser Cys Thr Gly Thr Ser Ser Asp Val Gly Ser Tyr
                 20                  25                  30

Asn Arg Val Ser Trp Tyr Gln Gln Pro Gly Thr Ala Pro Lys Leu
            35                  40                  45

Met Ile Tyr Glu Val Ser Asn Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Phe
```

<210> SEQ ID NO 40
<211> LENGTH: 4

```
<212> TYPE: PRT
<213> ORGANISM: Artificial sequence
<220> FEATURE:
<223> OTHER INFORMATION: Synthesized: optional sequence in ultralong
      CDR3
<220> FEATURE:
<221> NAME/KEY: MISC_FEATURE
<222> LOCATION: (1)..(1)
<223> OTHER INFORMATION: X is threonine or serine
<220> FEATURE:
<221> NAME/KEY: MISC_FEATURE
<222> LOCATION: (3)..(3)
<223> OTHER INFORMATION: X is histidine or threonine
<220> FEATURE:
<221> NAME/KEY: MISC_FEATURE
<222> LOCATION: (4)..(4)
<223> OTHER INFORMATION: X is glutamine or proline

<400> SEQUENCE: 40

Xaa Val Xaa Xaa
1

<210> SEQ ID NO 41
<211> LENGTH: 28
<212> TYPE: PRT
<213> ORGANISM: Artificial sequence
<220> FEATURE:
<223> OTHER INFORMATION: Synthesized: cysteine motif 1
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(27)
<223> OTHER INFORMATION: Xaa can be any naturally occurring amino acid

<400> SEQUENCE: 41

Cys Xaa Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Xaa Xaa Xaa Cys
            20                  25

<210> SEQ ID NO 42
<211> LENGTH: 43
<212> TYPE: PRT
<213> ORGANISM: Artificial sequence
<220> FEATURE:
<223> OTHER INFORMATION: Synthesized: cysteine motif 2
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
```

<221> NAME/KEY: misc_feature
<222> LOCATION: (28)..(42)
<223> OTHER INFORMATION: Xaa can be any naturally occurring amino acid

<400> SEQUENCE: 42

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Xaa Xaa Xaa Xaa Xaa Xaa Xaa Cys
        35                  40

<210> SEQ ID NO 43
<211> LENGTH: 21
<212> TYPE: PRT
<213> ORGANISM: Artificial sequence
<220> FEATURE:
<223> OTHER INFORMATION: Synthesized: cysteine motif 3
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(20)
<223> OTHER INFORMATION: Xaa can be any naturally occurring amino acid

<400> SEQUENCE: 43

Cys Xaa Xaa Xaa Xaa Xaa Xaa Xaa Xaa Xaa Xaa Cys Xaa Cys Xaa
1               5                   10                  15

Xaa Xaa Xaa Xaa Cys
            20

<210> SEQ ID NO 44
<211> LENGTH: 35
<212> TYPE: PRT
<213> ORGANISM: Artificial sequence
<220> FEATURE:
<223> OTHER INFORMATION: Synthesized: cysteine motif 4
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaa can be any naturally occurring amino acid

<400> SEQUENCE: 44

Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35

<210> SEQ ID NO 45
<211> LENGTH: 41
<212> TYPE: PRT
<213> ORGANISM: Artificial sequence
<220> FEATURE:
<223> OTHER INFORMATION: Synthesized: cysteine motif 5
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(40)
<223> OTHER INFORMATION: Xaa can be any naturally occurring amino acid

<400> SEQUENCE: 45

Cys Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Xaa Xaa Xaa Xaa Cys
        35                  40

<210> SEQ ID NO 46
<211> LENGTH: 34
<212> TYPE: PRT
<213> ORGANISM: Artificial sequence
<220> FEATURE:
<223> OTHER INFORMATION: Synthesized: cysteine motif 6
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(24)
<223> OTHER INFORMATION: Xaa can be any naturally occurring amino acid
<220> FEATURE:
<221> NAME/KEY: misc_feature
<222> LOCATION: (26)..(33)
<223> OTHER INFORMATION: Xaa can be any naturally occurring amino acid

<400> SEQUENCE: 46

Cys Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Cys Xaa Xaa Xaa Xaa Xaa Xaa
        20                  25                  30

Xaa Cys

```
<210> SEQ ID NO 47
<211> LENGTH: 36
<212> TYPE: PRT
<213> ORGANISM: Artificial sequence
<220> FEATURE:
<223> OTHER INFORMATION: Synthesized: cysteine motif 7
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(35)
<223> OTHER INFORMATION: Xaa can be any naturally occurring amino acid

<400> SEQUENCE: 47

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Xaa Cys Xaa Cys Xaa Xaa Xaa Xaa
                20                  25                  30

Xaa Xaa Xaa Cys
        35

<210> SEQ ID NO 48
<211> LENGTH: 36
<212> TYPE: PRT
<213> ORGANISM: Artificial sequence
<220> FEATURE:
<223> OTHER INFORMATION: Synthesized: cysteine motif 8
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid

<400> SEQUENCE: 48

Cys Xaa Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa Xaa
                20                  25                  30

Xaa Xaa Xaa Cys
        35
```

```
<210> SEQ ID NO 49
<211> LENGTH: 35
<212> TYPE: PRT
<213> ORGANISM: Artificial sequence
<220> FEATURE:
<223> OTHER INFORMATION: Synthesized: cysteine motif 9
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaa can be any naturally occurring amino acid

<400> SEQUENCE: 49

Cys Xaa Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa Xaa
            20                  25                  30

Xaa Xaa Cys
        35

<210> SEQ ID NO 50
<211> LENGTH: 33
<212> TYPE: PRT
<213> ORGANISM: Artificial sequence
<220> FEATURE:
<223> OTHER INFORMATION: Synthesized: cysteine motif 10
<220> FEATURE:
<221> NAME/KEY: misc_feature
<222> LOCATION: (2)..(14)
<223> OTHER INFORMATION: Xaa can be any naturally occurring amino acid
<220> FEATURE:
<221> NAME/KEY: misc_feature
<222> LOCATION: (16)..(23)
<223> OTHER INFORMATION: Xaa can be any naturally occurring amino acid
<220> FEATURE:
<221> NAME/KEY: misc_feature
<222> LOCATION: (25)..(32)
<223> OTHER INFORMATION: Xaa can be any naturally occurring amino acid

<400> SEQUENCE: 50

Cys Xaa Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Cys Xaa Xaa Xaa Xaa Xaa Xaa Xaa Xaa
            20                  25                  30

Cys

<210> SEQ ID NO 51
<211> LENGTH: 35
<212> TYPE: PRT
<213> ORGANISM: Artificial sequence
<220> FEATURE:
<223> OTHER INFORMATION: Synthesized: cysteine motif 11
<220> FEATURE:
<221> NAME/KEY: misc_feature
<222> LOCATION: (2)..(11)
```

```
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaa can be any naturally occurring amino acid

<400> SEQUENCE: 51

Cys Xaa Xaa Xaa Xaa Xaa Xaa Xaa Xaa Xaa Cys Xaa Xaa Xaa Xaa
 1               5                  10                  15

Xaa Xaa Cys Xaa Xaa Xaa Xaa Xaa Cys Xaa Cys Xaa Xaa Xaa Xaa Xaa
             20                  25                  30

Xaa Xaa Cys
         35

<210> SEQ ID NO 52
<211> LENGTH: 24
<212> TYPE: PRT
<213> ORGANISM: Artificial sequence
<220> FEATURE:
<223> OTHER INFORMATION: Synthesized: cysteine motif 12
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid

<400> SEQUENCE: 52

Cys Xaa Xaa Xaa Xaa Xaa Xaa Xaa Xaa Xaa Xaa Cys Xaa Xaa Xaa Xaa
 1               5                  10                  15

Xaa Cys Xaa Xaa Xaa Xaa Xaa Cys
             20

<210> SEQ ID NO 53
<211> LENGTH: 35
<212> TYPE: PRT
<213> ORGANISM: Artificial sequence
<220> FEATURE:
<223> OTHER INFORMATION: Synthesized: cysteine motif 13
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(24)
<223> OTHER INFORMATION: Xaa can be any naturally occurring amino acid
<220> FEATURE:
<221> NAME/KEY: misc_feature
<222> LOCATION: (26)..(26)
```

<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaa can be any naturally occurring amino acid

<400> SEQUENCE: 53

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Xaa Cys Xaa Cys Xaa Xaa Xaa Xaa Xaa
            20                  25                  30

Xaa Xaa Cys
        35

<210> SEQ ID NO 54
<211> LENGTH: 43
<212> TYPE: PRT
<213> ORGANISM: Artificial sequence
<220> FEATURE:
<223> OTHER INFORMATION: Synthesized: cysteine motif 14
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(32)
<223> OTHER INFORMATION: Xaa can be any naturally occurring amino acid
<220> FEATURE:
<221> NAME/KEY: misc_feature
<222> LOCATION: (34)..(42)
<223> OTHER INFORMATION: Xaa can be any naturally occurring amino acid

<400> SEQUENCE: 54

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Cys Xaa Xaa Xaa Xaa Xaa Xaa Xaa Xaa Xaa Cys
        35                  40

<210> SEQ ID NO 55
<211> LENGTH: 35
<212> TYPE: PRT
<213> ORGANISM: Artificial sequence
<220> FEATURE:
<223> OTHER INFORMATION: Synthesized: cysteine motif 15
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

```
<220> FEATURE:
<221> NAME/KEY: misc_feature
<222> LOCATION: (28)..(34)
<223> OTHER INFORMATION: Xaa can be any naturally occurring amino acid

<400> SEQUENCE: 55

Cys Xaa Xaa Xaa Xaa Xaa Xaa Xaa Xaa Cys Xaa Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Cys
        35

<210> SEQ ID NO 56
<211> LENGTH: 37
<212> TYPE: PRT
<213> ORGANISM: Artificial sequence
<220> FEATURE:
<223> OTHER INFORMATION: Synthesized: cysteine motif 16
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(36)
<223> OTHER INFORMATION: Xaa can be any naturally occurring amino acid

<400> SEQUENCE: 56

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Cys
        35

<210> SEQ ID NO 57
<211> LENGTH: 37
<212> TYPE: PRT
<213> ORGANISM: Artificial sequence
<220> FEATURE:
<223> OTHER INFORMATION: Synthesized: cysteine motif 17
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
```

<221> NAME/KEY: misc_feature
<222> LOCATION: (26)..(36)
<223> OTHER INFORMATION: Xaa can be any naturally occurring amino acid

<400> SEQUENCE: 57

Cys Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Cys Xaa Xaa Xaa Xaa Xaa Xaa Xaa
            20                  25                  30

Xaa Xaa Xaa Xaa Cys
            35

<210> SEQ ID NO 58
<211> LENGTH: 45
<212> TYPE: PRT
<213> ORGANISM: Artificial sequence
<220> FEATURE:
<223> OTHER INFORMATION: Synthesized: cysteine motif 18
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (35)..(44)
<223> OTHER INFORMATION: Xaa can be any naturally occurring amino acid

<400> SEQUENCE: 58

Cys Xaa Xaa Xaa Xaa Xaa Xaa Xaa Cys Xaa Xaa Xaa Cys Xaa Xaa
1               5                   10                  15

Xaa Xaa Xaa Cys Xaa Xaa Xaa Xaa Cys Xaa Cys Xaa Xaa Xaa Xaa
            20                  25                  30

Xaa Cys Xaa Xaa Xaa Xaa Xaa Xaa Xaa Xaa Xaa Xaa Cys
        35                  40                  45

<210> SEQ ID NO 59
<211> LENGTH: 34
<212> TYPE: PRT
<213> ORGANISM: Artificial sequence
<220> FEATURE:
<223> OTHER INFORMATION: Synthesized: cysteine motif 19
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature

```
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(33)
<223> OTHER INFORMATION: Xaa can be any naturally occurring amino acid

<400> SEQUENCE: 59

Cys Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Cys

<210> SEQ ID NO 60
<211> LENGTH: 26
<212> TYPE: PRT
<213> ORGANISM: Artificial sequence
<220> FEATURE:
<223> OTHER INFORMATION: Synthesized: cysteine motif 20
<220> FEATURE:
<221> NAME/KEY: misc_feature
<222> LOCATION: (2)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 60

Cys Xaa Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys
            20                  25

<210> SEQ ID NO 61
<211> LENGTH: 26
<212> TYPE: PRT
<213> ORGANISM: Artificial sequence
<220> FEATURE:
<223> OTHER INFORMATION: Synthesized: cysteine motif 21
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(19)
```

```
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid

<400> SEQUENCE: 61

Cys Xaa Xaa Xaa Xaa Xaa Xaa Cys Xaa Xaa Xaa Xaa Cys Xaa Cys Xaa
1               5                   10                  15

Xaa Xaa Xaa Cys Xaa Xaa Xaa Xaa Xaa Cys
            20                  25

<210> SEQ ID NO 62
<211> LENGTH: 35
<212> TYPE: PRT
<213> ORGANISM: Artificial sequence
<220> FEATURE:
<223> OTHER INFORMATION: Synthesized: cysteine motif 22
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(30)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid

<400> SEQUENCE: 62

Cys Xaa Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Cys Xaa
            20                  25                  30

Xaa Xaa Cys
        35

<210> SEQ ID NO 63
<211> LENGTH: 26
<212> TYPE: PRT
<213> ORGANISM: Artificial sequence
<220> FEATURE:
<223> OTHER INFORMATION: Synthesized: cysteine motif 23
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid

<400> SEQUENCE: 63
```

```
Cys Xaa Xaa Xaa Xaa Xaa Xaa Xaa Cys Xaa Xaa Cys Xaa Xaa Xaa
1               5                   10                  15

Xaa Xaa Xaa Cys Xaa Xaa Xaa Xaa Xaa Cys
            20                  25
```

<210> SEQ ID NO 64
<211> LENGTH: 37
<212> TYPE: PRT
<213> ORGANISM: Artificial sequence
<220> FEATURE:
<223> OTHER INFORMATION: Synthesized: cysteine motif 24
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(36)
<223> OTHER INFORMATION: Xaa can be any naturally occurring amino acid

<400> SEQUENCE: 64

```
Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa
            20                  25                  30

Xaa Xaa Xaa Xaa Cys
            35
```

<210> SEQ ID NO 65
<211> LENGTH: 28
<212> TYPE: PRT
<213> ORGANISM: Artificial sequence
<220> FEATURE:
<223> OTHER INFORMATION: Synthesized: cysteine motif 25
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(20)
<223> OTHER INFORMATION: Xaa can be any naturally occurring amino acid
<220> FEATURE:
<221> NAME/KEY: misc_feature
<222> LOCATION: (22)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 65

```
Cys Xaa Xaa Xaa Xaa Xaa Xaa Xaa Xaa Xaa Cys Xaa Cys Xaa Xaa
1               5                   10                  15

Xaa Xaa Xaa Xaa Cys Xaa Xaa Xaa Xaa Cys Xaa Cys
```

20              25

<210> SEQ ID NO 66
<211> LENGTH: 29
<212> TYPE: PRT
<213> ORGANISM: Artificial sequence
<220> FEATURE:
<223> OTHER INFORMATION: Synthesized: cysteine motif 26
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid

<400> SEQUENCE: 66

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Cys
            20                  25

<210> SEQ ID NO 67
<211> LENGTH: 27
<212> TYPE: PRT
<213> ORGANISM: Artificial sequence
<220> FEATURE:
<223> OTHER INFORMATION: Synthesized: cysteine motif 27
<220> FEATURE:
<221> NAME/KEY: misc_feature
<222> LOCATION: (2)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 67

Cys Xaa Xaa Xaa Xaa Xaa Xaa Xaa Xaa Xaa Xaa Xaa Xaa Xaa Xaa Cys
1               5                   10                  15

Xaa Xaa Cys Xaa Xaa Xaa Cys Xaa Cys Xaa Cys
            20                  25

<210> SEQ ID NO 68
<211> LENGTH: 25
<212> TYPE: PRT
<213> ORGANISM: Artificial sequence -continued

```
<220> FEATURE:
<223> OTHER INFORMATION: Synthesized: cysteine motif 28
<220> FEATURE:
<221> NAME/KEY: misc_feature
<222> LOCATION: (2)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 68

Cys Xaa Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Cys Xaa Cys
            20                  25

<210> SEQ ID NO 69
<211> LENGTH: 38
<212> TYPE: PRT
<213> ORGANISM: Artificial sequence
<220> FEATURE:
<223> OTHER INFORMATION: Synthesized: cysteine motif 29
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(12)
<223> OTHER INFORMATION: Xaa can be any naturally occurring amino acid
<220> FEATURE:
<221> NAME/KEY: misc_feature
<222> LOCATION: (14)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(37)
<223> OTHER INFORMATION: Xaa can be any naturally occurring amino acid

<400> SEQUENCE: 69

Cys Xaa Xaa Xaa Xaa Cys Xaa Xaa Xaa Xaa Xaa Xaa Cys Xaa Xaa Xaa
1               5                   10                  15

Xaa Xaa Xaa Xaa Xaa Xaa Cys Xaa Cys Xaa Xaa Xaa Xaa Xaa Xaa Xaa
            20                  25                  30

Xaa Xaa Xaa Xaa Xaa Cys
        35

<210> SEQ ID NO 70
<211> LENGTH: 38
<212> TYPE: PRT
<213> ORGANISM: Artificial sequence
<220> FEATURE:
<223> OTHER INFORMATION: Synthesized: cysteine motif 30
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
```

```
<222> LOCATION: (14)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(37)
<223> OTHER INFORMATION: Xaa can be any naturally occurring amino acid

<400> SEQUENCE: 70

Cys Xaa Xaa Xaa Xaa Xaa Xaa Cys Xaa Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Xaa Xaa Xaa Cys
        35

<210> SEQ ID NO 71
<211> LENGTH: 38
<212> TYPE: PRT
<213> ORGANISM: Artificial sequence
<220> FEATURE:
<223> OTHER INFORMATION: Synthesized: cysteine motif 31
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (23)..(27)
<223> OTHER INFORMATION: Xaa can be any naturally occurring amino acid
<220> FEATURE:
<221> NAME/KEY: misc_feature
<222> LOCATION: (29)..(37)
<223> OTHER INFORMATION: Xaa can be any naturally occurring amino acid

<400> SEQUENCE: 71

Cys Xaa Xaa Xaa Xaa Xaa Xaa Xaa Cys Xaa Xaa Xaa Cys Xaa Cys Xaa
1               5                   10                  15

Cys Xaa Xaa Xaa Xaa Cys Xaa Xaa Xaa Xaa Cys Xaa Xaa Xaa Xaa Xaa
            20                  25                  30

Xaa Xaa Xaa Xaa Xaa Cys
        35

<210> SEQ ID NO 72
<211> LENGTH: 25
<212> TYPE: PRT
<213> ORGANISM: Artificial sequence
<220> FEATURE:
<223> OTHER INFORMATION: Synthesized: cysteine motif 32
<220> FEATURE:
<221> NAME/KEY: misc_feature
<222> LOCATION: (2)..(11)
```

```
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid

<400> SEQUENCE: 72

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys
            20                  25

<210> SEQ ID NO 73
<211> LENGTH: 35
<212> TYPE: PRT
<213> ORGANISM: Artificial sequence
<220> FEATURE:
<223> OTHER INFORMATION: Synthesized: cysteine motif 33
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (14)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(34)
<223> OTHER INFORMATION: Xaa can be any naturally occurring amino acid

<400> SEQUENCE: 73

Cys Xaa Xaa Xaa Xaa Xaa Xaa Xaa Cys Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Xaa Cys
        35

<210> SEQ ID NO 74
<211> LENGTH: 20
<212> TYPE: PRT
<213> ORGANISM: Artificial sequence
<220> FEATURE:
<223> OTHER INFORMATION: Synthesized: cysteine motif 34
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
```

<223> OTHER INFORMATION: Xaa can be any naturally occurring amino acid

<400> SEQUENCE: 74

Cys Xaa Xaa Xaa Xaa Xaa Xaa Xaa Cys Xaa Xaa Xaa Xaa Cys Xaa
1               5                   10                  15

Cys Xaa Xaa Cys
            20

<210> SEQ ID NO 75
<211> LENGTH: 21
<212> TYPE: PRT
<213> ORGANISM: Artificial sequence
<220> FEATURE:
<223> OTHER INFORMATION: Synthesized: cysteine motif 35
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(20)
<223> OTHER INFORMATION: Xaa can be any naturally occurring amino acid

<400> SEQUENCE: 75

Cys Xaa Xaa Xaa Xaa Xaa Xaa Xaa Xaa Xaa Cys Xaa Cys Xaa Xaa
1               5                   10                  15

Xaa Xaa Xaa Xaa Cys
            20

<210> SEQ ID NO 76
<211> LENGTH: 43
<212> TYPE: PRT
<213> ORGANISM: Artificial sequence
<220> FEATURE:
<223> OTHER INFORMATION: Synthesized: cysteine motif 36
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid
<220> FEATURE:
<221> NAME/KEY: misc_feature
<222> LOCATION: (27)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(42)
<223> OTHER INFORMATION: Xaa can be any naturally occurring amino acid

<400> SEQUENCE: 76

Cys Xaa Xaa Xaa Xaa Xaa Xaa Xaa Xaa Xaa Xaa Cys Xaa Xaa Xaa Cys
1               5                   10                  15

```
Xaa Xaa Xaa Cys Xaa Xaa Xaa Xaa Cys Xaa Xaa Xaa Xaa Xaa
            20                  25                  30

Xaa Cys Xaa Cys Xaa Xaa Xaa Xaa Xaa Xaa Cys
        35                  40
```

<210> SEQ ID NO 77
<211> LENGTH: 39
<212> TYPE: PRT
<213> ORGANISM: Artificial sequence
<220> FEATURE:
<223> OTHER INFORMATION: Synthesized: cysteine motif 37
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid
<220> FEATURE:
<221> NAME/KEY: misc_feature
<222> LOCATION: (24)..(35)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid

<400> SEQUENCE: 77

```
Cys Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Cys Xaa Xaa Xaa Xaa Xaa Xaa Xaa Xaa
            20                  25                  30

Xaa Xaa Xaa Cys Xaa Xaa Cys
        35
```

<210> SEQ ID NO 78
<211> LENGTH: 43
<212> TYPE: PRT
<213> ORGANISM: Artificial sequence
<220> FEATURE:
<223> OTHER INFORMATION: Synthesized: cysteine motif 38
<220> FEATURE:
<221> NAME/KEY: misc_feature
<222> LOCATION: (2)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(38)
<223> OTHER INFORMATION: Xaa can be any naturally occurring amino acid
<220> FEATURE:
<221> NAME/KEY: misc_feature
<222> LOCATION: (40)..(42)

<223> OTHER INFORMATION: Xaa can be any naturally occurring amino acid

<400> SEQUENCE: 78

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Cys Xaa Cys Xaa Cys Xaa Xaa Xaa
            20                  25                  30

Xaa Xaa Xaa Xaa Xaa Xaa Cys Xaa Xaa Xaa Cys
        35                  40

<210> SEQ ID NO 79
<211> LENGTH: 41
<212> TYPE: PRT
<213> ORGANISM: Artificial sequence
<220> FEATURE:
<223> OTHER INFORMATION: Synthesized: cysteine motif 39
<220> FEATURE:
<221> NAME/KEY: misc_feature
<222> LOCATION: (2)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid

<400> SEQUENCE: 79

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Cys Xaa Xaa Xaa Xaa Xaa Xaa Xaa
            20                  25                  30

Xaa Xaa Xaa Xaa Xaa Cys Xaa Xaa Cys
        35                  40

<210> SEQ ID NO 80
<211> LENGTH: 39
<212> TYPE: PRT
<213> ORGANISM: Artificial sequence
<220> FEATURE:
<223> OTHER INFORMATION: Synthesized: cysteine motif 40
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(38)
<223> OTHER INFORMATION: Xaa can be any naturally occurring amino acid

```
<400> SEQUENCE: 80

Cys Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Cys Xaa Cys Xaa Xaa Xaa Xaa Xaa
            20                  25                  30

Xaa Xaa Xaa Xaa Xaa Xaa Cys
        35

<210> SEQ ID NO 81
<211> LENGTH: 43
<212> TYPE: PRT
<213> ORGANISM: Artificial sequence
<220> FEATURE:
<223> OTHER INFORMATION: Synthesized: cysteine motif 41
<220> FEATURE:
<221> NAME/KEY: misc_feature
<222> LOCATION: (2)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(42)
<223> OTHER INFORMATION: Xaa can be any naturally occurring amino acid

<400> SEQUENCE: 81

Cys Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys Xaa Cys Xaa Xaa Xaa
            20                  25                  30

Xaa Xaa Xaa Xaa Xaa Xaa Xaa Xaa Xaa Xaa Cys
        35                  40

<210> SEQ ID NO 82
<211> LENGTH: 36
<212> TYPE: PRT
<213> ORGANISM: Artificial sequence
<220> FEATURE:
<223> OTHER INFORMATION: Synthesized: cysteine motif 42
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(28)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
```

<400> SEQUENCE: 82

Cys Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Xaa Xaa Xaa Cys Xaa Xaa Xaa
            20                  25                  30

Xaa Xaa Xaa Cys
        35

<210> SEQ ID NO 83
<211> LENGTH: 37
<212> TYPE: PRT
<213> ORGANISM: Artificial sequence
<220> FEATURE:
<223> OTHER INFORMATION: Synthesized: cysteine motif 43
<220> FEATURE:
<221> NAME/KEY: misc_feature
<222> LOCATION: (2)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid

<400> SEQUENCE: 83

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Cys Xaa Xaa Cys
        35

<210> SEQ ID NO 84
<211> LENGTH: 37
<212> TYPE: PRT
<213> ORGANISM: Artificial sequence
<220> FEATURE:
<223> OTHER INFORMATION: Synthesized: cysteine motif 44
<220> FEATURE:
<221> NAME/KEY: misc_feature
<222> LOCATION: (2)..(13)
<223> OTHER INFORMATION: Xaa can be any naturally occurring amino acid
<220> FEATURE:
<221> NAME/KEY: misc_feature
<222> LOCATION: (15)..(19)
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(36)
<223> OTHER INFORMATION: Xaa can be any naturally occurring amino acid

<400> SEQUENCE: 84

```
Cys Xaa Xaa Xaa Xaa Xaa Xaa Xaa Xaa Xaa Xaa Cys Xaa Xaa
1               5                   10                  15

Xaa Xaa Xaa Cys Xaa Xaa Xaa Xaa Cys Xaa Cys Xaa Xaa Xaa Xaa
            20                  25              30

Xaa Xaa Xaa Xaa Cys
        35

<210> SEQ ID NO 85
<211> LENGTH: 44
<212> TYPE: PRT
<213> ORGANISM: Artificial sequence
<220> FEATURE:
<223> OTHER INFORMATION: Synthesized: cysteine motif 45
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(43)
<223> OTHER INFORMATION: Xaa can be any naturally occurring amino acid

<400> SEQUENCE: 85

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Cys Xaa Cys Xaa Xaa Xaa Xaa Cys
            20                  25              30

Xaa Cys Xaa Xaa Xaa Xaa Xaa Xaa Xaa Xaa Cys
        35                  40

<210> SEQ ID NO 86
<211> LENGTH: 36
<212> TYPE: PRT
<213> ORGANISM: Artificial sequence
<220> FEATURE:
<223> OTHER INFORMATION: Synthesized: cysteine motif 46
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(32)
```

```
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 86

Cys Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Xaa
            20                  25                  30

Cys Xaa Xaa Cys
        35

<210> SEQ ID NO 87
<211> LENGTH: 37
<212> TYPE: PRT
<213> ORGANISM: Artificial sequence
<220> FEATURE:
<223> OTHER INFORMATION: Synthesized: cysteine motif 47
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid

<400> SEQUENCE: 87

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Cys Xaa Xaa Cys
        35

<210> SEQ ID NO 88
<211> LENGTH: 36
<212> TYPE: PRT
<213> ORGANISM: Artificial sequence
<220> FEATURE:
<223> OTHER INFORMATION: Synthesized: cysteine motif 48
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
```

-continued

```
<220> FEATURE:
<221> NAME/KEY: misc_feature
<222> LOCATION: (28)..(35)
<223> OTHER INFORMATION: Xaa can be any naturally occurring amino acid

<400> SEQUENCE: 88

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Cys Xaa Cys Xaa Xaa Xaa Xaa Xaa
            20                  25                  30

Xaa Xaa Xaa Cys
        35

<210> SEQ ID NO 89
<211> LENGTH: 43
<212> TYPE: PRT
<213> ORGANISM: Artificial sequence
<220> FEATURE:
<223> OTHER INFORMATION: Synthesized: cysteine motif 49
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(39)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid

<400> SEQUENCE: 89

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Cys Xaa
            20                  25                  30

Xaa Xaa Xaa Xaa Xaa Xaa Xaa Cys Xaa Xaa Cys
        35                  40

<210> SEQ ID NO 90
<211> LENGTH: 38
<212> TYPE: PRT
<213> ORGANISM: Artificial sequence
<220> FEATURE:
<223> OTHER INFORMATION: Synthesized: cysteine motif 50
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
```

```
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (30)..(37)
<223> OTHER INFORMATION: Xaa can be any naturally occurring amino acid

<400> SEQUENCE: 90

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Cys Xaa Xaa Xaa
            20                  25                  30

Xaa Xaa Xaa Xaa Xaa Cys
        35

<210> SEQ ID NO 91
<211> LENGTH: 43
<212> TYPE: PRT
<213> ORGANISM: Artificial sequence
<220> FEATURE:
<223> OTHER INFORMATION: Synthesized: cysteine motif 51
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(36)
<223> OTHER INFORMATION: Xaa can be any naturally occurring amino acid
<220> FEATURE:
<221> NAME/KEY: misc_feature
<222> LOCATION: (38)..(42)
<223> OTHER INFORMATION: Xaa can be any naturally occurring amino acid

<400> SEQUENCE: 91

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Xaa Xaa Xaa Cys Xaa Xaa Xaa Xaa Xaa Cys
        35                  40

<210> SEQ ID NO 92
<211> LENGTH: 34
<212> TYPE: PRT
<213> ORGANISM: Artificial sequence
<220> FEATURE:
<223> OTHER INFORMATION: Synthesized: cysteine motif 52
<220> FEATURE:
<221> NAME/KEY: misc_feature
```

```
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (25)..(33)
<223> OTHER INFORMATION: Xaa can be any naturally occurring amino acid

<400> SEQUENCE: 92

Cys Xaa Xaa Xaa Xaa Xaa Xaa Xaa Cys Xaa Xaa Xaa Xaa Xaa Xaa Cys
1               5                   10                  15

Xaa Xaa Xaa Cys Xaa Xaa Xaa Cys Xaa Xaa Xaa Xaa Xaa Xaa Xaa Xaa
            20                  25                  30

Xaa Cys

<210> SEQ ID NO 93
<211> LENGTH: 39
<212> TYPE: PRT
<213> ORGANISM: Artificial sequence
<220> FEATURE:
<223> OTHER INFORMATION: Synthesized: cysteine motif 53
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(19)
<223> OTHER INFORMATION: Xaa can be any naturally occurring amino acid
<220> FEATURE:
<221> NAME/KEY: misc_feature
<222> LOCATION: (21)..(25)
<223> OTHER INFORMATION: Xaa can be any naturally occurring amino acid
<220> FEATURE:
<221> NAME/KEY: misc_feature
<222> LOCATION: (27)..(32)
<223> OTHER INFORMATION: Xaa can be any naturally occurring amino acid
<220> FEATURE:
<221> NAME/KEY: misc_feature
<222> LOCATION: (34)..(38)
<223> OTHER INFORMATION: Xaa can be any naturally occurring amino acid

<400> SEQUENCE: 93

Cys Xaa Xaa Xaa Xaa Xaa Xaa Xaa Xaa Xaa Cys Xaa Xaa Xaa Xaa Xaa
1               5                   10                  15

Xaa Xaa Xaa Cys Xaa Xaa Xaa Xaa Xaa Cys Xaa Xaa Xaa Xaa Xaa Xaa
            20                  25                  30

Cys Xaa Xaa Xaa Xaa Xaa Cys
        35

<210> SEQ ID NO 94
<211> LENGTH: 46
<212> TYPE: PRT
<213> ORGANISM: Artificial sequence
<220> FEATURE:
<223> OTHER INFORMATION: Synthesized: cysteine motif 54
<220> FEATURE:
<221> NAME/KEY: misc_feature
<222> LOCATION: (2)..(11)
<223> OTHER INFORMATION: Xaa can be any naturally occurring amino acid
```

-continued

```
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (19)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(39)
<223> OTHER INFORMATION: Xaa can be any naturally occurring amino acid
<220> FEATURE:
<221> NAME/KEY: misc_feature
<222> LOCATION: (41)..(45)
<223> OTHER INFORMATION: Xaa can be any naturally occurring amino acid

<400> SEQUENCE: 94

Cys Xaa Xaa Xaa Xaa Xaa Xaa Xaa Xaa Xaa Cys Xaa Xaa Cys Xaa
1               5                   10                  15

Xaa Cys Xaa Xaa Xaa Xaa Xaa Xaa Cys Xaa Cys Xaa Xaa Xaa Xaa
            20                  25                  30

Xaa Xaa Xaa Xaa Xaa Xaa Xaa Cys Xaa Xaa Xaa Xaa Xaa Cys
            35                  40                  45

<210> SEQ ID NO 95
<211> LENGTH: 44
<212> TYPE: PRT
<213> ORGANISM: Artificial sequence
<220> FEATURE:
<223> OTHER INFORMATION: Synthesized: cysteine motif 55
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (31)..(38)
<223> OTHER INFORMATION: Xaa can be any naturally occurring amino acid
<220> FEATURE:
<221> NAME/KEY: misc_feature
<222> LOCATION: (40)..(43)
<223> OTHER INFORMATION: Xaa can be any naturally occurring amino acid

<400> SEQUENCE: 95

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30
```

```
Xaa Xaa Xaa Xaa Xaa Xaa Cys Xaa Xaa Xaa Xaa Cys
        35                  40
```

<210> SEQ ID NO 96
<211> LENGTH: 42
<212> TYPE: PRT
<213> ORGANISM: Artificial sequence
<220> FEATURE:
<223> OTHER INFORMATION: Synthesized: cysteine motif 56
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(23)
<223> OTHER INFORMATION: Xaa can be any naturally occurring amino acid
<220> FEATURE:
<221> NAME/KEY: misc_feature
<222> LOCATION: (25)..(33)
<223> OTHER INFORMATION: Xaa can be any naturally occurring amino acid
<220> FEATURE:
<221> NAME/KEY: misc_feature
<222> LOCATION: (35)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 96

```
Cys Cys Xaa Xaa Xaa Cys Xaa Cys Xaa Xaa Xaa Cys Xaa Xaa Cys Cys
1               5                   10                  15

Xaa Cys Xaa Xaa Xaa Xaa Xaa Cys Xaa Xaa Xaa Xaa Xaa Xaa Xaa Xaa
            20                  25                  30

Xaa Cys Xaa Xaa Xaa Xaa Xaa Cys Xaa Cys
        35                  40
```

<210> SEQ ID NO 97
<211> LENGTH: 39
<212> TYPE: PRT
<213> ORGANISM: Artificial sequence
<220> FEATURE:
<223> OTHER INFORMATION: Synthesized: cysteine motif 57
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:

```
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid
<220> FEATURE:
<221> NAME/KEY: misc_feature
<222> LOCATION: (31)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 97

Cys Xaa Xaa Xaa Xaa Xaa Xaa Cys Xaa Xaa Cys Xaa Xaa Xaa Xaa Xaa
1               5                   10                  15

Cys Xaa Xaa Xaa Xaa Cys Cys Xaa Cys Xaa Xaa Xaa Xaa Cys Xaa Xaa
            20                  25                  30

Xaa Xaa Xaa Xaa Cys Xaa Cys
        35

<210> SEQ ID NO 98
<211> LENGTH: 38
<212> TYPE: PRT
<213> ORGANISM: Artificial sequence
<220> FEATURE:
<223> OTHER INFORMATION: Synthesized: cysteine motif 58
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 98

Cys Xaa Xaa Xaa Xaa Xaa Xaa Xaa Cys Xaa Cys Xaa Xaa Xaa Xaa Xaa
1               5                   10                  15

Cys Xaa Xaa Xaa Xaa Cys Cys Cys Xaa Xaa Xaa Xaa Cys Xaa Xaa Xaa
            20                  25                  30

Xaa Xaa Xaa Cys Xaa Cys
        35
```

```
<210> SEQ ID NO 99
<211> LENGTH: 36
<212> TYPE: PRT
<213> ORGANISM: Artificial sequence
<220> FEATURE:
<223> OTHER INFORMATION: Synthesized: cysteine motif 59
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(30)
<223> OTHER INFORMATION: Xaa can be any naturally occurring amino acid
<220> FEATURE:
<221> NAME/KEY: misc_feature
<222> LOCATION: (32)..(35)
<223> OTHER INFORMATION: Xaa can be any naturally occurring amino acid

<400> SEQUENCE: 99

Cys Xaa Xaa Xaa Xaa Xaa Xaa Xaa Xaa Xaa Cys Xaa Xaa Xaa Cys Xaa
 1               5                  10                  15

Cys Xaa Xaa Cys Xaa Cys Cys Cys Xaa Xaa Xaa Xaa Xaa Xaa Cys Xaa
            20                  25                  30

Xaa Xaa Xaa Cys
        35

<210> SEQ ID NO 100
<211> LENGTH: 39
<212> TYPE: PRT
<213> ORGANISM: Artificial sequence
<220> FEATURE:
<223> OTHER INFORMATION: Synthesized: cysteine motif 60
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (25)..(34)
<223> OTHER INFORMATION: Xaa can be any naturally occurring amino acid
<220> FEATURE:
<221> NAME/KEY: misc_feature
```

-continued

```
<222> LOCATION: (36)..(37)
<223> OTHER INFORMATION: Xaa can be any naturally occurring amino acid

<400> SEQUENCE: 100

Cys Xaa Xaa Xaa Xaa Xaa Cys Xaa Xaa Xaa Cys Xaa Cys Xaa Xaa Xaa
1               5                  10                  15

Xaa Cys Xaa Xaa Xaa Xaa Cys Cys Xaa Xaa Xaa Xaa Xaa Xaa Xaa Xaa
            20                  25                  30

Xaa Xaa Cys Xaa Xaa Cys Cys
        35

<210> SEQ ID NO 101
<211> LENGTH: 38
<212> TYPE: PRT
<213> ORGANISM: Artificial sequence
<220> FEATURE:
<223> OTHER INFORMATION: Synthesized: cysteine motif 61
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (28)..(37)
<223> OTHER INFORMATION: Xaa can be any naturally occurring amino acid

<400> SEQUENCE: 101

Cys Xaa Xaa Xaa Xaa Xaa Cys Xaa Cys Xaa Cys Xaa Cys Xaa Xaa Xaa
1               5                  10                  15

Cys Cys Xaa Xaa Xaa Cys Xaa Xaa Xaa Xaa Cys Xaa Xaa Xaa Xaa Xaa
            20                  25                  30

Xaa Xaa Xaa Xaa Xaa Cys
        35

<210> SEQ ID NO 102
<211> LENGTH: 37
<212> TYPE: PRT
<213> ORGANISM: Artificial sequence
<220> FEATURE:
<223> OTHER INFORMATION: Synthesized: cysteine motif 62
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (14)..(16)
```

<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (25)..(29)
<223> OTHER INFORMATION: Xaa can be any naturally occurring amino acid
<220> FEATURE:
<221> NAME/KEY: misc_feature
<222> LOCATION: (31)..(36)
<223> OTHER INFORMATION: Xaa can be any naturally occurring amino acid

<400> SEQUENCE: 102

Cys Xaa Xaa Xaa Xaa Xaa Xaa Xaa Xaa Cys Cys Cys Xaa Xaa Xaa
1               5                   10                  15

Cys Xaa Xaa Xaa Xaa Cys Cys Cys Xaa Xaa Xaa Xaa Cys Xaa Xaa
                20                  25                  30

Xaa Xaa Xaa Xaa Cys
        35

<210> SEQ ID NO 103
<211> LENGTH: 36
<212> TYPE: PRT
<213> ORGANISM: Artificial sequence
<220> FEATURE:
<223> OTHER INFORMATION: Synthesized: cysteine motif 63
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 103

Cys Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Xaa Xaa Xaa Cys Xaa Xaa Xaa Xaa Cys Cys
                20                  25                  30

Xaa Cys Xaa Cys
        35

<210> SEQ ID NO 104
<211> LENGTH: 41
<212> TYPE: PRT
<213> ORGANISM: Artificial sequence
<220> FEATURE:
<223> OTHER INFORMATION: Synthesized: cysteine motif 64

```
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (29)..(40)
<223> OTHER INFORMATION: Xaa can be any naturally occurring amino acid

<400> SEQUENCE: 104

Cys Cys Xaa Xaa Xaa Xaa Xaa Xaa Cys Cys Xaa Xaa Xaa Xaa Xaa Cys
1               5                   10                  15

Cys Cys Xaa Xaa Xaa Xaa Cys Xaa Xaa Xaa Xaa Cys Xaa Xaa Xaa Xaa
                20                  25                  30

Xaa Xaa Xaa Xaa Xaa Xaa Xaa Xaa Cys
            35                  40

<210> SEQ ID NO 105
<211> LENGTH: 36
<212> TYPE: PRT
<213> ORGANISM: Artificial sequence
<220> FEATURE:
<223> OTHER INFORMATION: Synthesized: cysteine motif 65
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (23)..(27)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid

<400> SEQUENCE: 105

Cys Xaa Xaa Xaa Xaa Xaa Xaa Cys Xaa Xaa Cys Xaa Xaa Xaa Cys Cys
1               5                   10                  15

Cys Xaa Xaa Xaa Xaa Cys Xaa Xaa Xaa Xaa Cys Xaa Xaa Xaa Cys Xaa Xaa Xaa Cys
                20                  25                  30

Xaa Xaa Xaa Cys
        35
```

```
<210> SEQ ID NO 106
<211> LENGTH: 39
<212> TYPE: PRT
<213> ORGANISM: Artificial sequence
<220> FEATURE:
<223> OTHER INFORMATION: Synthesized: cysteine motif 66
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (33)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid

<400> SEQUENCE: 106

Cys Xaa Xaa Xaa Cys Xaa Xaa Xaa Xaa Xaa Cys Xaa Xaa Xaa Xaa Xaa
1               5                   10                  15

Xaa Cys Xaa Xaa Xaa Xaa Cys Cys Xaa Cys Xaa Xaa Xaa Xaa Xaa Cys
                20                  25                  30

Xaa Xaa Xaa Xaa Cys Xaa Cys
        35

<210> SEQ ID NO 107
<211> LENGTH: 41
<212> TYPE: PRT
<213> ORGANISM: Artificial sequence
<220> FEATURE:
<223> OTHER INFORMATION: Synthesized: cysteine motif 67
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
```

```
<221> NAME/KEY: misc_feature
<222> LOCATION: (25)..(35)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 107

Cys Xaa Xaa Xaa Xaa Cys Xaa Xaa Xaa Cys Cys Xaa Xaa Xaa Xaa
1               5                   10                  15

Cys Xaa Xaa Xaa Xaa Cys Xaa Cys Xaa Xaa Xaa Xaa Xaa Xaa Xaa
            20                  25                  30

Xaa Xaa Xaa Cys Xaa Xaa Cys Xaa Cys
        35                  40

<210> SEQ ID NO 108
<211> LENGTH: 36
<212> TYPE: PRT
<213> ORGANISM: Artificial sequence
<220> FEATURE:
<223> OTHER INFORMATION: Synthesized: cysteine motif 68
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (29)..(35)
<223> OTHER INFORMATION: Xaa can be any naturally occurring amino acid

<400> SEQUENCE: 108

Cys Xaa Xaa Xaa Xaa Xaa Cys Xaa Xaa Cys Cys Xaa Xaa Xaa Xaa Xaa
1               5                   10                  15

Cys Xaa Xaa Xaa Xaa Cys Cys Xaa Xaa Xaa Cys Cys Xaa Xaa Xaa Xaa
            20                  25                  30

Xaa Xaa Xaa Cys
        35

<210> SEQ ID NO 109
<211> LENGTH: 38
<212> TYPE: PRT
<213> ORGANISM: Artificial sequence
<220> FEATURE:
<223> OTHER INFORMATION: Synthesized: cysteine motif 69
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
```

```
<222> LOCATION: (8)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (29)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 109

Cys Xaa Xaa Xaa Xaa Xaa Cys Xaa Xaa Xaa Xaa Xaa Cys Xaa Xaa Xaa
1               5                   10                  15

Cys Xaa Xaa Cys Xaa Cys Cys Xaa Xaa Xaa Xaa Cys Xaa Xaa Xaa Xaa
                20                  25                  30

Xaa Xaa Xaa Cys Xaa Cys
        35

<210> SEQ ID NO 110
<211> LENGTH: 37
<212> TYPE: PRT
<213> ORGANISM: Artificial sequence
<220> FEATURE:
<223> OTHER INFORMATION: Synthesized: cysteine motif 70
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid

<400> SEQUENCE: 110
```

Cys Xaa Xaa Xaa Cys Xaa Xaa Xaa Xaa Xaa Cys Xaa Xaa Xaa
1               5                   10                  15

Cys Xaa Xaa Xaa Xaa Cys Cys Xaa Xaa Xaa Cys Xaa Xaa Xaa
            20                  25                  30

Xaa Cys Xaa Xaa Cys
        35

<210> SEQ ID NO 111
<211> LENGTH: 38
<212> TYPE: PRT
<213> ORGANISM: Artificial sequence
<220> FEATURE:
<223> OTHER INFORMATION: Synthesized: cysteine motif 71
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: Xaa can be any naturally occurring amino acid
<220> FEATURE:
<221> NAME/KEY: misc_feature
<222> LOCATION: (32)..(37)
<223> OTHER INFORMATION: Xaa can be any naturally occurring amino acid

<400> SEQUENCE: 111

Cys Xaa Xaa Xaa Xaa Xaa Xaa Xaa Xaa Xaa Cys Xaa Xaa Xaa Cys Xaa
1               5                   10                  15

Cys Xaa Xaa Xaa Xaa Cys Cys Xaa Xaa Xaa Xaa Xaa Cys Cys Cys Xaa
            20                  25                  30

Xaa Xaa Xaa Xaa Xaa Cys
        35

<210> SEQ ID NO 112
<211> LENGTH: 38
<212> TYPE: PRT
<213> ORGANISM: Artificial sequence
<220> FEATURE:
<223> OTHER INFORMATION: Synthesized: cysteine motif 72
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)

```
<223> OTHER INFORMATION: Xaa can be any naturally occurring amino acid
<220> FEATURE:
<221> NAME/KEY: misc_feature
<222> LOCATION: (24)..(29)
<223> OTHER INFORMATION: Xaa can be any naturally occurring amino acid
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (35)..(37)
<223> OTHER INFORMATION: Xaa can be any naturally occurring amino acid

<400> SEQUENCE: 112

Cys Xaa Xaa Xaa Xaa Xaa Xaa Xaa Xaa Xaa Cys Xaa Xaa Xaa Cys Xaa
1               5                   10                  15

Cys Xaa Xaa Cys Xaa Cys Cys Xaa Xaa Xaa Xaa Xaa Cys Xaa Xaa
            20                  25                  30

Xaa Cys Xaa Xaa Xaa Cys
        35

<210> SEQ ID NO 113
<211> LENGTH: 33
<212> TYPE: PRT
<213> ORGANISM: Artificial sequence
<220> FEATURE:
<223> OTHER INFORMATION: Synthesized: cysteine motif 73
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(27)
<223> OTHER INFORMATION: Xaa can be any naturally occurring amino acid
<220> FEATURE:
<221> NAME/KEY: misc_feature
<222> LOCATION: (29)..(32)
<223> OTHER INFORMATION: Xaa can be any naturally occurring amino acid

<400> SEQUENCE: 113

Cys Xaa Xaa Xaa Xaa Xaa Xaa Xaa Xaa Cys Cys Xaa Cys Xaa Xaa Xaa
1               5                   10                  15

Cys Cys Xaa Xaa Xaa Cys Xaa Cys Xaa Xaa Xaa Cys Xaa Xaa Xaa Xaa
            20                  25                  30

Cys

<210> SEQ ID NO 114
<211> LENGTH: 34
<212> TYPE: PRT
<213> ORGANISM: Artificial sequence
<220> FEATURE:
<223> OTHER INFORMATION: Synthesized: cysteine motif 74
<220> FEATURE:
```

```
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid
<220> FEATURE:
<221> NAME/KEY: misc_feature
<222> LOCATION: (31)..(33)
<223> OTHER INFORMATION: Xaa can be any naturally occurring amino acid

<400> SEQUENCE: 114

Cys Xaa Xaa Xaa Xaa Xaa Xaa Xaa Xaa Xaa Cys Cys Xaa Xaa Xaa Xaa
1               5                   10                  15

Cys Xaa Xaa Cys Xaa Cys Cys Xaa Cys Xaa Cys Xaa Xaa Cys Xaa Xaa
            20                  25                  30

Xaa Cys

<210> SEQ ID NO 115
<211> LENGTH: 37
<212> TYPE: PRT
<213> ORGANISM: Artificial sequence
<220> FEATURE:
<223> OTHER INFORMATION: Synthesized: cysteine motif 75
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (30)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid

<400> SEQUENCE: 115
```

Cys Xaa Xaa Xaa Xaa Xaa Xaa Xaa Xaa Xaa Cys Xaa Cys Xaa Xaa
1               5                   10                  15

Xaa Cys Xaa Xaa Cys Xaa Cys Cys Xaa Xaa Xaa Cys Xaa Xaa Xaa
            20                  25                  30

Xaa Xaa Cys Xaa Cys
        35

<210> SEQ ID NO 116
<211> LENGTH: 36
<212> TYPE: PRT
<213> ORGANISM: Artificial sequence
<220> FEATURE:
<223> OTHER INFORMATION: Synthesized: cysteine motif 76
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (29)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 116

Cys Xaa Xaa Xaa Xaa Xaa Xaa Xaa Xaa Xaa Cys Xaa Cys Xaa Xaa Xaa
1               5                   10                  15

Cys Xaa Xaa Cys Xaa Cys Cys Xaa Xaa Xaa Cys Xaa Xaa Xaa Xaa
            20                  25                  30

Xaa Cys Xaa Cys
        35

<210> SEQ ID NO 117
<211> LENGTH: 34
<212> TYPE: PRT
<213> ORGANISM: Artificial sequence
<220> FEATURE:
<223> OTHER INFORMATION: Synthesized: cysteine motif 77
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(16)

<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid

<400> SEQUENCE: 117

Cys Xaa Xaa Xaa Xaa Xaa Xaa Cys Cys Xaa Cys Xaa Xaa Xaa Xaa Xaa
1               5                   10                  15

Cys Xaa Xaa Xaa Xaa Cys Cys Xaa Cys Xaa Xaa Xaa Xaa Xaa Cys Xaa
                20                  25                  30

Xaa Cys

<210> SEQ ID NO 118
<211> LENGTH: 28
<212> TYPE: PRT
<213> ORGANISM: Artificial sequence
<220> FEATURE:
<223> OTHER INFORMATION: Synthesized: cysteine motif 78
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid

<400> SEQUENCE: 118

Cys Xaa Xaa Xaa Xaa Xaa Xaa Cys Cys Xaa Cys Xaa Xaa Xaa Cys Xaa
1               5                   10                  15

Cys Cys Xaa Xaa Xaa Cys Xaa Xaa Xaa Xaa Cys Cys
                20                  25

<210> SEQ ID NO 119
<211> LENGTH: 36
<212> TYPE: PRT
<213> ORGANISM: Artificial sequence
<220> FEATURE:
<223> OTHER INFORMATION: Synthesized: cysteine motif 79
<220> FEATURE:
<221> NAME/KEY: misc_feature
<222> LOCATION: (2)..(7)
<223> OTHER INFORMATION: Xaa can be any naturally occurring amino acid -continued

```
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid

<400> SEQUENCE: 119

Cys Xaa Xaa Xaa Xaa Xaa Xaa Cys Cys Xaa Cys Xaa Xaa Xaa Cys Xaa
1               5                   10                  15

Cys Xaa Xaa Cys Xaa Cys Xaa Xaa Xaa Xaa Cys Xaa Xaa Xaa Xaa Xaa
            20                  25                  30

Xaa Xaa Xaa Cys
        35

<210> SEQ ID NO 120
<211> LENGTH: 29
<212> TYPE: PRT
<213> ORGANISM: Artificial sequence
<220> FEATURE:
<223> OTHER INFORMATION: Synthesized: cysteine motif 80
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid

<400> SEQUENCE: 120

Cys Xaa Xaa Xaa Xaa Cys Xaa Xaa Cys Cys Xaa Xaa Xaa Cys Xaa Cys
```

```
1               5                   10                  15
Xaa Xaa Xaa Xaa Cys Cys Xaa Xaa Cys Xaa Xaa Xaa Cys
            20                  25
```

<210> SEQ ID NO 121
<211> LENGTH: 32
<212> TYPE: PRT
<213> ORGANISM: Artificial sequence
<220> FEATURE:
<223> OTHER INFORMATION: Synthesized: cysteine motif 81
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid

<400> SEQUENCE: 121

```
Cys Xaa Xaa Xaa Cys Xaa Xaa Xaa Xaa Xaa Cys Xaa Xaa Xaa Cys Cys
1               5                   10                  15

Cys Xaa Xaa Xaa Xaa Cys Xaa Xaa Xaa Xaa Xaa Xaa Xaa Xaa Xaa Cys
            20                  25                  30
```

<210> SEQ ID NO 122
<211> LENGTH: 29
<212> TYPE: PRT
<213> ORGANISM: Artificial sequence
<220> FEATURE:
<223> OTHER INFORMATION: Synthesized: cysteine motif 82
<220> FEATURE:
<221> NAME/KEY: misc_feature
<222> LOCATION: (3)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(28)
<223> OTHER INFORMATION: Xaa can be any naturally occurring amino acid

<400> SEQUENCE: 122

```
Cys Cys Xaa Xaa Xaa Xaa Xaa Xaa Xaa Xaa Xaa Cys Xaa Xaa Xaa Cys
1               5                   10                  15

Xaa Cys Cys Xaa Xaa Xaa Cys Xaa Xaa Xaa Xaa Xaa Cys
            20                  25
```

<210> SEQ ID NO 123

```
<211> LENGTH: 35
<212> TYPE: PRT
<213> ORGANISM: Artificial sequence
<220> FEATURE:
<223> OTHER INFORMATION: Synthesized: cysteine motif 83
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (30)..(34)
<223> OTHER INFORMATION: Xaa can be any naturally occurring amino acid

<400> SEQUENCE: 123

Cys Xaa Xaa Xaa Xaa Xaa Xaa Xaa Xaa Xaa Cys Xaa Xaa Cys Xaa Xaa
 1               5                  10                  15

Xaa Cys Xaa Xaa Xaa Xaa Cys Cys Xaa Xaa Xaa Xaa Cys Xaa Xaa Xaa
            20                  25                  30

Xaa Xaa Cys
        35

<210> SEQ ID NO 124
<211> LENGTH: 39
<212> TYPE: PRT
<213> ORGANISM: Artificial sequence
<220> FEATURE:
<223> OTHER INFORMATION: Synthesized: cysteine motif 84
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(18)
<223> OTHER INFORMATION: Xaa can be any naturally occurring amino acid
<220> FEATURE:
<221> NAME/KEY: misc_feature
<222> LOCATION: (20)..(23)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(34)
<223> OTHER INFORMATION: Xaa can be any naturally occurring amino acid
<220> FEATURE:
<221> NAME/KEY: misc_feature
<222> LOCATION: (36)..(38)
<223> OTHER INFORMATION: Xaa can be any naturally occurring amino acid

<400> SEQUENCE: 124

Cys Xaa Xaa Xaa Xaa Xaa Xaa Xaa Xaa Xaa Cys Xaa Xaa Xaa Xaa Xaa
 1               5                  10                  15

Xaa Xaa Cys Xaa Xaa Xaa Xaa Cys Cys Xaa Cys Xaa Xaa Xaa Xaa Xaa
```

```
                    20                  25                  30

Xaa Xaa Cys Xaa Xaa Xaa Cys
        35

<210> SEQ ID NO 125
<211> LENGTH: 35
<212> TYPE: PRT
<213> ORGANISM: Artificial sequence
<220> FEATURE:
<223> OTHER INFORMATION: Synthesized: cysteine motif 85
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (18)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid

<400> SEQUENCE: 125

Cys Xaa Xaa Xaa Xaa Xaa Xaa Xaa Xaa Xaa Cys Xaa Xaa Xaa Cys Cys
1               5                   10                  15

Cys Xaa Xaa Xaa Xaa Xaa Xaa Xaa Xaa Xaa Cys Xaa Xaa Cys Xaa
            20                  25                  30

Xaa Xaa Cys
        35

<210> SEQ ID NO 126
<211> LENGTH: 41
<212> TYPE: PRT
<213> ORGANISM: Artificial sequence
<220> FEATURE:
<223> OTHER INFORMATION: Synthesized: cysteine motif 86
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(33)
<223> OTHER INFORMATION: Xaa can be any naturally occurring amino acid
<220> FEATURE:
<221> NAME/KEY: misc_feature
<222> LOCATION: (35)..(40)
<223> OTHER INFORMATION: Xaa can be any naturally occurring amino acid

<400> SEQUENCE: 126

Cys Xaa Xaa Xaa Cys Xaa Xaa Xaa Xaa Xaa Cys Xaa Xaa Xaa Xaa Xaa
```

```
                1               5                   10                  15
Cys Xaa Xaa Xaa Xaa Cys Cys Xaa Xaa Xaa Xaa Xaa Xaa Xaa
                20                  25                  30
Xaa Cys Xaa Xaa Xaa Xaa Xaa Xaa Cys
        35                  40
```

```
<210> SEQ ID NO 127
<211> LENGTH: 36
<212> TYPE: PRT
<213> ORGANISM: Artificial sequence
<220> FEATURE:
<223> OTHER INFORMATION: Synthesized: cysteine motif 87
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(30)
<223> OTHER INFORMATION: Xaa can be any naturally occurring amino acid
<220> FEATURE:
<221> NAME/KEY: misc_feature
<222> LOCATION: (32)..(35)
<223> OTHER INFORMATION: Xaa can be any naturally occurring amino acid

<400> SEQUENCE: 127

Cys Xaa Xaa Xaa Xaa Xaa Xaa Xaa Xaa Xaa Cys Xaa Xaa Xaa Xaa
1               5                   10                  15
Cys Xaa Xaa Xaa Xaa Cys Cys Xaa Cys Xaa Xaa Xaa Xaa Xaa Cys Xaa
                20                  25                  30
Xaa Xaa Xaa Cys
        35
```

```
<210> SEQ ID NO 128
<211> LENGTH: 36
<212> TYPE: PRT
<213> ORGANISM: Artificial sequence
<220> FEATURE:
<223> OTHER INFORMATION: Synthesized: cysteine motif 88
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (26)..(35)
<223> OTHER INFORMATION: Xaa can be any naturally occurring amino acid
```

<400> SEQUENCE: 128

Cys Xaa Xaa Xaa Xaa Xaa Xaa Cys Xaa Cys Xaa Xaa Xaa Xaa Xaa
1               5                   10                  15

Xaa Cys Xaa Xaa Xaa Cys Cys Xaa Xaa Xaa Xaa Xaa Xaa
            20                  25                  30

Xaa Xaa Xaa Cys
        35

<210> SEQ ID NO 129
<211> LENGTH: 32
<212> TYPE: PRT
<213> ORGANISM: Artificial sequence
<220> FEATURE:
<223> OTHER INFORMATION: Synthesized: cysteine motif 89
<220> FEATURE:
<221> NAME/KEY: misc_feature
<222> LOCATION: (2)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (20)..(23)
<223> OTHER INFORMATION: Xaa can be any naturally occurring amino acid
<220> FEATURE:
<221> NAME/KEY: misc_feature
<222> LOCATION: (25)..(27)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Xaa can be any naturally occurring amino acid

<400> SEQUENCE: 129

Cys Xaa Xaa Xaa Xaa Xaa Xaa Xaa Xaa Cys Xaa Xaa Cys Xaa Xaa Xaa
1               5                   10                  15

Xaa Cys Cys Xaa Xaa Xaa Xaa Cys Xaa Xaa Xaa Cys Xaa Xaa Xaa Cys
            20                  25                  30

<210> SEQ ID NO 130
<211> LENGTH: 36
<212> TYPE: PRT
<213> ORGANISM: Artificial sequence
<220> FEATURE:
<223> OTHER INFORMATION: Synthesized: cysteine motif 90
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid
<220> FEATURE:

<221> NAME/KEY: misc_feature
<222> LOCATION: (32)..(35)
<223> OTHER INFORMATION: Xaa can be any naturally occurring amino acid

<400> SEQUENCE: 130

Cys Xaa Xaa Xaa Xaa Xaa Xaa Cys Xaa Xaa Xaa Xaa Xaa Cys Xaa
1               5                   10                  15

Cys Xaa Xaa Xaa Xaa Cys Cys Xaa Xaa Xaa Xaa Xaa Xaa Cys Xaa
            20                  25                  30

Xaa Xaa Xaa Cys
        35

<210> SEQ ID NO 131
<211> LENGTH: 36
<212> TYPE: PRT
<213> ORGANISM: Artificial sequence
<220> FEATURE:
<223> OTHER INFORMATION: Synthesized: cysteine motif 91
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (25)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 131

Cys Xaa Xaa Xaa Xaa Xaa Xaa Xaa Xaa Xaa Xaa Xaa Cys Xaa Xaa Xaa
1               5                   10                  15

Cys Xaa Xaa Xaa Xaa Cys Cys Cys Xaa Xaa Xaa Xaa Xaa Xaa Xaa Xaa
            20                  25                  30

Cys Xaa Xaa Cys
        35

<210> SEQ ID NO 132
<211> LENGTH: 41
<212> TYPE: PRT
<213> ORGANISM: Artificial sequence
<220> FEATURE:
<223> OTHER INFORMATION: Synthesized: cysteine motif 92
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature

```
<222> LOCATION: (20)..(24)
<223> OTHER INFORMATION: Xaa can be any naturally occurring amino acid
<220> FEATURE:
<221> NAME/KEY: misc_feature
<222> LOCATION: (26)..(40)
<223> OTHER INFORMATION: Xaa can be any naturally occurring amino acid

<400> SEQUENCE: 132

Cys Xaa Xaa Cys Xaa Xaa Xaa Cys Xaa Xaa Xaa Xaa Cys Cys Xaa Xaa
1               5                   10                  15

Xaa Xaa Cys Xaa Xaa Xaa Xaa Cys Xaa Xaa Xaa Xaa Xaa Xaa
            20                  25                  30

Xaa Xaa Xaa Xaa Xaa Xaa Xaa Xaa Cys
        35                  40

<210> SEQ ID NO 133
<211> LENGTH: 31
<212> TYPE: PRT
<213> ORGANISM: Artificial sequence
<220> FEATURE:
<223> OTHER INFORMATION: Synthesized: cysteine motif 93
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(30)
<223> OTHER INFORMATION: Xaa can be any naturally occurring amino acid

<400> SEQUENCE: 133

Cys Xaa Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Cys
            20                  25                  30

<210> SEQ ID NO 134
<211> LENGTH: 33
<212> TYPE: PRT
<213> ORGANISM: Artificial sequence
<220> FEATURE:
<223> OTHER INFORMATION: Synthesized: cysteine motif 94
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(32)
<223> OTHER INFORMATION: Xaa can be any naturally occurring amino acid

<400> SEQUENCE: 134
```

```
Cys Xaa Xaa Xaa Xaa Xaa Xaa Xaa Xaa Cys Xaa Xaa Xaa Xaa Xaa
1               5                   10                  15

Xaa Xaa Cys Xaa Xaa Cys Xaa Xaa Cys Xaa Xaa Xaa Xaa Xaa
            20              25              30

Cys

<210> SEQ ID NO 135
<211> LENGTH: 38
<212> TYPE: PRT
<213> ORGANISM: Artificial sequence
<220> FEATURE:
<223> OTHER INFORMATION: Synthesized: cysteine motif 95
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(37)
<223> OTHER INFORMATION: Xaa can be any naturally occurring amino acid

<400> SEQUENCE: 135

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Xaa
            20              25              30

Xaa Xaa Xaa Xaa Xaa Cys
        35

<210> SEQ ID NO 136
<211> LENGTH: 32
<212> TYPE: PRT
<213> ORGANISM: Artificial sequence
<220> FEATURE:
<223> OTHER INFORMATION: Synthesized: cysteine motif 96
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid
<220> FEATURE:
<221> NAME/KEY: misc_feature
<222> LOCATION: (24)..(31)
<223> OTHER INFORMATION: Xaa can be any naturally occurring amino acid

<400> SEQUENCE: 136

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys Cys Xaa Xaa Xaa Xaa Xaa Xaa Xaa Cys
            20              25              30

<210> SEQ ID NO 137
<211> LENGTH: 26
```

```
<212> TYPE: PRT
<213> ORGANISM: Artificial sequence
<220> FEATURE:
<223> OTHER INFORMATION: Synthesized: cysteine motif 97
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 137

Cys Xaa Xaa Xaa Xaa Xaa Xaa Xaa Xaa Cys Xaa Xaa Xaa Xaa Xaa
1               5                   10                  15

Xaa Cys Xaa Xaa Xaa Xaa Cys Cys Xaa Cys
            20                  25

<210> SEQ ID NO 138
<211> LENGTH: 33
<212> TYPE: PRT
<213> ORGANISM: Artificial sequence
<220> FEATURE:
<223> OTHER INFORMATION: Synthesized: cysteine motif 98
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (22)..(33)
<223> OTHER INFORMATION: Xaa can be any naturally occurring amino acid

<400> SEQUENCE: 138

Cys Xaa Xaa Xaa Xaa Xaa Cys Cys Xaa Xaa Xaa Xaa Xaa Xaa Xaa Cys
1               5                   10                  15

Xaa Xaa Xaa Xaa Cys Xaa Xaa Xaa Xaa Xaa Xaa Xaa Xaa Xaa Xaa
            20                  25                  30

Xaa

<210> SEQ ID NO 139
<211> LENGTH: 27
<212> TYPE: PRT
<213> ORGANISM: Artificial sequence
<220> FEATURE:
<223> OTHER INFORMATION: Synthesized: cysteine motif 99
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
```

```
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid

<400> SEQUENCE: 139

Cys Xaa Xaa Xaa Xaa Xaa Xaa Xaa Xaa Xaa Cys Xaa Xaa Xaa Cys
1               5                   10                  15

Xaa Xaa Xaa Xaa Cys Cys Xaa Xaa Xaa Xaa Cys
            20                  25

<210> SEQ ID NO 140
<211> LENGTH: 28
<212> TYPE: PRT
<213> ORGANISM: Artificial sequence
<220> FEATURE:
<223> OTHER INFORMATION: Synthesized: cysteine motif 100
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (18)..(22)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid

<400> SEQUENCE: 140

Cys Xaa Xaa Xaa Xaa Xaa Xaa Xaa Xaa Xaa Cys Xaa Xaa Xaa Xaa Cys
1               5                   10                  15

Cys Xaa Xaa Xaa Xaa Xaa Cys Xaa Xaa Xaa Xaa Cys
            20                  25

<210> SEQ ID NO 141
<211> LENGTH: 31
<212> TYPE: PRT
<213> ORGANISM: Artificial sequence
<220> FEATURE:
<223> OTHER INFORMATION: Synthesized: cysteine motif 101
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (22)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 141

Cys Xaa Xaa Xaa Xaa Xaa Xaa Xaa Xaa Xaa Xaa Cys Xaa Xaa Xaa Cys
```

```
                1               5                   10                  15
Xaa Xaa Xaa Xaa Cys Xaa Xaa Xaa Xaa Xaa Xaa Cys Xaa Cys
                20                  25                  30
```

<210> SEQ ID NO 142
<211> LENGTH: 27
<212> TYPE: PRT
<213> ORGANISM: Artificial sequence
<220> FEATURE:
<223> OTHER INFORMATION: Synthesized: cysteine motif 102
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid

<400> SEQUENCE: 142

```
Cys Xaa Xaa Xaa Xaa Xaa Xaa Xaa Cys Xaa Xaa Xaa Xaa Xaa Xaa Xaa
1               5                   10                  15

Cys Xaa Xaa Cys Xaa Xaa Cys Xaa Xaa Xaa Cys
                20                  25
```

<210> SEQ ID NO 143
<211> LENGTH: 29
<212> TYPE: PRT
<213> ORGANISM: Artificial sequence
<220> FEATURE:
<223> OTHER INFORMATION: Synthesized: cysteine motif 103
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (23)..(28)
<223> OTHER INFORMATION: Xaa can be any naturally occurring amino acid

<400> SEQUENCE: 143

```
Cys Xaa Xaa Xaa Xaa Xaa Xaa Xaa Xaa Cys Xaa Xaa Xaa Xaa Cys
1               5                   10                  15

Xaa Xaa Xaa Xaa Cys Cys Xaa Xaa Xaa Xaa Xaa Xaa Cys
                20                  25
```

<210> SEQ ID NO 144
<211> LENGTH: 24
<212> TYPE: PRT
<213> ORGANISM: Artificial sequence
<220> FEATURE:

```
<223> OTHER INFORMATION: Synthesized: cysteine motif 104
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(23)
<223> OTHER INFORMATION: Xaa can be any naturally occurring amino acid

<400> SEQUENCE: 144

Cys Xaa Xaa Xaa Xaa Xaa Xaa Xaa Cys Xaa Cys Xaa Xaa Xaa Cys Xaa
1               5                   10                  15

Cys Xaa Xaa Xaa Xaa Xaa Xaa Cys
            20

<210> SEQ ID NO 145
<211> LENGTH: 23
<212> TYPE: PRT
<213> ORGANISM: Artificial sequence
<220> FEATURE:
<223> OTHER INFORMATION: Synthesized: cysteine motif 105
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid

<400> SEQUENCE: 145

Cys Xaa Xaa Xaa Xaa Xaa Xaa Xaa Cys Xaa Cys Xaa Xaa Xaa Xaa Cys
1               5                   10                  15

Xaa Cys Xaa Xaa Xaa Xaa Cys
            20

<210> SEQ ID NO 146
<211> LENGTH: 22
<212> TYPE: PRT
<213> ORGANISM: Artificial sequence
<220> FEATURE:
<223> OTHER INFORMATION: Synthesized: cysteine motif 106
<220> FEATURE:
<221> NAME/KEY: misc_feature
<222> LOCATION: (2)..(10)
<223> OTHER INFORMATION: Xaa can be any naturally occurring amino acid
<220> FEATURE:
<221> NAME/KEY: misc_feature
```

```
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(21)
<223> OTHER INFORMATION: Xaa can be any naturally occurring amino acid

<400> SEQUENCE: 146

Cys Xaa Xaa Xaa Xaa Xaa Xaa Xaa Xaa Cys Xaa Xaa Xaa Xaa Xaa
1               5                   10                  15

Cys Xaa Xaa Xaa Xaa Cys
            20

<210> SEQ ID NO 147
<211> LENGTH: 21
<212> TYPE: PRT
<213> ORGANISM: Artificial sequence
<220> FEATURE:
<223> OTHER INFORMATION: Synthesized: cysteine motif 107
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: misc_feature
<222> LOCATION: (13)..(20)
<223> OTHER INFORMATION: Xaa can be any naturally occurring amino acid

<400> SEQUENCE: 147

Cys Xaa Xaa Xaa Cys Xaa Xaa Xaa Xaa Xaa Xaa Cys Xaa Xaa Xaa Xaa
1               5                   10                  15

Xaa Xaa Xaa Xaa Cys
            20

<210> SEQ ID NO 148
<211> LENGTH: 19
<212> TYPE: PRT
<213> ORGANISM: Artificial sequence
<220> FEATURE:
<223> OTHER INFORMATION: Synthesized: cysteine motif 108
<220> FEATURE:
<221> NAME/KEY: misc_feature
<222> LOCATION: (2)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid

<400> SEQUENCE: 148

Cys Xaa Xaa Xaa Xaa Xaa Xaa Xaa Xaa Xaa Xaa Cys Xaa Cys Xaa Xaa
1               5                   10                  15

Xaa Xaa Cys

<210> SEQ ID NO 149
<211> LENGTH: 18
<212> TYPE: PRT
<213> ORGANISM: Artificial sequence
<220> FEATURE:
<223> OTHER INFORMATION: Synthesized: cysteine motif 109
<220> FEATURE:
<221> NAME/KEY: misc_feature
```

```
<222> LOCATION: (2)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 149

Cys Xaa Xaa Xaa Xaa Xaa Xaa Xaa Xaa Xaa Xaa Cys Cys Xaa Xaa Xaa
1               5                   10                  15

Xaa Cys

<210> SEQ ID NO 150
<211> LENGTH: 17
<212> TYPE: PRT
<213> ORGANISM: Artificial sequence
<220> FEATURE:
<223> OTHER INFORMATION: Synthesized: cysteine motif 110
<220> FEATURE:
<221> NAME/KEY: misc_feature
<222> LOCATION: (2)..(16)
<223> OTHER INFORMATION: Xaa can be any naturally occurring amino acid

<400> SEQUENCE: 150

Cys Xaa Xaa Xaa Xaa Xaa Xaa Xaa Xaa Xaa Xaa Xaa Xaa Xaa Xaa Xaa
1               5                   10                  15

Cys

<210> SEQ ID NO 151
<211> LENGTH: 12
<212> TYPE: PRT
<213> ORGANISM: Artificial sequence
<220> FEATURE:
<223> OTHER INFORMATION: Synthesized: cysteine motif 111
<220> FEATURE:
<221> NAME/KEY: misc_feature
<222> LOCATION: (2)..(11)
<223> OTHER INFORMATION: Xaa can be any naturally occurring amino acid

<400> SEQUENCE: 151

Cys Xaa Xaa Xaa Xaa Xaa Xaa Xaa Xaa Xaa Xaa Cys
1               5                   10

<210> SEQ ID NO 152
<211> LENGTH: 11
<212> TYPE: PRT
<213> ORGANISM: Artificial sequence
<220> FEATURE:
<223> OTHER INFORMATION: Synthesized: cysteine motif 112
<220> FEATURE:
<221> NAME/KEY: misc_feature
<222> LOCATION: (2)..(10)
<223> OTHER INFORMATION: Xaa can be any naturally occurring amino acid

<400> SEQUENCE: 152

Cys Xaa Xaa Xaa Xaa Xaa Xaa Xaa Xaa Xaa Cys
1               5                   10

<210> SEQ ID NO 153
<211> LENGTH: 5
<212> TYPE: PRT
<213> ORGANISM: Artificial sequence
<220> FEATURE:
<223> OTHER INFORMATION: Synthesized: X1X2X3X4X5 motif 1

<400> SEQUENCE: 153

Thr Thr Val His Gln
1               5
```

<210> SEQ ID NO 154
<211> LENGTH: 5
<212> TYPE: PRT
<213> ORGANISM: Artificial sequence
<220> FEATURE:
<223> OTHER INFORMATION: Synthesized: X1X2X3X4X5 motif 2

<400> SEQUENCE: 154

Thr Ser Val His Gln
1               5

<210> SEQ ID NO 155
<211> LENGTH: 5
<212> TYPE: PRT
<213> ORGANISM: Artificial sequence
<220> FEATURE:
<223> OTHER INFORMATION: Synthesized: X1X2X3X4X5 motif 3

<400> SEQUENCE: 155

Ser Ser Val Thr Gln
1               5

<210> SEQ ID NO 156
<211> LENGTH: 5
<212> TYPE: PRT
<213> ORGANISM: Artificial sequence
<220> FEATURE:
<223> OTHER INFORMATION: Synthesized: X1X2X3X4X5 motif 4

<400> SEQUENCE: 156

Ser Thr Val His Gln
1               5

<210> SEQ ID NO 157
<211> LENGTH: 5
<212> TYPE: PRT
<213> ORGANISM: Artificial sequence
<220> FEATURE:
<223> OTHER INFORMATION: Synthesized: X1X2X3X4X5 motif 5

<400> SEQUENCE: 157

Ala Thr Val Arg Gln
1               5

<210> SEQ ID NO 158
<211> LENGTH: 5
<212> TYPE: PRT
<213> ORGANISM: Artificial sequence
<220> FEATURE:
<223> OTHER INFORMATION: Synthesized: X1X2X3X4X5 motif 6

<400> SEQUENCE: 158

Thr Thr Val Tyr Gln
1               5

<210> SEQ ID NO 159
<211> LENGTH: 5
<212> TYPE: PRT
<213> ORGANISM: Artificial sequence
<220> FEATURE:
<223> OTHER INFORMATION: Synthesized: X1X2X3X4X5 motif 7

<400> SEQUENCE: 159

Ser Pro Val His Gln
1               5

```
<210> SEQ ID NO 160
<211> LENGTH: 5
<212> TYPE: PRT
<213> ORGANISM: Artificial sequence
<220> FEATURE:
<223> OTHER INFORMATION: Synthesized: X1X2X3X4X5 motif 8

<400> SEQUENCE: 160

Ala Thr Val Tyr Gln
1               5

<210> SEQ ID NO 161
<211> LENGTH: 5
<212> TYPE: PRT
<213> ORGANISM: Artificial sequence
<220> FEATURE:
<223> OTHER INFORMATION: Synthesized: X1X2X3X4X5 motif 9

<400> SEQUENCE: 161

Thr Ala Val Tyr Gln
1               5

<210> SEQ ID NO 162
<211> LENGTH: 5
<212> TYPE: PRT
<213> ORGANISM: Artificial sequence
<220> FEATURE:
<223> OTHER INFORMATION: Synthesized: X1X2X3X4X5 motif 10

<400> SEQUENCE: 162

Thr Asn Val His Gln
1               5

<210> SEQ ID NO 163
<211> LENGTH: 5
<212> TYPE: PRT
<213> ORGANISM: Artificial sequence
<220> FEATURE:
<223> OTHER INFORMATION: Synthesized: X1X2X3X4X5 motif 11

<400> SEQUENCE: 163

Ala Thr Val His Gln
1               5

<210> SEQ ID NO 164
<211> LENGTH: 5
<212> TYPE: PRT
<213> ORGANISM: Artificial sequence
<220> FEATURE:
<223> OTHER INFORMATION: Synthesized: X1X2X3X4X5 motif 12

<400> SEQUENCE: 164

Ser Thr Val Tyr Gln
1               5

<210> SEQ ID NO 165
<211> LENGTH: 5
<212> TYPE: PRT
<213> ORGANISM: Artificial sequence
<220> FEATURE:
<223> OTHER INFORMATION: Synthesized: X1X2X3X4X5 motif 13

<400> SEQUENCE: 165

Thr Ile Val His Gln
1               5
```

```
<210> SEQ ID NO 166
<211> LENGTH: 5
<212> TYPE: PRT
<213> ORGANISM: Artificial sequence
<220> FEATURE:
<223> OTHER INFORMATION: Synthesized: X1X2X3X4X5 motif 14

<400> SEQUENCE: 166

Ala Ile Val Tyr Gln
1               5

<210> SEQ ID NO 167
<211> LENGTH: 5
<212> TYPE: PRT
<213> ORGANISM: Artificial sequence
<220> FEATURE:
<223> OTHER INFORMATION: Synthesized: X1X2X3X4X5 motif 15

<400> SEQUENCE: 167

Thr Thr Val Phe Gln
1               5

<210> SEQ ID NO 168
<211> LENGTH: 5
<212> TYPE: PRT
<213> ORGANISM: Artificial sequence
<220> FEATURE:
<223> OTHER INFORMATION: Synthesized: X1X2X3X4X5 motif 16

<400> SEQUENCE: 168

Ala Ala Val Phe Gln
1               5

<210> SEQ ID NO 169
<211> LENGTH: 5
<212> TYPE: PRT
<213> ORGANISM: Artificial sequence
<220> FEATURE:
<223> OTHER INFORMATION: Synthesized: X1X2X3X4X5 motif 17

<400> SEQUENCE: 169

Gly Thr Val His Gln
1               5

<210> SEQ ID NO 170
<211> LENGTH: 5
<212> TYPE: PRT
<213> ORGANISM: Artificial sequence
<220> FEATURE:
<223> OTHER INFORMATION: Synthesized: X1X2X3X4X5 motif 18

<400> SEQUENCE: 170

Ala Ser Val His Gln
1               5

<210> SEQ ID NO 171
<211> LENGTH: 5
<212> TYPE: PRT
<213> ORGANISM: Artificial sequence
<220> FEATURE:
<223> OTHER INFORMATION: Synthesized: X1X2X3X4X5 motif 19

<400> SEQUENCE: 171

Thr Ala Val Phe Gln
1               5

<210> SEQ ID NO 172
```

```
<211> LENGTH: 5
<212> TYPE: PRT
<213> ORGANISM: Artificial sequence
<220> FEATURE:
<223> OTHER INFORMATION: Synthesized: X1X2X3X4X5 motif 20

<400> SEQUENCE: 172

Ala Thr Val Phe Gln
1               5

<210> SEQ ID NO 173
<211> LENGTH: 5
<212> TYPE: PRT
<213> ORGANISM: Artificial sequence
<220> FEATURE:
<223> OTHER INFORMATION: Synthesized: X1X2X3X4X5 motif 21

<400> SEQUENCE: 173

Ala Ala Ala His Gln
1               5

<210> SEQ ID NO 174
<211> LENGTH: 5
<212> TYPE: PRT
<213> ORGANISM: Artificial sequence
<220> FEATURE:
<223> OTHER INFORMATION: Synthesized: X1X2X3X4X5 motif 22

<400> SEQUENCE: 174

Val Val Val Tyr Gln
1               5

<210> SEQ ID NO 175
<211> LENGTH: 5
<212> TYPE: PRT
<213> ORGANISM: Artificial sequence
<220> FEATURE:
<223> OTHER INFORMATION: Synthesized: X1X2X3X4X5 motif 23

<400> SEQUENCE: 175

Gly Thr Val Phe Gln
1               5

<210> SEQ ID NO 176
<211> LENGTH: 5
<212> TYPE: PRT
<213> ORGANISM: Artificial sequence
<220> FEATURE:
<223> OTHER INFORMATION: Synthesized: X1X2X3X4X5 motif 24

<400> SEQUENCE: 176

Thr Ala Val His Gln
1               5

<210> SEQ ID NO 177
<211> LENGTH: 5
<212> TYPE: PRT
<213> ORGANISM: Artificial sequence
<220> FEATURE:
<223> OTHER INFORMATION: Synthesized: X1X2X3X4X5 motif 25

<400> SEQUENCE: 177

Ile Thr Val His Gln
1               5

<210> SEQ ID NO 178
<211> LENGTH: 5
```

-continued

```
<212> TYPE: PRT
<213> ORGANISM: Artificial sequence
<220> FEATURE:
<223> OTHER INFORMATION: Synthesized: X1X2X3X4X5 motif 26

<400> SEQUENCE: 178

Ile Thr Ala His Gln
1               5

<210> SEQ ID NO 179
<211> LENGTH: 5
<212> TYPE: PRT
<213> ORGANISM: Artificial sequence
<220> FEATURE:
<223> OTHER INFORMATION: Synthesized: X1X2X3X4X5 motif 27

<400> SEQUENCE: 179

Val Thr Val His Gln
1               5

<210> SEQ ID NO 180
<211> LENGTH: 5
<212> TYPE: PRT
<213> ORGANISM: Artificial sequence
<220> FEATURE:
<223> OTHER INFORMATION: Synthesized: X1X2X3X4X5 motif 28

<400> SEQUENCE: 180

Ala Ala Val His Gln
1               5

<210> SEQ ID NO 181
<211> LENGTH: 5
<212> TYPE: PRT
<213> ORGANISM: Artificial sequence
<220> FEATURE:
<223> OTHER INFORMATION: Synthesized: X1X2X3X4X5 motif 29

<400> SEQUENCE: 181

Gly Thr Val Tyr Gln
1               5

<210> SEQ ID NO 182
<211> LENGTH: 5
<212> TYPE: PRT
<213> ORGANISM: Artificial sequence
<220> FEATURE:
<223> OTHER INFORMATION: Synthesized: X1X2X3X4X5 motif 30

<400> SEQUENCE: 182

Thr Thr Val Leu Gln
1               5

<210> SEQ ID NO 183
<211> LENGTH: 5
<212> TYPE: PRT
<213> ORGANISM: Artificial sequence
<220> FEATURE:
<223> OTHER INFORMATION: Synthesized: X1X2X3X4X5 motif 31

<400> SEQUENCE: 183

Thr Thr Thr His Gln
1               5

<210> SEQ ID NO 184
<211> LENGTH: 5
<212> TYPE: PRT
```

```
<213> ORGANISM: Artificial sequence
<220> FEATURE:
<223> OTHER INFORMATION: Synthesized: X1X2X3X4X5 motif 32

<400> SEQUENCE: 184

Thr Thr Asp Tyr Gln
1               5

<210> SEQ ID NO 185
<211> LENGTH: 6
<212> TYPE: PRT
<213> ORGANISM: Artificial sequence
<220> FEATURE:
<223> OTHER INFORMATION: Synthesized: CX1X2X3X4X5 motif 1

<400> SEQUENCE: 185

Cys Thr Thr Val His Gln
1               5

<210> SEQ ID NO 186
<211> LENGTH: 6
<212> TYPE: PRT
<213> ORGANISM: Artificial sequence
<220> FEATURE:
<223> OTHER INFORMATION: Synthesized: CX1X2X3X4X5 motif 2

<400> SEQUENCE: 186

Cys Thr Ser Val His Gln
1               5

<210> SEQ ID NO 187
<211> LENGTH: 6
<212> TYPE: PRT
<213> ORGANISM: Artificial sequence
<220> FEATURE:
<223> OTHER INFORMATION: Synthesized: CX1X2X3X4X5 motif 3

<400> SEQUENCE: 187

Cys Ser Ser Val Thr Gln
1               5

<210> SEQ ID NO 188
<211> LENGTH: 6
<212> TYPE: PRT
<213> ORGANISM: Artificial sequence
<220> FEATURE:
<223> OTHER INFORMATION: Synthesized: CX1X2X3X4X5 motif 4

<400> SEQUENCE: 188

Cys Ser Thr Val His Gln
1               5

<210> SEQ ID NO 189
<211> LENGTH: 6
<212> TYPE: PRT
<213> ORGANISM: Artificial sequence
<220> FEATURE:
<223> OTHER INFORMATION: Synthesized: CX1X2X3X4X5 motif 5

<400> SEQUENCE: 189

Cys Ala Thr Val Arg Gln
1               5

<210> SEQ ID NO 190
<211> LENGTH: 6
<212> TYPE: PRT
<213> ORGANISM: Artificial sequence
```

```
<220> FEATURE:
<223> OTHER INFORMATION: Synthesized: CX1X2X3X4X5 motif 6

<400> SEQUENCE: 190

Cys Thr Thr Val Tyr Gln
1               5

<210> SEQ ID NO 191
<211> LENGTH: 6
<212> TYPE: PRT
<213> ORGANISM: Artificial sequence
<220> FEATURE:
<223> OTHER INFORMATION: Synthesized: CX1X2X3X4X5 motif 7

<400> SEQUENCE: 191

Cys Ser Pro Val His Gln
1               5

<210> SEQ ID NO 192
<211> LENGTH: 6
<212> TYPE: PRT
<213> ORGANISM: Artificial sequence
<220> FEATURE:
<223> OTHER INFORMATION: Synthesized: CX1X2X3X4X5 motif 8

<400> SEQUENCE: 192

Cys Ala Thr Val Tyr Gln
1               5

<210> SEQ ID NO 193
<211> LENGTH: 6
<212> TYPE: PRT
<213> ORGANISM: Artificial sequence
<220> FEATURE:
<223> OTHER INFORMATION: Synthesized: CX1X2X3X4X5 motif 9

<400> SEQUENCE: 193

Cys Thr Ala Val Tyr Gln
1               5

<210> SEQ ID NO 194
<211> LENGTH: 6
<212> TYPE: PRT
<213> ORGANISM: Artificial sequence
<220> FEATURE:
<223> OTHER INFORMATION: Synthesized: CX1X2X3X4X5 motif 10

<400> SEQUENCE: 194

Cys Thr Asn Val His Gln
1               5

<210> SEQ ID NO 195
<211> LENGTH: 6
<212> TYPE: PRT
<213> ORGANISM: Artificial sequence
<220> FEATURE:
<223> OTHER INFORMATION: Synthesized: CX1X2X3X4X5 motif 11

<400> SEQUENCE: 195

Cys Ala Thr Val His Gln
1               5

<210> SEQ ID NO 196
<211> LENGTH: 6
<212> TYPE: PRT
<213> ORGANISM: Artificial sequence
<220> FEATURE:
```

-continued

```
<223> OTHER INFORMATION: Synthesized: CX1X2X3X4X5 motif 12

<400> SEQUENCE: 196

Cys Ser Thr Val Tyr Gln
1               5

<210> SEQ ID NO 197
<211> LENGTH: 6
<212> TYPE: PRT
<213> ORGANISM: Artificial sequence
<220> FEATURE:
<223> OTHER INFORMATION: Synthesized: CX1X2X3X4X5 motif 13

<400> SEQUENCE: 197

Cys Thr Ile Val His Gln
1               5

<210> SEQ ID NO 198
<211> LENGTH: 6
<212> TYPE: PRT
<213> ORGANISM: Artificial sequence
<220> FEATURE:
<223> OTHER INFORMATION: Synthesized: CX1X2X3X4X5 motif 14

<400> SEQUENCE: 198

Cys Ala Ile Val Tyr Gln
1               5

<210> SEQ ID NO 199
<211> LENGTH: 6
<212> TYPE: PRT
<213> ORGANISM: Artificial sequence
<220> FEATURE:
<223> OTHER INFORMATION: Synthesized: CX1X2X3X4X5 motif 15

<400> SEQUENCE: 199

Cys Thr Thr Val Phe Gln
1               5

<210> SEQ ID NO 200
<211> LENGTH: 6
<212> TYPE: PRT
<213> ORGANISM: Artificial sequence
<220> FEATURE:
<223> OTHER INFORMATION: Synthesized: CX1X2X3X4X5 motif 16

<400> SEQUENCE: 200

Cys Ala Ala Val Phe Gln
1               5

<210> SEQ ID NO 201
<211> LENGTH: 6
<212> TYPE: PRT
<213> ORGANISM: Artificial sequence
<220> FEATURE:
<223> OTHER INFORMATION: Synthesized: CX1X2X3X4X5 motif 17

<400> SEQUENCE: 201

Cys Gly Thr Val His Gln
1               5

<210> SEQ ID NO 202
<211> LENGTH: 6
<212> TYPE: PRT
<213> ORGANISM: Artificial sequence
<220> FEATURE:
<223> OTHER INFORMATION: Synthesized: CX1X2X3X4X5 motif 18
```

```
<400> SEQUENCE: 202

Cys Ala Ser Val His Gln
1               5

<210> SEQ ID NO 203
<211> LENGTH: 6
<212> TYPE: PRT
<213> ORGANISM: Artificial sequence
<220> FEATURE:
<223> OTHER INFORMATION: Synthesized: CX1X2X3X4X5 motif 19

<400> SEQUENCE: 203

Cys Thr Ala Val Phe Gln
1               5

<210> SEQ ID NO 204
<211> LENGTH: 6
<212> TYPE: PRT
<213> ORGANISM: Artificial sequence
<220> FEATURE:
<223> OTHER INFORMATION: Synthesized: CX1X2X3X4X5 motif 20

<400> SEQUENCE: 204

Cys Ala Thr Val Phe Gln
1               5

<210> SEQ ID NO 205
<211> LENGTH: 6
<212> TYPE: PRT
<213> ORGANISM: Artificial sequence
<220> FEATURE:
<223> OTHER INFORMATION: Synthesized: CX1X2X3X4X5 motif 21

<400> SEQUENCE: 205

Cys Ala Ala Ala His Gln
1               5

<210> SEQ ID NO 206
<211> LENGTH: 6
<212> TYPE: PRT
<213> ORGANISM: Artificial sequence
<220> FEATURE:
<223> OTHER INFORMATION: Synthesized: CX1X2X3X4X5 motif 22

<400> SEQUENCE: 206

Cys Val Val Val Tyr Gln
1               5

<210> SEQ ID NO 207
<211> LENGTH: 6
<212> TYPE: PRT
<213> ORGANISM: Artificial sequence
<220> FEATURE:
<223> OTHER INFORMATION: Synthesized: CX1X2X3X4X5 motif 23

<400> SEQUENCE: 207

Cys Gly Thr Val Phe Gln
1               5

<210> SEQ ID NO 208
<211> LENGTH: 6
<212> TYPE: PRT
<213> ORGANISM: Artificial sequence
<220> FEATURE:
<223> OTHER INFORMATION: Synthesized: CX1X2X3X4X5 motif 24
```

```
<400> SEQUENCE: 208

Cys Thr Ala Val His Gln
1               5

<210> SEQ ID NO 209
<211> LENGTH: 6
<212> TYPE: PRT
<213> ORGANISM: Artificial sequence
<220> FEATURE:
<223> OTHER INFORMATION: Synthesized: CX1X2X3X4X5 motif 25

<400> SEQUENCE: 209

Cys Ile Thr Val His Gln
1               5

<210> SEQ ID NO 210
<211> LENGTH: 6
<212> TYPE: PRT
<213> ORGANISM: Artificial sequence
<220> FEATURE:
<223> OTHER INFORMATION: Synthesized: CX1X2X3X4X5 motif 26

<400> SEQUENCE: 210

Cys Ile Thr Ala His Gln
1               5

<210> SEQ ID NO 211
<211> LENGTH: 6
<212> TYPE: PRT
<213> ORGANISM: Artificial sequence
<220> FEATURE:
<223> OTHER INFORMATION: Synthesized: CX1X2X3X4X5 motif 27

<400> SEQUENCE: 211

Cys Val Thr Val His Gln
1               5

<210> SEQ ID NO 212
<211> LENGTH: 6
<212> TYPE: PRT
<213> ORGANISM: Artificial sequence
<220> FEATURE:
<223> OTHER INFORMATION: Synthesized: CX1X2X3X4X5 motif 28

<400> SEQUENCE: 212

Cys Ala Ala Val His Gln
1               5

<210> SEQ ID NO 213
<211> LENGTH: 6
<212> TYPE: PRT
<213> ORGANISM: Artificial sequence
<220> FEATURE:
<223> OTHER INFORMATION: Synthesized: CX1X2X3X4X5 motif 29

<400> SEQUENCE: 213

Cys Gly Thr Val Tyr Gln
1               5

<210> SEQ ID NO 214
<211> LENGTH: 6
<212> TYPE: PRT
<213> ORGANISM: Artificial sequence
<220> FEATURE:
<223> OTHER INFORMATION: Synthesized: CX1X2X3X4X5 motif 30

<400> SEQUENCE: 214
```

```
Cys Thr Thr Val Leu Gln
1               5

<210> SEQ ID NO 215
<211> LENGTH: 6
<212> TYPE: PRT
<213> ORGANISM: Artificial sequence
<220> FEATURE:
<223> OTHER INFORMATION: Synthesized: CX1X2X3X4X5 motif 31

<400> SEQUENCE: 215

Cys Thr Thr Thr His Gln
1               5

<210> SEQ ID NO 216
<211> LENGTH: 6
<212> TYPE: PRT
<213> ORGANISM: Artificial sequence
<220> FEATURE:
<223> OTHER INFORMATION: Synthesized: CX1X2X3X4X5 motif 32

<400> SEQUENCE: 216

Cys Thr Thr Asp Tyr Gln
1               5

<210> SEQ ID NO 217
<211> LENGTH: 8
<212> TYPE: PRT
<213> ORGANISM: Artificial sequence
<220> FEATURE:
<223> OTHER INFORMATION: Synthesized: XAXBZ motif 1

<400> SEQUENCE: 217

Cys Tyr Thr Tyr Asn Tyr Glu Phe
1               5

<210> SEQ ID NO 218
<211> LENGTH: 8
<212> TYPE: PRT
<213> ORGANISM: Artificial sequence
<220> FEATURE:
<223> OTHER INFORMATION: Synthesized: XAXBZ motif 2

<400> SEQUENCE: 218

His Tyr Thr Tyr Thr Tyr Asp Phe
1               5

<210> SEQ ID NO 219
<211> LENGTH: 8
<212> TYPE: PRT
<213> ORGANISM: Artificial sequence
<220> FEATURE:
<223> OTHER INFORMATION: Synthesized: XAXBZ motif 3

<400> SEQUENCE: 219

His Tyr Thr Tyr Thr Tyr Glu Trp
1               5

<210> SEQ ID NO 220
<211> LENGTH: 8
<212> TYPE: PRT
<213> ORGANISM: Artificial sequence
<220> FEATURE:
<223> OTHER INFORMATION: Synthesized: XAXBZ motif 4

<400> SEQUENCE: 220
```

Lys His Arg Tyr Thr Tyr Glu Trp
1               5

<210> SEQ ID NO 221
<211> LENGTH: 8
<212> TYPE: PRT
<213> ORGANISM: Artificial sequence
<220> FEATURE:
<223> OTHER INFORMATION: Synthesized: XAXBZ motif 5

<400> SEQUENCE: 221

Asn Tyr Ile Tyr Lys Tyr Ser Phe
1               5

<210> SEQ ID NO 222
<211> LENGTH: 8
<212> TYPE: PRT
<213> ORGANISM: Artificial sequence
<220> FEATURE:
<223> OTHER INFORMATION: Synthesized: XAXBZ motif 6

<400> SEQUENCE: 222

Pro Tyr Ile Tyr Thr Tyr Gln Phe
1               5

<210> SEQ ID NO 223
<211> LENGTH: 8
<212> TYPE: PRT
<213> ORGANISM: Artificial sequence
<220> FEATURE:
<223> OTHER INFORMATION: Synthesized: XAXBZ motif 7

<400> SEQUENCE: 223

Ser Phe Thr Tyr Thr Tyr Glu Trp
1               5

<210> SEQ ID NO 224
<211> LENGTH: 8
<212> TYPE: PRT
<213> ORGANISM: Artificial sequence
<220> FEATURE:
<223> OTHER INFORMATION: Synthesized: XAXBZ motif 8

<400> SEQUENCE: 224

Ser Tyr Ile Tyr Ile Tyr Gln Trp
1               5

<210> SEQ ID NO 225
<211> LENGTH: 8
<212> TYPE: PRT
<213> ORGANISM: Artificial sequence
<220> FEATURE:
<223> OTHER INFORMATION: Synthesized: XAXBZ motif 9

<400> SEQUENCE: 225

Ser Tyr Asn Tyr Thr Tyr Ser Trp
1               5

<210> SEQ ID NO 226
<211> LENGTH: 8
<212> TYPE: PRT
<213> ORGANISM: Artificial sequence
<220> FEATURE:
<223> OTHER INFORMATION: Synthesized: XAXBZ motif 10

<400> SEQUENCE: 226

Ser Tyr Ser Tyr Ser Tyr Glu Tyr

```
<210> SEQ ID NO 227
<211> LENGTH: 8
<212> TYPE: PRT
<213> ORGANISM: Artificial sequence
<220> FEATURE:
<223> OTHER INFORMATION: Synthesized: XAXBZ motif 11

<400> SEQUENCE: 227

Ser Tyr Thr Tyr Asn Tyr Asp Phe
1               5

<210> SEQ ID NO 228
<211> LENGTH: 8
<212> TYPE: PRT
<213> ORGANISM: Artificial sequence
<220> FEATURE:
<223> OTHER INFORMATION: Synthesized: XAXBZ motif 12

<400> SEQUENCE: 228

Ser Tyr Thr Tyr Asn Tyr Glu Trp
1               5

<210> SEQ ID NO 229
<211> LENGTH: 8
<212> TYPE: PRT
<213> ORGANISM: Artificial sequence
<220> FEATURE:
<223> OTHER INFORMATION: Synthesized: XAXBZ motif 13

<400> SEQUENCE: 229

Ser Tyr Thr Tyr Asn Tyr Gln Phe
1               5

<210> SEQ ID NO 230
<211> LENGTH: 8
<212> TYPE: PRT
<213> ORGANISM: Artificial sequence
<220> FEATURE:
<223> OTHER INFORMATION: Synthesized: XAXBZ motif 14

<400> SEQUENCE: 230

Ser Tyr Val Trp Thr His Asn Phe
1               5

<210> SEQ ID NO 231
<211> LENGTH: 8
<212> TYPE: PRT
<213> ORGANISM: Artificial sequence
<220> FEATURE:
<223> OTHER INFORMATION: Synthesized: XAXBZ motif 15

<400> SEQUENCE: 231

Thr Tyr Lys Tyr Val Tyr Glu Trp
1               5

<210> SEQ ID NO 232
<211> LENGTH: 8
<212> TYPE: PRT
<213> ORGANISM: Artificial sequence
<220> FEATURE:
<223> OTHER INFORMATION: Synthesized: XAXBZ motif 16

<400> SEQUENCE: 232

Thr Tyr Thr Tyr Thr Tyr Glu Phe
1               5
```

<210> SEQ ID NO 233
<211> LENGTH: 8
<212> TYPE: PRT
<213> ORGANISM: Artificial sequence
<220> FEATURE:
<223> OTHER INFORMATION: Synthesized: XAXBZ motif 17

<400> SEQUENCE: 233

Thr Tyr Thr Tyr Thr Tyr Glu Trp
1               5

<210> SEQ ID NO 234
<211> LENGTH: 8
<212> TYPE: PRT
<213> ORGANISM: Artificial sequence
<220> FEATURE:
<223> OTHER INFORMATION: Synthesized: XAXBZ motif 18

<400> SEQUENCE: 234

Val Phe Thr Tyr Thr Tyr Glu Phe
1               5

<210> SEQ ID NO 235
<211> LENGTH: 6
<212> TYPE: PRT
<213> ORGANISM: Artificial sequence
<220> FEATURE:
<223> OTHER INFORMATION: Synthesized: XAXBZ motif 19

<400> SEQUENCE: 235

Ala Tyr Thr Tyr Glu Trp
1               5

<210> SEQ ID NO 236
<211> LENGTH: 6
<212> TYPE: PRT
<213> ORGANISM: Artificial sequence
<220> FEATURE:
<223> OTHER INFORMATION: Synthesized: XAXBZ motif 20

<400> SEQUENCE: 236

Asp Tyr Ile Tyr Thr Tyr
1               5

<210> SEQ ID NO 237
<211> LENGTH: 6
<212> TYPE: PRT
<213> ORGANISM: Artificial sequence
<220> FEATURE:
<223> OTHER INFORMATION: Synthesized: XAXBZ motif 21

<400> SEQUENCE: 237

Ile His Ser Tyr Glu Phe
1               5

<210> SEQ ID NO 238
<211> LENGTH: 6
<212> TYPE: PRT
<213> ORGANISM: Artificial sequence
<220> FEATURE:
<223> OTHER INFORMATION: Synthesized: XAXBZ motif 22

<400> SEQUENCE: 238

Ser Phe Thr Tyr Glu Phe
1               5

<210> SEQ ID NO 239
<211> LENGTH: 6
<212> TYPE: PRT
<213> ORGANISM: Artificial sequence
<220> FEATURE:
<223> OTHER INFORMATION: Synthesized: XAXBZ motif 23

<400> SEQUENCE: 239

Ser His Ser Tyr Glu Phe
1               5

<210> SEQ ID NO 240
<211> LENGTH: 6
<212> TYPE: PRT
<213> ORGANISM: Artificial sequence
<220> FEATURE:
<223> OTHER INFORMATION: Synthesized: XAXBZ motif 24

<400> SEQUENCE: 240

Thr His Thr Tyr Glu Phe
1               5

<210> SEQ ID NO 241
<211> LENGTH: 6
<212> TYPE: PRT
<213> ORGANISM: Artificial sequence
<220> FEATURE:
<223> OTHER INFORMATION: Synthesized: XAXBZ motif 25

<400> SEQUENCE: 241

Thr Trp Thr Tyr Glu Phe
1               5

<210> SEQ ID NO 242
<211> LENGTH: 6
<212> TYPE: PRT
<213> ORGANISM: Artificial sequence
<220> FEATURE:
<223> OTHER INFORMATION: Synthesized: XAXBZ motif 26

<400> SEQUENCE: 242

Thr Tyr Asn Tyr Glu Trp
1               5

<210> SEQ ID NO 243
<211> LENGTH: 6
<212> TYPE: PRT
<213> ORGANISM: Artificial sequence
<220> FEATURE:
<223> OTHER INFORMATION: Synthesized: XAXBZ motif 27

<400> SEQUENCE: 243

Thr Tyr Ser Tyr Glu Phe
1               5

<210> SEQ ID NO 244
<211> LENGTH: 6
<212> TYPE: PRT
<213> ORGANISM: Artificial sequence
<220> FEATURE:
<223> OTHER INFORMATION: Synthesized: XAXBZ motif 28

<400> SEQUENCE: 244

Thr Tyr Ser Tyr Glu His
1               5

```
<210> SEQ ID NO 245
<211> LENGTH: 6
<212> TYPE: PRT
<213> ORGANISM: Artificial sequence
<220> FEATURE:
<223> OTHER INFORMATION: Synthesized: XAXBZ motif 29

<400> SEQUENCE: 245

Thr Tyr Thr Tyr Asp Phe
1               5

<210> SEQ ID NO 246
<211> LENGTH: 6
<212> TYPE: PRT
<213> ORGANISM: Artificial sequence
<220> FEATURE:
<223> OTHER INFORMATION: Synthesized: XAXBZ motif 30

<400> SEQUENCE: 246

Thr Tyr Thr Tyr Glu Phe
1               5

<210> SEQ ID NO 247
<211> LENGTH: 6
<212> TYPE: PRT
<213> ORGANISM: Artificial sequence
<220> FEATURE:
<223> OTHER INFORMATION: Synthesized: XAXBZ motif 31

<400> SEQUENCE: 247

Thr Tyr Thr Tyr Glu Trp
1               5

<210> SEQ ID NO 248
<211> LENGTH: 4
<212> TYPE: PRT
<213> ORGANISM: Artificial sequence
<220> FEATURE:
<223> OTHER INFORMATION: Synthesized: XAXBZ motif 32

<400> SEQUENCE: 248

Ala Tyr Glu Phe
1

<210> SEQ ID NO 249
<211> LENGTH: 4
<212> TYPE: PRT
<213> ORGANISM: Artificial sequence
<220> FEATURE:
<223> OTHER INFORMATION: Synthesized: XAXBZ motif 33

<400> SEQUENCE: 249

Ala Tyr Ser Phe
1

<210> SEQ ID NO 250
<211> LENGTH: 4
<212> TYPE: PRT
<213> ORGANISM: Artificial sequence
<220> FEATURE:
<223> OTHER INFORMATION: Synthesized: XAXBZ motif 34

<400> SEQUENCE: 250

Ala Tyr Ser Tyr
1

<210> SEQ ID NO 251
```

```
<211> LENGTH: 4
<212> TYPE: PRT
<213> ORGANISM: Artificial sequence
<220> FEATURE:
<223> OTHER INFORMATION: Synthesized: XAXBZ motif 35

<400> SEQUENCE: 251

Cys Tyr Ser Phe
1

<210> SEQ ID NO 252
<211> LENGTH: 4
<212> TYPE: PRT
<213> ORGANISM: Artificial sequence
<220> FEATURE:
<223> OTHER INFORMATION: Synthesized: XAXBZ motif 36

<400> SEQUENCE: 252

Asp Tyr Thr Tyr
1

<210> SEQ ID NO 253
<211> LENGTH: 4
<212> TYPE: PRT
<213> ORGANISM: Artificial sequence
<220> FEATURE:
<223> OTHER INFORMATION: Synthesized: XAXBZ motif 37

<400> SEQUENCE: 253

Lys Tyr Glu His
1

<210> SEQ ID NO 254
<211> LENGTH: 4
<212> TYPE: PRT
<213> ORGANISM: Artificial sequence
<220> FEATURE:
<223> OTHER INFORMATION: Synthesized: XAXBZ motif 38

<400> SEQUENCE: 254

Lys Tyr Glu Trp
1

<210> SEQ ID NO 255
<211> LENGTH: 4
<212> TYPE: PRT
<213> ORGANISM: Artificial sequence
<220> FEATURE:
<223> OTHER INFORMATION: Synthesized: XAXBZ motif 39

<400> SEQUENCE: 255

Met Tyr Glu Phe
1

<210> SEQ ID NO 256
<211> LENGTH: 4
<212> TYPE: PRT
<213> ORGANISM: Artificial sequence
<220> FEATURE:
<223> OTHER INFORMATION: Synthesized: XAXBZ motif 40

<400> SEQUENCE: 256

Asn Trp Ile Tyr
1

<210> SEQ ID NO 257
<211> LENGTH: 4
```

```
<212> TYPE: PRT
<213> ORGANISM: Artificial sequence
<220> FEATURE:
<223> OTHER INFORMATION: Synthesized: XAXBZ motif 41

<400> SEQUENCE: 257

Asn Tyr Asp Tyr
1

<210> SEQ ID NO 258
<211> LENGTH: 4
<212> TYPE: PRT
<213> ORGANISM: Artificial sequence
<220> FEATURE:
<223> OTHER INFORMATION: Synthesized: XAXBZ motif 42

<400> SEQUENCE: 258

Asn Tyr Gln Trp
1

<210> SEQ ID NO 259
<211> LENGTH: 4
<212> TYPE: PRT
<213> ORGANISM: Artificial sequence
<220> FEATURE:
<223> OTHER INFORMATION: Synthesized: XAXBZ motif 43

<400> SEQUENCE: 259

Asn Tyr Ser Phe
1

<210> SEQ ID NO 260
<211> LENGTH: 4
<212> TYPE: PRT
<213> ORGANISM: Artificial sequence
<220> FEATURE:
<223> OTHER INFORMATION: Synthesized: XAXBZ motif 44

<400> SEQUENCE: 260

Pro Tyr Glu Trp
1

<210> SEQ ID NO 261
<211> LENGTH: 4
<212> TYPE: PRT
<213> ORGANISM: Artificial sequence
<220> FEATURE:
<223> OTHER INFORMATION: Synthesized: XAXBZ motif 45

<400> SEQUENCE: 261

Arg Tyr Asn Trp
1

<210> SEQ ID NO 262
<211> LENGTH: 4
<212> TYPE: PRT
<213> ORGANISM: Artificial sequence
<220> FEATURE:
<223> OTHER INFORMATION: Synthesized: XAXBZ motif 46

<400> SEQUENCE: 262

Arg Tyr Thr Tyr
1

<210> SEQ ID NO 263
<211> LENGTH: 4
<212> TYPE: PRT
```

```
<213> ORGANISM: Artificial sequence
<220> FEATURE:
<223> OTHER INFORMATION: Synthesized: XAXBZ motif 47

<400> SEQUENCE: 263

Ser Tyr Glu Phe
1

<210> SEQ ID NO 264
<211> LENGTH: 4
<212> TYPE: PRT
<213> ORGANISM: Artificial sequence
<220> FEATURE:
<223> OTHER INFORMATION: Synthesized: XAXBZ motif 48

<400> SEQUENCE: 264

Ser Tyr Glu His
1

<210> SEQ ID NO 265
<211> LENGTH: 4
<212> TYPE: PRT
<213> ORGANISM: Artificial sequence
<220> FEATURE:
<223> OTHER INFORMATION: Synthesized: XAXBZ motif 49

<400> SEQUENCE: 265

Ser Tyr Glu Trp
1

<210> SEQ ID NO 266
<211> LENGTH: 4
<212> TYPE: PRT
<213> ORGANISM: Artificial sequence
<220> FEATURE:
<223> OTHER INFORMATION: Synthesized: XAXBZ motif 50

<400> SEQUENCE: 266

Ser Tyr Lys Trp
1

<210> SEQ ID NO 267
<211> LENGTH: 4
<212> TYPE: PRT
<213> ORGANISM: Artificial sequence
<220> FEATURE:
<223> OTHER INFORMATION: Synthesized: XAXBZ motif 51

<400> SEQUENCE: 267

Ser Tyr Thr Tyr
1

<210> SEQ ID NO 268
<211> LENGTH: 4
<212> TYPE: PRT
<213> ORGANISM: Artificial sequence
<220> FEATURE:
<223> OTHER INFORMATION: Synthesized: XAXBZ motif 52

<400> SEQUENCE: 268

Thr Tyr Asp Phe
1

<210> SEQ ID NO 269
<211> LENGTH: 4
<212> TYPE: PRT
<213> ORGANISM: Artificial sequence
```

```
<220> FEATURE:
<223> OTHER INFORMATION: Synthesized: XAXBZ motif 53

<400> SEQUENCE: 269

Thr Tyr Glu Phe
1

<210> SEQ ID NO 270
<211> LENGTH: 4
<212> TYPE: PRT
<213> ORGANISM: Artificial sequence
<220> FEATURE:
<223> OTHER INFORMATION: Synthesized: XAXBZ motif 54

<400> SEQUENCE: 270

Thr Tyr Glu Trp
1

<210> SEQ ID NO 271
<211> LENGTH: 4
<212> TYPE: PRT
<213> ORGANISM: Artificial sequence
<220> FEATURE:
<223> OTHER INFORMATION: Synthesized: XAXBZ motif 55

<400> SEQUENCE: 271

Thr Tyr Gln Trp
1

<210> SEQ ID NO 272
<211> LENGTH: 4
<212> TYPE: PRT
<213> ORGANISM: Artificial sequence
<220> FEATURE:
<223> OTHER INFORMATION: Synthesized: XAXBZ motif 56

<400> SEQUENCE: 272

Thr Tyr Thr Tyr
1

<210> SEQ ID NO 273
<211> LENGTH: 4
<212> TYPE: PRT
<213> ORGANISM: Artificial sequence
<220> FEATURE:
<223> OTHER INFORMATION: Synthesized: XAXBZ motif 57

<400> SEQUENCE: 273

Val Tyr Glu Trp
1

<210> SEQ ID NO 274
<211> LENGTH: 48
<212> TYPE: PRT
<213> ORGANISM: Artificial sequence
<220> FEATURE:
<223> OTHER INFORMATION: Synthesized: DH2 Germline sequence

<400> SEQUENCE: 274

Ser Cys Pro Asp Gly Tyr Ser Tyr Gly Tyr Gly Cys Gly Tyr Gly Tyr
1               5                   10                  15

Gly Cys Ser Gly Tyr Asp Cys Tyr Gly Tyr Gly Gly Tyr Gly Gly Tyr
                20                  25                  30

Gly Gly Tyr Gly Tyr Ser Ser Tyr Ser Tyr Ser Tyr Thr Tyr Glu Tyr
            35                  40                  45
```

<210> SEQ ID NO 275
<211> LENGTH: 15
<212> TYPE: PRT
<213> ORGANISM: Artificial sequence
<220> FEATURE:
<223> OTHER INFORMATION: Synthesized: JH1 Germline sequence

<400> SEQUENCE: 275

Tyr Val Asp Ala Trp Gly Gln Gly Leu Leu Val Thr Val Ser Ser
1               5                   10                  15

<210> SEQ ID NO 276
<211> LENGTH: 65
<212> TYPE: PRT
<213> ORGANISM: Artificial sequence
<220> FEATURE:
<223> OTHER INFORMATION: Synthesized: BLV1H12

<400> SEQUENCE: 276

Cys Thr Ser Val His Gln Glu Thr Lys Lys Tyr Gln Ser Cys Pro Asp
1               5                   10                  15

Gly Tyr Arg Glu Arg Ser Asp Cys Ser Asn Arg Pro Ala Cys Gly Thr
                20                  25                  30

Ser Asp Cys Cys Arg Val Ser Val Phe Gly Asn Cys Leu Thr Thr Leu
            35                  40                  45

Pro Val Ser Tyr Ser Tyr Thr Tyr Asn Tyr Glu Trp His Val Asp Val
        50                  55                  60

Trp
65

<210> SEQ ID NO 277
<211> LENGTH: 60
<212> TYPE: PRT
<213> ORGANISM: Artificial sequence
<220> FEATURE:
<223> OTHER INFORMATION: Synthesized: BLV5B8

<400> SEQUENCE: 277

Cys Thr Thr Val His Gln Glu Thr Arg Lys Thr Cys Ser Asp Gly Tyr
1               5                   10                  15

Ile Ala Val Asp Ser Cys Gly Arg Gly Gln Ser Asp Gly Cys Val Asn
                20                  25                  30

Asp Cys Asn Ser Cys Tyr Tyr Gly Trp Arg Asn Cys Arg Arg Gln Pro
            35                  40                  45

Ala Ile His Ser Tyr Glu Phe His Val Asp Ala Trp
        50                  55                  60

<210> SEQ ID NO 278
<211> LENGTH: 61
<212> TYPE: PRT
<213> ORGANISM: Artificial sequence
<220> FEATURE:
<223> OTHER INFORMATION: Synthesized: BLV5D3

<400> SEQUENCE: 278

Cys Ser Ser Val Thr Gln Arg Thr His Val Ser Arg Ser Cys Pro Asp
1               5                   10                  15

Gly Cys Ser Asp Gly Asp Gly Cys Val Asp Gly Cys Cys Cys Ser Ala
                20                  25                  30

Tyr Arg Cys Tyr Thr Pro Gly Val Arg Asp Leu Ser Cys Thr Ser Tyr
            35                  40                  45

Ser Ile Thr Tyr Thr Tyr Glu Trp Asn Val Asp Ala Trp
    50                  55                  60

<210> SEQ ID NO 279
<211> LENGTH: 62
<212> TYPE: PRT
<213> ORGANISM: Artificial sequence
<220> FEATURE:
<223> OTHER INFORMATION: Synthesized: BLV8C11

<400> SEQUENCE: 279

Cys Thr Thr Val His Gln Lys Thr Arg Lys Thr Cys Cys Ser Asp
1               5                   10                  15

Ala Tyr Arg Tyr Asp Ser Gly Cys Gly Ser Gly Cys Asp Cys Cys Gly
                20                  25                  30

Ala Asp Cys Tyr Val Phe Gly Ala Cys Thr Phe Gly Leu Asp Ser Ser
            35                  40                  45

Tyr Ser Tyr Ile Tyr Ile Tyr Gln Trp Tyr Val Asp Ala Trp
    50                  55                  60

<210> SEQ ID NO 280
<211> LENGTH: 60
<212> TYPE: PRT
<213> ORGANISM: Artificial sequence
<220> FEATURE:
<223> OTHER INFORMATION: Synthesized: BF4E9

<400> SEQUENCE: 280

Cys Thr Thr Val His Gln Ile Phe Cys Pro Asp Gly Tyr Ser Tyr Gly
1               5                   10                  15

Tyr Gly Cys Gly Tyr Gly Tyr Gly Cys Ser Gly Tyr Asp Cys Tyr Gly
                20                  25                  30

Tyr Gly Gly Tyr Gly Tyr Gly Gly Tyr Gly Gly Tyr Ser Ser Tyr Ser
            35                  40                  45

Tyr Ser Tyr Ser Tyr Glu Tyr Tyr Gly Asp Ala Trp
    50                  55                  60

<210> SEQ ID NO 281
<211> LENGTH: 70
<212> TYPE: PRT
<213> ORGANISM: Artificial sequence
<220> FEATURE:
<223> OTHER INFORMATION: Synthesized: B-L1

<400> SEQUENCE: 281

Cys Ser Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 282
<211> LENGTH: 63
<212> TYPE: PRT
<213> ORGANISM: Artificial sequence
<220> FEATURE:
<223> OTHER INFORMATION: Synthesized: B-L2

```
<400> SEQUENCE: 282

Cys Ala Thr Val Arg Gln Thr Thr Leu Arg Asp Cys Pro Gly Gly Tyr
1               5                   10                  15

Thr Glu Asp Arg Ser Cys Val Asn Thr Tyr Ser Cys Gly Ala Asp Asp
            20                  25                  30

Cys Cys Gly Arg Gly Asp Val Gly Tyr Pro Ala Leu Tyr Gly Tyr Arg
        35                  40                  45

Cys Ala Ala His Ile Gln Arg Tyr Asn Trp His Ala Asp Ala Trp
    50                  55                  60

<210> SEQ ID NO 283
<211> LENGTH: 71
<212> TYPE: PRT
<213> ORGANISM: Artificial sequence
<220> FEATURE:
<223> OTHER INFORMATION: Synthesized: UL1

<400> SEQUENCE: 283

Cys Ser Thr Val His Gln Lys Thr Arg Thr Thr Gln Gly Glu Tyr Leu
1               5                   10                  15

Ser Leu Met Val Thr Leu Leu Lys Asp Asp Cys Pro Arg Cys Arg Gly
            20                  25                  30

Gly Cys Asp Gly Tyr Asp Cys Cys Trp Gly Asp Ala Cys Arg Ser Ser
        35                  40                  45

Gly Leu Cys Trp Gly His Asn Pro Leu Val Thr Glu Thr Tyr Thr Tyr
    50                  55                  60

Glu Phe Tyr Ile Asp Ala Trp
65                  70

<210> SEQ ID NO 284
<211> LENGTH: 71
<212> TYPE: PRT
<213> ORGANISM: Artificial sequence
<220> FEATURE:
<223> OTHER INFORMATION: Synthesized: UL2

<400> SEQUENCE: 284

Cys Ser Thr Val His Gln Lys Thr Arg Thr Thr Gln Gly Asn Asn Leu
1               5                   10                  15

Ser Leu Met Val Thr Leu Leu Lys Asp Asp Cys Pro Arg Cys Arg Gly
            20                  25                  30

Gly Cys Asp Gly Tyr Asp Cys Cys Trp Gly Asp Ala Cys Arg Ser Ser
        35                  40                  45

Gly Leu Cys Trp Gly His Asn Pro Leu Val Thr Glu Thr Tyr Thr Tyr
    50                  55                  60

Glu Phe Tyr Ile Asp Ala Trp
65                  70

<210> SEQ ID NO 285
<211> LENGTH: 70
<212> TYPE: PRT
<213> ORGANISM: Artificial sequence
<220> FEATURE:
<223> OTHER INFORMATION: Synthesized: UL3

<400> SEQUENCE: 285

Cys Ser Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
```

-continued

```
                20                  25                  30

Cys Asp Gly Tyr Asp Cys Cys Trp Gly Asp Ala Cys Arg Ser Ser Gly
                35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 286
<211> LENGTH: 70
<212> TYPE: PRT
<213> ORGANISM: Artificial sequence
<220> FEATURE:
<223> OTHER INFORMATION: Synthesized: UL4

<400> SEQUENCE: 286

Cys Ser Thr Val His Gln Lys Thr Arg Thr Thr Gln Gly Asn Thr Cys
1               5                   10                  15

Pro Asp Gly Tyr Thr Phe Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
                35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 287
<211> LENGTH: 70
<212> TYPE: PRT
<213> ORGANISM: Artificial sequence
<220> FEATURE:
<223> OTHER INFORMATION: Synthesized: UL5

<400> SEQUENCE: 287

Cys Thr Thr Val His Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
                35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 288
<211> LENGTH: 70
<212> TYPE: PRT
<213> ORGANISM: Artificial sequence
<220> FEATURE:
<223> OTHER INFORMATION: Synthesized: UL6

<400> SEQUENCE: 288

Cys Ser Thr Val His Gln Lys Thr Arg Thr Thr Gln Gly Asn Thr Cys
1               5                   10                  15

Pro Asp Gly Tyr Thr Leu Lys Asn Asp Cys Pro Arg Cys Arg Gly Gly
                20                  25                  30

Cys Asp Gly Tyr Asp Cys Cys Trp Gly Asp Ala Cys Arg Ser Ser Gly
                35                  40                  45
```

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 289
<211> LENGTH: 70
<212> TYPE: PRT
<213> ORGANISM: Artificial sequence
<220> FEATURE:
<223> OTHER INFORMATION: Synthesized: UL7

<400> SEQUENCE: 289

Cys Thr Thr Val Tyr Gln Lys Thr Arg Thr Thr Gln Gly Asn Thr Cys
1               5                   10                  15

Pro Asp Gly Tyr Thr Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 290
<211> LENGTH: 70
<212> TYPE: PRT
<213> ORGANISM: Artificial sequence
<220> FEATURE:
<223> OTHER INFORMATION: Synthesized: UL8

<400> SEQUENCE: 290

Cys Ser Thr Val His Gln Lys Pro Gly Gln His Lys Gly Ile Leu Val
1               5                   10                  15

Leu Met Val Thr Leu Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
    50                  55                  60

Phe Tyr Ile Asp Ala Trp
65                  70

<210> SEQ ID NO 291
<211> LENGTH: 70
<212> TYPE: PRT
<213> ORGANISM: Artificial sequence
<220> FEATURE:
<223> OTHER INFORMATION: Synthesized: UL9

<400> SEQUENCE: 291

Cys Ser Thr Val His Gln Lys Thr Arg Thr Thr Gln Gly Ile Leu Val
1               5                   10                  15

Leu Met Val Thr Leu Leu Lys Asp Asp Cys Pro Arg Cys Arg Gly Gly
                20                  25                  30

Cys Asp Gly Tyr Asp Cys Cys Trp Gly Asp Ala Cys Arg Ser Ser Gly
            35                  40                  45

Leu Cys Trp Gly His Asn Pro Leu Val Thr Glu Thr Tyr Thr Tyr Glu
    50                  55                  60

Phe Tyr Ile Asp Ala Trp
 65                  70

<210> SEQ ID NO 292
<211> LENGTH: 63
<212> TYPE: PRT
<213> ORGANISM: Artificial sequence
<220> FEATURE:
<223> OTHER INFORMATION: Synthesized: UL10

<400> SEQUENCE: 292

Cys Ser Pro Val His Gln Glu Ile Arg Lys Cys Cys Pro Ala Gly Cys
 1               5                  10                  15

Gln Cys Gly Arg Ser Cys Gly Ala Cys Cys Gly Cys Ala Gly Asp Glu
             20                  25                  30

Phe Cys Gly Ile Asn Val Tyr Gly Tyr Val Thr Cys Gly Gly Tyr Arg
         35                  40                  45

Thr Cys Ser Cys Ile Asp Thr Tyr Asp Phe Tyr Val Asp Ala Trp
     50                  55                  60

<210> SEQ ID NO 293
<211> LENGTH: 63
<212> TYPE: PRT
<213> ORGANISM: Artificial sequence
<220> FEATURE:
<223> OTHER INFORMATION: Synthesized: UL11

<400> SEQUENCE: 293

Cys Ser Pro Val His Gln Gln Thr Arg Lys Cys Cys Pro Ala Gly Cys
 1               5                  10                  15

Gln Cys Gly Arg Ser Cys Gly Ala Cys Cys Gly Cys Ala Gly Asp Glu
             20                  25                  30

Phe Cys Gly Ile Asn Val Tyr Gly Tyr Ile Thr Cys Gly Gly Tyr Arg
         35                  40                  45

Thr Cys Ser Cys Ile Asp Thr Tyr Asp Phe Tyr Val Glu Ala Trp
     50                  55                  60

<210> SEQ ID NO 294
<211> LENGTH: 68
<212> TYPE: PRT
<213> ORGANISM: Artificial sequence
<220> FEATURE:
<223> OTHER INFORMATION: Synthesized: UL12

<400> SEQUENCE: 294

Cys Ala Thr Val Tyr Gln Lys Thr Asn Gln Ser Lys Asn Cys Pro Glu
 1               5                  10                  15

Gly Ser Ala Trp Cys Arg Ser Cys Asp Gly Gly Ala Gly Cys Ala Asp
             20                  25                  30

Tyr Glu Cys Cys Arg Cys Gly Trp Ser Gly Cys Ser Trp Arg Asn Gly
         35                  40                  45

Ala Cys Glu Cys Ser Ser Leu Ser Ser Ser Tyr Thr Tyr Glu Leu His
     50                  55                  60

Val Asp Ala Trp
 65

<210> SEQ ID NO 295
<211> LENGTH: 65
<212> TYPE: PRT
<213> ORGANISM: Artificial sequence
<220> FEATURE:
<223> OTHER INFORMATION: Synthesized: UL13

```
<400> SEQUENCE: 295

Cys Ser Thr Val His Gln Thr Thr Gln Ile His Thr Cys Pro Asn
1               5                   10                  15

Gly Trp Thr Gly Gly Cys Val Cys Ser Ser Arg Phe Asn Cys Arg Gly
                20                  25                  30

Asn Asn Cys Cys Cys Arg Thr Ala Tyr Cys Ser Val Asp Arg Tyr Val
            35                  40                  45

Cys Ala Cys Pro Thr Val Thr Tyr Thr Tyr Glu Phe Asn Val Asp Ser
        50                  55                  60

Trp
65

<210> SEQ ID NO 296
<211> LENGTH: 65
<212> TYPE: PRT
<213> ORGANISM: Artificial sequence
<220> FEATURE:
<223> OTHER INFORMATION: Synthesized: UL14

<400> SEQUENCE: 296

Cys Thr Ala Val Tyr Gln Lys Thr Ser Ile Arg Ser Cys Pro Gly
1               5                   10                  15

Gly Thr Thr Leu Arg Asn Gly Cys Arg Ser Ala Cys Gly Cys Asn Asp
                20                  25                  30

Cys Asp Cys Cys Cys Gly Ser Ser Trp Asp Ile Cys Tyr Met Ser Lys
            35                  40                  45

Cys Thr Ser Ala Pro Glu Thr Tyr Thr Tyr Glu Leu His Ile Asp Ala
        50                  55                  60

Trp
65

<210> SEQ ID NO 297
<211> LENGTH: 65
<212> TYPE: PRT
<213> ORGANISM: Artificial sequence
<220> FEATURE:
<223> OTHER INFORMATION: Synthesized: UL15

<400> SEQUENCE: 297

Cys Thr Asn Val His Gln Lys Thr Lys Lys Thr Cys Pro Asp Asp Tyr
1               5                   10                  15

Thr Cys Gly Val Ser Cys Ser Cys Ser Ser Ser Gly Cys Ala Asp Tyr
                20                  25                  30

Gly Cys Cys Ser Tyr Ile Thr Tyr Gly Val Pro Gly Asp Cys Gly Gly
            35                  40                  45

Cys Cys Ser Tyr Lys His Arg Tyr Thr Tyr Glu Trp Asn Val Asp Ala
        50                  55                  60

Trp
65

<210> SEQ ID NO 298
<211> LENGTH: 63
<212> TYPE: PRT
<213> ORGANISM: Artificial sequence
<220> FEATURE:
<223> OTHER INFORMATION: Synthesized: UL16

<400> SEQUENCE: 298

Cys Thr Thr Val His Gln Lys Thr Lys Lys Leu Cys Pro Asn Gly Arg
```

```
1               5                   10                  15
Thr Cys Gly Cys Gly Cys Asp Cys Gly Ser Gly Cys Cys Thr Ser Tyr
                    20                  25                  30
Cys Asp Ser Phe Gly Cys Trp Gly Gly Arg Asp Thr Phe Gly Ser Ser
                35                  40                  45
Cys Thr Ser Ala Thr Tyr Thr Tyr Glu Trp Gly Val Asp Ala Trp
            50                  55                  60
```

<210> SEQ ID NO 299
<211> LENGTH: 64
<212> TYPE: PRT
<213> ORGANISM: Artificial sequence
<220> FEATURE:
<223> OTHER INFORMATION: Synthesized: UL17

<400> SEQUENCE: 299

```
Cys Ala Thr Val His Gln His Thr Asn Lys Lys Arg Cys Pro Asp Gly
1               5                   10                  15
Tyr Glu Phe Ser Ala Gly Cys Cys Cys Gly Glu Gly Cys Ser Gly Ser
                    20                  25                  30
Asp Cys Cys Cys Asn Ser Arg Leu Arg Cys Ser Trp Tyr Glu Ile Tyr
                35                  40                  45
Cys Ser Val Ser Pro Ser Asp Thr Tyr Glu Phe His Val Asp Ala Trp
            50                  55                  60
```

<210> SEQ ID NO 300
<211> LENGTH: 64
<212> TYPE: PRT
<213> ORGANISM: Artificial sequence
<220> FEATURE:
<223> OTHER INFORMATION: Synthesized: UL18

<400> SEQUENCE: 300

```
Cys Thr Thr Val His Gln His Thr Asn Lys Lys Arg Cys Pro Asp Gly
1               5                   10                  15
Tyr Arg Phe Ser Ala Ala Cys Cys Cys Gly Glu Gly Cys Ser Gly Asn
                    20                  25                  30
Glu Cys Cys Cys Asn Thr Arg Leu Arg Cys Ser Trp Tyr Glu Ile Tyr
                35                  40                  45
Cys Ser Val Ser Pro Ser Asp Thr Tyr Glu Phe His Val Asp Ala Trp
            50                  55                  60
```

<210> SEQ ID NO 301
<211> LENGTH: 64
<212> TYPE: PRT
<213> ORGANISM: Artificial sequence
<220> FEATURE:
<223> OTHER INFORMATION: Synthesized: UL19

<400> SEQUENCE: 301

```
Cys Thr Thr Val His Gln His Thr Asn Gln Asn Arg Cys Pro Thr Gly
1               5                   10                  15
Tyr Lys His Ser Ala Gly Cys Cys Cys Gly Val Gly Cys Ser Gly Asn
                    20                  25                  30
Asp Cys Cys Cys Asn Ser Arg Leu Arg Cys Ser Trp Tyr Glu Thr Tyr
                35                  40                  45
Cys Ser Leu Ser Pro Thr Asp Met Tyr Glu Phe Tyr Val Asp Ala Trp
            50                  55                  60
```

<210> SEQ ID NO 302

```
<211> LENGTH: 64
<212> TYPE: PRT
<213> ORGANISM: Artificial sequence
<220> FEATURE:
<223> OTHER INFORMATION: Synthesized: UL20

<400> SEQUENCE: 302

Cys Ser Thr Val His Gln His Thr Asn Gln Asn Arg Cys Pro Ala Gly
1               5                   10                  15

Tyr Lys His Ser Ala Gly Cys Cys Gly Val Gly Cys Ser Gly Asn
            20                  25                  30

Asp Cys Cys Cys Asn Ser Arg Leu Arg Cys Ser Trp Tyr Glu Thr Tyr
        35                  40                  45

Cys Ser Leu Ser Pro Thr Asp Met Tyr Glu Phe Tyr Val Asp Ala Trp
    50                  55                  60

<210> SEQ ID NO 303
<211> LENGTH: 63
<212> TYPE: PRT
<213> ORGANISM: Artificial sequence
<220> FEATURE:
<223> OTHER INFORMATION: Synthesized: UL21

<400> SEQUENCE: 303

Cys Thr Thr Val His Gln Lys Thr Asn Glu Arg Cys Cys Arg Val Val
1               5                   10                  15

Ser Asp Asp Gly Glu Cys Gly Asp Gly Asn Ser Cys His Arg Trp Leu
            20                  25                  30

Cys Ser Asp Tyr Cys Tyr Ser Gly Asp Cys Cys Ala Cys Gly Cys Arg
        35                  40                  45

Ala Tyr His Tyr Thr Tyr Thr Tyr Glu Trp Asn Ile Asp Ala Trp
    50                  55                  60

<210> SEQ ID NO 304
<211> LENGTH: 63
<212> TYPE: PRT
<213> ORGANISM: Artificial sequence
<220> FEATURE:
<223> OTHER INFORMATION: Synthesized: UL22

<400> SEQUENCE: 304

Cys Thr Thr Val His Gln Lys Thr Asn Glu Arg Cys Cys Arg Val Val
1               5                   10                  15

Ser Asp Asp Gly Glu Cys Gly Asp Gly Asn Ser Cys His Arg Trp Leu
            20                  25                  30

Cys Ser Asp Tyr Cys Tyr Ser Gly Asp Cys Cys Ala Cys Gly Cys Arg
        35                  40                  45

Ala Tyr His Tyr Thr Tyr Thr Tyr Asp Phe Arg Ile Asp Val Trp
    50                  55                  60

<210> SEQ ID NO 305
<211> LENGTH: 64
<212> TYPE: PRT
<213> ORGANISM: Artificial sequence
<220> FEATURE:
<223> OTHER INFORMATION: Synthesized: UL23

<400> SEQUENCE: 305

Cys Thr Thr Val His Gln Lys Thr Asn Arg Glu Arg Cys Cys Pro Asp
1               5                   10                  15

Gly Tyr Tyr Tyr Cys Cys Arg Ser Val Ser Asp Cys Cys Cys Ser Thr
            20                  25                  30
```

```
Arg Ala Cys Val Gly Asp Ser Cys Gly Trp Thr Asp Phe Gly Ser Thr
        35                  40                  45

His Asn Val Asp Cys Ser Phe Thr Tyr Glu Phe His Val Asp Ala Trp
 50                  55                  60

<210> SEQ ID NO 306
<211> LENGTH: 63
<212> TYPE: PRT
<213> ORGANISM: Artificial sequence
<220> FEATURE:
<223> OTHER INFORMATION: Synthesized: UL24

<400> SEQUENCE: 306

Cys Thr Thr Val His Gln Gln Thr Arg Lys Ser Cys Pro Asp Gly Tyr
1               5                   10                  15

Thr Tyr Cys His Asp Cys Gly Tyr Gly Cys Cys Gly Ala Ser Phe
            20                  25                  30

Cys Arg Asp Tyr Gly Gly Cys Gly Ser Leu Cys Gly Arg Tyr Cys Thr
        35                  40                  45

Ser Phe Asp Tyr Ile Tyr Thr Tyr Glu Asn Tyr Val Glu Thr Trp
 50                  55                  60

<210> SEQ ID NO 307
<211> LENGTH: 64
<212> TYPE: PRT
<213> ORGANISM: Artificial sequence
<220> FEATURE:
<223> OTHER INFORMATION: Synthesized: UL25

<400> SEQUENCE: 307

Cys Thr Thr Val His Gln Glu Thr Lys Lys Asn Cys Pro Asp Asn Cys
1               5                   10                  15

Tyr Tyr Glu Asn Ser Cys Gly Asp Tyr Gly Ser Gly Cys Asn Gly Gly
            20                  25                  30

Asp Cys Cys Arg Cys Gly Thr Trp Leu Thr Cys Ser Val Ser Gly Cys
        35                  40                  45

Thr Cys Ile Arg Ala Thr Asn Thr Tyr Gln Trp Tyr Val Asn Ala Trp
 50                  55                  60

<210> SEQ ID NO 308
<211> LENGTH: 64
<212> TYPE: PRT
<213> ORGANISM: Artificial sequence
<220> FEATURE:
<223> OTHER INFORMATION: Synthesized: UL26

<400> SEQUENCE: 308

Cys Thr Thr Val His Gln Ser Thr Asn Lys Lys Ser Cys Pro Asp Arg
1               5                   10                  15

Val Cys Trp Ala Val Gly Cys Cys Phe Gly Glu Asp Cys Thr Ser Ser
            20                  25                  30

Asp Cys Thr Cys Tyr Ala Ser Pro Gly Asn Pro Tyr Arg His Asp Cys
        35                  40                  45

Gly Asn Cys Asp Cys Arg Ser Ser Tyr Glu His His Val Asp Ala Trp
 50                  55                  60

<210> SEQ ID NO 309
<211> LENGTH: 63
<212> TYPE: PRT
<213> ORGANISM: Artificial sequence
<220> FEATURE:
```

<223> OTHER INFORMATION: Synthesized: UL27

<400> SEQUENCE: 309

Cys Thr Thr Val Arg Gln Glu Thr Leu Ile Arg Cys Arg Asp Gly Pro
1               5                   10                  15

Ser Cys Ala Ala Cys Cys Arg Ser Gly Arg Arg Cys Ser Gly Tyr Gly
            20                  25                  30

Cys Cys Thr Asp Gly Cys Ser Asp Asn Asp Tyr Ala Asp Cys Ile
        35                  40                  45

Arg Gly Glu Phe Val Asp Val Tyr Glu Trp Asn Val Asp Ala Trp
    50                  55                  60

<210> SEQ ID NO 310
<211> LENGTH: 63
<212> TYPE: PRT
<213> ORGANISM: Artificial sequence
<220> FEATURE:
<223> OTHER INFORMATION: Synthesized: UL28

<400> SEQUENCE: 310

Cys Ser Thr Val Tyr Gln Lys Thr Arg Thr Thr Cys Pro Asp Gly Tyr
1               5                   10                  15

Thr Cys Gly Asp Gly Ala Arg Cys Glu Lys Ala Cys Arg Gly Cys Asp
            20                  25                  30

Cys Cys Arg Thr Thr Val Cys Asp Thr Val Trp Ser Ser Tyr Cys Ser
        35                  40                  45

Cys Tyr Ser Phe Thr Asp Ser Tyr Glu Phe Tyr Val Asp Ala Trp
    50                  55                  60

<210> SEQ ID NO 311
<211> LENGTH: 66
<212> TYPE: PRT
<213> ORGANISM: Artificial sequence
<220> FEATURE:
<223> OTHER INFORMATION: Synthesized: UL29

<400> SEQUENCE: 311

Cys Ala Thr Val Tyr Gln Lys Thr Asn Arg Glu Met Ser Cys Pro Asp
1               5                   10                  15

Gly Cys Arg Ile His Asn Ala Arg Leu Cys Leu Ser Gly Cys Ser Gly
            20                  25                  30

Ser Asp Cys Cys Ser Cys Gly Asp Cys Val Ser Asp Ala Arg Cys Tyr
        35                  40                  45

Asn Cys Arg Ser Ala Val Phe Thr Tyr Thr Tyr Glu Phe His Val Asp
    50                  55                  60

Ala Trp
65

<210> SEQ ID NO 312
<211> LENGTH: 63
<212> TYPE: PRT
<213> ORGANISM: Artificial sequence
<220> FEATURE:
<223> OTHER INFORMATION: Synthesized: UL30

<400> SEQUENCE: 312

Cys Thr Ile Val His Gln Glu Thr Lys Arg Ser Cys Pro Asp Gly Tyr
1               5                   10                  15

Asn Thr Gly Thr Arg Cys Phe Gly Ser Cys Gly Cys Ile Gly Ser Asn
            20                  25                  30

```
Cys Cys Arg Ser Thr Thr Ser Cys Cys Ala Gly Ile Tyr Ser Gln
        35                  40                  45

Cys Thr Thr Ser Thr Leu Thr Tyr Glu Trp His Ala Asp Val Trp
    50                  55                  60

<210> SEQ ID NO 313
<211> LENGTH: 63
<212> TYPE: PRT
<213> ORGANISM: Artificial sequence
<220> FEATURE:
<223> OTHER INFORMATION: Synthesized: UL31

<400> SEQUENCE: 313

Cys Ala Ile Val Tyr Gln Arg Thr Arg Gln Arg Cys Pro Asp Gly Tyr
1               5                   10                  15

Asn Thr Gly Thr Arg Cys Phe Gly Thr Cys Gly Cys Asn Gly Ser Asn
            20                  25                  30

Cys Cys Arg Phe Thr Thr Ser Cys Cys Ala Gly Val Tyr Ser Gln
        35                  40                  45

Cys Thr Thr Ser Thr Leu Thr Tyr Glu Trp His Ala Asp Val Trp
    50                  55                  60

<210> SEQ ID NO 314
<211> LENGTH: 63
<212> TYPE: PRT
<213> ORGANISM: Artificial sequence
<220> FEATURE:
<223> OTHER INFORMATION: Synthesized: UL32

<400> SEQUENCE: 314

Cys Thr Thr Val His Gln Lys Thr Glu Thr Arg Cys Pro Asp Gly Tyr
1               5                   10                  15

Ser Ser Thr Asn Gly Cys Asp Ala Arg Cys Gly Cys Ser Asp Cys Asp
            20                  25                  30

Cys Cys Asn Val Gly Arg Trp Gly Cys Pro Leu Ile Cys Ser Arg Asn
        35                  40                  45

Cys Arg Ser Phe Thr Tyr Thr Tyr Glu Trp Tyr Ala Asp Ala Trp
    50                  55                  60

<210> SEQ ID NO 315
<211> LENGTH: 63
<212> TYPE: PRT
<213> ORGANISM: Artificial sequence
<220> FEATURE:
<223> OTHER INFORMATION: Synthesized: UL33

<400> SEQUENCE: 315

Cys Thr Thr Val His Gln Lys Thr Asn Lys Lys Glu Ser Cys Pro Asp
1               5                   10                  15

Gly Tyr Thr Met Asn Glu Cys Cys Gly Cys Gly Tyr Gly Cys Cys Arg
            20                  25                  30

Gly Gly Cys Val Cys Ser Ala Tyr Cys Ser Arg Pro Asn Cys Trp Arg
        35                  40                  45

Glu Leu Thr Tyr Thr Tyr Thr Tyr Glu Phe Tyr Val Asp Thr Trp
    50                  55                  60

<210> SEQ ID NO 316
<211> LENGTH: 63
<212> TYPE: PRT
<213> ORGANISM: Artificial sequence
<220> FEATURE:
<223> OTHER INFORMATION: Synthesized: UL34
```

<400> SEQUENCE: 316

Cys Thr Thr Val Tyr Gln Lys Ser Arg Lys Glu Ser Cys Pro Asn
1               5                   10                  15

Gly Trp Ile Tyr Gly Lys Asp Cys Cys Ser Trp Ser Tyr Cys Thr Asp
            20                  25                  30

Cys Asp Cys Cys Leu Cys Gly Asp Leu His Cys Tyr Asp Gly Cys Ser
        35                  40                  45

Ser Phe Gly Val Thr Trp Thr Tyr Glu Phe His Val Asp Ala Trp
    50                  55                  60

<210> SEQ ID NO 317
<211> LENGTH: 62
<212> TYPE: PRT
<213> ORGANISM: Artificial sequence
<220> FEATURE:
<223> OTHER INFORMATION: Synthesized: UL35

<400> SEQUENCE: 317

Cys Thr Thr Val Phe Gln Glu Thr Arg Lys Ser Cys Pro Thr Gly Phe
1               5                   10                  15

Tyr Val Asp Gly Ser Thr Cys Gly Cys Ala Thr Tyr Cys Arg Thr Cys
            20                  25                  30

Asp Cys Cys Gly Gly Tyr Arg Cys Ser Gly Gly Ser Cys Ala Cys
        35                  40                  45

Ser Ser Tyr Thr Tyr Asn Tyr Asp Phe His Val Asp Ala Trp
    50                  55                  60

<210> SEQ ID NO 318
<211> LENGTH: 61
<212> TYPE: PRT
<213> ORGANISM: Artificial sequence
<220> FEATURE:
<223> OTHER INFORMATION: Synthesized: UL36

<400> SEQUENCE: 318

Cys Ala Ala Val Phe Gln Glu Thr Arg Thr Asn Cys Pro Ser Gly Tyr
1               5                   10                  15

Gly Asn Ala Phe Ser Cys Gly Cys Pro Ile Ala Cys Arg Asp Cys Asp
            20                  25                  30

Cys Cys Gly Gly Tyr Trp Cys Ser Gly Gly Ala Asp Cys His Cys Val
        35                  40                  45

Ser Tyr Asn Tyr Thr Tyr Ser Trp His Val Asp Ala Trp
    50                  55                  60

<210> SEQ ID NO 319
<211> LENGTH: 62
<212> TYPE: PRT
<213> ORGANISM: Artificial sequence
<220> FEATURE:
<223> OTHER INFORMATION: Synthesized: UL37

<400> SEQUENCE: 319

Cys Ala Thr Val Tyr Gln Lys Thr Glu Lys His Cys Pro Leu Phe His
1               5                   10                  15

Ser Ile Cys Cys His Cys Gly Glu Gly Val Gly Cys Ser Gly Gly Asp
            20                  25                  30

Cys Cys Gly Cys Glu Arg Arg Ser Gly Cys Val Val Cys Thr Met Arg
        35                  40                  45

Asn Ser Tyr Thr Tyr Asn Tyr Gln Phe His Val Asp Ala Trp

```
                50                  55                  60
```

<210> SEQ ID NO 320
<211> LENGTH: 63
<212> TYPE: PRT
<213> ORGANISM: Artificial sequence
<220> FEATURE:
<223> OTHER INFORMATION: Synthesized: UL38

<400> SEQUENCE: 320

```
Cys Gly Thr Val His Gln Lys Thr Lys Glu Leu Cys Pro Asp Asp Ser
1               5                   10                  15

Thr Tyr Cys Cys Gly Cys Val Ser Gly Cys Ala Cys Cys Thr Tyr Gly
            20                  25                  30

Cys Asp Gly Val Gly Cys Cys Arg Val Ser Leu Trp Thr Thr Tyr Ile
        35                  40                  45

Lys Asp Ile Val Gly Val Ser Tyr Glu Trp His Val Asp Ala Trp
    50                  55                  60
```

<210> SEQ ID NO 321
<211> LENGTH: 61
<212> TYPE: PRT
<213> ORGANISM: Artificial sequence
<220> FEATURE:
<223> OTHER INFORMATION: Synthesized: UL39

<400> SEQUENCE: 321

```
Cys Ala Ser Val His Gln His Thr Glu Pro Thr Cys Pro Ala Gly Tyr
1               5                   10                  15

Thr Tyr Cys Cys Gly Cys Leu Tyr Lys Cys Asn Cys Gly Asp Cys Gly
            20                  25                  30

Cys Tyr Asn Val Gly Cys Gly Ser Gly Trp Leu Gly Lys Ala Cys Gly
        35                  40                  45

Asp Tyr Arg Glu Thr Tyr Glu Trp Tyr Val Asp Ala Trp
    50                  55                  60
```

<210> SEQ ID NO 322
<211> LENGTH: 61
<212> TYPE: PRT
<213> ORGANISM: Artificial sequence
<220> FEATURE:
<223> OTHER INFORMATION: Synthesized: UL40

<400> SEQUENCE: 322

```
Cys Ala Ser Val His Gln His Thr Glu Pro Thr Cys Pro Ala Gly Tyr
1               5                   10                  15

Thr Tyr Cys Cys Gly Cys Leu Tyr Lys Cys Asn Cys Gly Asp Cys Gly
            20                  25                  30

Cys Tyr Asn Ala Gly Cys Gly Ser Gly Trp Leu Gly Lys Ala Cys Gly
        35                  40                  45

Asp Tyr Arg Glu Thr Tyr Glu Trp Tyr Val Asp Ala Trp
    50                  55                  60
```

<210> SEQ ID NO 323
<211> LENGTH: 61
<212> TYPE: PRT
<213> ORGANISM: Artificial sequence
<220> FEATURE:
<223> OTHER INFORMATION: Synthesized: UL41

<400> SEQUENCE: 323

```
Cys Thr Thr Val Phe Gln Glu Thr Arg Lys Ser Cys Pro Ser Gly Phe
```

```
              1               5                  10                 15
Arg Asp Arg Asp Ala Cys Gly Cys Ala Val Thr Cys Arg Asn Cys Asp
              20                 25                 30
Cys Cys Gly Gly Gly Pro Cys Asn Gly Gly Gly Ser Cys Arg Cys Asn
              35                 40                 45
Asn Tyr Ile Tyr Lys Tyr Ser Phe His Val Asp Ala Trp
              50                 55                 60

<210> SEQ ID NO 324
<211> LENGTH: 61
<212> TYPE: PRT
<213> ORGANISM: Artificial sequence
<220> FEATURE:
<223> OTHER INFORMATION: Synthesized: UL42

<400> SEQUENCE: 324

Cys Thr Ala Val Phe Gln Glu Thr Arg Lys Asp Cys Pro Ser Gly Tyr
1               5                  10                 15
Gly Ser Ala Phe Thr Cys Gly Cys Leu Ala Ala Cys His Gly Cys Asp
              20                 25                 30
Cys Cys Gly Gly Gly Trp Cys Ser Gly Gly Asp Cys Arg Cys Arg
              35                 40                 45
Ser Tyr Ser Thr Ala Tyr Ser Phe His Ile Asp Ala Trp
              50                 55                 60

<210> SEQ ID NO 325
<211> LENGTH: 61
<212> TYPE: PRT
<213> ORGANISM: Artificial sequence
<220> FEATURE:
<223> OTHER INFORMATION: Synthesized: UL43

<400> SEQUENCE: 325

Cys Ala Thr Val Phe Gln Glu Thr Arg Lys Ser Cys Pro Ser Gly Tyr
1               5                  10                 15
Ala Asp Arg Phe Thr Cys Asp Cys Val Tyr Tyr Cys Gln Thr Cys Asp
              20                 25                 30
Cys Cys Gly Gly Asn Arg Cys Ser Gly Gly Pro Cys Arg Cys Ser
              35                 40                 45
Ser Tyr Ser Ile Asn Tyr Ser Phe His Val Asp Thr Trp
              50                 55                 60

<210> SEQ ID NO 326
<211> LENGTH: 58
<212> TYPE: PRT
<213> ORGANISM: Artificial sequence
<220> FEATURE:
<223> OTHER INFORMATION: Synthesized: UL44

<400> SEQUENCE: 326

Cys Ala Ala Ala His Gln Glu Thr Lys Lys Ser Cys Pro Asp Gly Thr
1               5                  10                 15
Cys Arg Gln Cys Cys Gly Gly Val Cys Arg Cys His Ala Ser Gly Cys
              20                 25                 30
Cys Tyr Trp Cys Thr Thr Gly Cys Val Gly Arg Ala Leu Ser Glu Ser
              35                 40                 45
His Ser Tyr Glu Phe His Val Asp Thr Trp
              50                 55

<210> SEQ ID NO 327
```

<211> LENGTH: 70
<212> TYPE: PRT
<213> ORGANISM: Artificial sequence
<220> FEATURE:
<223> OTHER INFORMATION: Synthesized: UL45

<400> SEQUENCE: 327

Cys Ser Thr Val His Gln Lys Thr Arg Thr Thr Gln Gly Asn Thr Cys
1               5                   10                  15
Pro Asp Gly Tyr Thr Leu Lys Asp Asp Cys Pro Arg Cys Arg Gly Gly
            20                  25                  30
Cys Asp Gly Tyr Asp Cys Cys Trp Gly Asp Ala Cys Arg Ser Ser Gly
        35                  40                  45
Leu Cys Trp Gly His Asn Pro Leu Val Thr Glu Thr Tyr Thr Tyr Glu
    50                  55                  60
Phe Tyr Ile Asp Ala Trp
65                  70

<210> SEQ ID NO 328
<211> LENGTH: 68
<212> TYPE: PRT
<213> ORGANISM: Artificial sequence
<220> FEATURE:
<223> OTHER INFORMATION: Synthesized: UL46

<400> SEQUENCE: 328

Cys Val Val Val Tyr Gln Lys Thr Asn Ser Gln Lys Ser Cys Pro Arg
1               5                   10                  15
Gly Tyr Thr Glu Arg Glu Thr Cys Asn Arg Arg Tyr Gly Trp Gly Cys
            20                  25                  30
Gly Arg Tyr Asp Cys Cys Asp Cys Asp Arg Trp Val Ser Gly Asn Cys
        35                  40                  45
Ala Asn Ile Cys Thr Asp Tyr Thr Asp Thr His Thr Tyr Glu Phe His
    50                  55                  60
Ala Asp Ala Trp
65

<210> SEQ ID NO 329
<211> LENGTH: 64
<212> TYPE: PRT
<213> ORGANISM: Artificial sequence
<220> FEATURE:
<223> OTHER INFORMATION: Synthesized: UL47

<400> SEQUENCE: 329

Cys Gly Thr Val Phe Gln Gln Thr His Lys Val Arg Asp Cys Pro Asp
1               5                   10                  15
Gly Phe Thr Ala Ala Pro Arg Cys Gly Gly Glu Cys Cys Cys Ser Asn
            20                  25                  30
Val Asn Ser Arg Ser Gly Gly Trp Cys Arg Tyr Cys Gly Arg Asp Cys
        35                  40                  45
Thr Ala Pro Thr Glu Thr Ser Thr Tyr Glu Phe His Val Asp Ala Trp
    50                  55                  60

<210> SEQ ID NO 330
<211> LENGTH: 63
<212> TYPE: PRT
<213> ORGANISM: Artificial sequence
<220> FEATURE:
<223> OTHER INFORMATION: Synthesized: UL48

<400> SEQUENCE: 330

```
Cys Thr Ala Val Tyr Gln Arg Thr Gly Gln Lys Cys Pro Glu Gly Cys
1               5                   10                  15

Glu Ser Arg Asn Thr Cys Leu Tyr Ser Arg Asn Cys Gly Asp Tyr Thr
            20                  25                  30

Cys Cys Gly Gly Ser Arg Ala Ser Gly Ser Gly Ala Cys Gly Trp Asn
        35                  40                  45

Ser Val Asp Cys Lys Asn Lys Tyr Glu His His Val Asp Ala Trp
    50                  55                  60

<210> SEQ ID NO 331
<211> LENGTH: 63
<212> TYPE: PRT
<213> ORGANISM: Artificial sequence
<220> FEATURE:
<223> OTHER INFORMATION: Synthesized: UL49

<400> SEQUENCE: 331

Cys Thr Thr Val Tyr Gln Lys Thr Lys Gln Asn Cys Pro Asp Gly Tyr
1               5                   10                  15

Asp Phe Arg Asp Thr Cys Gly Ser Gln Ser Tyr Cys Ser Gly Tyr Asp
            20                  25                  30

Cys Cys Arg Cys Ser Arg Phe Gly Gly Cys Ser Ile Gly Thr Cys Ile
        35                  40                  45

Ser Tyr Ser Asp Ala Tyr Thr Tyr Glu Trp Tyr Val Asp Ala Trp
    50                  55                  60

<210> SEQ ID NO 332
<211> LENGTH: 63
<212> TYPE: PRT
<213> ORGANISM: Artificial sequence
<220> FEATURE:
<223> OTHER INFORMATION: Synthesized: UL50

<400> SEQUENCE: 332

Cys Thr Thr Val His Gln Gln Thr His Glu Lys Arg Ser Cys Pro Glu
1               5                   10                  15

Ser Tyr Ser Tyr Ser Cys Ser Cys Ala Ser Gly Val Val Gly Cys Gly
            20                  25                  30

Pro Asp Asp Cys Cys Cys Thr Tyr Arg Ile Ser Ile Arg Gly Tyr Thr
        35                  40                  45

Cys Ser Ser Leu Ser Asn Ser Tyr Glu Trp Tyr Val Asp Ala Trp
    50                  55                  60

<210> SEQ ID NO 333
<211> LENGTH: 61
<212> TYPE: PRT
<213> ORGANISM: Artificial sequence
<220> FEATURE:
<223> OTHER INFORMATION: Synthesized: UL51

<400> SEQUENCE: 333

Cys Thr Ala Val His Gln Gln Thr Lys Arg Lys Ser Gly Cys Pro Asp
1               5                   10                  15

Gly Tyr Ser Asp Glu Ser Cys Tyr Cys Gly Ser Ser Trp Cys Cys
            20                  25                  30

Pro Val Tyr Trp Cys Gly Ser Pro Cys Ser Tyr Arg Cys Leu Arg His
        35                  40                  45

Thr Asp Thr Tyr Ser Tyr Glu His His Val Asp Ala Trp
    50                  55                  60
```

<210> SEQ ID NO 334
<211> LENGTH: 60
<212> TYPE: PRT
<213> ORGANISM: Artificial sequence
<220> FEATURE:
<223> OTHER INFORMATION: Synthesized: UL52

<400> SEQUENCE: 334

Cys Ala Thr Val Tyr Gln Glu Thr Lys Arg Thr Cys Ala Gly Gly His
1               5                   10                  15

Ser Val Glu Cys Asp Ser Pro Tyr Asp Cys Asn Cys Arg Gly Gly Asp
            20                  25                  30

Cys Cys Arg Ser Pro Ile Phe Asn Asp Cys Trp Ala Ala Ser Cys Ser
        35                  40                  45

Ala Thr Lys Thr Tyr Glu Trp His Val Glu Ser Trp
    50                  55                  60

<210> SEQ ID NO 335
<211> LENGTH: 58
<212> TYPE: PRT
<213> ORGANISM: Artificial sequence
<220> FEATURE:
<223> OTHER INFORMATION: Synthesized: UL53

<400> SEQUENCE: 335

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Lys
            20                  25                  30

Cys Cys Cys Gly Arg Thr Trp Leu Ser Ser Gly Cys Leu Pro Cys Arg
        35                  40                  45

Tyr Thr Tyr Asn Leu His Val Asp Ala Trp
    50                  55

<210> SEQ ID NO 336
<211> LENGTH: 58
<212> TYPE: PRT
<213> ORGANISM: Artificial sequence
<220> FEATURE:
<223> OTHER INFORMATION: Synthesized: UL54

<400> SEQUENCE: 336

Cys Ile Thr Val His Gln Glu Thr Gln Lys Ser Cys Pro Asp Asp Tyr
1               5                   10                  15

Thr Ser Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 337
<211> LENGTH: 58
<212> TYPE: PRT
<213> ORGANISM: Artificial sequence
<220> FEATURE:
<223> OTHER INFORMATION: Synthesized: UL55

<400> SEQUENCE: 337

Cys Ile Thr Val His Gln Glu Thr Gln Lys Ser Cys Phe Asp Asp Tyr
1               5                   10                  15

Thr Tyr Tyr Gly Asp Ala Ser Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 338
<211> LENGTH: 58
<212> TYPE: PRT
<213> ORGANISM: Artificial sequence
<220> FEATURE:
<223> OTHER INFORMATION: Synthesized: UL56

<400> SEQUENCE: 338

Cys Ile Thr Ala His Gln Glu Thr Gln Lys Ser Cys Ser Asp Asp Tyr
1               5                   10                  15

Thr Tyr Tyr Gly Asp Ala Thr Cys Ala Tyr Val Cys Ser Thr Asp Glu
            20                  25                  30

Cys Cys Cys Gly Arg Thr Trp Leu Ser Ala Gly Cys Arg Pro Cys Arg
        35                  40                  45

Tyr Thr Tyr Asn Leu His Val Asp Ala Trp
    50                  55

<210> SEQ ID NO 339
<211> LENGTH: 58
<212> TYPE: PRT
<213> ORGANISM: Artificial sequence
<220> FEATURE:
<223> OTHER INFORMATION: Synthesized: UL57

<400> SEQUENCE: 339

Cys Ile Thr Val His Gln Glu Thr Gln Lys Ser Cys Pro Asp Asp Tyr
1               5                   10                  15

Thr Tyr Tyr Gly Asp Gly Thr Cys Ala Tyr Val Cys Ser Ile Asp Asn
            20                  25                  30

Cys Cys Cys Gly Arg Thr Trp Leu Ser Ser Gly Cys Leu Pro Cys Arg
        35                  40                  45

Tyr Thr Tyr Asn Leu His Val Asp Ala Trp
    50                  55

<210> SEQ ID NO 340
<211> LENGTH: 61
<212> TYPE: PRT
<213> ORGANISM: Artificial sequence
<220> FEATURE:
<223> OTHER INFORMATION: Synthesized: UL58

<400> SEQUENCE: 340

Cys Val Thr Val His Gln Gln Thr His Ala Thr Arg Arg Cys Pro Asp
1               5                   10                  15

Gly Tyr Gly Asp Ser Tyr Ala Cys Lys Ser Asn Tyr Gly Cys Ser Ala
            20                  25                  30

Glu Gly Cys Cys Arg Trp Gly Pro Gly Ser Gly Ala Cys Thr Gly Ala
        35                  40                  45

Ile Tyr Thr Ser Pro Tyr Glu Trp Tyr Val Asp Ala Trp
    50                  55                  60

<210> SEQ ID NO 341
<211> LENGTH: 60
<212> TYPE: PRT

-continued

```
<213> ORGANISM: Artificial sequence
<220> FEATURE:
<223> OTHER INFORMATION: Synthesized: UL59

<400> SEQUENCE: 341

Cys Ala Ala Val His Gln Arg Thr Glu Gly Gln Gln Ser Cys Pro Asp
1               5                   10                  15

Gly Tyr Leu Glu Thr Arg Val Cys Pro Tyr Arg Met Tyr Arg Cys Ile
            20                  25                  30

Gly Trp Asp Cys Cys Arg Cys Ser Asp Gly Ser Arg Asp Asn Tyr Ile
        35                  40                  45

Met Thr Tyr Ser Tyr Glu Phe His Val Asp Val Trp
    50                  55                  60

<210> SEQ ID NO 342
<211> LENGTH: 59
<212> TYPE: PRT
<213> ORGANISM: Artificial sequence
<220> FEATURE:
<223> OTHER INFORMATION: Synthesized: UL60

<400> SEQUENCE: 342

Cys Thr Thr Val Tyr Gln Glu Thr Lys Thr Lys Ser Gly Cys Pro Asp
1               5                   10                  15

Gly Tyr Ser Cys Cys Tyr Asn Gly Arg Ser Arg Ser Cys Arg Pro Asn
            20                  25                  30

Asp Cys Ser Thr Tyr Gly Glu Val Arg Ser Leu Ser Arg Ser Cys Tyr
        35                  40                  45

Thr Tyr Asn Tyr Glu Phe Tyr Val Asp Ala Trp
    50                  55

<210> SEQ ID NO 343
<211> LENGTH: 58
<212> TYPE: PRT
<213> ORGANISM: Artificial sequence
<220> FEATURE:
<223> OTHER INFORMATION: Synthesized: UL61

<400> SEQUENCE: 343

Cys Gly Thr Val Tyr Gln His Thr Lys Glu Ile Lys Thr Cys Pro Asp
1               5                   10                  15

Gly Tyr Ser Asp Val Phe Thr Tyr Cys Pro Val Thr Cys Pro Gly Trp
            20                  25                  30

Asp Cys Cys Arg Arg Asn Asp Cys Gly Arg Thr Arg Tyr Thr Val Ala
        35                  40                  45

Tyr Ser Tyr Ala Leu His Val Asp Val Trp
    50                  55

<210> SEQ ID NO 344
<211> LENGTH: 57
<212> TYPE: PRT
<213> ORGANISM: Artificial sequence
<220> FEATURE:
<223> OTHER INFORMATION: Synthesized: UL62

<400> SEQUENCE: 344

Cys Thr Thr Val Leu Gln Glu Thr His Gln Gln Arg Gly Cys Pro Ala
1               5                   10                  15

Gly Tyr Gln Val Val Asp Gly Cys Pro Tyr Gly Asp Cys Cys Arg Thr
            20                  25                  30

Ser Tyr Val Cys Gly Pro Leu Thr Cys Thr Ser Asn Thr Ala Thr Arg
```

Asn Tyr Gln Trp Tyr Val Asp Ala Trp
    50                  55

<210> SEQ ID NO 345
<211> LENGTH: 56
<212> TYPE: PRT
<213> ORGANISM: Artificial sequence
<220> FEATURE:
<223> OTHER INFORMATION: Synthesized: UL63

<400> SEQUENCE: 345

Cys Ser Thr Val Tyr Gln Lys Thr Glu Lys Lys Cys Pro Asp Gly Tyr
1               5                   10                  15

Thr Asp Arg Arg Asp Glu Cys Pro Asn Thr Cys Lys Asn Phe Asp Cys
            20                  25                  30

Glu Asn Glu Gly Gly Leu Arg Cys Leu Cys Ser Ala Tyr Ile Ser Ala
        35                  40                  45

Tyr Glu Phe His Val Asp Ala Trp
    50                  55

<210> SEQ ID NO 346
<211> LENGTH: 55
<212> TYPE: PRT
<213> ORGANISM: Artificial sequence
<220> FEATURE:
<223> OTHER INFORMATION: Synthesized: UL64

<400> SEQUENCE: 346

Cys Thr Thr Thr His Gln Arg Thr Gln Lys Ser Cys Pro Asp Tyr Ala
1               5                   10                  15

Ser Tyr Asp Cys Gly Ser Pro Asp Asp Glu Glu Cys Ser Ser Cys Arg
            20                  25                  30

Ser Cys Thr Arg Trp Cys Ala Pro Thr Ala Pro Tyr Ile Tyr Thr Tyr
        35                  40                  45

Gln Phe Tyr Ile Asp Ala Trp
    50                  55

<210> SEQ ID NO 347
<211> LENGTH: 54
<212> TYPE: PRT
<213> ORGANISM: Artificial sequence
<220> FEATURE:
<223> OTHER INFORMATION: Synthesized: UL65

<400> SEQUENCE: 347

Cys Thr Thr Val His Gln Gln Thr Asn Lys Arg Cys Pro Thr Gly Tyr
1               5                   10                  15

Asn Ser Gly Thr Leu Cys Asn Met Ile Gly Cys Ser Gly Asp Glu Cys
            20                  25                  30

Cys Asn Tyr Gly Arg Val Glu Cys Thr Ser Tyr Val Trp Thr His Asn
        35                  40                  45

Phe Tyr Val Asp Ala Trp
    50

<210> SEQ ID NO 348
<211> LENGTH: 53
<212> TYPE: PRT
<213> ORGANISM: Artificial sequence
<220> FEATURE:
<223> OTHER INFORMATION: Synthesized: UL66

```
<400> SEQUENCE: 348

Cys Thr Thr Val His Gln Glu Thr Gln Arg Thr Ser Cys Pro Ser Gly
1               5                   10                  15

Trp Thr Tyr Thr Cys Asn Cys Arg Asn Gly Cys Gly Cys Tyr Arg Pro
            20                  25                  30

Ser Gln Leu Cys Gly Ala Tyr Val Ala Val Thr His Thr Tyr Glu Phe
        35                  40                  45

His Val Asp Ala Trp
    50

<210> SEQ ID NO 349
<211> LENGTH: 53
<212> TYPE: PRT
<213> ORGANISM: Artificial sequence
<220> FEATURE:
<223> OTHER INFORMATION: Synthesized: UL67

<400> SEQUENCE: 349

Cys Ala Thr Val His Gln Lys Asp Lys His Cys Pro Ala Gly Tyr Arg
1               5                   10                  15

Ser Gly Thr Leu Cys Arg Met Ile Gly Cys Thr Gly Asp Asp Cys Cys
            20                  25                  30

Asn Tyr Asp Arg Val Glu Cys Thr Asn Tyr Asp Tyr Thr Asn Asn Phe
        35                  40                  45

Tyr Val Asp Ala Trp
    50

<210> SEQ ID NO 350
<211> LENGTH: 52
<212> TYPE: PRT
<213> ORGANISM: Artificial sequence
<220> FEATURE:
<223> OTHER INFORMATION: Synthesized: UL68

<400> SEQUENCE: 350

Cys Thr Ala Val His Gln Gln Thr Thr Glu Lys Gly Lys Thr Cys Pro
1               5                   10                  15

Pro Arg Ser Arg Asp Met Gly Thr Arg Cys Arg Asp Asp Arg Tyr Tyr
            20                  25                  30

Pro Trp Arg Tyr Ser Asp Tyr Thr Tyr Thr Thr Tyr Glu Trp His
        35                  40                  45

Val Asp Ala Trp
    50

<210> SEQ ID NO 351
<211> LENGTH: 51
<212> TYPE: PRT
<213> ORGANISM: Artificial sequence
<220> FEATURE:
<223> OTHER INFORMATION: Synthesized: UL69

<400> SEQUENCE: 351

Cys Thr Ser Val His Gln Lys Thr Asp Val Thr Cys Pro Ser Gly Ala
1               5                   10                  15

Thr Tyr Arg Cys Asp Cys Gly Gly Arg Gly Cys Gly Cys Tyr Asp Pro
            20                  25                  30

Trp Cys Ser Thr Thr Tyr Arg Gly Thr Tyr Tyr Asp Phe His Val
        35                  40                  45

Glu Thr Trp
    50
```

<210> SEQ ID NO 352
<211> LENGTH: 50
<212> TYPE: PRT
<213> ORGANISM: Artificial sequence
<220> FEATURE:
<223> OTHER INFORMATION: Synthesized: UL70

<400> SEQUENCE: 352

Cys Gly Thr Val His Gln Glu Thr His Thr Gln Arg Thr Cys Pro Asp
1               5                   10                  15

Ala Cys Asp Val Thr Gly Asp Asn Cys Lys Val Arg Arg Asn Gly Asp
            20                  25                  30

Trp Cys Gly Arg Ala Ser Lys Thr Asp Thr Tyr Asp Phe Tyr Val Asp
        35                  40                  45

Ala Trp
    50

<210> SEQ ID NO 353
<211> LENGTH: 49
<212> TYPE: PRT
<213> ORGANISM: Artificial sequence
<220> FEATURE:
<223> OTHER INFORMATION: Synthesized: UL71

<400> SEQUENCE: 353

Cys Thr Thr Asp Tyr Gln Lys Thr Glu Lys Ser Cys Pro Glu Asn Tyr
1               5                   10                  15

Tyr Ala Glu Thr Gly Tyr Cys Met Cys Gly Ser Trp Arg Cys Gly Tyr
            20                  25                  30

Gly Ser Thr Thr Ser Leu Ile Val Ser Tyr Lys Trp Tyr Val Asp Ala
        35                  40                  45

Trp

<210> SEQ ID NO 354
<211> LENGTH: 49
<212> TYPE: PRT
<213> ORGANISM: Artificial sequence
<220> FEATURE:
<223> OTHER INFORMATION: Synthesized: UL72

<400> SEQUENCE: 354

Cys Thr Thr Val His Gln Lys Thr Asn Gln Lys Trp Gly Cys Pro Asp
1               5                   10                  15

Gly Tyr Val His Met Ser Gly Ser Cys Cys Arg Gly Ser Ile Cys Thr
            20                  25                  30

Asn Gly Leu Phe Arg Asn Thr Tyr Thr Tyr Glu Phe Asn Val Glu Ala
        35                  40                  45

Trp

<210> SEQ ID NO 355
<211> LENGTH: 48
<212> TYPE: PRT
<213> ORGANISM: Artificial sequence
<220> FEATURE:
<223> OTHER INFORMATION: Synthesized: UL73

<400> SEQUENCE: 355

Cys Thr Thr Val Tyr Gln Glu Thr Arg Thr Asn Cys Pro Asp Gly Tyr
1               5                   10                  15

Asn Tyr Arg Ser Gly Asp Cys Arg Arg Trp Asn His Trp Leu Gly Glu

```
                20                  25                  30

Gln Arg Val Ser Pro Thr Tyr Asn Tyr Glu Trp Tyr Val Asp Ser Trp
        35                  40                  45

<210> SEQ ID NO 356
<211> LENGTH: 47
<212> TYPE: PRT
<213> ORGANISM: Artificial sequence
<220> FEATURE:
<223> OTHER INFORMATION: Synthesized: UL74

<400> SEQUENCE: 356

Cys Thr Thr Val Tyr Gln Lys Thr Thr Thr Lys Ser Cys Pro Gly
1               5                   10                  15

Gly Phe Asp Asn Gly Arg Arg Cys Ile Met Gly Leu Gly Asp Leu Arg
                20                  25                  30

Asp Tyr Thr Tyr Phe Asn Lys Tyr Glu Trp Tyr Val Glu Thr Trp
        35                  40                  45

<210> SEQ ID NO 357
<211> LENGTH: 46
<212> TYPE: PRT
<213> ORGANISM: Artificial sequence
<220> FEATURE:
<223> OTHER INFORMATION: Synthesized: UL75

<400> SEQUENCE: 357

Cys Ser Thr Val His Gln Lys Thr Glu Gln Arg Cys Leu Asp Gly Tyr
1               5                   10                  15

Asp Asp Arg Gly Ala Tyr Cys Tyr Asp Ser Val Arg Gly Leu Met Ser
                20                  25                  30

Trp Thr Tyr Lys Tyr Val Tyr Glu Trp Arg Val Asp Thr Trp
        35                  40                  45

<210> SEQ ID NO 358
<211> LENGTH: 45
<212> TYPE: PRT
<213> ORGANISM: Artificial sequence
<220> FEATURE:
<223> OTHER INFORMATION: Synthesized: UL76

<400> SEQUENCE: 358

Cys Thr Asn Val His Gln Met Thr Ile Lys Thr Cys Pro Asp Gly Gly
1               5                   10                  15

Ser Tyr Gly Trp Tyr Trp Pro Tyr Gly Tyr Gly Cys Asn Gly Gly Val
                20                  25                  30

Ser Ala Thr Tyr Thr Tyr Glu Phe Tyr Val Asp Ala Trp
        35                  40                  45

<210> SEQ ID NO 359
<211> LENGTH: 44
<212> TYPE: PRT
<213> ORGANISM: Artificial sequence
<220> FEATURE:
<223> OTHER INFORMATION: Synthesized: UL77

<400> SEQUENCE: 359

Cys Thr Thr Val Tyr Gln Lys Thr Glu Ser Val Arg Ser Cys Pro Asp
1               5                   10                  15

Gly Ser Met Asp Gly Trp Arg Cys Arg Leu Gly Thr Met Asn Trp Ile
                20                  25                  30

Tyr Ser Asn Thr Tyr Glu Phe Tyr Val Asp Ala Trp
```

<210> SEQ ID NO 360
<211> LENGTH: 75
<212> TYPE: PRT
<213> ORGANISM: Artificial sequence
<220> FEATURE:
<223> OTHER INFORMATION: Synthesized: BLV1H12

<400> SEQUENCE: 360

Cys Thr Ser Val His Gln Glu Thr Lys Lys Tyr Gln Ser Cys Pro Asp
1               5                   10                  15

Gly Tyr Arg Glu Arg Ser Asp Cys Ser Asn Arg Pro Ala Cys Gly Thr
            20                  25                  30

Ser Asp Cys Cys Arg Val Ser Val Phe Gly Asn Cys Leu Thr Thr Leu
        35                  40                  45

Pro Val Ser Tyr Ser Tyr Thr Tyr Asn Tyr Glu Trp His Val Asp Val
    50                  55                  60

Trp Gly Gln Gly Leu Leu Val Thr Val Ser Ser
65                  70                  75

<210> SEQ ID NO 361
<211> LENGTH: 70
<212> TYPE: PRT
<213> ORGANISM: Artificial sequence
<220> FEATURE:
<223> OTHER INFORMATION: Synthesized: BLV5B8

<400> SEQUENCE: 361

Cys Thr Thr Val His Gln Glu Thr Arg Lys Thr Cys Ser Asp Gly Tyr
1               5                   10                  15

Ile Ala Val Asp Ser Cys Gly Arg Gly Gln Ser Asp Gly Cys Val Asn
            20                  25                  30

Asp Cys Asn Ser Cys Tyr Tyr Gly Trp Arg Asn Cys Arg Arg Gln Pro
        35                  40                  45

Ala Ile His Ser Tyr Glu Phe His Val Asp Ala Trp Gly Arg Gly Leu
    50                  55                  60

Leu Val Thr Val Ser Ser
65                  70

<210> SEQ ID NO 362
<211> LENGTH: 71
<212> TYPE: PRT
<213> ORGANISM: Artificial sequence
<220> FEATURE:
<223> OTHER INFORMATION: Synthesized: BLV5D3

<400> SEQUENCE: 362

Cys Ser Ser Val Thr Gln Arg Thr His Val Ser Arg Ser Cys Pro Asp
1               5                   10                  15

Gly Cys Ser Asp Gly Asp Gly Cys Val Asp Gly Cys Cys Ser Ala
            20                  25                  30

Tyr Arg Cys Tyr Thr Pro Gly Val Arg Asp Leu Ser Cys Thr Ser Tyr
        35                  40                  45

Ser Ile Thr Tyr Thr Tyr Glu Trp Asn Val Asp Ala Trp Gly Arg Gly
    50                  55                  60

Leu Leu Val Thr Val Ser Ser
65                  70

<210> SEQ ID NO 363

```
<211> LENGTH: 72
<212> TYPE: PRT
<213> ORGANISM: Artificial sequence
<220> FEATURE:
<223> OTHER INFORMATION: Synthesized: BLV8C11

<400> SEQUENCE: 363

Cys Thr Thr Val His Gln Lys Thr Thr Arg Lys Thr Cys Cys Ser Asp
1               5                   10                  15

Ala Tyr Arg Tyr Asp Ser Gly Cys Gly Ser Gly Cys Asp Cys Cys Gly
            20                  25                  30

Ala Asp Cys Tyr Val Phe Gly Ala Cys Thr Phe Gly Leu Asp Ser Ser
        35                  40                  45

Tyr Ser Tyr Ile Tyr Ile Tyr Gln Trp Tyr Val Asp Ala Trp Gly Gln
    50                  55                  60

Gly Leu Leu Val Thr Val Ser Ser
65                  70

<210> SEQ ID NO 364
<211> LENGTH: 70
<212> TYPE: PRT
<213> ORGANISM: Artificial sequence
<220> FEATURE:
<223> OTHER INFORMATION: Synthesized: BF4E9

<400> SEQUENCE: 364

Cys Thr Thr Val His Gln Ile Phe Cys Pro Asp Gly Tyr Ser Tyr Gly
1               5                   10                  15

Tyr Gly Cys Gly Tyr Gly Tyr Gly Cys Ser Gly Tyr Asp Cys Tyr Gly
            20                  25                  30

Tyr Gly Gly Tyr Gly Tyr Gly Gly Tyr Gly Tyr Ser Ser Tyr Ser
        35                  40                  45

Tyr Ser Tyr Ser Tyr Glu Tyr Tyr Gly Asp Ala Trp Gly Gln Gly Leu
    50                  55                  60

Leu Val Thr Val Ser Ser
65                  70

<210> SEQ ID NO 365
<211> LENGTH: 50
<212> TYPE: PRT
<213> ORGANISM: Artificial sequence
<220> FEATURE:
<223> OTHER INFORMATION: Synthesized: BF1H1

<400> SEQUENCE: 365

Cys Thr Thr Val His Pro Ser Pro Asp Gly Tyr Ser Tyr Gly Tyr Gly
1               5                   10                  15

Cys Gly Tyr Gly Tyr Gly Cys Ser Gly Tyr Asp Cys Tyr Gly Tyr Gly
            20                  25                  30

Gly Tyr Gly Tyr Gly Gly Tyr Gly Gly Tyr Ser Ser Tyr Ser Tyr Ser
        35                  40                  45

Tyr Ser
    50

<210> SEQ ID NO 366
<211> LENGTH: 50
<212> TYPE: PRT
<213> ORGANISM: Artificial sequence
<220> FEATURE:
<223> OTHER INFORMATION: Synthesized: F18

<400> SEQUENCE: 366
```

Cys Thr Thr Val His Gln Ile Arg Cys Pro Asp Gly Tyr Gly Tyr Gly
1               5                   10                  15

Tyr Gly Cys Gly Tyr Gly Ser Tyr Gly Tyr Ser Gly Tyr Asp Cys Tyr
                20                  25                  30

Gly Tyr Gly Gly Tyr Gly Gly Tyr Gly Gly Tyr Gly Tyr Ser Ser
            35                  40                  45

Tyr Ser
    50

<210> SEQ ID NO 367
<211> LENGTH: 300
<212> TYPE: DNA
<213> ORGANISM: Artificial sequence
<220> FEATURE:
<223> OTHER INFORMATION: Synthesized: Bovine VH-UL

<400> SEQUENCE: 367
caggtgcagc tgcgggagtc gggcccagc ctggtgaagc cctcacagac cctctcgctc      60
acctgcacgg cctctggatt ctcattgagc gacaaggctg taggctgggt ccgccaggct    120
ccagggaagg cgctggagtg gctcggtggt atagacactg gtggaagcac aggctataac    180
ccaggcctga atcccggct cagcatcacc aaggacaact ccaagagcca agtctctctg     240
tcagtgagca gcgtgacaac tgaggactcg gccacatact actgtactac tgtgcaccag   300

<210> SEQ ID NO 368
<211> LENGTH: 311
<212> TYPE: DNA
<213> ORGANISM: Artificial sequence
<220> FEATURE:
<223> OTHER INFORMATION: Synthesized: 4-39

<400> SEQUENCE: 368
cagctgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaaggggct ggagtggatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg cgagacac      300 acagtgaggg g                                                         311

<210> SEQ ID NO 369
<211> LENGTH: 288
<212> TYPE: DNA
<213> ORGANISM: Artificial sequence
<220> FEATURE:
<223> OTHER INFORMATION: Synthesized: 4-59*03

<400> SEQUENCE: 369
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
ccctccctca gagtcgagt caccatatca gtagacacg ccaagaacca attctccctg      240
aagctgagct ctgtgaccgc tgcggacacg gccgtgtatt actgtgcg                 288

<210> SEQ ID NO 370
<211> LENGTH: 291
<212> TYPE: DNA

<213> ORGANISM: Artificial sequence
<220> FEATURE:
<223> OTHER INFORMATION: Synthesized: 4-34*09

<400> SEQUENCE: 370

```
caggtgcagc tgcaggagtc gggcccagga ctggtgaagc cttcacagac cctgtccctc    60
acctgcgctg tctatggtgg gtccttcagt ggttactact ggagctggat ccgccagccc   120
ccagggaagg gactggagtg gattggggaa atcaatcata gtggaagcac caactacaac   180
ccgtccctca agagtcgagt taccatatca gtagacacgt ctaagaacca gttctccctg   240
aagctgagct ctgtgactgc cgcggacacg gccgtgtatt actgtgcgag a            291
```

<210> SEQ ID NO 371
<211> LENGTH: 293
<212> TYPE: DNA
<213> ORGANISM: Artificial sequence
<220> FEATURE:
<223> OTHER INFORMATION: Synthesized: 4-34*02

<400> SEQUENCE: 371

```
caggtgcagc tacaacagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag agg          293
```

<210> SEQ ID NO 372
<211> LENGTH: 330
<212> TYPE: DNA
<213> ORGANISM: Artificial sequence
<220> FEATURE:
<223> OTHER INFORMATION: Synthesized: BLV1H12 VL

<400> SEQUENCE: 372

```
caggctgtgc tgaatcagcc atcatccgtg tccgggtccc tgggccagag ggtctccatc    60
acctgctctg gaagcagcag caatgttgga aatggatatg tgagctggta ccaactgatc   120
ccaggatcgg cccccagaac cctcatctat ggtgacacca gtcgagcctc gggggtcccc   180
gaccgattct ccggctccag gtctgggaac acagccaccc tgaccatcag ctcgctccag   240
gctgaggacg aggcagatta tttctgtgca tctgctgagg atagtagcag taatgctgtt   300
ttcggcagcg ggaccacact gaccgtcctg                                     330
```

<210> SEQ ID NO 373
<211> LENGTH: 296
<212> TYPE: DNA
<213> ORGANISM: Artificial sequence
<220> FEATURE:
<223> OTHER INFORMATION: Synthesized: Vl1-47

<400> SEQUENCE: 373

```
cagtctgtgc tgactcagcc accctcagcg tctgggaccc ccgggcagag ggtcaccatc    60
tcttgttctg gaagcagctc caacatcgga agtaattatg tatactggta ccagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtcc       296
```

```
<210> SEQ ID NO 374
<211> LENGTH: 299
<212> TYPE: DNA
<213> ORGANISM: Artificial sequence
<220> FEATURE:
<223> OTHER INFORMATION: Synthesized: Vl1-40*1

<400> SEQUENCE: 374
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttc    299

<210> SEQ ID NO 375
<211> LENGTH: 296
<212> TYPE: DNA
<213> ORGANISM: Artificial sequence
<220> FEATURE:
<223> OTHER INFORMATION: Synthesized: Vl1-51 *01

<400> SEQUENCE: 375
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct    180 gaccgattct ctggctccaa gtctggcacg tcagccaccc tgggcatcac cggactccag   240
actggggacg aggccgatta ttactgcgga acatgggata gcagcctgag tgctgg       296

<210> SEQ ID NO 376
<211> LENGTH: 297
<212> TYPE: DNA
<213> ORGANISM: Artificial sequence
<220> FEATURE:
<223> OTHER INFORMATION: Synthesized: Vl2-18*02

<400> SEQUENCE: 376
cagtctgccc tgactcagcc tccctccgtg tccgggtctc ctggacagtc agtcaccatc    60
tcctgcactg gaaccagcag tgacgttggt agttataacc gtgtctcctg gtaccagcag   120
cccccaggca gcccccaa actcatgatt tatgaggtca gtaatcggcc ctcaggggtc     180
cctgatcgct tctctgggtc caagtctggc aacacggcct ccctgaccat ctctgggctc   240
caggctgagg acgaggctga ttattactgc agctcatata caagcagcag cactttc      297

<210> SEQ ID NO 377
<211> LENGTH: 514
<212> TYPE: DNA
<213> ORGANISM: Artificial sequence
<220> FEATURE:
<223> OTHER INFORMATION: Synthesized: partially human antibody
     comprising an ultralong CDR3

<400> SEQUENCE: 377
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaagggact ggagtggatt gggagtatct attatagtgg gagcacctac   180
tacaacccgt ccctcaagag tcgagtcacc atatccgtag acacgtccaa gaaccagttc   240
tccctgaagc tgagctctgt gaccgccgca gacacggctg tgtattactg tactactgtg   300
```

```
caccaggaaa caaaaaaata ccaaagttgt cctgatgggt atagagaacg ttcggattgt    360
agtaacagac ctgcttgtgg tactagtgat tgttgtcgtg ttagtgtttt tggtaattgt    420
cttactactc ttcctgtgag ttatagttat acttacaatt acgaatggca cgtcgatgtc    480
tggggccagg gaaccctggt caccgtctcc tcag                                514
```

<210> SEQ ID NO 378
<211> LENGTH: 171
<212> TYPE: PRT
<213> ORGANISM: Artificial sequence
<220> FEATURE:
<223> OTHER INFORMATION: Synthesized: partially human antibody
    comprising an ultralong CDR3 amino acid sequence

<400> SEQUENCE: 378

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Thr Val His Gln Glu Thr Lys Lys Tyr Gln Ser Cys Pro Asp
            100                 105                 110

Gly Tyr Arg Glu Arg Ser Asp Cys Ser Asn Arg Pro Ala Cys Gly Thr
        115                 120                 125

Ser Asp Cys Cys Arg Val Ser Val Phe Gly Asn Cys Leu Thr Thr Leu
    130                 135                 140

Pro Val Ser Tyr Ser Tyr Thr Tyr Asn Tyr Glu Trp His Val Asp Val
145                 150                 155                 160

Trp Gly Gln Gly Thr Leu Val Thr Val Ser Ser
                165                 170
```

<210> SEQ ID NO 379
<211> LENGTH: 493
<212> TYPE: DNA
<213> ORGANISM: Artificial sequence
<220> FEATURE:
<223> OTHER INFORMATION: Synthesized: partially human antibody V region
    comprised of an ultralong CDR3

<400> SEQUENCE: 379

```
caggtgcagc tacaacagtg gggcgcagga ctgttgaagc cttcggagac cctgtccctc     60
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca gagtcgagt caccatatca gtagacacgt ccaagaacca gttctccctg    240
aagctgagct ctgtgaccgc cgcggacacg gctgtgtatt actgtactac tgtgcaccag    300
gaaaccagaa aaacctgttc tgatggttat atgctgtag atagttgtgg tcgtggtcag    360
agtgatggtt gtgtcaatga ttgcaattgt tgttattatg gttggcggaa ctgtcgcagg    420
cagcctgcaa ttcaaagtta cgaatttcac gtcgatgcct ggggccgtgg caccctggtc    480
```
actgtctcct cag                                                                493

```
<210> SEQ ID NO 380
<211> LENGTH: 164
<212> TYPE: PRT
<213> ORGANISM: Artificial sequence
<220> FEATURE:
<223> OTHER INFORMATION: Synthesized: partially human antibody V region
      comprised of an ultralong CDR3

<400> SEQUENCE: 380
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Thr Val His Gln Glu Thr Arg Lys Thr Cys Ser Asp Gly Tyr Met Ala
            100                 105                 110

Val Asp Ser Cys Gly Arg Gly Gln Ser Asp Gly Cys Val Asn Asp Cys
        115                 120                 125

Asn Cys Cys Tyr Tyr Gly Trp Arg Asn Cys Arg Arg Gln Pro Ala Ile
    130                 135                 140

Gln Ser Tyr Glu Phe His Val Asp Ala Trp Gly Arg Gly Thr Leu Val
145                 150                 155                 160

Thr Val Ser Ser

```
<210> SEQ ID NO 381
<211> LENGTH: 63
<212> TYPE: DNA
<213> ORGANISM: Artificial sequence
<220> FEATURE:
<223> OTHER INFORMATION: Synthesized: MID1 FW

<400> SEQUENCE: 381
```
cctatcccct gtgtgccttg gcagtctcag acgagtgcgt ttgagcgaca aggctgtagg      60
ctg                                                                   63

```
<210> SEQ ID NO 382
<211> LENGTH: 62
<212> TYPE: DNA
<213> ORGANISM: Artificial sequence
<220> FEATURE:
<223> OTHER INFORMATION: Synthesized: MID1 RV

<400> SEQUENCE: 382
```
ccatctcatc cctgcgtgtc tccgactcag acgagtgcgt ctttcggggc tgtggtggag      60
gc                                                                    62

```
<210> SEQ ID NO 383
<211> LENGTH: 63
<212> TYPE: DNA
<213> ORGANISM: Artificial sequence
```

```
<220> FEATURE:
<223> OTHER INFORMATION: Synthesized: MID10 FW

<400> SEQUENCE: 383
cctatcccct gtgtgccttg gcagtctcag tctctatgcg ttgagcgaca aggctgtagg      60
ctg                                                                   63

<210> SEQ ID NO 384
<211> LENGTH: 66
<212> TYPE: DNA
<213> ORGANISM: Artificial sequence
<220> FEATURE:
<223> OTHER INFORMATION: Synthesized: MID10 RV

<400> SEQUENCE: 384
ccatctcatc cctgcgtgtc tccgactcag tctctatgcg agtgaagact ctcgggtgtg      60
attcac                                                                66

<210> SEQ ID NO 385
<211> LENGTH: 63
<212> TYPE: DNA
<213> ORGANISM: Artificial sequence
<220> FEATURE:
<223> OTHER INFORMATION: Synthesized: MID11 FW

<400> SEQUENCE: 385
cctatcccct gtgtgccttg gcagtctcag tgatacgtct ttgagcgaca aggctgtagg      60
ctg                                                                   63

<210> SEQ ID NO 386
<211> LENGTH: 66
<212> TYPE: DNA
<213> ORGANISM: Artificial sequence
<220> FEATURE:
<223> OTHER INFORMATION: Synthesized: MID11 RV

<400> SEQUENCE: 386
ccatctcatc cctgcgtgtc tccgactcag tgatacgtct agtgaagact ctcgggtgtg      60
attcac                                                                66

<210> SEQ ID NO 387
<211> LENGTH: 23
<212> TYPE: DNA
<213> ORGANISM: Artificial sequence
<220> FEATURE:
<223> OTHER INFORMATION: Synthesized: primer 1 for bovine VH region

<400> SEQUENCE: 387
ttgagcgaca aggctgtagg ctg                                             23

<210> SEQ ID NO 388
<211> LENGTH: 22
<212> TYPE: DNA
<213> ORGANISM: Artificial sequence
<220> FEATURE:
<223> OTHER INFORMATION: Synthesized: primer 2 for bovine VH region

<400> SEQUENCE: 388
ctttcggggc tgtggtggag gc                                              22

<210> SEQ ID NO 389
<211> LENGTH: 20
<212> TYPE: DNA
```

```
<213> ORGANISM: Artificial sequence
<220> FEATURE:
<223> OTHER INFORMATION: Synthesized: sequencing primer

<400> SEQUENCE: 389
agatccaagc tgtgaccggc                                                    20

<210> SEQ ID NO 390
<211> LENGTH: 1002
<212> TYPE: DNA
<213> ORGANISM: Artificial sequence
<220> FEATURE:
<223> OTHER INFORMATION: Synthesized: CH1 CH2 CH3 of human IgG1
<220> FEATURE:
<221> NAME/KEY: CDS
<222> LOCATION: (1)..(1002)

<400> SEQUENCE: 390
```

| | | | | | | | | | | | | | | | | |
|---|---|---|---|---|---|---|---|---|---|---|---|---|---|---|---|---|
| gct | agc | acc | aag | ggc | cca | tcg | gtc | ttc | ccc | ctg | gca | ccc | tcc | tcc | aag | 48 |
| Ala | Ser | Thr | Lys | Gly | Pro | Ser | Val | Phe | Pro | Leu | Ala | Pro | Ser | Ser | Lys | |
| 1 | | | | 5 | | | | | 10 | | | | | 15 | | |
| agc | acc | tct | ggg | ggc | aca | gcg | gcc | ctg | ggc | tgc | ctg | gtc | aag | gac | tac | 96 |
| Ser | Thr | Ser | Gly | Gly | Thr | Ala | Ala | Leu | Gly | Cys | Leu | Val | Lys | Asp | Tyr | |
| | | | 20 | | | | | 25 | | | | | 30 | | | |
| ttc | ccc | gag | ccg | gtg | acg | gtg | tcg | tgg | aac | tca | ggc | gcc | ctg | acc | agc | 144 |
| Phe | Pro | Glu | Pro | Val | Thr | Val | Ser | Trp | Asn | Ser | Gly | Ala | Leu | Thr | Ser | |
| | 35 | | | | | 40 | | | | | 45 | | | | | |
| ggc | gtg | cac | acc | ttc | ccg | gct | gtc | cta | cag | tcc | tca | gga | ctc | tac | tcc | 192 |
| Gly | Val | His | Thr | Phe | Pro | Ala | Val | Leu | Gln | Ser | Ser | Gly | Leu | Tyr | Ser | |
| 50 | | | | | 55 | | | | | 60 | | | | | | |
| ctc | agc | agc | gtg | gtg | acc | gtg | ccc | tcc | agc | agc | ttg | ggc | acc | cag | acc | 240 |
| Leu | Ser | Ser | Val | Val | Thr | Val | Pro | Ser | Ser | Ser | Leu | Gly | Thr | Gln | Thr | |
| 65 | | | | | 70 | | | | | 75 | | | | | 80 | |
| tac | atc | tgc | aac | gtg | aat | cac | aag | ccc | agc | aac | acc | aag | gtg | gac | aag | 288 |
| Tyr | Ile | Cys | Asn | Val | Asn | His | Lys | Pro | Ser | Asn | Thr | Lys | Val | Asp | Lys | |
| | | | | 85 | | | | | 90 | | | | | 95 | | |
| aaa | gtt | gag | ccc | aaa | tct | tgt | gac | aaa | act | cac | aca | tgc | cca | ccg | tgc | 336 |
| Lys | Val | Glu | Pro | Lys | Ser | Cys | Asp | Lys | Thr | His | Thr | Cys | Pro | Pro | Cys | |
| | | | 100 | | | | | 105 | | | | | 110 | | | |
| cca | gca | cct | gaa | ctc | ctg | ggg | gga | ccg | tca | gtc | ttc | ctc | ttc | ccc | cca | 384 |
| Pro | Ala | Pro | Glu | Leu | Leu | Gly | Gly | Pro | Ser | Val | Phe | Leu | Phe | Pro | Pro | |
| | 115 | | | | | 120 | | | | | 125 | | | | | |
| aaa | ccc | aag | gac | acc | ctc | atg | atc | tcc | cgg | acc | cct | gag | gtc | aca | tgc | 432 |
| Lys | Pro | Lys | Asp | Thr | Leu | Met | Ile | Ser | Arg | Thr | Pro | Glu | Val | Thr | Cys | |
| 130 | | | | | 135 | | | | | 140 | | | | | | |
| gtg | gtg | gtg | gac | gtg | agc | cac | gaa | gac | cct | gag | gtc | aag | ttc | aac | tgg | 480 |
| Val | Val | Val | Asp | Val | Ser | His | Glu | Asp | Pro | Glu | Val | Lys | Phe | Asn | Trp | |
| 145 | | | | | 150 | | | | | 155 | | | | | 160 | |
| tac | gtg | gac | ggc | gtg | gag | gtg | cat | aat | gcc | aag | aca | aag | ccg | cgg | gag | 528 |
| Tyr | Val | Asp | Gly | Val | Glu | Val | His | Asn | Ala | Lys | Thr | Lys | Pro | Arg | Glu | |
| | | | | 165 | | | | | 170 | | | | | 175 | | |
| gag | cag | tac | aac | agc | acg | tac | cgt | gtg | gtc | agc | gtc | ctc | acc | gtc | ctg | 576 |
| Glu | Gln | Tyr | Asn | Ser | Thr | Tyr | Arg | Val | Val | Ser | Val | Leu | Thr | Val | Leu | |
| | | | 180 | | | | | 185 | | | | | 190 | | | |
| cac | cag | gac | tgg | ctg | aat | ggc | aag | gag | tac | aag | tgc | aag | gtc | tcc | aac | 624 |
| His | Gln | Asp | Trp | Leu | Asn | Gly | Lys | Glu | Tyr | Lys | Cys | Lys | Val | Ser | Asn | |
| | 195 | | | | | 200 | | | | | 205 | | | | | |
| aaa | gcc | ctc | cca | gcc | ccc | atc | gag | aaa | acc | atc | tcc | aaa | gcc | aaa | ggg | 672 |
| Lys | Ala | Leu | Pro | Ala | Pro | Ile | Glu | Lys | Thr | Ile | Ser | Lys | Ala | Lys | Gly | |
| 210 | | | | | 215 | | | | | 220 | | | | | | |
| cag | ccc | cga | gaa | cca | cag | gtg | tac | acc | ctg | ccc | cca | tcc | cgg | gat | gag | 720 |
| Gln | Pro | Arg | Glu | Pro | Gln | Val | Tyr | Thr | Leu | Pro | Pro | Ser | Arg | Asp | Glu | |

```
ctg acc aag aac cag gtc agc ctg acc tgc ctg gtc aaa ggc ttc tat         768
Leu Thr Lys Asn Gln Val Ser Leu Thr Cys Leu Val Lys Gly Phe Tyr
            245                 250                 255 ccc agc gac atc gcc gtg gag tgg gag agc aat ggg cag ccg gag aac         816
Pro Ser Asp Ile Ala Val Glu Trp Glu Ser Asn Gly Gln Pro Glu Asn
        260                 265                 270 aac tac aag acc acg cct ccc gtg ctg gac tcc gac ggc tcc ttc ttc         864
Asn Tyr Lys Thr Thr Pro Pro Val Leu Asp Ser Asp Gly Ser Phe Phe
    275                 280                 285 ctc tac agc aag ctc acc gtg gac aag agc agg tgg cag cag ggg aac         912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg         960
Val Phe Ser Cys Ser Val Met His Glu Ala Leu His Asn His Tyr Thr
305                 310                 315                 320 cag aag agc ctc tcc ctg tct ccg ggt aaa tga taa tct aga              1002
Gln Lys Ser Leu Ser Leu Ser Pro Gly Lys         Ser Arg
                325                 330
```

<210> SEQ ID NO 391
<211> LENGTH: 330
<212> TYPE: PRT
<213> ORGANISM: Artificial sequence
<220> FEATURE:
<223> OTHER INFORMATION: Synthetic Construct

<400> SEQUENCE: 391

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 392
<211> LENGTH: 513
<212> TYPE: DNA
<213> ORGANISM: Artificial sequence
<220> FEATURE:
<223> OTHER INFORMATION: Synthesized: BLV1H12 V region

<400> SEQUENCE: 392
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga gagcagact gtccattacc aaggacaact ctaaaagtca ggtgtcactg      240
agcgtgagct ccgtcaccac agaggatagt gcaacttact attgcacctc tgtgcaccag     300
gaaactaaga ataccagag ctgtcctgac ggctatcggg agagatctga ttgcagtaat      360
aggccagctt gtggcacatc cgactgctgt cgcgtgtctg tcttcgggaa ctgcctgact     420
accctgcctg tgtcctactc ttatacctac aattatgaat ggcatgtgga tgtctgggga    480
cagggcctgc tggtgacagt ctctagtgct agc                                  513

<210> SEQ ID NO 393
<211> LENGTH: 1563
<212> TYPE: DNA
<213> ORGANISM: Artificial sequence
<220> FEATURE:
<223> OTHER INFORMATION: Synthesized: (Sig Seq- VRegion - CH1CH2CH3)
      BLV1H12 V in human IgG
<220> FEATURE:
<221> NAME/KEY: CDS
<222> LOCATION: (1)..(1563)

<400> SEQUENCE: 393 atg cgc agg atg caa ctc ctg ttg ctg att gca cta agt ctt gca ctt       48
Met Arg Arg Met Gln Leu Leu Leu Leu Ile Ala Leu Ser Leu Ala Leu
1               5                   10                  15 gtc acg aat tcg cag gtc cag ctg aga gag agc ggc cct tca ctg gtc       96
Val Thr Asn Ser Gln Val Gln Leu Arg Glu Ser Gly Pro Ser Leu Val
                20                  25                  30 aag cca tcc cag aca ctg agc ctg aca tgc aca gca agc ggg ttt tca      144
Lys Pro Ser Gln Thr Leu Ser Leu Thr Cys Thr Ala Ser Gly Phe Ser
            35                  40                  45 ctg agc gac aag gca gtg gga tgg gtc cga cag gca cca gga aaa gcc      192
Leu Ser Asp Lys Ala Val Gly Trp Val Arg Gln Ala Pro Gly Lys Ala
        50                  55                  60 ctg gaa tgg ctg ggc agc atc gat acc ggc ggg aac aca ggg tac aat      240
Leu Glu Trp Leu Gly Ser Ile Asp Thr Gly Gly Asn Thr Gly Tyr Asn
    65                  70                  75                  80
```

-continued

| | | |
|---|---|---|
| Leu Glu Trp Leu Gly Ser Ile Asp Thr Gly Gly Asn Thr Gly Tyr Asn<br>65                                70                            75                            80 | | |
| ccc gga ctg aag agc aga ctg tcc att acc aag gac aac tct aaa agt<br>Pro Gly Leu Lys Ser Arg Leu Ser Ile Thr Lys Asp Asn Ser Lys Ser<br>                      85                            90                            95 | 288 |
| cag gtg tca ctg agc gtg agc tcc gtc acc aca gag gat agt gca act<br>Gln Val Ser Leu Ser Val Ser Ser Val Thr Thr Glu Asp Ser Ala Thr<br>                100                           105                        110 | 336 |
| tac tat tgc acc tct gtg cac cag gaa act aag aaa tac cag agc tgt<br>Tyr Tyr Cys Thr Ser Val His Gln Glu Thr Lys Lys Tyr Gln Ser Cys<br>          115                        120                        125 | 384 |
| cct gac ggc tat cgg gag aga tct gat tgc agt aat agg cca gct tgt<br>Pro Asp Gly Tyr Arg Glu Arg Ser Asp Cys Ser Asn Arg Pro Ala Cys<br>130                              135                        140 | 432 |
| ggc aca tcc gac tgc tgt cgc gtg tct gtc ttc ggg aac tgc ctg act<br>Gly Thr Ser Asp Cys Cys Arg Val Ser Val Phe Gly Asn Cys Leu Thr<br>145                              150                        155                        160 | 480 |
| acc ctg cct gtg tcc tac tct tat acc tac aat tat gaa tgg cat gtg<br>Thr Leu Pro Val Ser Tyr Ser Tyr Thr Tyr Asn Tyr Glu Trp His Val<br>                          165                            170                        175 | 528 |
| gat gtc tgg gga cag ggc ctg ctg gtg aca gtc tct agt gct agc acc<br>Asp Val Trp Gly Gln Gly Leu Leu Val Thr Val Ser Ser Ala Ser Thr<br>              180                           185                        190 | 576 |
| aag ggc cca tcg gtc ttc ccc ctg gca ccc tcc tcc aag agc acc tct<br>Lys Gly Pro Ser Val Phe Pro Leu Ala Pro Ser Ser Lys Ser Thr Ser<br>          195                        200                        205 | 624 |
| ggg ggc aca gcg gcc ctg ggc tgc ctg gtc aag gac tac ttc ccc gag<br>Gly Gly Thr Ala Ala Leu Gly Cys Leu Val Lys Asp Tyr Phe Pro Glu<br>210                              215                        220 | 672 |
| ccg gtg acg gtg tcg tgg aac tca ggc gcc ctg acc agc ggc gtg cac<br>Pro Val Thr Val Ser Trp Asn Ser Gly Ala Leu Thr Ser Gly Val His<br>225                              230                        235                        240 | 720 |
| acc ttc ccg gct gtc cta cag tcc tca gga ctc tac tcc ctc agc agc<br>Thr Phe Pro Ala Val Leu Gln Ser Ser Gly Leu Tyr Ser Leu Ser Ser<br>              245                           250                        255 | 768 |
| gtg gtg acc gtg ccc tcc agc agc ttg ggc acc cag acc tac atc tgc<br>Val Val Thr Val Pro Ser Ser Ser Leu Gly Thr Gln Thr Tyr Ile Cys<br>                    260                           265                        270 | 816 |
| aac gtg aat cac aag ccc agc aac acc aag gtg gac aag aaa gtt gag<br>Asn Val Asn His Lys Pro Ser Asn Thr Lys Val Asp Lys Lys Val Glu<br>          275                        280                        285 | 864 |
| ccc aaa tct tgt gac aaa act cac aca tgc cca ccg tgc cca gca cct<br>Pro Lys Ser Cys Asp Lys Thr His Thr Cys Pro Pro Cys Pro Ala Pro<br>290                              295                        300 | 912 |
| gaa ctc ctg ggg gga ccg tca gtc ttc ctc ttc ccc cca aaa ccc aag<br>Glu Leu Leu Gly Gly Pro Ser Val Phe Leu Phe Pro Pro Lys Pro Lys<br>305                              310                        315                        320 | 960 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>                    325                           330                        335 | 1008 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>          340                        345                        350 | 1056 |
| ggc gtg gag gtg cat aat gcc aag aca aag ccg cgg gag gag cag tac<br>Gly Val Glu Val His Asn Ala Lys Thr Lys Pro Arg Glu Glu Gln Tyr<br>                  355                           360                        365 | 1104 |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>370                              375                        380 | 1152 |

```
tgg ctg aat ggc aag gag tac aag tgc aag gtg tcc aac aaa gcc ctc      1200
Trp Leu Asn Gly Lys Glu Tyr Lys Cys Lys Val Ser Asn Lys Ala Leu
385                 390                 395                 400 cca gcc ccc atc gag aaa acc atc tcc aaa gcc aaa ggg cag ccc cga      1248
Pro Ala Pro Ile Glu Lys Thr Ile Ser Lys Ala Lys Gly Gln Pro Arg
                405                 410                 415 gaa cca cag gtg tac acc ctg ccc cca tcc cgg gat gag ctg acc aag      1296
Glu Pro Gln Val Tyr Thr Leu Pro Pro Ser Arg Asp Glu Leu Thr Lys
            420                 425                 430 aac cag gtc agc ctg acc tgc ctg gtc aaa ggc ttc tat ccc agc gac      1344
Asn Gln Val Ser Leu Thr Cys Leu Val Lys Gly Phe Tyr Pro Ser Asp
        435                 440                 445 atc gcc gtg gag tgg gag agc aat ggg cag ccg gag aac aac tac aag      1392
Ile Ala Val Glu Trp Glu Ser Asn Gly Gln Pro Glu Asn Asn Tyr Lys
    450                 455                 460 acc acg cct ccc gtg ctg gac tcc gac ggc tcc ttc ttc ctc tac agc      1440
Thr Thr Pro Pro Val Leu Asp Ser Asp Gly Ser Phe Phe Leu Tyr Ser
465                 470                 475                 480 aag ctc acc gtg gac aag agc agg tgg cag cag ggg aac gtc ttc tca      1488
Lys Leu Thr Val Asp Lys Ser Arg Trp Gln Gln Gly Asn Val Phe Ser
                485                 490                 495 tgc tcc gtg atg cat gag gct ctg cac aac cac tac acg cag aag agc      1536
Cys Ser Val Met His Glu Ala Leu His Asn His Tyr Thr Gln Lys Ser
                500                 505                 510 ctc tcc ctg tct ccg ggt aaa tga taa                                   1563
Leu Ser Leu Ser Pro Gly Lys
                515

<210> SEQ ID NO 394
<211> LENGTH: 519
<212> TYPE: PRT
<213> ORGANISM: Artificial sequence
<220> FEATURE:
<223> OTHER INFORMATION: Synthetic Construct

<400> SEQUENCE: 394

Met Arg Arg Met Gln Leu Leu Leu Leu Ile Ala Leu Ser Leu Ala Leu
1               5                   10                  15

Val Thr Asn Ser Gln Val Gln Leu Arg Glu Ser Gly Pro Ser Leu Val
            20                  25                  30

Lys Pro Ser Gln Thr Leu Ser Leu Thr Cys Thr Ala Ser Gly Phe Ser
        35                  40                  45

Leu Ser Asp Lys Ala Val Gly Trp Val Arg Gln Ala Pro Gly Lys Ala
    50                  55                  60

Leu Glu Trp Leu Gly Ser Ile Asp Thr Gly Gly Asn Thr Gly Tyr Asn
65                  70                  75                  80

Pro Gly Leu Lys Ser Arg Leu Ser Ile Thr Lys Asp Asn Ser Lys Ser
                85                  90                  95

Gln Val Ser Leu Ser Val Ser Ser Val Thr Thr Glu Asp Ser Ala Thr
            100                 105                 110

Tyr Tyr Cys Thr Ser Val His Gln Glu Thr Lys Lys Tyr Gln Ser Cys
        115                 120                 125

Pro Asp Gly Tyr Arg Glu Arg Ser Asp Cys Ser Asn Arg Pro Ala Cys
    130                 135                 140

Gly Thr Ser Asp Cys Cys Arg Val Ser Val Phe Gly Asn Cys Leu Thr
145                 150                 155                 160

Thr Leu Pro Val Ser Tyr Ser Tyr Thr Tyr Asn Tyr Glu Trp His Val
                165                 170                 175
```

Asp Val Trp Gly Gln Gly Leu Leu Val Thr Val Ser Ala Ser Thr
            180                 185                 190

Lys Gly Pro Ser Val Phe Pro Leu Ala Pro Ser Ser Lys Ser Thr Ser
        195                 200                 205

Gly Gly Thr Ala Ala Leu Gly Cys Leu Val Lys Asp Tyr Phe Pro Glu
        210                 215                 220

Pro Val Thr Val Ser Trp Asn Ser Gly Ala Leu Thr Ser Gly Val His
225                 230                 235                 240

Thr Phe Pro Ala Val Leu Gln Ser Ser Gly Leu Tyr Ser Leu Ser Ser
                245                 250                 255

Val Val Thr Val Pro Ser Ser Ser Leu Gly Thr Gln Thr Tyr Ile Cys
            260                 265                 270

Asn Val Asn His Lys Pro Ser Asn Thr Lys Val Asp Lys Lys Val Glu
        275                 280                 285

Pro Lys Ser Cys Asp Lys Thr His Thr Cys Pro Pro Cys Pro Ala Pro
    290                 295                 300

Glu Leu Leu Gly Gly Pro Ser Val Phe Leu Phe Pro Pro Lys Pro Lys
305                 310                 315                 320

Asp Thr Leu Met Ile Ser Arg Thr Pro Glu Val Thr Cys Val Val Val
                325                 330                 335

Asp Val Ser His Glu Asp Pro Glu Val Lys Phe Asn Trp Tyr Val Asp
            340                 345                 350

Gly Val Glu Val His Asn Ala Lys Thr Lys Pro Arg Glu Glu Gln Tyr
        355                 360                 365

Asn Ser Thr Tyr Arg Val Val Ser Val Leu Thr Val Leu His Gln Asp
    370                 375                 380

Trp Leu Asn Gly Lys Glu Tyr Lys Cys Lys Val Ser Asn Lys Ala Leu
385                 390                 395                 400

Pro Ala Pro Ile Glu Lys Thr Ile Ser Lys Ala Lys Gly Gln Pro Arg
                405                 410                 415

Glu Pro Gln Val Tyr Thr Leu Pro Pro Ser Arg Asp Glu Leu Thr Lys
            420                 425                 430

Asn Gln Val Ser Leu Thr Cys Leu Val Lys Gly Phe Tyr Pro Ser Asp
        435                 440                 445

Ile Ala Val Glu Trp Glu Ser Asn Gly Gln Pro Glu Asn Asn Tyr Lys
    450                 455                 460

Thr Thr Pro Pro Val Leu Asp Ser Asp Gly Ser Phe Phe Leu Tyr Ser
465                 470                 475                 480

Lys Leu Thr Val Asp Lys Ser Arg Trp Gln Gln Gly Asn Val Phe Ser
                485                 490                 495

Cys Ser Val Met His Glu Ala Leu His Asn His Tyr Thr Gln Lys Ser
            500                 505                 510

Leu Ser Leu Ser Pro Gly Lys
        515

<210> SEQ ID NO 395
<211> LENGTH: 1470
<212> TYPE: DNA
<213> ORGANISM: Artificial sequence
<220> FEATURE:
<223> OTHER INFORMATION: Synthesized: BLV1H12 V in human IgG with BsaI
      cassette in CDR3
<220> FEATURE:
<221> NAME/KEY: CDS
<222> LOCATION: (1)..(1470)

<400> SEQUENCE: 395

| | | |
|---|---|---|
| atg cgc agg atg caa ctc ctg ttg ctg att gca cta agt ctt gca ctt<br>Met Arg Arg Met Gln Leu Leu Leu Leu Ile Ala Leu Ser Leu Ala Leu<br>1               5                   10                  15 | | 48 |
| gtc acg aat tcg cag gtc cag ctg aga gag agc ggc cct tca ctg gtc<br>Val Thr Asn Ser Gln Val Gln Leu Arg Glu Ser Gly Pro Ser Leu Val<br>            20                  25                  30 | | 96 |
| aag cca tcc cag aca ctg agc ctg aca tgc aca gca agc ggg ttt tca<br>Lys Pro Ser Gln Thr Leu Ser Leu Thr Cys Thr Ala Ser Gly Phe Ser<br>        35                  40                  45 | | 144 |
| ctg agc gac aag gca gtg gga tgg gtc cga cag gca cca gga aaa gcc<br>Leu Ser Asp Lys Ala Val Gly Trp Val Arg Gln Ala Pro Gly Lys Ala<br>    50                  55                  60 | | 192 |
| ctg gaa tgg ctg ggc agc atc gat acc ggg ggg aac aca ggg tac aat<br>Leu Glu Trp Leu Gly Ser Ile Asp Thr Gly Gly Asn Thr Gly Tyr Asn<br>65                  70                  75                  80 | | 240 |
| ccc gga ctg aag agc aga ctg tcc att acc aag gac aac tct aaa agt<br>Pro Gly Leu Lys Ser Arg Leu Ser Ile Thr Lys Asp Asn Ser Lys Ser<br>                85                  90                  95 | | 288 |
| cag gtg tca ctg agc gtg agc tcc gtc acc aca gag gat agt gca act<br>Gln Val Ser Leu Ser Val Ser Ser Val Thr Thr Glu Asp Ser Ala Thr<br>            100                 105                 110 | | 336 |
| tac tat tgc acc tct gtg cac cag gaa act aag aaa tac cag agc gag<br>Tyr Tyr Cys Thr Ser Val His Gln Glu Thr Lys Lys Tyr Gln Ser Glu<br>        115                 120                 125 | | 384 |
| acc tac tat ggt tcg ggt ctc tct tat acc tac aat tat gaa tgg cat<br>Thr Tyr Tyr Gly Ser Gly Leu Ser Tyr Thr Tyr Asn Tyr Glu Trp His<br>    130                 135                 140 | | 432 |
| gtg gat gtc tgg gga cag ggc ctg ctg gtg aca gtc tct agt gct agc<br>Val Asp Val Trp Gly Gln Gly Leu Leu Val Thr Val Ser Ser Ala Ser<br>145                 150                 155                 160 | | 480 |
| acc aag ggc cca tcg gtc ttc ccc ctg gca ccc tcc tcc aag agc acc<br>Thr Lys Gly Pro Ser Val Phe Pro Leu Ala Pro Ser Ser Lys Ser Thr<br>                165                 170                 175 | | 528 |
| tct ggg ggc aca gcg gcc ctg ggc tgc ctg gtc aag gac tac ttc ccc<br>Ser Gly Gly Thr Ala Ala Leu Gly Cys Leu Val Lys Asp Tyr Phe Pro<br>            180                 185                 190 | | 576 |
| gag ccg gtg acg gtg tcg tgg aac tca ggc gcc ctg acc agc ggc gtg<br>Glu Pro Val Thr Val Ser Trp Asn Ser Gly Ala Leu Thr Ser Gly Val<br>        195                 200                 205 | | 624 |
| cac acc ttc ccg gct gtc cta cag tcc tca gga ctc tac tcc ctc agc<br>His Thr Phe Pro Ala Val Leu Gln Ser Ser Gly Leu Tyr Ser Leu Ser<br>    210                 215                 220 | | 672 |
| agc gtg gtg acc gtg ccc tcc agc agc ttg ggc acc cag acc tac atc<br>Ser Val Val Thr Val Pro Ser Ser Ser Leu Gly Thr Gln Thr Tyr Ile<br>225                 230                 235                 240 | | 720 |
| tgc aac gtg aat cac aag ccc agc aac acc aag gtg gac aag aaa gtt<br>Cys Asn Val Asn His Lys Pro Ser Asn Thr Lys Val Asp Lys Lys Val<br>                245                 250                 255 | | 768 |
| gag ccc aaa tct tgt gac aaa act cac aca tgc cca ccg tgc cca gca<br>Glu Pro Lys Ser Cys Asp Lys Thr His Thr Cys Pro Pro Cys Pro Ala<br>            260                 265                 270 | | 816 |
| cct gaa ctc ctg ggg gga ccg tca gtc ttc ctc ttc ccc cca aaa ccc<br>Pro Glu Leu Leu Gly Gly Pro Ser Val Phe Leu Phe Pro Pro Lys Pro<br>        275                 280                 285 | | 864 |
| aag gac acc ctc atg atc tcc cgg acc cct gag gtc aca tgc gtg gtg<br>Lys Asp Thr Leu Met Ile Ser Arg Thr Pro Glu Val Thr Cys Val Val<br>    290                 295                 300 | | 912 |
| gtg gac gtg agc cac gaa gac cct gag gtc aag ttc aac tgg tac gtg<br>Val Asp Val Ser His Glu Asp Pro Glu Val Lys Phe Asn Trp Tyr Val | | 960 |

```
                    305                 310                 315                 320
gac ggc gtg gag gtg cat aat gcc aag aca aag ccg cgg gag gag cag      1008
Asp Gly Val Glu Val His Asn Ala Lys Thr Lys Pro Arg Glu Glu Gln
                    325                 330                 335 tac aac agc acg tac cgt gtg gtc agc gtc ctc acc gtc ctg cac cag      1056
Tyr Asn Ser Thr Tyr Arg Val Val Ser Val Leu Thr Val Leu His Gln
                340                 345                 350 gac tgg ctg aat ggc aag gag tac aag tgc aag gtg tcc aac aaa gcc      1104
Asp Trp Leu Asn Gly Lys Glu Tyr Lys Cys Lys Val Ser Asn Lys Ala
            355                 360                 365 ctc cca gcc ccc atc gag aaa acc atc tcc aaa gcc aaa ggg cag ccc      1152
Leu Pro Ala Pro Ile Glu Lys Thr Ile Ser Lys Ala Lys Gly Gln Pro
        370                 375                 380 cga gaa cca cag gtg tac acc ctg ccc cca tcc cgg gat gag ctg acc      1200
Arg Glu Pro Gln Val Tyr Thr Leu Pro Pro Ser Arg Asp Glu Leu Thr
385                 390                 395                 400 aag aac cag gtc agc ctg acc tgc ctg gtc aaa ggc ttc tat ccc agc      1248
Lys Asn Gln Val Ser Leu Thr Cys Leu Val Lys Gly Phe Tyr Pro Ser
                405                 410                 415 gac atc gcc gtg gag tgg gag agc aat ggg cag ccg gag aac aac tac      1296
Asp Ile Ala Val Glu Trp Glu Ser Asn Gly Gln Pro Glu Asn Asn Tyr
            420                 425                 430 aag acc acg cct ccc gtg ctg gac tcc gac ggc tcc ttc ttc ctc tac      1344
Lys Thr Thr Pro Pro Val Leu Asp Ser Asp Gly Ser Phe Phe Leu Tyr
        435                 440                 445 agc aag ctc acc gtg gac aag agc agg tgg cag cag ggg aac gtc ttc      1392
Ser Lys Leu Thr Val Asp Lys Ser Arg Trp Gln Gln Gly Asn Val Phe
    450                 455                 460 tca tgc tcc gtg atg cat gag gct ctg cac aac cac tac acg cag aag      1440
Ser Cys Ser Val Met His Glu Ala Leu His Asn His Tyr Thr Gln Lys
465                 470                 475                 480 agc ctc tcc ctg tct ccg ggt aaa tga taa                              1470
Ser Leu Ser Leu Ser Pro Gly Lys
                485

<210> SEQ ID NO 396
<211> LENGTH: 488
<212> TYPE: PRT
<213> ORGANISM: Artificial sequence
<220> FEATURE:
<223> OTHER INFORMATION: Synthetic Construct

<400> SEQUENCE: 396

Met Arg Arg Met Gln Leu Leu Leu Ile Ala Leu Ser Leu Ala Leu
1               5                   10                  15

Val Thr Asn Ser Gln Val Gln Leu Arg Glu Ser Gly Pro Ser Leu Val
            20                  25                  30

Lys Pro Ser Gln Thr Leu Ser Leu Thr Cys Thr Ala Ser Gly Phe Ser
        35                  40                  45

Leu Ser Asp Lys Ala Val Gly Trp Val Arg Gln Ala Pro Gly Lys Ala
    50                  55                  60

Leu Glu Trp Leu Gly Ser Ile Asp Thr Gly Gly Asn Thr Gly Tyr Asn
65                  70                  75                  80

Pro Gly Leu Lys Ser Arg Leu Ser Ile Thr Lys Asp Asn Ser Lys Ser
                85                  90                  95

Gln Val Ser Leu Ser Val Ser Ser Val Thr Thr Glu Asp Ser Ala Thr
            100                 105                 110

Tyr Tyr Cys Thr Ser Val His Gln Glu Thr Lys Lys Tyr Gln Ser Glu
        115                 120                 125
```

Thr Tyr Tyr Gly Ser Gly Leu Ser Tyr Thr Tyr Asn Tyr Glu Trp His
    130                 135                 140

Val Asp Val Trp Gly Gln Gly Leu Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175

Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
    210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 397
<211> LENGTH: 258
<212> TYPE: DNA
<213> ORGANISM: Artificial sequence
<220> FEATURE:
<223> OTHER INFORMATION: Synthesized: IL-8 26-99 Insert
<220> FEATURE:
<221> NAME/KEY: CDS

<222> LOCATION: (1)..(258)

<400> SEQUENCE: 397

```
aat tcg ggt ctc aag agc cca agg agt gct aaa gaa ctt aga tgt cag      48
Asn Ser Gly Leu Lys Ser Pro Arg Ser Ala Lys Glu Leu Arg Cys Gln
1               5                   10                  15 tgc ata aag aca tac tcc aaa cct ttc cac ccc aag ttc atc aag gag      96
Cys Ile Lys Thr Tyr Ser Lys Pro Phe His Pro Lys Phe Ile Lys Glu
            20                  25                  30 ctg aga gtg att gag agt gga cca cac tgc gcc aac aca gag att att     144
Leu Arg Val Ile Glu Ser Gly Pro His Cys Ala Asn Thr Glu Ile Ile
        35                  40                  45 gta aag ctt tct gat ggg aga gag ctc tgc ctg gac ccc aag gaa aac     192
Val Lys Leu Ser Asp Gly Arg Glu Leu Cys Leu Asp Pro Lys Glu Asn
    50                  55                  60 tgg gtg cag agg gtc gtg gag aag ttc ttg aag agg gct gag aac tca     240
Trp Val Gln Arg Val Val Glu Lys Phe Leu Lys Arg Ala Glu Asn Ser
65                  70                  75                  80 tct tat gag acc agc taa                                             258
Ser Tyr Glu Thr Ser
                85
```

<210> SEQ ID NO 398
<211> LENGTH: 85
<212> TYPE: PRT
<213> ORGANISM: Artificial sequence
<220> FEATURE:
<223> OTHER INFORMATION: Synthetic Construct

<400> SEQUENCE: 398

```
Asn Ser Gly Leu Lys Ser Pro Arg Ser Ala Lys Glu Leu Arg Cys Gln
1               5                   10                  15

Cys Ile Lys Thr Tyr Ser Lys Pro Phe His Pro Lys Phe Ile Lys Glu
            20                  25                  30

Leu Arg Val Ile Glu Ser Gly Pro His Cys Ala Asn Thr Glu Ile Ile
        35                  40                  45

Val Lys Leu Ser Asp Gly Arg Glu Leu Cys Leu Asp Pro Lys Glu Asn
    50                  55                  60

Trp Val Gln Arg Val Val Glu Lys Phe Leu Lys Arg Ala Glu Asn Ser
65                  70                  75                  80

Ser Tyr Glu Thr Ser
                85
```

<210> SEQ ID NO 399
<211> LENGTH: 267
<212> TYPE: DNA
<213> ORGANISM: Artificial sequence
<220> FEATURE:
<223> OTHER INFORMATION: Synthesized: IL8 26-99 + GlySerGly Linker
      Insert
<220> FEATURE:
<221> NAME/KEY: CDS
<222> LOCATION: (1)..(267)

<400> SEQUENCE: 399

```
aat tcg ggt ctc aag agc cca agg agt gct aaa gaa ctt aga tgt cag      48
Asn Ser Gly Leu Lys Ser Pro Arg Ser Ala Lys Glu Leu Arg Cys Gln
1               5                   10                  15 tgc ata aag aca tac tcc aaa cct ttc cac ccc aag ttc atc aag gag      96
Cys Ile Lys Thr Tyr Ser Lys Pro Phe His Pro Lys Phe Ile Lys Glu
            20                  25                  30 ctg aga gtg att gag agt gga cca cac tgc gcc aac aca gag att att     144
```

```
Leu Arg Val Ile Glu Ser Gly Pro His Cys Ala Asn Thr Glu Ile Ile
            35                  40                  45 gta aag ctt tct gat ggg aga gag ctc tgc ctg gac ccc aag gaa aac    192
Val Lys Leu Ser Asp Gly Arg Glu Leu Cys Leu Asp Pro Lys Glu Asn
 50                  55                  60 tgg gtg cag agg gtc gtg gag aag ttc ttg aag agg gct gag aac tca    240
Trp Val Gln Arg Val Val Glu Lys Phe Leu Lys Arg Ala Glu Asn Ser
 65                  70                  75                  80 ggc agc ggt tct tat gag acc agc taa                                267
Gly Ser Gly Ser Tyr Glu Thr Ser
                 85
```

```
<210> SEQ ID NO 400
<211> LENGTH: 88
<212> TYPE: PRT
<213> ORGANISM: Artificial sequence
<220> FEATURE:
<223> OTHER INFORMATION: Synthetic Construct

<400> SEQUENCE: 400

Asn Ser Gly Leu Lys Ser Pro Arg Ser Ala Lys Glu Leu Arg Cys Gln
 1               5                  10                  15

Cys Ile Lys Thr Tyr Ser Lys Pro Phe His Pro Lys Phe Ile Lys Glu
            20                  25                  30

Leu Arg Val Ile Glu Ser Gly Pro His Cys Ala Asn Thr Glu Ile Ile
            35                  40                  45

Val Lys Leu Ser Asp Gly Arg Glu Leu Cys Leu Asp Pro Lys Glu Asn
 50                  55                  60

Trp Val Gln Arg Val Val Glu Lys Phe Leu Lys Arg Ala Glu Asn Ser
 65                  70                  75                  80

Gly Ser Gly Ser Tyr Glu Thr Ser
                 85
```

```
<210> SEQ ID NO 401
<211> LENGTH: 435
<212> TYPE: DNA
<213> ORGANISM: Artificial sequence
<220> FEATURE:
<223> OTHER INFORMATION: Synthesized: IL-21 Insert
<220> FEATURE:
<221> NAME/KEY: CDS
<222> LOCATION: (1)..(435)

<400> SEQUENCE: 401 aat tcg ggt ctc aag agc caa ggt caa gat cgc cac atg atc aga atg     48
Asn Ser Gly Leu Lys Ser Gln Gly Gln Asp Arg His Met Ile Arg Met
 1               5                  10                  15 cgt cag ctc ata gat att gtt gat cag ctg aag aac tac gtg aac gac     96
Arg Gln Leu Ile Asp Ile Val Asp Gln Leu Lys Asn Tyr Val Asn Asp
            20                  25                  30 ttg gtc cct gaa ttt ctg cca gct ccc gaa gat gta gag aca aac tgt    144
Leu Val Pro Glu Phe Leu Pro Ala Pro Glu Asp Val Glu Thr Asn Cys
            35                  40                  45 gag tgg tca gcc ttc tcc tgc ttt cag aag gcc caa cta aag tca gca    192
Glu Trp Ser Ala Phe Ser Cys Phe Gln Lys Ala Gln Leu Lys Ser Ala
 50                  55                  60 aat acc ggc aac aac gag agg ata atc aat gta tca atc aaa aag ctg    240
Asn Thr Gly Asn Asn Glu Arg Ile Ile Asn Val Ser Ile Lys Lys Leu
 65                  70                  75                  80 aag agg aag cca cct tcc aca aat gca ggg aga cgg cag aaa cac cgc    288
Lys Arg Lys Pro Pro Ser Thr Asn Ala Gly Arg Arg Gln Lys His Arg
                 85                  90                  95
```

```
ctg aca tgc cct tca tgt gat tct tac gag aag aag cca ccc aaa gag      336
Leu Thr Cys Pro Ser Cys Asp Ser Tyr Glu Lys Lys Pro Pro Lys Glu
            100                 105                 110 ttc cta gag cgg ttc aag tca ctt ctc gac aag atg att gat cag cat      384
Phe Leu Glu Arg Phe Lys Ser Leu Leu Asp Lys Met Ile Asp Gln His
        115                 120                 125 ctg tcc tct cgc aca cac gga agt gaa gat tcc tct tat gag acc agc      432
Leu Ser Ser Arg Thr His Gly Ser Glu Asp Ser Ser Tyr Glu Thr Ser
    130                 135                 140 taa                                                                  435
```

<210> SEQ ID NO 402
<211> LENGTH: 144
<212> TYPE: PRT
<213> ORGANISM: Artificial sequence
<220> FEATURE:
<223> OTHER INFORMATION: Synthetic Construct

<400> SEQUENCE: 402

Asn Ser Gly Leu Lys Ser Gln Gly Gln Asp Arg His Met Ile Arg Met
1               5                   10                  15

Arg Gln Leu Ile Asp Ile Val Asp Gln Leu Lys Asn Tyr Val Asn Asp
            20                  25                  30

Leu Val Pro Glu Phe Leu Pro Ala Pro Glu Asp Val Glu Thr Asn Cys
        35                  40                  45

Glu Trp Ser Ala Phe Ser Cys Phe Gln Lys Ala Gln Leu Lys Ser Ala
    50                  55                  60

Asn Thr Gly Asn Asn Glu Arg Ile Ile Asn Val Ser Ile Lys Lys Leu
65                  70                  75                  80

Lys Arg Lys Pro Pro Ser Thr Asn Ala Gly Arg Arg Gln Lys His Arg
                85                  90                  95

Leu Thr Cys Pro Ser Cys Asp Ser Tyr Glu Lys Lys Pro Pro Lys Glu
            100                 105                 110

Phe Leu Glu Arg Phe Lys Ser Leu Leu Asp Lys Met Ile Asp Gln His
        115                 120                 125

Leu Ser Ser Arg Thr His Gly Ser Glu Asp Ser Ser Tyr Glu Thr Ser
    130                 135                 140

<210> SEQ ID NO 403
<211> LENGTH: 435
<212> TYPE: DNA
<213> ORGANISM: Artificial sequence
<220> FEATURE:
<223> OTHER INFORMATION: Synthesized: IL-21 (Q116D, H120D) Insert
<220> FEATURE:
<221> NAME/KEY: CDS
<222> LOCATION: (1)..(435)

<400> SEQUENCE: 403

```
aat tcg ggt ctc aag agc caa ggt caa gat cgc cac atg atc aga atg       48
Asn Ser Gly Leu Lys Ser Gln Gly Gln Asp Arg His Met Ile Arg Met
1               5                   10                  15 cgt cag ctc ata gat att gtt gat cag ctg aag aac tac gtg aac gac       96
Arg Gln Leu Ile Asp Ile Val Asp Gln Leu Lys Asn Tyr Val Asn Asp
            20                  25                  30 ttg gtc cct gaa ttt ctg cca gct ccc gaa gat gta gag aca aac tgt      144
Leu Val Pro Glu Phe Leu Pro Ala Pro Glu Asp Val Glu Thr Asn Cys
        35                  40                  45 gag tgg tca gcc ttc tcc tgc ttt cag aag gcc caa cta aag tca gca      192
Glu Trp Ser Ala Phe Ser Cys Phe Gln Lys Ala Gln Leu Lys Ser Ala
    50                  55                  60
```

```
aat acc ggc aac aac gag agg ata atc aat gta tca atc aaa aag ctg    240
Asn Thr Gly Asn Asn Glu Arg Ile Ile Asn Val Ser Ile Lys Lys Leu
 65              70                  75                  80 aag agg aag cca cct tcc aca aat gca ggg aga cgg cag aaa cac cgc    288
Lys Arg Lys Pro Pro Ser Thr Asn Ala Gly Arg Arg Gln Lys His Arg
                 85                  90                  95 ctg aca tgc cct tca tgt gat tct tac gag aag aag cca ccc aaa gag    336
Leu Thr Cys Pro Ser Cys Asp Ser Tyr Glu Lys Lys Pro Pro Lys Glu
            100                 105                 110 ttc cta gag cgg ttc aag tca ctt ctc gac aag atg att gat cag cat    384
Phe Leu Glu Arg Phe Lys Ser Leu Leu Asp Lys Met Ile Asp Gln His
        115                 120                 125 ctg tcc tct cgc aca cac gga agt gaa gat tcc tct tat gag acc agc    432
Leu Ser Ser Arg Thr His Gly Ser Glu Asp Ser Ser Tyr Glu Thr Ser
    130                 135                 140 taa                                                                435

<210> SEQ ID NO 404
<211> LENGTH: 144
<212> TYPE: PRT
<213> ORGANISM: Artificial sequence
<220> FEATURE:
<223> OTHER INFORMATION: Synthetic Construct

<400> SEQUENCE: 404

Asn Ser Gly Leu Lys Ser Gln Gly Gln Asp Arg His Met Ile Arg Met
 1               5                  10                  15

Arg Gln Leu Ile Asp Ile Val Asp Gln Leu Lys Asn Tyr Val Asn Asp
                20                  25                  30

Leu Val Pro Glu Phe Leu Pro Ala Pro Glu Asp Val Glu Thr Asn Cys
            35                  40                  45

Glu Trp Ser Ala Phe Ser Cys Phe Gln Lys Ala Gln Leu Lys Ser Ala
        50                  55                  60

Asn Thr Gly Asn Asn Glu Arg Ile Ile Asn Val Ser Ile Lys Lys Leu
 65              70                  75                  80

Lys Arg Lys Pro Pro Ser Thr Asn Ala Gly Arg Arg Gln Lys His Arg
                 85                  90                  95

Leu Thr Cys Pro Ser Cys Asp Ser Tyr Glu Lys Lys Pro Pro Lys Glu
            100                 105                 110

Phe Leu Glu Arg Phe Lys Ser Leu Leu Asp Lys Met Ile Asp Gln His
        115                 120                 125

Leu Ser Ser Arg Thr His Gly Ser Glu Asp Ser Ser Tyr Glu Thr Ser
    130                 135                 140

<210> SEQ ID NO 405
<211> LENGTH: 249
<212> TYPE: DNA
<213> ORGANISM: Artificial sequence
<220> FEATURE:
<223> OTHER INFORMATION: Synthesized: SDF-1alpha-GSG Insert

<400> SEQUENCE: 405
aattcgggtc tcaagagcaa gcccgtcagc ctgagctaca gatgcccatg ccgattcttc     60
gaaagccatg ttgccagagc caacgtcaag catctcaaaa ttctcaacac tccaaactgt    120
gcccttcaga ttgtagcccg gctgaagaac aacaacagac aagtgtgcat tgacccgaag    180
ctaaagtgga ttcaggagta cctggagaaa gctttaaaca agggcagcgg ttcttatgag    240
accagctaa                                                           249
```

<210> SEQ ID NO 406
<211> LENGTH: 78
<212> TYPE: DNA
<213> ORGANISM: Artificial sequence
<220> FEATURE:
<223> OTHER INFORMATION: Synthesized: Somatostatin-14
<220> FEATURE:
<221> NAME/KEY: CDS
<222> LOCATION: (1)..(78)

<400> SEQUENCE: 406 aat tcg ggt ctc aag agc gct ggc tgc aag aat ttc ttc tgg aag act    48
Asn Ser Gly Leu Lys Ser Ala Gly Cys Lys Asn Phe Phe Trp Lys Thr
1               5                   10                  15 ttc aca tcc tgt tct tat gag acc agc taa                            78
Phe Thr Ser Cys Ser Tyr Glu Thr Ser
            20                  25

<210> SEQ ID NO 407
<211> LENGTH: 25
<212> TYPE: PRT
<213> ORGANISM: Artificial sequence
<220> FEATURE:
<223> OTHER INFORMATION: Synthetic Construct

<400> SEQUENCE: 407

Asn Ser Gly Leu Lys Ser Ala Gly Cys Lys Asn Phe Phe Trp Lys Thr
1               5                   10                  15

Phe Thr Ser Cys Ser Tyr Glu Thr Ser
            20                  25

<210> SEQ ID NO 408
<211> LENGTH: 126
<212> TYPE: DNA
<213> ORGANISM: Artificial sequence
<220> FEATURE:
<223> OTHER INFORMATION: Synthesized: ProTx-II Insert
<220> FEATURE:
<221> NAME/KEY: CDS
<222> LOCATION: (1)..(126)

<400> SEQUENCE: 408 aat tcg ggt ctc aag agc tat tgc cag aag tgg atg tgg acc tgc gat    48
Asn Ser Gly Leu Lys Ser Tyr Cys Gln Lys Trp Met Trp Thr Cys Asp
1               5                   10                  15 agc gaa cgg aaa tgt tgc gaa ggc atg gtg tgc cgc ctg tgg tgc aag    96
Ser Glu Arg Lys Cys Cys Glu Gly Met Val Cys Arg Leu Trp Cys Lys
            20                  25                  30 aag aaa ctc tgg tct tat gag acc agc taa                            126
Lys Lys Leu Trp Ser Tyr Glu Thr Ser
        35                  40

<210> SEQ ID NO 409
<211> LENGTH: 41
<212> TYPE: PRT
<213> ORGANISM: Artificial sequence
<220> FEATURE:
<223> OTHER INFORMATION: Synthetic Construct

<400> SEQUENCE: 409

Asn Ser Gly Leu Lys Ser Tyr Cys Gln Lys Trp Met Trp Thr Cys Asp
1               5                   10                  15

Ser Glu Arg Lys Cys Cys Glu Gly Met Val Cys Arg Leu Trp Cys Lys
            20                  25                  30

Lys Lys Leu Trp Ser Tyr Glu Thr Ser

```
                 35                  40

<210> SEQ ID NO 410
<211> LENGTH: 138
<212> TYPE: DNA
<213> ORGANISM: Artificial sequence
<220> FEATURE:
<223> OTHER INFORMATION: Synthesized: Chlorotoxin Insert

<400> SEQUENCE: 410
aattcgggtc tcaagagcat gtgtatgccc tgcttcacga ccgatcacca gatggcgcgc      60
aaatgcgatg actgttgcgg cggtaaaggt cgcggaaagt gctatggccc gcagtgtctg     120
tcttatgaga ccagctaa                                                    138

<210> SEQ ID NO 411
<211> LENGTH: 111
<212> TYPE: DNA
<213> ORGANISM: Artificial sequence
<220> FEATURE:
<223> OTHER INFORMATION: Synthesized: Ziconotide Insert

<400> SEQUENCE: 411
aattcgggtc tcaagagctg caagggcaaa ggtgcgaaat gcagccgcct gatgtatgat      60
tgctgtaccg gtcctgccg cagtggcaag tgctcttatg agaccagcta a                111

<210> SEQ ID NO 412
<211> LENGTH: 672
<212> TYPE: DNA
<213> ORGANISM: Artificial sequence
<220> FEATURE:
<223> OTHER INFORMATION: Synthesized: BLV1H12 Light Chain
<220> FEATURE:
<221> NAME/KEY: CDS
<222> LOCATION: (1)..(672)

<400> SEQUENCE: 412 tca cga att cgc agg ccg tcc tga acc agc caa gca gcg tct ccg ggt       48
Ser Arg Ile Arg Arg Pro Ser     Thr Ser Gln Ala Ala Ser Pro Gly
1               5                   10                  15 ctc tgg ggc agc ggg tct caa tca cct gta gcg ggt ctt cct cca atg       96
Leu Trp Gly Ser Gly Ser Gln Ser Pro Val Ala Gly Leu Pro Pro Met
            20                  25                  30 tcg gca acg gct acg tgt ctt ggt atc agc tga tcc ctg gca gtg ccc      144
Ser Ala Thr Ala Thr Cys Leu Gly Ile Ser     Ser Leu Ala Val Pro
        35                  40                  45 cac gaa ccc tga tct acg gcg aca cat cca gag ctt ctg ggg tcc ccg      192
His Glu Pro     Ser Thr Ala Thr His Pro Glu Leu Leu Gly Ser Pro
    50                  55                  60 atc ggt tct cag gga gca gat ccg gaa aca cag cta ctc tga cca tca      240
Ile Gly Ser Gln Gly Ala Asp Pro Glu Thr Gln Leu Leu     Pro Ser
65                  70                  75 gct ccc tgc agg ctg agg acg aag cag att att tct gcg cat ctg ccg      288
Ala Pro Cys Arg Leu Arg Thr Lys Gln Ile Ile Ser Ala His Leu Pro
            80                  85                  90 agg act cta gtt caa atg ccg tgt ttg gaa gcg gca cca cac tga cag      336
Arg Thr Leu Val Gln Met Pro Cys Leu Glu Ala Ala Pro His     Gln
        95                  100                 105 tcc tgg ggc agc cca aga gtc ccc ctt cag tga ctc tgt tcc cac cct      384
Ser Trp Gly Ser Pro Arg Val Pro Leu Gln     Leu Cys Ser His Pro
    110                 115                 120 cta ccg agg aac tga acg gaa aca agg cca cac tgg tgt gtc tga tca      432
Leu Pro Arg Asn     Thr Glu Thr Arg Pro His Trp Cys Val     Ser
```

```
                    125                 130                 135
gcg act ttt acc ctg gat ccg tca ctg tgg tct gga agg cag atg gca    480
Ala Thr Phe Thr Leu Asp Pro Ser Leu Trp Ser Gly Arg Gln Met Ala
140                 145                 150 gca caa tta cta gga acg tgg aaa cta ccc gcg cct cca agc agt cta    528
Ala Gln Leu Leu Gly Thr Trp Lys Leu Pro Ala Pro Pro Ser Ser Leu
            155                 160                 165 ata gta aat acg ccg cca gct cct atc tga gcc tga cct cta gtg att    576
Ile Val Asn Thr Pro Pro Ala Pro Ile     Ala     Pro Leu Val Ile
        170                 175                             180 gga agt cca aag ggt cat ata gct gcg aag tga ccc atg aag gct caa    624
Gly Ser Pro Lys Gly His Ile Ala Ala Lys     Pro Met Lys Ala Gln
                185                 190                 195 ccg tga cta aga ctg tga aac cat ccg agt gct cct agg cta gct ggc    672
Pro     Leu Arg Leu     Asn His Pro Ser Ala Pro Arg Leu Ala Gly
    200                     205                 210

<210> SEQ ID NO 413
<211> LENGTH: 7
<212> TYPE: PRT
<213> ORGANISM: Artificial sequence
<220> FEATURE:
<223> OTHER INFORMATION: Synthetic Construct

<400> SEQUENCE: 413

Ser Arg Ile Arg Arg Pro Ser
1               5

<210> SEQ ID NO 414
<211> LENGTH: 34
<212> TYPE: PRT
<213> ORGANISM: Artificial sequence
<220> FEATURE:
<223> OTHER INFORMATION: Synthetic Construct

<400> SEQUENCE: 414

Thr Ser Gln Ala Ala Ser Pro Gly Leu Trp Gly Ser Gly Ser Gln Ser
1               5                   10                  15

Pro Val Ala Gly Leu Pro Pro Met Ser Ala Thr Ala Thr Cys Leu Gly
            20                  25                  30

Ile Ser

<210> SEQ ID NO 415
<211> LENGTH: 8
<212> TYPE: PRT
<213> ORGANISM: Artificial sequence
<220> FEATURE:
<223> OTHER INFORMATION: Synthetic Construct

<400> SEQUENCE: 415

Ser Leu Ala Val Pro His Glu Pro
1               5

<210> SEQ ID NO 416
<211> LENGTH: 25
<212> TYPE: PRT
<213> ORGANISM: Artificial sequence
<220> FEATURE:
<223> OTHER INFORMATION: Synthetic Construct

<400> SEQUENCE: 416

Ser Thr Ala Thr His Pro Glu Leu Leu Gly Ser Pro Ile Gly Ser Gln
1               5                   10                  15
```

Gly Ala Asp Pro Glu Thr Gln Leu Leu
            20                  25

<210> SEQ ID NO 417
<211> LENGTH: 32
<212> TYPE: PRT
<213> ORGANISM: Artificial sequence
<220> FEATURE:
<223> OTHER INFORMATION: Synthetic Construct

<400> SEQUENCE: 417

Pro Ser Ala Pro Cys Arg Leu Arg Thr Lys Gln Ile Ile Ser Ala His
1               5                   10                  15

Leu Pro Arg Thr Leu Val Gln Met Pro Cys Leu Glu Ala Ala Pro His
            20                  25                  30

<210> SEQ ID NO 418
<211> LENGTH: 11
<212> TYPE: PRT
<213> ORGANISM: Artificial sequence
<220> FEATURE:
<223> OTHER INFORMATION: Synthetic Construct

<400> SEQUENCE: 418

Gln Ser Trp Gly Ser Pro Arg Val Pro Leu Gln
1               5                   10

<210> SEQ ID NO 419
<211> LENGTH: 9
<212> TYPE: PRT
<213> ORGANISM: Artificial sequence
<220> FEATURE:
<223> OTHER INFORMATION: Synthetic Construct

<400> SEQUENCE: 419

Leu Cys Ser His Pro Leu Pro Arg Asn
1               5

<210> SEQ ID NO 420
<211> LENGTH: 9
<212> TYPE: PRT
<213> ORGANISM: Artificial sequence
<220> FEATURE:
<223> OTHER INFORMATION: Synthetic Construct

<400> SEQUENCE: 420

Thr Glu Thr Arg Pro His Trp Cys Val
1               5

<210> SEQ ID NO 421
<211> LENGTH: 42
<212> TYPE: PRT
<213> ORGANISM: Artificial sequence
<220> FEATURE:
<223> OTHER INFORMATION: Synthetic Construct

<400> SEQUENCE: 421

Ser Ala Thr Phe Thr Leu Asp Pro Ser Leu Trp Ser Gly Arg Gln Met
1               5                   10                  15

Ala Ala Gln Leu Leu Gly Thr Trp Lys Leu Pro Ala Pro Pro Ser Ser
            20                  25                  30

Leu Ile Val Asn Thr Pro Pro Ala Pro Ile
        35                  40

<210> SEQ ID NO 422

```
<211> LENGTH: 14
<212> TYPE: PRT
<213> ORGANISM: Artificial sequence
<220> FEATURE:
<223> OTHER INFORMATION: Synthetic Construct

<400> SEQUENCE: 422

Pro Leu Val Ile Gly Ser Pro Lys Gly His Ile Ala Ala Lys
1               5                   10

<210> SEQ ID NO 423
<211> LENGTH: 6
<212> TYPE: PRT
<213> ORGANISM: Artificial sequence
<220> FEATURE:
<223> OTHER INFORMATION: Synthetic Construct

<400> SEQUENCE: 423

Pro Met Lys Ala Gln Pro
1               5

<210> SEQ ID NO 424
<211> LENGTH: 10
<212> TYPE: PRT
<213> ORGANISM: Artificial sequence
<220> FEATURE:
<223> OTHER INFORMATION: Synthetic Construct

<400> SEQUENCE: 424

Asn His Pro Ser Ala Pro Arg Leu Ala Gly
1               5                   10

<210> SEQ ID NO 425
<211> LENGTH: 641
<212> TYPE: DNA
<213> ORGANISM: Artificial sequence
<220> FEATURE:
<223> OTHER INFORMATION: Synthesized: VH1-24+CDR3-IL8

<400> SEQUENCE: 425
tcacgaattc gcaggtccag ctggtacagt ctggggctga ggtgaagaag cctggggcct      60
cagtgaaggt gtcctgcaag gtttccggat acaccctcac tgaattatcc atgcactggg     120
tgcgacaggc tcctggaaaa gggcttgagt ggatgggagg ttttgatcct gaagatggtg     180
aaacaatcta cgcacagaag ttccagggca gagtcaccat gaccgaggac acatctacag     240
acacagccta catggagctg agcagcctga gatctgagga cacggccgtg tattactgca     300
cctctgtgca ccaggaaact aagaaatacc agagcccaag gagtgctaaa gaacttagat     360
gtcagtgcat aaagacatac tccaaacctt ccacccccaa gttcatcaag gagctgagag     420
tgattgagag tggaccacac tgcgccaaca cagagattat tgtaaagctt tctgatggga     480
gagagctctg cctggacccc aaggaaaact gggtgcagag ggtcgtggag aagttcttga     540
agagggctga gaactcaggc agcggttctt atacctacaa ttatgaatgg catgtggatg     600
tctggggaca gggcctgctg gtgacagtct ctagtgctag c                        641

<210> SEQ ID NO 426
<211> LENGTH: 641
<212> TYPE: DNA
<213> ORGANISM: Artificial sequence
<220> FEATURE:
<223> OTHER INFORMATION: Synthesized: VH1-46+CDR3-IL8

<400> SEQUENCE: 426
```

```
tcacgaattc gcaggtgcag ctggtgcagt ctggggctga ggtgaagaag cctggggcct      60
cagtgaaggt ttcctgcaag gcatctggat acaccttcac cagctactat atgcactggg     120
tgcgacaggc ccctggacaa gggcttgagt ggatgggaat aatcaaccct agtggtggta     180
gcacaagcta cgcacagaag ttccagggca gagtcaccat gaccagggac acgtccacga     240
gcacagtcta catggagctg agcagcctga gatctgagga cacggccgtg tattactgca     300
cctctgtgca ccaggaaact aagaaatacc agagcccaag gagtgctaaa gaacttagat     360
gtcagtgcat aaagacatac tccaaacctt ccacccccaa gttcatcaag gagctgagag     420
tgattgagag tggaccacac tgcgccaaca cagagattat tgtaaagctt tctgatggga     480
gagagctctg cctggacccc aaggaaaact gggtgcagag gtcgtggag  aagttcttga     540 agagggctga gaactcaggc agcggttctt atacctacaa ttatgaatgg catgtggatg     600
tctggggaca gggcctgctg gtgacagtct ctagtgctag c                         641
```

<210> SEQ ID NO 427
<211> LENGTH: 641
<212> TYPE: DNA
<213> ORGANISM: Artificial sequence
<220> FEATURE:
<223> OTHER INFORMATION: Synthesized: VH1-69+CDR3-IL8

<400> SEQUENCE: 427

```
tcacgaattc gcaggtgcag ctggtgcagt ctggggctga ggtgaagaag cctgggtcct      60
cggtgaaggt gtcctgcaag gcttctggag gcaccttcag cagctatgct atcagctggg     120
tgcgacaggc ccctggacaa gggcttgagt ggatgggagg gatcatccct atctttggta     180
cagcaaacta cgcacagaag ttccagggca gagtcacgat taccgcggac aaatccacga     240
gcacagccta catggagctg agcagcctga gatctgagga cacggccgtg tattactgca     300
cctctgtgca ccaggaaact aagaaatacc agagcccaag gagtgctaaa gaacttagat     360
gtcagtgcat aaagacatac tccaaacctt ccacccccaa gttcatcaag gagctgagag     420
tgattgagag tggaccacac tgcgccaaca cagagattat tgtaaagctt tctgatggga     480
gagagctctg cctggacccc aaggaaaact gggtgcagag gtcgtggag  aagttcttga     540 agagggctga gaactcaggc agcggttctt atacctacaa ttatgaatgg catgtggatg     600
tctggggaca gggcctgctg gtgacagtct ctagtgctag c                         641
```

<210> SEQ ID NO 428
<211> LENGTH: 641
<212> TYPE: DNA
<213> ORGANISM: Artificial sequence
<220> FEATURE:
<223> OTHER INFORMATION: Synthesized: VH3-23+CDR3-IL8

<400> SEQUENCE: 428

```
tcacgaattc ggaggtgcag ctgttggagt ctgggggagg cttggtacag cctggggggt      60
ccctgagact ctcctgtgca gcctctggat tcacctttag cagctatgcc atgagctggg     120
tccgccaggc tccagggaag gggctggagt gggtgagcgc aattagtggt agtggcggta     180
gcacatacta cgcagactcc gtgaagggcc ggttcaccat ctcacgtgac aattccaaga     240
acacgctgta tctgcaaatg aacagcctga gagccgagga cacggccgtg tattactgca     300
cctctgtgca ccaggaaact aagaaatacc agagcccaag gagtgctaaa gaacttagat     360
gtcagtgcat aaagacatac tccaaacctt ccacccccaa gttcatcaag gagctgagag     420
tgattgagag tggaccacac tgcgccaaca cagagattat tgtaaagctt tctgatggga     480
```

```
gagagctctg cctggacccc aaggaaaact gggtgcagag ggtcgtggag aagttcttga      540
agagggctga aactcaggc agcggttctt atacctacaa ttatgaatgg catgtggatg      600
tctggggaca gggcctgctg gtgacagtct ctagtgctag c                         641
```

<210> SEQ ID NO 429
<211> LENGTH: 638
<212> TYPE: DNA
<213> ORGANISM: Artificial sequence
<220> FEATURE:
<223> OTHER INFORMATION: Synthesized: VH4-4+CDR3-IL8

<400> SEQUENCE: 429

```
tcacgaattc gcaggtgcag ctgcaggagt cgggcccagg actggtgaag ccttcggaga      60
cgctgtccct cacctgcact gtctctggtg gctccatcag tagttactac tggagctgga     120
ttcggcagcc cgccgggaag gactggagt ggattgggcg tatctatacc agtgggagca      180
ccaactacaa cccctccctc aagagtcgag tcaccatgtc agtagacacg tccaagaacc     240
agttctccct gaagctgagc tctgtgaccg ccgcggacac ggccgtgtat tactgcacct     300
ctgtgcacca ggaaactaag aaataccaga gcccaaggag tgctaaagaa cttagatgtc     360
agtgcataaa gacatactcc aaacctttcc accccaagtt catcaaggag ctgagagtga     420
ttgagagtgg accacactgc gccaacacag agattattgt aaagctttct gatgggagag     480
agctctgcct ggaccccaag gaaaactggg tgcagagggt cgtggagaag ttcttgaaga     540
gggctgagaa ctcaggcagc ggttcttata cctacaatta tgaatggcat gtggatgtct     600
ggggacaggg cctgctggtg acagtctcta gtgctagc                             638
```

<210> SEQ ID NO 430
<211> LENGTH: 638
<212> TYPE: DNA
<213> ORGANISM: Artificial sequence
<220> FEATURE:
<223> OTHER INFORMATION: Synthesized: VH4-34+CDR3-IL8

<400> SEQUENCE: 430

```
tcacgaattc gcaggtgcag ctacagcagt ggggcgcagg actgttgaag ccttcggaga      60
cgctgtccct cacctgcgct gtctatggtg ggtccttcag tggttactac tggagctgga     120
ttcgccagcc cccagggaag gggctggagt ggattgggga atcaatcat agtggaagca      180 ccaactacaa cccgtccctc aagagtcgag tcaccatatc agtagacacg tccaagaacc     240
agttctccct gaagctgagc tctgtgaccg ccgcggacac ggctgtgtat tactgtacct     300
ctgtgcacca ggaaactaag aaataccaga gcccaaggag tgctaaagaa cttagatgtc     360
agtgcataaa gacatactcc aaacctttcc accccaagtt catcaaggag ctgagagtga     420
ttgagagtgg accacactgc gccaacacag agattattgt aaagctttct gatgggagag     480
agctctgcct ggaccccaag gaaaactggg tgcagagggt cgtggagaag ttcttgaaga     540
gggctgagaa ctcaggcagc ggttcttata cctacaatta tgaatggcat gtggatgtct     600
ggggacaggg cctgctggtg acagtctcta gtgctagc                             638
```

<210> SEQ ID NO 431
<211> LENGTH: 431
<212> TYPE: DNA
<213> ORGANISM: Artificial sequence
<220> FEATURE:
<223> OTHER INFORMATION: Synthesized: IgGVH4-4 CDR3 BsaI (lacking the
     IL-8 insert)

<400> SEQUENCE: 431

```
tcacgaattc gcaggtgcag ctgcaggagt cgggcccagg actggtgaag ccttcggaga    60
cgctgtccct cacctgcact gtctctggtg gctccatcag tagttactac tggagctgga   120
ttcggcagcc cgccgggaag ggactggagt ggattgggcg tatctatacc agtgggagca   180
ccaactacaa ccccteectc aagagtcgag tcaccatgtc agtagacacg tccaagaacc   240
agttctccct gaagctgagc tctgtgaccg ccgcggacac ggccgtgtat tactgcacct   300
ctgtgcacca ggaaactaag aaataccaga gcgagaccta ctatggttcg ggtctctctt   360
atacctacaa ttatgaatgg catgtggatg tctggggaca gggcctgctg gtgacagtct   420
ctagtgctag c                                                        431
```

<210> SEQ ID NO 432
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 Cow

<400> SEQUENCE: 432

```
tcacgaattc gcaggtgcag ctacagcagt ggggcgcagg actgttgaag ccttcggaga    60
cgctgtccct cacctgcaca gcaagcgggt tttcactgag cgacaaggca gtgggatgga   120
ttcgccagcc cccagggaag gggctggagt ggattgggga atcaatcat agtggaagca   180
ccaactacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
gggctgagaa ctcaggcagc ggttcttata cctacaatta tgaatggcat gtggatgtct   600
ggggacaggg cctgctggtg acagtctcta gtgctagc                           638
```

<210> SEQ ID NO 433
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR2 Cow

<400> SEQUENCE: 433

```
tcacgaattc gcaggtgcag ctacagcagt ggggcgcagg actgttgaag ccttcggaga    60
cgctgtccct cacctgcgct gtctatggtg ggtccttcag tggttactac tggagctgga   120
ttcgccagcc cccagggaag gggctggagt ggctgggcag catcgatacc ggcgggaaca   180
cagggtacaa cccgtccctc aagagtcgag tcaccatatc agtagacacg tccaagaacc   240
agttctccct gaagctgagc tctgtgaccg ccgcggacac ggctgtgtat tactgtacct   300
ctgtgcacca ggaaactaag aaataccaga gcccaaggag tgctaaagaa cttagatgtc   360
agtgcataaa gacatactcc aaacctttcc accccaagtt catcaaggag ctgagagtga   420
ttgagagtgg accacactgc gccaacacag agattattgt aaagctttct gatgggagag   480
agctctgcct ggaccccaag gaaaactggg tgcagagggt cgtggagaag ttcttgaaga   540
```

```
gggctgagaa ctcaggcagc ggttcttata cctacaatta tgaatggcat gtggatgtct      600
ggggacaggg cctgctggtg acagtctcta gtgctagc                              638
```

<210> SEQ ID NO 434
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 G31D, Y32K

<400> SEQUENCE: 434

```
tcacgaattc gcaggtgcag ctacagcagt ggggcgcagg actgttgaag ccttcggaga      60
cgctgtccct cacctgcgct gtctatggtg ggtccttcag tgacaagtac tggagctgga     120
ttcgccagcc cccagggaag gggctggagt ggattgggga aatcaatcat agtggaagca     180
ccaactacaa cccgtccctc aagagtcgag tcaccatatc agtagacacg tccaagaacc     240
agttctccct gaagctgagc tctgtgaccg ccgcggacac ggctgtgtat tactgtacct     300
ctgtgcacca ggaaactaag aaataccaga gcccaaggag tgctaaagaa cttagatgtc     360
agtgcataaa gacatactcc aaaccttttcc accccaagtt catcaaggag ctgagagtga    420
ttgagagtgg accacactgc gccaacacag agattattgt aaagctttct gatgggagag     480
agctctgcct ggaccccaag gaaaactggg tgcagagggt cgtggagaag ttcttgaaga     540
gggctgagaa ctcaggcagc ggttcttata cctacaatta tgaatggcat gtggatgtct     600
ggggacaggg cctgctggtg acagtctcta gtgctagc                             638
```

<210> SEQ ID NO 435
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR2 E50S

<400> SEQUENCE: 435

```
tcacgaattc gcaggtgcag ctacagcagt ggggcgcagg actgttgaag ccttcggaga      60
cgctgtccct cacctgcgct gtctatggtg ggtccttcag tggttactac tggagctgga    120
ttcgccagcc cccagggaag gggctggagt ggattgggag catcaatcat agtggaagca    180
ccaactacaa cccgtccctc aagagtcgag tcaccatatc agtagacacg tccaagaacc    240
agttctccct gaagctgagc tctgtgaccg ccgcggacac ggctgtgtat tactgtacct    300
ctgtgcacca ggaaactaag aaataccaga gcccaaggag tgctaaagaa cttagatgtc    360
agtgcataaa gacatactcc aaaccttttcc accccaagtt catcaaggag ctgagagtga   420
ttgagagtgg accacactgc gccaacacag agattattgt aaagctttct gatgggagag    480
agctctgcct ggaccccaag gaaaactggg tgcagagggt cgtggagaag ttcttgaaga    540
gggctgagaa ctcaggcagc ggttcttata cctacaatta tgaatggcat gtggatgtct    600
ggggacaggg cctgctggtg acagtctcta gtgctagc                            638
```

<210> SEQ ID NO 436
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 Cow_CDR2 Cow

<400> SEQUENCE: 436

```
tcacgaattc gcaggtgcag ctacagcagt ggggcgcagg actgttgaag ccttcggaga      60
```

```
cgctgtccct cacctgcaca gcaagcgggt tttcactgag cgacaaggca gtgggatgga    120
ttcgccagcc cccagggaag gggctggagt ggctgggcag catcgatacc ggcgggaaca    180
cagggtacaa cccgtccctc aagagtcgag tcaccatatc agtagacacg tccaagaacc    240
agttctccct gaagctgagc tctgtgaccg ccgcggacac ggctgtgtat tactgtacct    300
ctgtgcacca ggaaactaag aaataccaga gcccaaggag tgctaaagaa cttagatgtc    360
agtgcataaa gacatactcc aaacctttcc accccaagtt catcaaggag ctgagagtga    420
ttgagagtgg accacactgc gccaacacag agattattgt aaagctttct gatgggagag    480
agctctgcct ggaccccaag gaaaactggg tgcagagggt cgtggagaag ttcttgaaga    540
gggctgagaa ctcaggcagc ggttcttata cctacaatta tgaatggcat gtggatgtct    600
ggggacaggg cctgctggtg acagtctcta gtgctagc                           638
```

<210> SEQ ID NO 437
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 Cow_CDR2 E50S

<400> SEQUENCE: 437

```
tcacgaattc gcaggtgcag ctacagcagt ggggcgcagg actgttgaag ccttcggaga     60
cgctgtccct cacctgcaca gcaagcgggt tttcactgag cgacaaggca gtgggatgga    120
ttcgccagcc cccagggaag gggctggagt ggattgggag catcaatcat agtggaagca    180
ccaactacaa cccgtccctc aagagtcgag tcaccatatc agtagacacg tccaagaacc    240
agttctccct gaagctgagc tctgtgaccg ccgcggacac ggctgtgtat tactgtacct    300
ctgtgcacca ggaaactaag aaataccaga gcccaaggag tgctaaagaa cttagatgtc    360
agtgcataaa gacatactcc aaacctttcc accccaagtt catcaaggag ctgagagtga    420
ttgagagtgg accacactgc gccaacacag agattattgt aaagctttct gatgggagag    480
agctctgcct ggaccccaag gaaaactggg tgcagagggt cgtggagaag ttcttgaaga    540
gggctgagaa ctcaggcagc ggttcttata cctacaatta tgaatggcat gtggatgtct    600
ggggacaggg cctgctggtg acagtctcta gtgctagc                           638
```

<210> SEQ ID NO 438
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 G31D, Y32K_CDR2 Cow

<400> SEQUENCE: 438

```
tcacgaattc gcaggtgcag ctacagcagt ggggcgcagg actgttgaag ccttcggaga     60
cgctgtccct cacctgcgct gtctatggtg ggtccttcag tgacaagtac tggagctgga    120
ttcgccagcc cccagggaag gggctggagt ggctgggcag catcgatacc ggcgggaaca    180
cagggtacaa cccgtccctc aagagtcgag tcaccatatc agtagacacg tccaagaacc    240
agttctccct gaagctgagc tctgtgaccg ccgcggacac ggctgtgtat tactgtacct    300
ctgtgcacca ggaaactaag aaataccaga gcccaaggag tgctaaagaa cttagatgtc    360
agtgcataaa gacatactcc aaacctttcc accccaagtt catcaaggag ctgagagtga    420
ttgagagtgg accacactgc gccaacacag agattattgt aaagctttct gatgggagag    480
```

-continued

```
agctctgcct ggaccccaag gaaaactggg tgcagagggt cgtggagaag ttcttgaaga      540
gggctgagaa ctcaggcagc ggttcttata cctacaatta tgaatggcat gtggatgtct      600
ggggacaggg cctgctggtg acagtctcta gtgctagc                              638
```

<210> SEQ ID NO 439
<211> LENGTH: 638
<212> TYPE: DNA
<213> ORGANISM: Artificial sequence
<220> FEATURE:
<223> OTHER INFORMATION: Synthesized: VH4-34+CDR3-IL8_CDR1 G31D,
      Y32K_CDR2 E50S

<400> SEQUENCE: 439

```
tcacgaattc gcaggtgcag ctacagcagt ggggcgcagg actgttgaag ccttcggaga       60
cgctgtccct cacctgcgct gtctatggtg ggtccttcag tgacaagtac tggagctgga      120
ttcgccagcc cccagggaag gggctggagt ggattgggag catcaatcat agtggaagca      180
ccaactacaa cccgtccctc aagagtcgag tcaccatatc agtagacacg tccaagaacc      240
agttctccct gaagctgagc tctgtgaccg ccgcggacac ggctgtgtat tactgtacct      300
ctgtgcacca ggaaactaag aaataccaga gcccaaggag tgctaaagaa cttagatgtc      360
agtgcataaa gacatactcc aaacctttcc accccaagtt catcaaggag ctgagagtga      420
ttgagagtgg accacactgc gccaacacag agattattgt aaagctttct gatgggagag      480
agctctgcct ggaccccaag gaaaactggg tgcagagggt cgtggagaag ttcttgaaga      540
gggctgagaa ctcaggcagc ggttcttata cctacaatta tgaatggcat gtggatgtct      600
ggggacaggg cctgctggtg acagtctcta gtgctagc                              638
```

<210> SEQ ID NO 440
<211> LENGTH: 671
<212> TYPE: DNA
<213> ORGANISM: Artificial sequence
<220> FEATURE:
<223> OTHER INFORMATION: Synthesized: V1-51, I29V, N32G

<400> SEQUENCE: 440

```
tcacgaattc gcagtccgtg ctgacccaac ccccgtcagt gtctgctgcc cccgggcaga       60
aggtgactat cagctgctct ggctcatcct ccaatgtcgg caacggctac gtcagctggt      120
accagcagct gcctggaaca gctcctaaac tgctcattta tgacaataac aagcgcccat      180
ccggaatccc tgaccgattc agcggaagca aatcagggac ctctgcaact ctgggaatca      240
ctgggcttca gacaggagat gaggcagatt actattgcgc ctctgcagag gacagctcca      300
gcaatgccgt gttcgggtct ggtaccactc ttacagtcct aggtcagccc aaggctgccc      360
cctcggtcac tctgttcccg ccctcctctg aggagcttca agccaacaag gccacactgg      420
tgtgtctcat aagtgacttc tacccggag ccgtgacagt ggcctggaag cagatagca       480 gccccgtcaa ggcgggagtg gaaacaacca cacctccaa acaaagcaac aacaagtacg       540
cggccagcag ctatctgagc ctgacgcctg agcagtggaa gtcccacaga agctacagct      600
gccaggtcac gcatgaaggg agcaccgtgg agaagacagt ggcccctaca gaatgttcat      660
aatgagctag c                                                           671
```

<210> SEQ ID NO 441
<211> LENGTH: 671
<212> TYPE: DNA
<213> ORGANISM: Artificial sequence
<220> FEATURE:
<223> OTHER INFORMATION: Synthesized: V1-51, DNN (aa51-53) changed to GDT

<400> SEQUENCE: 441

```
tcacgaattc gcagtccgtg ctgacccaac cccgtcagt gtctgctgcc cccgggcaga      60
aggtgactat cagctgctct ggctcatcaa gcaacatcgg gaataattac gtcagctggt    120
accagcagct gcctggaaca gctcctaaac tgctcattta tggcgacaca aagcgcccat    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca gccaacaag gccacactgg     420
tgtgtctcat aagtgacttc tacccgggag ccgtgacagt ggcctggaag gcagatagca    480
gccccgtcaa ggcgggagtg gaaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                         671
```

<210> SEQ ID NO 442
<211> LENGTH: 671
<212> TYPE: DNA
<213> ORGANISM: Artificial sequence
<220> FEATURE:
<223> OTHER INFORMATION: Synthesized: V1-51, DNNKRP (aa51-56) changed to GDTSRA

<400> SEQUENCE: 442

```
tcacgaattc gcagtccgtg ctgacccaac cccgtcagt gtctgctgcc cccgggcaga      60
aggtgactat cagctgctct ggctcatcaa gcaacatcgg gaataattac gtcagctggt    120
accagcagct gcctggaaca gctcctaaac tgctcattta tggcgacaca tccagagctt    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca gccaacaag gccacactgg     420
tgtgtctcat aagtgacttc tacccgggag ccgtgacagt ggcctggaag gcagatagca    480
gccccgtcaa ggcgggagtg gaaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                         671
```

<210> SEQ ID NO 443
<211> LENGTH: 671
<212> TYPE: DNA
<213> ORGANISM: Artificial sequence
<220> FEATURE:
<223> OTHER INFORMATION: Synthesized: V1-51, S2A,T5N,P8S,A12G,A13S, and P14L

<400> SEQUENCE: 443

```
tcacgaattc gcaggccgtc ctgaaccagc caagcagcgt ctccgggtct ctggggcaga     60
aggtgactat cagctgctct ggctcatcaa gcaacatcgg gaataattac gtcagctggt    120
```

```
accagcagct gcctggaaca gctcctaaac tgctcattta tgacaataac aagcgcccat    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca agccaacaag gccacactgg    420
tgtgtctcat aagtgacttc tacccggag ccgtgacagt ggcctggaag gcagatagca    480
gccccgtcaa ggcgggagtg aaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                         671
```

<210> SEQ ID NO 444
<211> LENGTH: 671
<212> TYPE: DNA
<213> ORGANISM: Artificial sequence
<220> FEATURE:
<223> OTHER INFORMATION: Synthesized: V1-51, S2A,T5N,P8S,A12G,A13S,
      P14L, and DNN (aa51-53) changed to GDT

<400> SEQUENCE: 444

```
tcacgaattc gcaggccgtc ctgaaccagc caagcagcgt ctccgggtct ctggggcaga     60
aggtgactat cagctgctct ggctcatcaa gcaacatcgg gaataattac gtcagctggt    120
accagcagct gcctggaaca gctcctaaac tgctcattta tggcgacaca aagcgcccat    180
ccggaatccc tgaccgattc agcggaagca aatcagggac ctctgcaact ctgggaatca    240
ctgggcttca gacaggagat gaggcagatt actattgcgc ctctgcagag gacagctcca    300
gcaatgccgt gttcgggtct ggtaccactc ttacagtcct aggtcagccc aaggctgccc    360
cctcggtcac tctgttcccg ccctcctctg aggagcttca agccaacaag gccacactgg    420
tgtgtctcat aagtgacttc tacccgggag ccgtgacagt ggcctggaag gcagatagca    480
gccccgtcaa ggcgggagtg aaacaacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aatgagctag c                                                         671
```

<210> SEQ ID NO 445
<211> LENGTH: 657
<212> TYPE: DNA
<213> ORGANISM: Artificial sequence
<220> FEATURE:
<223> OTHER INFORMATION: Synthesized: A20J1

<400> SEQUENCE: 445

```
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccctccgtg acgttcggc    300 caagggacca aggtggaaat caaacgtacg gtggctgcac catctgtctt catcttcccg    360
ccatctgatg agcagttgaa atctggaact gcctctgttg tgtgcctgct gaataacttc    420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaatg agctagc      657
```

<210> SEQ ID NO 446
<211> LENGTH: 657
<212> TYPE: DNA
<213> ORGANISM: Artificial sequence
<220> FEATURE:
<223> OTHER INFORMATION: Synthesized: L6J1

<400> SEQUENCE: 446

```
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgtg acgttcggc    300 caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttaatg agctagc      657
```

<210> SEQ ID NO 447
<211> LENGTH: 660
<212> TYPE: DNA
<213> ORGANISM: Artificial sequence
<220> FEATURE:
<223> OTHER INFORMATION: Synthesized: L25J1

<400> SEQUENCE: 447

```
gaaatagtga tgacgcagtc tccagccacc ctgtctttgt ctccagggga aagagccacc     60
ctctcctgca gggccagtca gagtgttagc agcagctact atcctggta ccagcagaaa    120 cctgggcagg ctcccaggct cctcatctat ggtgcatcca ccagggccac tggcatccca    180
gccaggttca gtggcagtgg gtctgggaca gacttcactc tcaccatcag cagcctgcag    240
cctgaagatt ttgcagttta ttactgtcag caggattata acttacctcc gtggacgttc    300
ggccaaggga ccaaggtgga aatcaaacgt acggtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta atgagctagc    660
```

<210> SEQ ID NO 448
<211> LENGTH: 663
<212> TYPE: DNA
<213> ORGANISM: Artificial sequence
<220> FEATURE:

<223> OTHER INFORMATION: Synthesized: V1-2J7

<400> SEQUENCE: 448

| | | |
|---|---|---|
| cagtctgccc tgactcagcc tccctccgcg tccgggtctc ctggacagtc agtcaccatc | 60 | |
| tcctgcactg gaaccagcag tgacgttggt ggttataact atgtctcctg gtaccaacag | 120 | |
| cacccaggca aagcccccaa actcatgatt tatgaggtca gtaagcggcc ctcagggggtc | 180 | |
| cctgatcgct tctctggctc caagtctggc aacacggcct ccctgaccgt ctctgggctc | 240 | |
| caggctgagg atgaggctga ttattactgc agctcatatg caggcagcaa caatttcgct | 300 | |
| gtgttcggag gaggcaccca gctgaccgtc ctaggtcagc ccaaggctgc cccctcggtc | 360 | |
| actctgttcc cgccctcctc tgaggagctt caagccaaca aggccacact ggtgtgtctc | 420 | |
| ataagtgact tctacccggg agccgtgaca gtggcctgga aggcagatag cagccccgtc | 480 | |
| aaggcgggag tggagaccac cacaccctcc aaacaaagca acaacaagta cgcggccagc | 540 | |
| agctatctga gcctgacgcc tgagcagtgg aagtcccaca aagctacag ctgccaggtc | 600 | |
| acgcatgaag ggagcaccgt ggagaagaca gtggccccta cagaatgttc ataatgagct | 660 | |
| agc | 663 | |

<210> SEQ ID NO 449
<211> LENGTH: 663
<212> TYPE: DNA
<213> ORGANISM: Artificial sequence
<220> FEATURE:
<223> OTHER INFORMATION: Synthesized: V1-7J1

<400> SEQUENCE: 449

| | | |
|---|---|---|
| cagtctgccc tgactcagcc tgcctccgtg tctggctccc ctggacagtc gatcaccatc | 60 | |
| tcctgcactg gaaccagcag tgatgttggg agttataacc ttgtctcctg gtaccaacag | 120 | |
| cacccaggca aagcccccaa actcatgatt tatgagggca gtaagcggcc ctcagggggtt | 180 | |
| tctaatcgct tctctggctc caagtctggc aacacggcct ccctgacaat ctctgggctc | 240 | |
| caggctgagg acgaggctga ttattactgc tgctcatatg caggtagtag cactttctat | 300 | |
| gtcttcggaa ctgggaccaa ggtcaccgtc ctaggtcagc ccaaggctgc cccctcggtc | 360 | |
| actctgttcc cgccctcctc tgaggagctt caagccaaca aggccacact ggtgtgtctc | 420 | |
| ataagtgact tctacccggg agccgtgaca gtggcctgga aggcagatag cagccccgtc | 480 | |
| aaggcgggag tggagaccac cacaccctcc aaacaaagca acaacaagta cgcggccagc | 540 | |
| agctatctga gcctgacgcc tgagcagtgg aagtcccaca aagctacag ctgccaggtc | 600 | |
| acgcatgaag ggagcaccgt ggagaagaca gtggccccta cagaatgttc ataatgagct | 660 | |
| agc | 663 | |

<210> SEQ ID NO 450
<211> LENGTH: 663
<212> TYPE: DNA
<213> ORGANISM: Artificial sequence
<220> FEATURE:
<223> OTHER INFORMATION: Synthesized: V1-11J2

<400> SEQUENCE: 450

| | | |
|---|---|---|
| cagtctgtgc tgactcagcc accctcggtg tctgaagccc ccaggcagag ggtcaccatc | 60 | |
| tcctgttctg gaagcagctc caacatcgga aataatgctg taaactggta ccagcagctc | 120 | |
| ccaggaaagg ctcccaaact cctcatctat tatgatgatc tgctgccctc aggggtctct | 180 | |
| gaccgattct ctggctccaa gtctggcacc tcagcctccc tggccatcag tgggctccag | 240 | |

-continued

```
tctgaggatg aggctgatta ttactgtgca gcatgggatg acagcctgaa tggtcctgtg      300
gtattcggcg agggaccaa gctgaccgtc ctaggtcagc ccaaggctgc ccctcggtc         360 actctgttcc cgccctcctc tgaggagctt caagccaaca aggccacact ggtgtgtctc      420
ataagtgact tctacccggg agccgtgaca gtggcctgga aggcagatag cagccccgtc      480
aaggcgggag tggagaccac cacaccctcc aaacaaagca acaacaagta cgcggccagc     540
agctatctga gcctgacgcc tgagcagtgg aagtcccaca aagctacag ctgccaggtc       600 acgcatgaag ggagcaccgt ggagaagaca gtggccccta cagaatgttc ataatgagct     660
agc                                                                    663
```

<210> SEQ ID NO 451
<211> LENGTH: 336
<212> TYPE: DNA
<213> ORGANISM: Artificial sequence
<220> FEATURE:
<223> OTHER INFORMATION: Synthesized: V1-16J6

<400> SEQUENCE: 451

```
ccagtctgtg ctgactcagc caccctcagc gtctgggacc cccgggcaga gggtcaccat      60
ctcttgttct ggaagcagct ccaacatcgg aagtaatact gtaaactggt accagcagct     120
cccaggaacg gcccccaaac tcctcatcta tagtaataat cagcggccct caggggtccc     180
tgaccgattc tctggctcca agtctggcac ctcagcctcc ctggccatca gtgggctcca    240
gtctgaggat gaggctgatt attactgtgc agcatgggat gacagcctga atggtcctaa     300
tgtgttcggc agtggcacca aggtgaccgt cctagg                               336
```

<210> SEQ ID NO 452
<211> LENGTH: 657
<212> TYPE: DNA
<213> ORGANISM: Artificial sequence
<220> FEATURE:
<223> OTHER INFORMATION: Synthesized: V2-17J2

<400> SEQUENCE: 452

```
tcctatgagc tgacacagcc accctcggtg tcagtgtccc caggacagac ggccaggatc      60
acctgctctg gagatgcatt gccaaagcaa tatgcttatt ggtaccagca gaagccaggc     120
caggcccctg tgctggtgat atataaagac agtgagaggc cctcaggcat ccctgagcga     180
ttctctggct ccagctcagg gacaacagtc acgttgacca tcagtggagt ccaggcagaa     240
gatgaggctg actattactg tcaatcagca gacagcagtg gtacttatcc tgtggtattc     300
ggcggaggga ccaagctgac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaaa caaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttcataatg agctagc        657
```

<210> SEQ ID NO 453
<211> LENGTH: 663
<212> TYPE: DNA
<213> ORGANISM: Artificial sequence
<220> FEATURE:
<223> OTHER INFORMATION: Synthesized: V3-4J1

<400> SEQUENCE: 453

```
cagactgtgg tgacccagga gccatcgttc tcagtgtccc ctggagggac agtcacactc      60
acttgtggct tgagctctgg ctcagtctct actagttact accccagctg gtaccagcag     120
accccaggcc aggctccacg cacgctcatc tacagcacaa acactcgctc ttctggggtc     180
cctgatcgct tctctggctc catccttggg aacaaagctg ccctcaccat cacggggggcc    240
caggcagatg atgaatctga ttattactgt gtgctgtata tgggtagtgg catttcttat     300
gtcttcggaa ctgggaccaa ggtcaccgtc ctaggtcagc ccaaggctgc cccctcggtc     360
actctgttcc cgccctcctc tgaggagctt caagccaaca aggccacact ggtgtgtctc     420
ataagtgact tctacccggg agccgtgaca gtggcctgga aggcagatag cagccccgtc     480
aaggcgggag tggagaccac cacaccctcc aaacaaagca caacaagta cgcggccagc      540
agctatctga gcctgacgcc tgagcagtgg aagtcccaca aagctacag ctgccaggtc      600
acgcatgaag ggagcaccgt ggagaagaca gtggccccta cagaatgttc ataatgagct     660
agc                                                                   663
```

<210> SEQ ID NO 454
<211> LENGTH: 666
<212> TYPE: DNA
<213> ORGANISM: Artificial sequence
<220> FEATURE:
<223> OTHER INFORMATION: Synthesized: V5-4J2

<400> SEQUENCE: 454

```
cagcctgtgc tgactcaatc atcctctgcc tctgcttccc tgggctcctc ggtcaagctc      60
acctgcactc tgagcagtgg gcacagtagc tacatcatcg catggcatca gcagcagcca    120
gggaaggccc ctcggtactt gatgaagctt gaaggtagtg gaagctacaa caaggggagc    180
ggagttcctg atcgcttctc aggctccagc tctgggggctg accgctacct caccatctcc    240
aacctccagt tgaggatga ggctgattat tactgtgaga cctgggacag taacactcat      300
gtggtattcg gcggagggac caagctgacc gtcctaggtc agcccaaggc tgccccctcg    360
gtcactctgt tcccgccctc ctctgaggag cttcaagcca acaaggccac actggtgtgt    420
ctcataagtg acttctaccc gggagccgtg acagtggcct ggaaggcaga tagcagcccc    480
gtcaaggcgg gagtggagac caccacaccc tccaaacaaa gcaacaacaa gtacgcggcc    540
agcagctatc tgagcctgac gcctgagcag tggaagtccc acagaagcta cagctgccag    600
gtcacgcatg aagggagcac cgtggagaag acagtggccc ctacagaatg ttcataatga    660
gctagc                                                                666
```

<210> SEQ ID NO 455
<211> LENGTH: 660
<212> TYPE: DNA
<213> ORGANISM: Artificial sequence
<220> FEATURE:
<223> OTHER INFORMATION: Synthesized: V1-47

<400> SEQUENCE: 455

```
caatcagttt tgacccagcc accctccgca tccggcaccc cgggcaacg cgttacaata      60
agctgtagcg gcagctcatc taatattggc agcaactacg tttattggta ccagcagctt    120
ccagggaccg cccccaaatt gcttatctac cggaataatc agaggccttc cggggtgcca    180
gataggttct ctgggagtaa atctggcact agcgcaagtc tggctatcag cgggctccgg    240
tctgaggatg aagccgacta ttattgcgcg agcgctgagg actcatcttc taatgctgtg    300
```

```
tttggctccg gtaccacact caccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg aaacaaccac accctccaaa caaagcaaca caagtacgc ggccagcagc       540 tatctgagcc tgacgcctga gcagtggaag tcccacagaa gctacagctg ccaggtcacg      600
catgaaggga gcaccgtgga gaagacagtg gcccctacag aatgttcata atgagctagc      660
```

<210> SEQ ID NO 456
<211> LENGTH: 660
<212> TYPE: DNA
<213> ORGANISM: Artificial sequence
<220> FEATURE:
<223> OTHER INFORMATION: Synthesized: V1-51

<400> SEQUENCE: 456

```
cagtccgtgc tgacccaacc cccgtcagtg tctgctgccc ccgggcagaa ggtgactatc       60
agctgctctg gctcatcaag caacatcggg aataattacg tcagctggta ccagcagctg      120
cctggaacag ctcctaaact gctcatttat gacaataaca gcgcccatc cggaatccct       180 gaccgattca gcggaagcaa atcagggacc tctgcaactc tgggaatcac tgggcttcag      240
acaggagatg aggcagatta ctattgcgcc tctgcagagg acagctccag caatgccgtg      300
ttcgggtctg gtaccactct tacagtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg aaacaaccac accctccaaa caaagcaaca caagtacgc ggccagcagc       540 tatctgagcc tgacgcctga gcagtggaag tcccacagaa gctacagctg ccaggtcacg      600
catgaaggga gcaccgtgga gaagacagtg gcccctacag aatgttcata atgagctagc      660
```

<210> SEQ ID NO 457
<211> LENGTH: 4188
<212> TYPE: DNA
<213> ORGANISM: Artificial sequence
<220> FEATURE:
<223> OTHER INFORMATION: Synthesized: vector pFUSE-hIgG2-Fc2

<400> SEQUENCE: 457

```
ggatctgcga tcgctccggt gcccgtcagt gggcagagcg cacatcgccc acagtccccg       60
agaagttggg gggaggggtc ggcaattgaa cgggtgccta gagaaggtgg cgcggggtaa      120
actgggaaag tgatgtcgtg tactggctcc gcctttttcc cgagggtggg ggagaaccgt      180
atataagtgc agtagtcgcc gtgaacgttc tttttcgcaa cgggtttgcc gccagaacac      240
agctgaagct cgagggggct cgcatctctc cttcacgcgc ccgccgccct acctgaggcc      300
gccatccacg ccggttgagt cgcgttctgc cgcctcccgc ctgtggtgcc tcctgaactg      360
cgtccgccgt ctaggtaagt ttaaagctca ggtcgagacc gggcctttgt ccggcgctcc      420
cttggagcct acctagactc agccggctct ccacgctttg cctgaccctg cttgctcaac      480
tctacgtctt tgtttcgttt tctgttctgc gccgttacag atccaagctg tgaccggcgc      540
ctacctgaga tcaccggcga aggagggcca ccatgtacag gatgcaactc ctgtcttgca      600
ttgcactaag tcttgcactt gtcacgaatt cgatatcggc catggttaga tctgtggagt      660
gcccaccttg cccagcacca cctgtggcag gaccttcagt cttcctcttc cccccaaaac      720
```

```
ccaaggacac cctgatgatc tccagaaccc ctgaggtcac gtgcgtggtg gtggacgtga      780
gccacgaaga ccccgaggtc cagttcaact ggtacgtgga cggcatggag gtgcataatg      840
ccaagacaaa gccacgggag gagcagttca acagcacgtt ccgtgtggtc agcgtcctca      900
ccgtcgtgca ccaggactgg ctgaacggca aggagtacaa gtgcaaggtc tccaacaaag      960
gcctcccagc ccccatcgag aaaaccatct ccaaaaccaa agggcagccc cgagaaccac     1020
aggtgtacac cctgccccca tcccgggagg agatgaccaa gaaccaggtc agcctgacct     1080
gcctggtcaa aggcttctac cccagcgaca tcgccgtgga gtgggagagc aatgggcagc     1140
cggagaacaa ctacaagacc acacctccca tgctggactc cgacggctcc ttcttcctct     1200
acagcaagct caccgtggac aagagcaggt ggcagcaggg gaacgtcttc tcatgctccg     1260
tgatgcatga ggctctgcac aaccactaca cacagaagag cctctccctg tctccgggta     1320
aatgagtgcc acggctagct ggccagacat gataagatac attgatgagt ttggacaaac     1380
cacaactaga atgcagtgaa aaaaatgctt tatttgtgaa atttgtgatg ctattgcttt     1440
atttgtaacc attataagct gcaataaaca agttaacaac aacaattgca ttcattttat     1500
gtttcaggtt cagggggagg tgtgggaggt tttttaaagc aagtaaaacc tctacaaatg     1560
tggtatggaa ttaattctaa aatacagcat agcaaaactt taacctccaa atcaagcctc     1620
tacttgaatc cttttctgag ggatgaataa ggcataggca tcaggggctg ttgccaatgt     1680
gcattagctg tttgcagcct caccttcttt catggagttt aagatatagt gtattttccc     1740
aaggtttgaa ctagctcttc atttctttat gttttaaatg cactgacctc ccacattccc     1800
tttttagtaa aatattcaga aataatttaa atacatcatt gcaatgaaaa taatgttttt     1860
ttattaggca gaatccagat gctcaaggcc cttcataata tcccccagtt tagtagttgg     1920
acttaggaa caaaggaacc tttaatagaa attggacagc aagaaagcga gcttctagct      1980
tatcctcagt cctgctcctc tgccacaaag tgcacgcagt tgccggccgg gtcgcgcagg     2040
gcgaactccc gccccacgg ctgctcgccg atctcggtca tggccggccc ggaggcgtcc       2100
cggaagttcg tggacacgac ctccgaccac tcggcgtaca gctcgtccag ccgcgcacc       2160
cacacccagg ccagggtgtt gtccggcacc acctggtcct ggaccgcgct gatgaacagg     2220
gtcacgtcgt cccggaccac accggcgaag tcgtcctcca cgaagtcccg ggagaacccg     2280
agccggtcgg tccagaactc gaccgctccg gcgacgtcgc gcgcggtgag caccggaacg     2340
gcactggtca acttggccat gatggctcct cctgtcagga gaggaaagag aagaaggtta     2400
gtacaattgc tatagtgagt tgtattatac tatgcagata tactatgcca atgattaatt     2460
gtcaaactag gctgcagggg ttcatagtgc cacttttcct gcactgcccc atctcctgcc     2520
cacccttttcc caggcataga cagtcagtga cttaccaaac tcacaggagg agaaggcag     2580
aagcttgaga cagacccgcg ggaccgccga actgcgaggg gacgtggcta ggcggcttc      2640
ttttatggtg cgccggccct cggaggcagg gcgctcgggg aggcctagcg gccaatctgc     2700
ggtggcagga ggcggggccg aaggccgtgc ctgaccaatc cggagcacat aggagtctca     2760
gccccccgcc ccaaagcaag gggaagtcac gcgcctgtag cgccagcgtg ttgtgaaatg     2820
ggggcttggg ggggttgggg ccctgactag tcaaaacaaa ctcccattga cgtcaatggg     2880
gtggagactt ggaaatcccc gtgagtcaaa ccgctatcca cgcccattga tgtactgcca     2940
aaaccgcatc atcatggtaa tagcgatgac taatacgtag atgtactgcc aagtaggaaa     3000
gtcccataag gtcatgtact gggcataatg ccaggcgggc catttaccgt cattgacgtc     3060
aataggggc gtacttggca tatgatacac ttgatgtact gccaagtggg cagtttaccg     3120
```

-continued

```
taaatactcc acccattgac gtcaatggaa agtccctatt ggcgttacta tgggaacata    3180
cgtcattatt gacgtcaatg ggcgggggtc gttgggcggt cagccaggcg ggccatttac    3240
cgtaagttat gtaacgcctg caggttaatt aagaacatgt gagcaaaagg ccagcaaaag    3300
gccaggaacc gtaaaaaggc cgcgttgctg gcgtttttcc ataggctccg ccccctgac    3360 gagcatcaca aaaatcgacg ctcaagtcag aggtggcgaa acccgacagg actataaaga    3420
taccaggcgt ttccccctgg aagctccctc gtgcgctctc ctgttccgac cctgccgctt    3480
accggatacc tgtccgcctt tctcccttcg ggaagcgtgg cgctttctca tagctcacgc    3540
tgtaggtatc tcagttcggt gtaggtcgtt cgctccaagc tgggctgtgt gcacgaaccc    3600
cccgttcagc ccgaccgctg cgccttatcc ggtaactatc gtcttgagtc caacccggta    3660
agacacgact tatcgccact ggcagcagcc actggtaaca ggattagcag agcgaggtat    3720
gtaggcggtg ctacagagtt cttgaagtgg tggcctaact acggctacac tagaagaaca    3780
gtatttggta tctgcgctct gctgaagcca gttaccttcg gaaaaagagt ggtagctct    3840 tgatccggca acaaaccac cgctggtagc ggtggttttt ttgtttgcaa gcagcagatt    3900
acgcgcagaa aaaaggatc tcaagaagat cctttgatct tttctacggg gtctgacgct    3960
cagtggaacg aaaactcacg ttaagggatt ttggtcatgg ctagttaatt aacatttaaa    4020
tcagcggccg caataaaata tctttatttt cattacatct gtgtgttggt tttttgtgtg    4080
aatcgtaact aacatacgct ctccatcaaa acaaaacgaa acaaaacaaa ctagcaaaat    4140
aggctgtccc cagtgcaagt gcaggtgcca gaacatttct ctatcgaa                 4188
```

<210> SEQ ID NO 458
<211> LENGTH: 4495
<212> TYPE: DNA
<213> ORGANISM: Artificial sequence
<220> FEATURE:
<223> OTHER INFORMATION: Synthesized: vector HC pFuse

<400> SEQUENCE: 458

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtccagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg taccggcgc    540 ctacctgaga tcaccggcga aggagggcca ccatgcgcag gatgcaactc ctgttgctga    600
ttgcactaag tcttgcactt gtcacgaatt cgccatggct cctcagctag caccaagggc    660
ccatcggtct tccccctggc acctcctcc aagagcacct ctggggcac agcggccctg    720 ggctgcctgg tcaaggacta cttccccgag ccggtgacgg tgtcgtggaa ctcaggcgcc    780
ctgaccagcg gcgtgcacac cttcccggct gtcctacagt cctcaggact ctactccctc    840
agcagcgtgg tgaccgtgcc ctccagcagc ttgggcaccc agacctacat ctgcaacgtg    900
aatcacaagc ccagcaacac caaggtggac aagaaagttg agcccaaatc ttgtgacaaa    960
```

```
actcacacat gcccaccgtg cccagcacct gaactcctgg ggggaccgtc agtcttcctc    1020 ttcccccaa  aacccaagga caccctcatg atctcccgga cccctgaggt cacatgcgtg    1080
gtggtggacg tgagccacga agaccctgag gtcaagttca actggtacgt ggacggcgtg    1140
gaggtgcata atgccaagac aaagccgcgg gaggagcagt acaacagcac gtaccgtgtg    1200
gtcagcgtcc tcaccgtcct gcaccaggac tggctgaatg gcaaggagta caagtgcaag    1260
gtgtccaaca aagccctccc agcccccatc gagaaaacca tctccaaagc caagggcag    1320 ccccgagaac cacaggtgta caccctgccc ccatcccggg atgagctgac caagaaccag    1380
gtcagcctga cctgcctggt caaaggcttc tatcccagcg acatcgccgt ggagtgggag    1440
agcaatgggc agccggagaa caactacaag accacgcctc ccgtgctgga ctccgacggc    1500
tccttcttcc tctacagcaa gctcaccgtg gacaagagca ggtggcagca ggggaacgtc    1560
ttctcatgct ccgtgatgca tgaggctctg cacaaccact acacgcagaa gagcctctcc    1620
ctgtctccgg gtaaatgata atctagtggc cagacatgat aagatacatt gatgagtttg    1680
gacaaaccac aactagaatg cagtgaaaaa aatgctttat ttgtgaaatt tgtgatgcta    1740
ttgctttatt tgtaaccatt ataagctgca ataaacaagt taacaacaac aattgcattc    1800
attttatgtt tcaggttcag ggggaggtgt gggaggtttt ttaaagcaag taaaacctct    1860
acaaatgtgg tatggaatta attctaaaat acagcatagc aaaactttaa cctccaaatc    1920
aagcctctac ttgaatcctt ttctgaggga tgaataaggc ataggcatca ggggctgttg    1980
ccaatgtgca ttagctgttt gcagcctcac cttctttcat ggagtttaag atatagtgta    2040
ttttcccaag gtttgaacta gctcttcatt tctttatgtt ttaaatgcac tgacctccca    2100
cattcccttt ttagtaaaat attcagaaat aatttaaata catcattgca atgaaaataa    2160 atgttttta  ttaggcagaa tccagatgct caaggccctt cataatatcc cccagtttag    2220
tagttggact tagggaacaa aggaaccttt aatagaaatt ggacagcaag aaagcgagct    2280
tctagcttat cctcagtcct gctcctctgc cacaaagtgc acgcagttgc cggccgggtc    2340
gcgcagggcg aactcccgcc cccacggctg ctcgccgatc tcggtcatgg ccggcccgga    2400
ggcgtcccgg aagttcgtgg acacgacctc cgaccactcg gcgtacagct cgtccaggcc    2460
gcgcacccac acccaggcca gggtgttgtc cggcaccacc tggtcctgga ccgcgctgat    2520
gaacagggtc acgtcgtccc ggaccacacc ggcgaagtcg tcctccacga agtcccggga    2580
gaacccgagc cggtcggtcc agaactcgac cgctccggcg acgtcgcgcg cggtgagcac    2640
cggaacggca ctggtcaact tggccatgat ggctcctcct gtcaggagag gaaagagaag    2700
aaggttagta caattgctat agtgagttgt attatactat gcagatatac tatgccaatg    2760
attaattgtc aaactagggc tgcagggttc atagtgccac ttttcctgca ctgccccatc    2820
tcctgcccac cctttcccag gcatagacag tcagtgactt accaaactca caggagggag    2880
aaggcagaag cttgagacag acccgcggga ccgccgaact gcgagggac gtggctaggg    2940 cggcttcttt tatggtgcgc cggccctcgg aggcagggcg ctcggggagg cctagcggcc    3000
aatctgcggt ggcaggaggc ggggccgaag gccgtgcctg accaatccgg agcacatagg    3060
agtctcagcc ccccgcccca aagcaagggg aagtcacgcg cctgtagcgc cagcgtgttg    3120
tgaaatgggg gcttgggggg gttggggccc tgactagtca aaacaaactc ccattgacgt    3180
caatggggtg gagacttgga aatccccgtg agtcaaaccg ctatccacgc ccattgatgt    3240
actgccaaaa ccgcatcatc atggtaatag cgatgactaa tacgtagatg tactgccaag    3300
taggaaagtc ccataaggtc atgtactggg cataatgcca ggcgggccat ttaccgtcat    3360
```

```
tgacgtcaat aggggggcgta cttggcatat gatacacttg atgtactgcc aagtgggcag    3420
tttaccgtaa atactccacc cattgacgtc aatggaaagt ccctattggc gttactatgg    3480
gaacatacgt cattattgac gtcaatgggc ggggtcgtt gggcggtcag ccaggcgggc    3540
catttaccgt aagttatgta acgcctgcag gttaattaag aacatgtgag caaaaggcca    3600
gcaaaaggcc aggaaccgta aaaaggccgc gttgctggcg ttttttccata ggctccgccc    3660 ccctgacgag catcacaaaa atcgacgctc aagtcagagg tggcgaaacc cgacaggact    3720
ataaagatac caggcgtttc ccctggaag ctccctcgtg cgctctcctg ttccgaccct    3780
gccgcttacc ggatacctgt ccgcctttct cccttcggga agcgtggcgc tttctcatag    3840
ctcacgctgt aggtatctca gttcggtgta ggtcgttcgc tccaagctgg gctgtgtgca    3900
cgaacccccc gttcagcccg accgctgcgc cttatccggt aactatcgtc ttgagtccaa    3960
cccggtaaga cacgacttat cgccactggc agcagccact ggtaacagga ttagcagagc    4020
gaggtatgta ggcggtgcta cagagttctt gaagtggtgg cctaactacg gctacactag    4080
aagaacagta tttggtatct gcgctctgct gaagccagtt accttcggaa aaagagttgg    4140
tagctcttga tccggcaaac aaaccaccgc tggtagcggt ggtttttttg tttgcaagca    4200
gcagattacg cgcagaaaaa aaggatctca agaagatcct ttgatctttt ctacggggtc    4260
tgacgctcag tggaacgaaa actcacgtta agggattttg gtcatggcta gttaattaac    4320
atttaaatca gcggccgcaa taaaatatct ttattttcat tacatctgtg tgttggtttt    4380
ttgtgtgaat cgtaactaac atacgctctc catcaaaaca aaacgaaaca aaacaaacta    4440
gcaaaatagg ctgtccccag tgcaagtgca ggtgccagaa catttctcta tcgaa         4495

<210> SEQ ID NO 459
<211> LENGTH: 3822
<212> TYPE: DNA
<213> ORGANISM: Artificial sequence
<220> FEATURE:
<223> OTHER INFORMATION: Synthesized: vector LC-pFuse

<400> SEQUENCE: 459
ggatctgcga tcgctccggt gcccgtcagt gggcagagcg cacatcgccc acagtccccg      60
agaagttggg ggagggggtc ggcaattgaa cgggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtccagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg taccggcgc     540 ctacctgaga tcaccggcga aggagggcca ccatgcgcag gatgcaactc ctgttgctga     600
ttgcactaag tcttgcactt gtcacgaatt cgccatggcc ctaggtcagc ccaaggctgc     660
cccctcggtc actctgttcc cgccctcctc tgaggagctt caagccaaca aggccacact     720
ggtgtgtctc ataagtgact tctacccggg agccgtgaca gtggcctgga aggcagatag     780
cagccccgtc aaggcgggag tggaaacaac cacaccctcc aaacaaagca acaacaagta     840
cgcggccagc agctatctga gcctgacgcc tgagcagtgg aagtcccaca aagctacag    900
```

```
ctgccaggtc acgcatgaag ggagcaccgt ggagaagaca gtggcccta cagaatgttc      960
ataatgagct agctgccag acatgataag atacattgat gagtttggac aaaccacaac     1020
tagaatgcag tgaaaaaaat gctttatttg tgaaatttgt gatgctattg ctttatttgt    1080
aaccattata agctgcaata aacaagttaa caacaacaat tgcattcatt ttatgtttca    1140
ggttcagggg gaggtgtggg aggtttttta aagcaagtaa aacctctaca aatgtggtat    1200
ggaattaatt ctaaaataca gcatagcaaa actttaacct ccaaatcaag cctctacttg    1260
aatccttttc tgagggatga ataaggcata ggcatcaggg gctgttgcca atgtgcatta    1320
gctgtttgca gcctcacctt cttcatgga gtttaagata tagtgtattt tcccaaggtt     1380
tgaactagct cttcatttct ttatgtttta aatgcactga cctcccacat tccttttta    1440
gtaaaatatt cagaaataat ttaaatacat cattgcaatg aaaataaatg ttttttatta    1500
ggcagaatcc agatgctcaa ggcccttcat aatatccccc agtttagtag ttggacttag    1560
ggaacaaagg aacctttaat agaaattgga cagcaagaaa gcgagcttct agcttatcct    1620
cagtcctgct cctctgccac aaagtgcacg cagttgccgg ccgggtcgcg cagggcgaac    1680
tcccgcccc acggctgctc gccgatctcg gtcatggccg gcccggaggc gtcccggaag    1740
ttcgtggaca cgacctccga ccactcggcg tacagctcgt ccaggccgcg cacccacacc    1800
caggccaggg tgttgtccgg caccacctgg tcctggaccg cgctgatgaa cagggtcacg    1860
tcgtcccgga ccacaccggc gaagtcgtcc tcccgaagt cccgggagaa cccgagccgg    1920
tcggtccaga actcgaccgc tccggcgacg tcgcgcgcgg tgagcaccgg aacggcactg    1980
gtcaacttgg ccatgatggc tcctcctgtc aggagaggaa agagaagaag gttagtacaa    2040
ttgctatagt gagttgtatt atactatgca gatatactat gccaatgatt aattgtcaaa    2100
ctagggctgc agggttcata gtgccacttt tcctgcactg ccccatctcc tgcccaccct    2160
ttcccaggca tagacagtca gtgacttacc aaactcacag gagggagaag gcagaagctt    2220
gagacagacc cgcggaccg ccgaactgcg aggggacgtg gctagggcgg cttcttttat    2280
ggtgcgccgg ccctcggagg cagggcgctc ggggaggcct agcggccaat ctgcggtggc    2340
aggaggcggg gccgaaggcc gtgcctgacc aatccggagc ataggagt ctcagccccc     2400
cgccccaaag caaggggaag tcacgcgcct gtagcgccag cgtgttgtga atgggggct    2460
tgggggggtt gggggccctga ctagtcaaaa caaactccca ttgacgtcaa tggggtggag   2520
acttggaaat ccccgtgagt caaaccgcta tccacgccca ttgatgtact gccaaaaccg    2580
catcatcatg gtaatagcga tgactaatac gtagatgtac tgccaagtag gaaagtccca    2640
taaggtcatg tactgggcat aatgccaggc gggccattta ccgtcattga cgtcaatagg    2700
gggcgtactt ggcatatgat acacttgatg tactgccaag tggcagttt accgtaaata    2760
ctccacccat tgacgtcaat ggaaagtccc tattggcgtt actatgggaa catacgtcat    2820
tattgacgtc aatgggcggg ggtcgttggg cggtcagcca gcgggccat ttaccgtaag    2880
ttatgtaacg cctgcaggtt aattaagaac atgtgagcaa aaggccagca aaaggccagg    2940
aaccgtaaaa aggccgcgtt gctggcgttt tccataggc tccgccccc tgacgagcat     3000
cacaaaaatc gacgctcaag tcagaggtgg cgaaacccga caggactata agataccag    3060
gcgtttcccc ctggaagctc cctcgtgcgc tctcctgttc cgaccctgcc gcttaccgga    3120
tacctgtccg cctttctccc ttcgggaagc gtggcgcttt ctcatagctc acgctgtagg    3180
tatctcagtt cggtgtaggt cgttcgctcc aagctgggct gtgtgcacga accccccgtt    3240
cagcccgacc gctgcgcctt atccggtaac tatcgtcttg agtccaaccc ggtaagacac    3300
```

```
gacttatcgc cactggcagc agccactggt aacaggatta gcagagcgag gtatgtaggc    3360
ggtgctacag agttcttgaa gtggtggcct aactacggct acactagaag aacagtattt    3420
ggtatctgcg ctctgctgaa gccagttacc ttcggaaaaa gagttggtag ctcttgatcc    3480
ggcaaacaaa ccaccgctgg tagcggtggt ttttttgttt gcaagcagca gattacgcgc    3540
agaaaaaaag gatctcaaga agatcctttg atctttccta cggggtctga cgctcagtgg    3600
aacgaaaact cacgttaagg gattttggtc atggctagtt aattaacatt taaatcagcg    3660
gccgcaataa aatatcttta ttttcattac atctgtgtgt tggttttttg tgtgaatcgt    3720
aactaacata cgctctccat caaaacaaaa cgaaacaaaa caaactagca aaataggctg    3780
tccccagtgc aagtgcaggt gccagaacat ttctctatcg aa                      3822
```

<210> SEQ ID NO 460
<211> LENGTH: 107
<212> TYPE: PRT
<213> ORGANISM: Artificial sequence
<220> FEATURE:
<223> OTHER INFORMATION: Synthesized: VH4-34+CDR3

<400> SEQUENCE: 460

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser
            100                 105

<210> SEQ ID NO 461
<211> LENGTH: 107
<212> TYPE: PRT
<213> ORGANISM: Artificial sequence
<220> FEATURE:
<223> OTHER INFORMATION: Synthesized: VH4-34+CDR3_CDR1 Cow

<400> SEQUENCE: 461

Gln Val Gln Leu Gln Gln Trp Gly Ala Gly Leu Leu Lys Pro Ser Glu
1               5                   10                  15

Thr Leu Ser Leu Thr Cys Thr Ala Ser Gly Phe Ser Leu Ser Asp Lys
            20                  25                  30

Ala Val Gly Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser

<210> SEQ ID NO 462
<211> LENGTH: 107
<212> TYPE: PRT
<213> ORGANISM: Artificial sequence
<220> FEATURE:
<223> OTHER INFORMATION: Synthesized: VH4-34+CDR3_CDR2 Cow

<400> SEQUENCE: 462

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Leu
        35                  40                  45

Gly Ser Ile Asp Thr Gly Gly Asn Thr Gly Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser
            100                 105

<210> SEQ ID NO 463
<211> LENGTH: 107
<212> TYPE: PRT
<213> ORGANISM: Artificial sequence
<220> FEATURE:
<223> OTHER INFORMATION: Synthesized: VH4-34+CDR3_CDR1 G31D, Y32K

<400> SEQUENCE: 463

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Lys
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser
            100                 105

<210> SEQ ID NO 464
<211> LENGTH: 107
<212> TYPE: PRT
<213> ORGANISM: Artificial sequence
<220> FEATURE:
<223> OTHER INFORMATION: Synthesized: VH4-34+CDR3_CDR2 E50S

<400> SEQUENCE: 464

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

```
Tyr Trp Ser Trp Ile Arg Gln Pro Pro Gly Lys Gly Leu Glu Trp Ile
            35                  40                  45

Gly Ser Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Thr
                 85                  90                  95

Ser Val His Gln Glu Thr Lys Lys Tyr Gln Ser
            100                 105

<210> SEQ ID NO 465
<211> LENGTH: 107
<212> TYPE: PRT
<213> ORGANISM: Artificial sequence
<220> FEATURE:
<223> OTHER INFORMATION: Synthesized: VH4-34+CDR3_CDR1 Cow_CDR2 Cow

<400> SEQUENCE: 465

Gln Val Gln Leu Gln Gln Trp Gly Ala Gly Leu Leu Lys Pro Ser Glu
1               5                   10                  15

Thr Leu Ser Leu Thr Cys Thr Ala Ser Gly Phe Ser Leu Ser Asp Lys
            20                  25                  30

Ala Val Gly Trp Ile Arg Gln Pro Pro Gly Lys Gly Leu Glu Trp Leu
            35                  40                  45

Gly Ser Ile Asp Thr Gly Gly Asn Thr Gly Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Thr
                 85                  90                  95

Ser Val His Gln Glu Thr Lys Lys Tyr Gln Ser
            100                 105

<210> SEQ ID NO 466
<211> LENGTH: 107
<212> TYPE: PRT
<213> ORGANISM: Artificial sequence
<220> FEATURE:
<223> OTHER INFORMATION: Synthesized: VH4-34+CDR3_CDR1 Cow_CDR2 E50S

<400> SEQUENCE: 466

Gln Val Gln Leu Gln Gln Trp Gly Ala Gly Leu Leu Lys Pro Ser Glu
1               5                   10                  15

Thr Leu Ser Leu Thr Cys Thr Ala Ser Gly Phe Ser Leu Ser Asp Lys
            20                  25                  30

Ala Val Gly Trp Ile Arg Gln Pro Pro Gly Lys Gly Leu Glu Trp Ile
            35                  40                  45

Gly Ser Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Thr
                 85                  90                  95

Ser Val His Gln Glu Thr Lys Lys Tyr Gln Ser
            100                 105
```

```
<210> SEQ ID NO 467
<211> LENGTH: 107
<212> TYPE: PRT
<213> ORGANISM: Artificial sequence
<220> FEATURE:
<223> OTHER INFORMATION: Synthesized: VH4-34+CDR3_CDR1 G31D,Y32K_CDR2
      Cow

<400> SEQUENCE: 467
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Lys
            20                  25                  30

Tyr Trp Ser Trp Ile Arg Gln Pro Pro Gly Lys Gly Leu Glu Trp Leu
        35                  40                  45

Gly Ser Ile Asp Thr Gly Gly Asn Thr Gly Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser
            100                 105

```
<210> SEQ ID NO 468
<211> LENGTH: 107
<212> TYPE: PRT
<213> ORGANISM: Artificial sequence
<220> FEATURE:
<223> OTHER INFORMATION: Synthesized: VH4-34+CDR3_CDR1 G31D,Y32K_CDR2
      E50S

<400> SEQUENCE: 468
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Lys
            20                  25                  30

Tyr Trp Ser Trp Ile Arg Gln Pro Pro Gly Lys Gly Leu Glu Trp Ile
        35                  40                  45

Gly Ser Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser
            100                 105

```
<210> SEQ ID NO 469
<211> LENGTH: 25
<212> TYPE: PRT
<213> ORGANISM: Artificial sequence
<220> FEATURE:
<223> OTHER INFORMATION: Synthesized: J region of antibody comprising UL
      CDR3

<400> SEQUENCE: 469
```

Ser Tyr Thr Tyr Asn Tyr Glu Trp His Val Asp Val Trp Gly Gln Gly
1               5                   10                  15

Leu Leu Val Thr Val Ser Ser Ala Ser
            20                  25

-continued

<210> SEQ ID NO 470
<211> LENGTH: 6
<212> TYPE: PRT
<213> ORGANISM: Artificial sequence
<220> FEATURE:
<223> OTHER INFORMATION: Synthesized: VL1-51 CDR2 substituted amino acid
      resides

<400> SEQUENCE: 470

Asp Asn Asn Lys Arg Pro
1               5

<210> SEQ ID NO 471
<211> LENGTH: 6
<212> TYPE: PRT
<213> ORGANISM: Artificial sequence
<220> FEATURE:
<223> OTHER INFORMATION: Synthesized: VL1-51 CDR2 substituted amino
      acids

<400> SEQUENCE: 471

Gly Asp Thr Ser Arg Ala
1               5

<210> SEQ ID NO 472
<211> LENGTH: 420
<212> TYPE: DNA
<213> ORGANISM: Artificial sequence
<220> FEATURE:
<223> OTHER INFORMATION: Synthesized: HC-pFuse vector with BsaI cassette

<400> SEQUENCE: 472
caggtgcagc tacagcagtg gggcgcagga ctgttgaagc cttcggagac gctgtccctc      60
acctgcacag caagcgggtt ttcactgagc gacaaggcag tgggatggat tcgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtacctc tgtgcaccag     300
gaaactaaga ataccagag cgagacctac tatggttcgg gtctctctta tacctacaat     360
tatgaatggc atgtggatgt ctggggacag ggcctgctgg tgacagtctc tagtgctagc     420

<210> SEQ ID NO 473
<211> LENGTH: 133
<212> TYPE: PRT
<213> ORGANISM: Artificial sequence
<220> FEATURE:
<223> OTHER INFORMATION: Synthesized: Hc-pFuse vector with non-bovine
      sequence insert
<220> FEATURE:
<221> NAME/KEY: MISC_FEATURE
<222> LOCATION: (107)..(107)
<223> OTHER INFORMATION: X is an insert of a non-bovine sequence
<220> FEATURE:
<221> NAME/KEY: misc_feature
<222> LOCATION: (108)..(108)
<223> OTHER INFORMATION: Xaa can be any naturally occurring amino acid

<400> SEQUENCE: 473

Gln Val Gln Leu Gln Gln Trp Gly Ala Gly Leu Leu Lys Pro Ser Glu
1               5                   10                  15

Thr Leu Ser Leu Thr Cys Thr Ala Ser Gly Phe Ser Leu Ser Asp Lys
            20                  25                  30

Ala Val Gly Trp Ile Arg Gln Pro Pro Gly Lys Gly Leu Glu Trp Ile

```
                35                  40                  45
Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Ser Val His Gln Glu Thr Lys Lys Tyr Gln Ser Xaa Ser Tyr Thr Tyr
            100                 105                 110

Asn Tyr Glu Trp His Val Asp Val Trp Gly Gln Gly Leu Leu Val Thr
            115                 120                 125

Val Ser Ser Ala Ser
        130

<210> SEQ ID NO 474
<211> LENGTH: 662
<212> TYPE: DNA
<213> ORGANISM: Artificial sequence
<220> FEATURE:
<223> OTHER INFORMATION: Synthesized: BLV1H12 LV-human lambda LC

<400> SEQUENCE: 474
tcacgaattc gcaggccgtc ctgaaccagc caagcagcgt ctccgggtct ctggggcagc     60
gggtctcaat cacctgtagc gggtcttcct ccaatgtcgg caacggctac gtgtcttggt    120
atcagctgat ccctggcagt gccccacgaa ccctgatcta cggcgacaca tccagagctt    180
ctggggtccc cgatcggttc tcagggagca gatccggaaa cacagctact ctgaccatca    240
gctccctgca ggctgaggac gaagcagatt atttctgcgc atctgccgag gactctagtt    300
caaatgccgt gtttggaagc ggcaccacac tgacagtcct aggtcagccc aaggctgccc    360
cctcggtcac tctgttcccg ccctcctctg aggagcttca agccaacaag gccacactgg    420
tgtgtctcat aagtgacttc tacccgggag ccgtgacagt ggcctggaag cagatagca    480 gccccgtcaa ggcgggagtg agaccacca caccctccaa acaaagcaac aacaagtacg    540
cggccagcag ctatctgagc ctgacgcctg agcagtggaa gtcccacaga agctacagct    600
gccaggtcac gcatgaaggg agcaccgtgg agaagacagt ggcccctaca gaatgttcat    660
aa                                                                   662

<210> SEQ ID NO 475
<211> LENGTH: 74
<212> TYPE: PRT
<213> ORGANISM: Artificial sequence
<220> FEATURE:
<223> OTHER INFORMATION: Synthesized: IL-8 sequence

<400> SEQUENCE: 475

Pro Arg Ser Ala Lys Glu Leu Arg Cys Gln Cys Ile Lys Thr Tyr Ser
1               5                   10                  15

Lys Pro Phe His Pro Lys Phe Ile Lys Glu Leu Arg Val Ile Glu Ser
            20                  25                  30

Gly Pro His Cys Ala Asn Thr Glu Ile Ile Val Lys Leu Ser Asp Gly
        35                  40                  45

Arg Glu Leu Cys Leu Asp Pro Lys Glu Asn Trp Val Gln Arg Val Val
    50                  55                  60

Glu Lys Phe Leu Lys Arg Ala Glu Asn Ser
65                  70
```

```
<210> SEQ ID NO 476
<211> LENGTH: 25
<212> TYPE: PRT
<213> ORGANISM: Artificial sequence
<220> FEATURE:
<223> OTHER INFORMATION: Synthesized: ziconotide sequence

<400> SEQUENCE: 476

Cys Lys Gly Lys Gly Ala Lys Cys Ser Arg Leu Met Tyr Asp Cys Cys
1               5                   10                  15

Thr Gly Ser Cys Arg Ser Gly Lys Cys
            20                  25

<210> SEQ ID NO 477
<211> LENGTH: 15
<212> TYPE: PRT
<213> ORGANISM: Artificial sequence
<220> FEATURE:
<223> OTHER INFORMATION: Synthesized: somatostatin sequence

<400> SEQUENCE: 477

Ala Gly Cys Lys Asn Phe Phe Trp Lys Thr Phe Thr Ser Cys Gly
1               5                   10                  15

<210> SEQ ID NO 478
<211> LENGTH: 34
<212> TYPE: PRT
<213> ORGANISM: Artificial sequence
<220> FEATURE:
<223> OTHER INFORMATION: Synthesized: chlorotoxin sequence

<400> SEQUENCE: 478

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu

<210> SEQ ID NO 479
<211> LENGTH: 68
<212> TYPE: PRT
<213> ORGANISM: Artificial sequence
<220> FEATURE:
<223> OTHER INFORMATION: Synthesized: SDF1(alpha) sequence

<400> SEQUENCE: 479

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 480
<211> LENGTH: 133
<212> TYPE: PRT
<213> ORGANISM: Artificial sequence
<220> FEATURE:
<223> OTHER INFORMATION: Synthesized: IL-21 sequence
```

<400> SEQUENCE: 480

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 481
<211> LENGTH: 30
<212> TYPE: PRT
<213> ORGANISM: Artificial sequence
<220> FEATURE:
<223> OTHER INFORMATION: Synthesized: ProTxII sequence

<400> SEQUENCE: 481

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 482
<211> LENGTH: 274
<212> TYPE: PRT
<213> ORGANISM: Artificial sequence
<220> FEATURE:
<223> OTHER INFORMATION: Synthesized: Hc BLV1H12

<400> SEQUENCE: 482

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Pro Asp Gly Tyr
            100                 105                 110

Arg Glu Arg Ser Asp Cys Ser Asn Arg Pro Ala Cys Gly Thr Ser Asp
        115                 120                 125

```
Cys Cys Arg Val Ser Val Phe Gly Asn Cys Leu Thr Thr Leu Pro Val
            130                 135                 140

Ser Tyr Ser Tyr Thr Tyr Asn Tyr Glu Trp His Val Asp Val Trp Gly
145                 150                 155                 160

Gln Gly Leu Leu Val Thr Val Ser Ser Ala Ser Thr Thr Ala Pro Lys
                165                 170                 175

Val Tyr Pro Leu Ser Ser Cys Cys Gly Asp Lys Ser Ser Ser Thr Val
            180                 185                 190

Thr Leu Gly Cys Leu Val Ser Ser Tyr Met Pro Glu Pro Val Thr Val
            195                 200                 205

Thr Trp Asn Ser Gly Ala Leu Lys Ser Gly Val His Thr Phe Pro Ala
            210                 215                 220

Val Leu Gln Ser Ser Gly Leu Tyr Ser Leu Ser Ser Met Val Thr Val
225                 230                 235                 240

Pro Gly Ser Thr Ser Gly Gln Thr Phe Thr Cys Asn Val Ala His Pro
                245                 250                 255

Ala Ser Ser Thr Lys Val Asp Lys Ala Val Glu Pro Lys Ser Cys Asp
                260                 265                 270

Gly Ser
```

<210> SEQ ID NO 483
<211> LENGTH: 216
<212> TYPE: PRT
<213> ORGANISM: Artificial sequence
<220> FEATURE:
<223> OTHER INFORMATION: Synthesized: Lc BLV1H12

<400> SEQUENCE: 483

```
Gln Ala Val Leu Asn Gln Pro Ser Ser Val Ser Gly Ser Leu Gly Gln
1               5                   10                  15

Arg Val Ser Ile Thr Cys Ser Gly Ser Ser Asn Val Gly Asn Gly
            20                  25                  30

Tyr Val Ser Trp Tyr Gln Leu Ile Pro Gly Ser Ala Pro Arg Thr Leu
            35                  40                  45

Ile Tyr Gly Asp Thr Ser Arg Ala Ser Gly Val Pro Asp Arg Phe Ser
50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Pro Ser Val Thr Leu Phe Pro Pro Ser Thr Glu Glu
            115                 120                 125

Leu Asn Gly Asn Lys Ala Thr Leu Val Cys Leu Ile Ser Asp Phe Tyr
130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
            180                 185                 190

Gly Ser Tyr Ser Cys Glu Val Thr His Glu Gly Ser Thr Val Thr Lys
            195                 200                 205
```

```
Thr Val Lys Pro Ser Glu Cys Ser
    210                 215
```

<210> SEQ ID NO 484
<211> LENGTH: 269
<212> TYPE: PRT
<213> ORGANISM: Artificial sequence
<220> FEATURE:
<223> OTHER INFORMATION: Synthesized: Hc BLV5B8

<400> SEQUENCE: 484

```
Gln Val Gln Leu Arg Glu Ser Gly Pro Ser Leu Val Gln Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Ser Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Thr Val His Gln Glu Thr Arg Lys Thr Cys Ser Asp Gly Tyr Ile Ala
            100                 105                 110

Val Asp Ser Cys Gly Arg Gly Gln Ser Asp Gly Cys Val Asn Asp Cys
        115                 120                 125

Asn Ser Cys Tyr Tyr Gly Trp Arg Asn Cys Arg Arg Gln Pro Ala Ile
    130                 135                 140

His Ser Tyr Glu Phe His Val Asp Ala Trp Gly Arg Gly Leu Leu Val
145                 150                 155                 160

Thr Val Ser Ser Ala Ser Thr Thr Ala Pro Lys Val Tyr Pro Leu Ser
                165                 170                 175

Ser Cys Cys Gly Asp Lys Ser Ser Ser Thr Val Thr Leu Gly Cys Leu
            180                 185                 190

Val Ser Ser Tyr Met Pro Glu Pro Val Thr Val Thr Trp Asn Ser Gly
        195                 200                 205

Ala Leu Lys Ser Gly Val His Thr Phe Pro Ala Val Leu Gln Ser Ser
    210                 215                 220

Gly Leu Tyr Ser Leu Ser Ser Met Val Thr Val Pro Gly Ser Thr Ser
225                 230                 235                 240

Gly Gln Thr Phe Thr Cys Asn Val Ala His Pro Ala Ser Ser Thr Lys
                245                 250                 255

Val Asp Lys Ala Val Glu Pro Lys Ser Cys Asp Gly Ser
            260                 265
```

<210> SEQ ID NO 485
<211> LENGTH: 216
<212> TYPE: PRT
<213> ORGANISM: Artificial sequence
<220> FEATURE:
<223> OTHER INFORMATION: Synthesized: Lc BLV5B8

<400> SEQUENCE: 485

```
Gln Ala Val Leu Asn Gln Pro Ser Ser Val Ser Gly Ser Leu Gly Gln
1               5                   10                  15

Arg Val Ser Ile Thr Cys Ser Gly Ser Ser Ser Asn Val Gly Asn Gly
            20                  25                  30
```

-continued

```
Tyr Val Ser Trp Tyr Gln Leu Ile Pro Gly Ser Ala Pro Arg Thr Leu
        35              40              45

Ile Tyr Gly Asp Thr Ser Arg Ala Ser Gly Val Pro Asp Arg Phe Ser
    50              55              60

Gly Ser Arg Ser Gly Asn Thr Ala Thr Leu Thr Ile Ser Ser Leu Gln
65              70              75              80

Ala Glu Asp Glu Ala Asp Tyr Phe Cys Ala Ser Ala Glu Asp Ser Ser
            85              90              95

Ser Asn Ala Val Phe Gly Ser Gly Thr Thr Leu Thr Val Leu Gly Gln
            100             105             110

Pro Lys Ser Pro Pro Ser Val Thr Leu Phe Pro Pro Ser Thr Glu Glu
        115             120             125

Leu Asn Gly Asn Lys Ala Thr Leu Val Cys Leu Ile Ser Asp Phe Tyr
    130             135             140

Pro Gly Ser Val Thr Val Val Trp Lys Ala Asp Gly Ser Thr Ile Thr
145             150             155             160

Arg Asn Val Glu Thr Thr Arg Ala Ser Lys Gln Ser Asn Ser Lys Tyr
                165             170             175

Ala Ala Ser Ser Tyr Leu Ser Leu Thr Ser Ser Asp Trp Lys Ser Lys
            180             185             190

Gly Ser Tyr Ser Cys Glu Val Thr His Glu Gly Ser Thr Val Thr Lys
        195             200             205

Thr Val Lys Pro Ser Glu Cys Ser
    210             215
```